US008841326B2

(12) United States Patent
Vander Jagt et al.

(10) Patent No.: US 8,841,326 B2
(45) Date of Patent: Sep. 23, 2014

(54) THERAPEUTIC CURCUMIN DERIVATIVES

(75) Inventors: David L. Vander Jagt, Albuquerque, NM (US); Lorraine M Deck, Albuquerque, NM (US); Steve F. Abcouwer, Hummelstown, PA (US); Robert A. Orlando, Placitas, NM (US); Robert E. Royer, Bosque Farms, NM (US); Waylon M. Weber, Albuquerque, NM (US); Ekaterina V. Bobrovnikova-Marjon, Philadelphia, PA (US); Lucy A. Hunsaker, Albuquerque, NM (US)

(73) Assignee: STC.UNM, Alburquerque, NM (US)

( * ) Notice: Subject to any disclaimer, the term of this patent is extended or adjusted under 35 U.S.C. 154(b) by 1842 days.

(21) Appl. No.: 11/478,073

(22) Filed: Jun. 29, 2006

(65) Prior Publication Data

US 2007/0060644 A1    Mar. 15, 2007

Related U.S. Application Data

(63) Continuation-in-part of application No. 11/373,444, filed on Mar. 10, 2006, now abandoned, which is a continuation-in-part of application No. 11/057,736, filed on Feb. 14, 2005, now abandoned.

(60) Provisional application No. 60/787,694, filed on Mar. 30, 2006, provisional application No. 60/787,695, filed on Mar. 30, 2006, provisional application No. 60/544,424, filed on Feb. 12, 2004, provisional application No. 60/695,046, filed on Jun. 29, 2005.

(51) Int. Cl.
*A61K 31/44* (2006.01)
*A61K 31/12* (2006.01)

(52) U.S. Cl.
USPC ............................................ 514/332; 514/679

(58) Field of Classification Search
USPC ....................................... 514/332, 679
See application file for complete search history.

(56) References Cited

U.S. PATENT DOCUMENTS

| 3,691,210 A | 9/1972 | Solodar |
| 4,045,487 A | 8/1977 | Cleeland, Jr. et al. |
| 4,938,949 A | 7/1990 | Borch et al. |
| 5,395,692 A | 3/1995 | White et al. |
| 5,891,924 A * | 4/1999 | Aggarwal ..................... 514/679 |
| 6,887,898 B1 | 5/2005 | Kim |
| 2001/0025034 A1 | 9/2001 | Arbiser |

(Continued)

FOREIGN PATENT DOCUMENTS

| EP | 0507013 | 10/1992 |
| EP | 370461 B1 | 6/1995 |

(Continued)

OTHER PUBLICATIONS

Abcouwer, S.F., et al. "Response of VEGF Expression to Amino Acid Deprivation and Inducers of Endoplasmic Reticulum Stress" *Investigative Ophthalmology & Visual Science* 43:2791 (2002).

(Continued)

*Primary Examiner* — San-Ming Hui
(74) *Attorney, Agent, or Firm* — Henry D. Coleman; R. Neil Sudol

(57) ABSTRACT

Curcumin analogs and methods are provided for treatment of disease.

13 Claims, 39 Drawing Sheets
(10 of 39 Drawing Sheet(s) Filed in Color)

(56) References Cited

U.S. PATENT DOCUMENTS

| | | | |
|---|---|---|---|
| 2001/0051184 | A1 | 12/2001 | Heng |
| 2002/0006966 | A1 | 1/2002 | Arbiser |
| 2002/0019382 | A1 | 2/2002 | Snyder et al. |
| 2003/0007961 | A1 | 1/2003 | Wilburn |
| 2003/0078231 | A1 | 4/2003 | Wilburn |
| 2003/0092772 | A1* | 5/2003 | Reksohadiprodjo et al. .. 514/646 |
| 2003/0147979 | A1 | 8/2003 | Mae et al. |
| 2003/0149113 | A1 | 8/2003 | Caplan et al. |
| 2003/0153512 | A1 | 8/2003 | Hergenhahn et al. |
| 2003/0236300 | A1 | 12/2003 | Caplan et al. |
| 2004/0014721 | A1* | 1/2004 | Hensley et al. ................. 514/64 |
| 2004/0028673 | A1 | 2/2004 | Netzer et al. |
| 2004/0058021 | A1 | 3/2004 | Aggarwal |
| 2004/0146551 | A1 | 7/2004 | Mannino et al. |
| 2004/0176384 | A1 | 9/2004 | Snyder et al. |
| 2004/0220242 | A1 | 11/2004 | Shapiro |
| 2004/0253329 | A1 | 12/2004 | Mae et al. |
| 2004/0266883 | A1 | 12/2004 | Caplan et al. |
| 2005/0129791 | A1 | 6/2005 | Babish et al. |
| 2005/0181036 | A1 | 8/2005 | Aggarwal et al. |

FOREIGN PATENT DOCUMENTS

| | | |
|---|---|---|
| GB | 1109270 | 4/1968 |
| WO | WO 95/30670 | 11/1995 |
| WO | WO 98/20891 | 5/1998 |
| WO | WO 01/40188 A1 | 6/2001 |
| WO | WO 01/46110 A2 | 6/2001 |
| WO | WO 2004/047716 A2 | 6/2004 |

OTHER PUBLICATIONS

Heynekamp, J.J., et al. "Substituted trans-Stilbenes, Including Analogues of the Natural Product Resveratrol, Inhibit the Human Tumor Necrosis Factor Alpha-Induced Activataion of Transcription Factor Nuclear Factor KappaB" *J. Med. Chem.* 49:7182.
Roybal, C.N., et al., "Homocysteine Increases the Expression of Vascular Endothelial Growth Factor by a Mechanism Involving Endoplasmic Reticulum Stress and Transcription Factor ATF4" *J. Biol. Chem.* 279:14844 (2004).
Roybal, C.N., et al., "The Oxidative StressorArsenite Activates Vascular Endothelial Growth Factor mRNA Transcription by an ATF4-dependent Mechanism" *J. Biol. Chem.* 280:20331 (2005).
Roybal, C.N., et al., "Aberrant Accumulation of Fibulin-3 in the Endoplasmic Reticulum Leads to Activation of the Unfolded Protein Response and VEGF Expression" *Investigative Ophthalmology & Visual Science* 46:3973 (2005).
Adams, et al., *Anti-Cancer Drug.*, 2005; 16(3):263-275.
U.S. Appl. No. 11/057,736, filed Feb. 14, 2005, Vander Jagt et al.
U.S. Appl. No. 11/373,444, filed Mar. 10, 2006, Vander Jagt et al.
Adler et al., "Regulation of JNK signaling by GSTp" *EMBO J.*, Mar. 1, 1999; 18(5):1321-1334.
Aggarwal et al., "Suppression of the nuclear factor-kappaB activation pathway by spice-derived phytochemicals: reasoning for the seasoning" *Ann NY Acad Sci.*, 2004;1030:434-441.
Ahmed et al., *Dhaka Univ J Sci.*, 1998; 46(2):253-260.
Ahmed et al., "Molecular targets of diabetic cardiovascular complications" *Curr Drug Targets*, 2005; 6:487-494.
Aisen, "Inflammation and Alzheimer's disease: mechanisms and therapeutic strategies" *Gerontology*, 1997; 43(1-2):143-149.
Ali et al., *Indian J. Chem.*, 1995; 34B:884.
Allsop et al., "Fibrillogenesis of beta-amyloid" *Biochem Soc Trans.*, 1998; 26:459-463.
Amere et al., "Effect of Hsp90 inhibitors, geldanamycin, 17-allylamino-17-demethoxygeldanamycin and curcumin on human neuroblastoma cells, IMR-32", Abstract No. G1-008P, Federation of European Biochemical Societies 2005 Congress, Budapest, Hungary, Jul. 2-7, 2005. [Retrieved on Nov. 5, 2005] Retrieved from the Internet<URL:http://www.blackwellpublishing.com/febsabstracts2005/abstract.asp?id=41229>, 1 pg.

Ammon et al., "Pharmacology of Curcuma longa" *Planta Med.*, 1991; 57:1-7.
Andela et al., "NflcappaB: a pivotal transcription factor in prostate cancer metastasis to bone" *Clin Orthop Relat Res.*, Oct. 2003; (415 Suppl):S75-S85.
Andreasson et al., "Age-dependent cognitive deficits and neuronal apoptosis in cyclooxygenase-2 transgenic mice" *J. Neurosci.*, Oct. 15, 2001; 21(20):8198-8209.
Angel et al., "Phorbol ester-inducible genes contain a common cis element recognized by a TPA-modulated trans-acting factor" *Cell*, Jun. 19, 1987; 49(6):729-739.
Angel et al., "The role of Jun, Fos and the AP-1 complex in cell-proliferation and transformation" *Biochim Biophys Acta.*, Dec. 10, 1991; 1072(2-3):129-157.
Anto et al., "L-929 cells harboring ectopically expressed Re1A resist curcumin-induced apoptosis" *J Biol Chem.*, May 26, 2000; 275(21):15601-15604.
Antonioletti et al., "A new route to 2-alkenyl-1,3-dicarbonyl compounds, intermediates in the synthesis of dihydrofurans" *Tetrahedron*, Jan. 14, 2002; 58(3):589-596.
Araujo et al., "Beta-amyloid stimulates glial cells in vitro to produce growth factors that accumulate in senile plaques in Alzheimer's disease" *Brain Res.*, 1992; 569:141-145.
Araujo et al., "Biological activities of Curcuma longa L" *Mem Inst Oswaldo Cruz*, 2001; 96:723-728.
Arkan et al., "IKK-$\beta$ links inflammation to obesity-induced insulin resistance" *Nature Medicine*, Feb. 2005; 11(2):191-198.
Arsura et al., "Role of the IkappaB kinase complex in oncogenic Ras- and Raf-mediated transformation of rat liver epithelial cells" *Mol Cell Biol.*, Aug. 2000; 20(15):5381-5391.
Artico et al., *J Med Chem.*, 1998; 41(21):3948-3960.
Arty et al., *Eur J Med Chem.*, 2000; 35(4):449-457.
Arun et al., "Efficacy of turmeric on blood sugar and polyol pathway in diabetic albino rats" *Plant Foods Hum Ntr.*, 2002; 57:41-52.
Athamaprasangsa et al., "A 17-diarylheptanoid from *Alpinia chonchigera*" *Phytochemistry*, 1994; 37(3):871-873.
Awasthi et al., "Physiological substrates of glutathione S-transferases" *Chemico Biological Interactions*, 2001; 133:217-223.
Baeyer et al., *Chem Ber.*, 1902; 35:3013-3033.
Bagatell et al., "Altered Hsp90 function in cancer: a unique therapeutic opportunity" *Molecular Cancer Therapeutics*, Aug. 2004; 3(8):1021-1030.
Baker et al., "Jun is phosphorylated by several protein kinases at the same sites that are modified in serum-stimulated fibroblasts" *Mol Cell Biol.*, Oct. 1992; 12(10):4694-4705.
Balasubramanyam et al., "Curcumin-induced inhibition of cellular reactive oxygen species generation: novel therapeutic implications" *J Biosci.*, 2003; 28:715-721.
Baldwin, "The NF-kappa B and I kappa B proteins: new discoveries and insights" *Annu Rev Immunol.*, 1996; 14:649-683.
Baldwin, "Control of oncogenesis and cancer therapy resistance by the transcription factor NF-kappaB" *J Clin Invest.*, Feb. 2001; 107(3):241-246.
Bales et al., "The NF-kappaB/Rel family of proteins mediates Abeta-induced neurotoxicity and glial activation" *Brain Res Mol Brain Res.*, 1998; 57:63-72.
Barclay et al., "On the antioxidant mechanism of curcumin: classical methods are needed to determine antioxidant mechanism and activity" *Org Lett.*, 2000; 2:2841-2843.
Barkett et al., "Control of apoptosis by Rel/NF-kappaB transcription factors" *Oncogene*, Nov. 22, 1999; 18(49):6910-6924.
Barnes et al., "Nuclear factor-kappaB: a pivotal transcription factor in chronic inflammatory diseases" *N Engl J Med.*, Apr. 10, 1977; 336(15):1066-1071.
Baum et al., "Curcumin interaction with copper and iron suggests one possible mechanism of action in Alzheimer's disease animal models" *J Alzheimers Dis.*, Aug. 2004; 6(4):367-377; discussion 443-449.
Bayon et al., "Inhibition of IkappaB kinase by a new class of retinoid-related anticancer agents that induce apoptosis" *Mol Cell Biol.*, Feb. 2003; 23(3):1061-1074.
Begum et al., *Ind J Chem., Section B*, 1988; 27B(5):464.

(56) References Cited

OTHER PUBLICATIONS

*Beilsteins Handbuch der organischen Chemie.* 4. Aufl., Springer-Verlag, Berlin, Germany. Title page, copyright page and table of contents. 1991.
Benjamin, "Glucose, VEGF-A, and diabetic complications" *Am J Pathol.*, 2001; 158:1181-1184.
Bernstein et al., "AP1/jun function is differentially induced in promotion-sensitive and resistant JB6 cells" *Science*, May 5, 1989; 244(4904):566-569.
Benzie, et al., "Ferric reducing/antioxidant power assay: direct measure of total antioxidant activity of biological fluids and modified version for simultaneous measurement of total antioxidant power and ascorbic acid concentration" *Methods Enzymol.*, 1999; 299:15-27.
Bharti et al., "Curcumin (diferuloylmethane) down-regulates the constitutive activation of nuclear factor-kappa B and IkappaBalpha kinase in human multiple myeloma cells, leading to suppression of proliferation and induction of apoptosis" *Blood*, 2003; 101:1053-1062.
Bianchini et al., "In situ and reactor study of the enantioselective hydrogenation of acetylacetone by ruthenium catalysis with the new chiral diphosphine ligand (R)-(R)-3-benzyl-2,4-bis(diphenylphosphino)pentane" *Organometallics*, 2000; 19(13):2450-2461.
Bieler et al., "Beta-sheet breakers for Alzheimer's disease therapy" *Curr Drug Targets*, 2004; 5:553-558.
Blenis, "Signal transduction via the MAP kinases: proceed at your own RSK" *Proc Natl Acad Sci USA*, Jul. 1, 1993; 90(13):5889-5892.
Bocchini et al., "An immortalized cell line expresses properties of activated microglial cells" *J Neurosci Res.*, Apr. 1992; 31(4):616-621.
Boeri et al., "Modification of tissue factor mRNA and protein response to thrombin and interleukin 1 by high glucose in cultured human endothelial cells" *Diabetes*, 1989; 38:212-218.
Bologa et al., "Virtual and biomolecular screening coverage on a selective agonist for GPR30" *Nature Chem Biol.*, Apr. 2006; 2(4):207-212. Epub Mar. 5, 2006.
Bonte et al., "Protective effect of curcuminoids on epidermal skin cells under free oxygen radical stress" *Planta Med.*, Jun. 1997; 63(3):265-266.
Brahmbhatt et al., Ind J Chem Section B, 2003; 42B:145-149.
Bremner et al., "Natural products as targeted modulators of the nuclear factor-kappaB pathway" *J Pharm Pharmacol.*, 2002; 54:453-472.
Brennan et al , "Inhibition of nuclear factor kappaB by direct modification in whole cells—mechanism of action of nordihydroguaiaritic acid, curcumin and thiol modifiers" *Biochem Pharmacol.*, Apr. 1, 1998; 55(7):965-973.
Brown et al., "Creating artificial binding pocket boundaries to improve the efficiency of flexible ligand docking" *J Chem Inf Comput Sci.*, Jul.-Aug. 2004; 44(4):1412-1422.
Buchschacher et al., "Development of lentiviral vectors for gene therapy for human diseases" *Blood*, Apr. 15, 2000; 95(8):2499-2504.
Burditt et al., *J Chem Soc., Section C*, 1967; 22:2273-2275.
Bushby et al., *J Chem Soc Perkin Trans 1*, 2001; 18:2183-2193.
Cagliero et al., "Increased expression of basement membrane components in human endothelial cells cultured in high glucose" *J Clin Invest.*, 1988; 82:735-738.
Cai et al., "BACE1 is the major beta-secretase for generation of Abeta peptides by neurons" *Nature Neuroscience*, 2001; 4:233-234.
Carde et al., *J Chem Soc Perkin Trans 1*, 2000; 15:2455-2463.
Ceriello, "Acute hyperglycaemia and oxidative stress generation" *Diabet Med.*, 1997; 14:S45-S49.
Chainani-Wu, "Safety and anti-inflammatory activity of curcumin: a component of tumeric (Curcuma longa)" *J Altern Complement Med.*, 2003; 9:161-168.
Chan, "Inhibition of tumor necrosis factor by curcumin, a phytochemical" *Biochem Pharmacol.*May 26, 1995; 49(11):1551-1556.
Chan, "Effect of resveratrol on high glucose-induced stress in human leukemia K562 cells" *J Cell Biochem.*, 2005; 94:1267-1279.
Chandra et al., "Incidence of Alzheimer's disease in a rural community in India: the Indo-US study" *Neurology*, 2001; 57:985-989.
Chaudhary et al., "Regulation of interleukin-8 gene expression by interleukin-1beta, osteotropic hormones, and protein kinase inhibitors in normal human bone marrow stromal cells" *J Biol Chem.*, Jul. 12, 1996; 271(28):16591-16596.
Chaykovsky et al., *J Med Chem.*, 1973; 16(3):188-191.
Chem Abstr., 68; P115550a, 1968.
Chem Abstr., 78, 45071a, 1973.
Chem Abstr., 87, P167872u, 1977.
Chem Abstr., 113, P230963x, 1990.
Chem Abstr., 115, P207660d, 1992.
Chem Abstr., 123, P84361n, 1995.
Chem Abstr., 124, P232245r, 1996.
Chem Abstr., 129, P23452v, 1998.
Chem Abstr., 135, P19497v, 2001.
Chem Abstr., 135, P76687f, 2001.
Chem Abstr., 141, 38433, 2004.
Chen et al., "Simultaneous assessment of conformation and aggregation of beta-amyloid peptide using electrospray ionization mass spectrometry" *FASEB Journal*, 1997; 11:817-823.
Chen et al., "New insights into the role of Nuclear Factor-κB, a ubiquitous transcription factor in the initiation of diseases" *Clinical Chemistry*, 1999; 45(1):7-17.
Chen et al., "TNF-induced recruitment and activation of the IKK complex require Cdc37 and Hsp90" *Mol Cell*, Feb. 2002; 9(2):401-410.
Chung et al., "Inhibition of activator protein 1 activity and cell growth by purified green tea and black tea polyphenols in H-ras-transformed cells: structure-activity relationship and mechanisms involved" *Cancer Res.*, Sep. 15, 1999; 59(18):4610-4617.
Citron, "Beta-secretase inhibition for the treatment of Alzheimer's disease—promise and challenge" *Trends Pharmacol Sci.*, 2004; 25:92-97.
Cockerill et al., *J Chem Soc Perkin Trans 2*, 1972; 14:2076-2081.
Cohly, "Effect of turmeric, turmerin and curcumin on H2O2-induced renal epithelial (LLC-PK1) cell injury" *Free Radic Biol Med.*, Jan. 1, 1998; 24(1):49-54.
Cole et al., "NSAID and antioxidant prevention of Alzheimer's disease: lessons from in vitro and animal models" *Ann NY Acad Sci.*, Dec. 2004; 1035:68-84.
Coles et al., "Solution structure of amyloid beta-peptide(1-40) in a water-micelle environment. Is the membrane-spanning domain where we think it is?" *Biochemistry*, 1998; 37:11064-11077.
Combs et al., "beta-Amyloid stimulation of microglia and monocytes results in TNFalpha-dependent expression of inducible nitric oxide synthase and neuronal apoptosis" *J Neurosci.*, Feb. 15, 2001; 21(4):1179-1188.
Crescenzi et al., 2002. "Solution structure of the Alzheimer amyloid beta-peptide (1-42) in an apolar microenvironment. Similarity with a virus fusion domain" *Eur J Biochem.*, 2002; 269:5642-5648.
Czekay et al., "Endocytic trafficking of megalin/RAP complexes: dissociation of the complexes in late endosomes" *Mol Biol Cell*, 1997; 8:517-532.
Dalla Vestra et al., "Acute-phase markers of inflammation and glomerular structure in patients with type 2 diabetes" *J Am Soc Nephrol.*, 2005; 16:S78-S82.
Datki et al., "Method for measuring neurotoxicity of aggregating polypeptides with the MTT assay on differentiated neuroblastoma cells" *Brain Res Bull.*, 2003; 62:223-229.
Davis, "The mitogen-activated protein kinase signal transduction pathway" *J Biol Chem.*, Jul. 15, 1993; 268(20):14553-14556.
de Castro Reffeira Gomes et al., Arzneimittel.-Forsch., 2002; 52(9):695-698.
De Strooper, "Aph-1, Pen-2, and Nicastrin with Presenilin generate an active gamma-Secretase complex" *Neuron*, 2003; 38:9-12.
Dhar et al., "The role of AP-1, NF-kappaB and ROS/NOS in skin carcinogenesis: the JB6 model is predictive" *Mol Cell Biochem.*, May-Jun. 2002; 234-235(1-2):185-193.
Dietze et al., *Phannazie*, 1997; 52(4):302-306.
Dong et al., "Blocking of tumor promoter-induced AP-1 activity inhibits induced transformation in JB6 mouse epidermal cells" *Proc Natl Acad Sci USA*, Jan. 18, 1994; 91(2):609-613.

(56) References Cited

OTHER PUBLICATIONS

Du et al., "Methylglyoxal induces apoptosis in Jurkat leukemia T cells by activating c-jun N-terminal kinase" *J Cell Biochem.*, Mar. 2000; 77(2):333-344.
Du et al., "Inhibition of GAPDH activity by poly(ADP-ribose) polymerase activates three major pathways of hyperglycemic damage in endothelial cells" *J Clin Invest.*, 2003;112:1049-1057.
Ducat Sigala et al., "Activation of transcription factor NF-kappaB requires ELKS, an IkappaB kinase regulatory subunit" *Science*, Jun. 25, 2004; 304(5679): 1963-1967.
Dull et al., "A third-generation lentivirus vector with a conditional packaging system" *J Virol.*, Nov. 1998; 72(11):8463-8471.
Durant et al., "Reoptimization of MDL keys for use in drug discovery" *J Chem Inf Comput Sci.*, 2002; 42:1273-1280.
Duvoix et al., "Induction of apoptosis by curcumin: mediation by glutathione S-transferase P1-1 inhibition" *Biochem Pharmacol.*, Oct. 15, 2003; 66(8):1475-1483.
Dyrks et al., "Generation of beta A4 from the amyloid protein precursor and fragments thereof" *FEBS Letters*, 1993; 335:89-93.
Edwards et al., *J Med Chem.*, 1983; 26(3):431-436.
Edwards et al., "Flow cytometry for high-throughput, high-content screening" *Curr Opin Chem Biol.*, Aug. 2004; 8(4):392-398.
Egan et al., "Curcumin, a major constituent of turmeric, corrects cystic fibrosis defects" *Science*, Apr. 23, 2004; 304(5670):600-602.
Elias et al., *Eur J Med Chem.*, 1988, 23(4):379-380.
Emre et al., "The acute neurotoxicity and effects upon cholinergic axons of intracerebrally injected beta-amyloid in the rat brain" *Neurobiol Aging*, 1992; 13:553-559.
Engelhart et al., "Dietary intake of antioxidants and risk of Alzheimer disease" *JAMA*, Jun. 26, 2002; 287(24):3223-3229.
Etcheberrigaray et al., "Calcium responses in fibroblasts from asymptomatic members of Alzheimer's disease families" *Neurobiol Dis.*, 1998; 5:37-45.
Evans et al., "Apolipoprotein E is a kinetic but not a thermodynamic inhibitor of amyloid formation: implications for the pathogenesis and treatment of Alzheimer disease" *Proc Natl Acad Sci USA*, 1995; 92:763-767.
Fernandez-Real et al., "Insulin resistance and chronic cardiovascular inflammatory syndrome" Endocrine Reviews, Jun. 2003; 24(3):278-301.
Festa et al., "Elevated levels of acute-phase proteins and plasminogen activator inhibitor-1 predict the development of type 2 diabetes: the insulin resistance atherosclerosis study" *Diabetes*, Apr. 2002; 51(4):1131-1137.
Fieser et al., *Reagents for Organic Synthesis*, v. 1-19, Wiley, New York, NY, 1967-1999. Title page copyright page and table of contents.
Fontecave et al., "Resveratrol, a remarkable inhibitor of ribonucleotide reductase" *FEBS Lett.*, Jan. 16, 1998; 421(3):277-279.
Funakoshi-Tago et al., "Functional role of c-Src in IL-1-induced NF-kappa B activation: c-Src is a component of the IKK complex" *J Biochem* (Tokyo), Feb. 2005; 137(2):189-197.
Funato et al., "Quantitation of amyloid beta-protein (A beta) in the cortex during aging and in Alzheimer's disease" *Am J Pathol.*, 1998; 152:1633-1640.
Games et al., "Alzheimer-type neuropathology in transgenic mice overexpressing V717F beta-amyloid precursor protein" *Nature*, 1995; 373:523-527.
Garcea et al., "Detection of curcumin and its metabolites in hepatic tissue and portal blood of patients following oral administration" *Br J Cancer*, 2004; 90:1011-1015.
Gasic-Milenkovic et al., "Beta-amyloid peptide potentiates inflammatory responses induced by lipopolysaccharide, interferon-gamma and 'advanced glycation endproducts' in a murine microglia cell line" *Eur J Neurosci.*, 2003; 17:813-821.
Gasparini et al., "Activity of flurbiprofen and chemically related anti-inflammatory drugs in models of Alzheimer's disease" *Brain Res Brain Res Rev.*, Apr. 2005; 48(2):400-408. Epub Jan. 28, 2005.
Geula, "Abnormalities of neural circuitry in Alzheimer's disease: hippocampus and cortical cholinergic innervation" *Neurology*, 1998; 51(1 Suppl 1):S18-29; discussion S65-67.
Ghosh et al., "Structure-based design: potent inhibitors of human brain memapsin 2 (beta-secretase)" *J Med Chem.*, 2001; 44:2865-2868.
Ghosh et al., "Missing pieces in the NF-kappaB puzzle" *Cell*, Apr. 2002; 109 *Suppl*:S81-96.
Glabe, "Does Alzheimer disease tilt the scales of amyloid degradation versus accumulation?" *Nat Med.*, 2000; 6:133-134.
Glabe, "Conformation-dependent antibodies target diseases of protein misfolding" *Trends Biochem Sci.*, 2004; 29:542-547.
Glenner et al., "The amyloid deposits in Alzheimer's disease: their nature and pathogenesis" *Applied Pathology*, 1984; 2:357-369.
Glover et al., "Crystal structure of the heterodimeric bZIP transcription factor c-Fos-c-Jun bound to DNA" *Nature*, Jan. 19, 1995; 373(6511):257-261.
Goate et al., "Segregation of a missense mutation in the amyloid precursor protein gene with familial Alzheimer's disease" *Nature*, 1991; 349:704-706.
Goldgaber et al., "Characterization and chromosomal localization of a cDNA encoding brain amyloid of Alzheimer's disease" *Science*, 1987; 235:877-880.
Goodwin et al., "Microglial release of nitric oxide by the synergistic action of beta-amyloid and IFN-gamma" *Brain Res.*,1995; 692:207-214.
Govindarajan, "Turmeric—chemistry, technology, and quality" *Crit Rev Food Sci Nutr.*, 1980;12(3):199-301.
Graier et al., "Intracellular mechanism of high D-glucose-induced modulation of vascular cell proliferation" *Eur J Pharmacol.*, 1995; 294:221-229.
Grant et al., "A smooth permittivity function for Poisson-Boltzmann solvation methods" *J. Comput. Chem.*, 2001; 22(6):608-640. Published online: Mar. 20, 2001.
Greenberg et al., "Prostate cancer in a transgenic mouse" *Proc Natl Acad Sci USA*, Apr. 11, 1995; 92(8):3439-3443.
Greenhalgh et al., "12-O-tetradecanoylphorbol-13-acetate promotion of transgenic mice expressing epidermal-targeted v-fos induces rasHA-activated papillomas and carcinomas without p53 mutation: association of v-fos expression with promotion and tumor autonomy" *Cell Growth Differ.*, May 1995; 6(5):579-586.
Griffin et al., "Glial-neuronal in teractions in Alzheimer's disease: the potential role of a 'cytokine cycle' in disease progression" *Brain Pathol.*, Jan. 1998; 8(1):65-72.
Gupta et al., "Curcuma longa inhibits TNF-alpha induced expression of adhesion molecules on human umbilical vein endothelial cells" *Int J Immunopharmacol.*, Nov. 1999; 21(11):745-757.
Gursky et al., "Temperature-dependent beta-sheet formation in beta-amyloid Abeta(1-40) peptide in water: uncoupling beta-structure folding from aggregation" *Biochimica et Biophysica Acta*, 2000; 1476:93-102.
Haass et al., "Amyloid beta-peptide is produced by cultured cells during normal metabolism" *Nature*, 1992; 359:322-325.
Hahm et al., "New and known symmetrical curcumin derivatives inhibit the formation of Fos-Jun-DNA complex" *Cancer Lett.*, Oct. 8, 2002; 184(1):89-96.
Hahn et al., "A cell based assay system for monitoring NF-kappa-B activity in human HaCat transfectant cells" *Anal Biochem.*, 2001; 292:17-21.
Hardy et al., "The amyloid hypothesis of Alzheimer's disease: progress and problems on the road to therapeutics" *Science*, 2002; 297:353-356.
Harper et al., "Models of amyloid seeding in Alzheimer's disease and scrapie: mechanistic truths and physiological consequences of the time-dependent solubility of amyloid proteins" *Annu Rev Biochem.*, 1997; 66:385-407.
Hartley et al., "Protofibrillar intermediates of amyloid beta-protein induce acute electrophysiological changes and progressive neurotoxicity in cortical neurons" *J Neurosci.*, 1999; 19:8876-8884.
Hass et al., *J Am Chem Soc.*, 1949; 71:1767-1769.
Hayes et al., *J Org Chem.*, 2002; 67(3):935-942.

(56) References Cited

OTHER PUBLICATIONS

Hebert et al., "Alzheimer disease in the US population: prevalence estimates using the 2000 census" *Arch Neurol.*, Aug. 2003; 60(8):1119-1122.

Hess et al., "AP-1 subunits: quarrel and harmony among siblings" *Journal of Cell Science*, 2004;117:5965-5973.

Hink et al., "Mechanisms underlying endothelial dysfunction in diabetes mellitus: therapeutic implications" *Treat Endocrinol.*, 2003; 2:293-304.

Hirosumi et al., "A central role for JNK in obesity and insulin resistance" *Nature*, Nov. 21, 2002; 420(6913):333-336.

Hiscott et al., "Hostile takeovers: viral appropriation of the NF-kappaB pathway" *J Clin Invest.*, Jan. 2001; 107(2):143-151.

Holcomb et al., "Behavioral changes in transgenic mice expressing both amyloid precursor protein and presenilin-1 mutations: lack of association with amyloid deposits" *Behav Genet.*,1999; 29:177-185.

Hong et al., "Curcumin inhibits tyrosine kinase activity of p185neu and also depletes p185neu" *Clin Cancer Res.*, Jul. 1999; 5(7):1884-1891.

Hooper et al., "The search for alpha-secretase and its potential as a therapeutic approach to Alzheimer s disease" *Curr Med Chem.*, 2002; 9:1107-1119.

Hotamisligil, "Inflammatory pathways and insulin action" *Int J Obes Relat Metab Disord.*, Dec. 2003; 27(Suppl 3):S53-S55.

Hsia et al., "Plaque-independent disruption of neural circuits in Alzheimer's disease mouse models" *Proc Natl Acad Sci USA*, 1999; 96:3228-3233.

Hsiao, "Transgenic mice expressing Alzheimer amyloid precursor proteins" *Exp Gerontol.*, 1998; 33:883-889.

Hu et al., "Amyloid-beta peptide activates cultured astrocytes: morphological alterations, cytokine induction and nitric oxide release" *Brain Res.*, 1998; 785:195-206.

Huang et al., "Suppression of c-Jun/AP-1 activation by an inhibitor of tumor promotion in mouse fibroblast cells" *Proc Natl Acad Sci USA*, Jun. 15, 1991; 88(12):5292-5296.

Huxford et al., "The crystal structure of the IkappaBalpha/NF-kappaB complex reveals mechanisms of NF-kappaB inactivation" *Cell*, Dec. 11, 1998; 95(6):759-770.

Ingels, "Food for thought: curcumin may prevent Alzheimer's disease" Healthnotes Newswire, Nov. 21, 2001 [online]. Numark Pharmacists, copyright 2001 Healthnotes, Inc. [Retrieved on Nov. 5, 2005]. Retrieved from the Internet: <URL:http://www.numarkpharmacists.com/nw/page_nw_nov_curcumin_prevents_alzheimers.html>; 1 page.

Iwata et al., "Identification of the major Abeta1-42-degrading catabolic pathway in brain parenchyma: suppression leads to biochemical and pathological deposition" *Nat Med.*, 2000; 6:143-150.

• Jiang et al., "Curcumin induces apoptosis in immortalized NIH 3T3 and malignant cancer cell lines" *Nutr Cancer*, 1996; 26(1):111-120.

Jarrett et al., "Amyloid fibril formation requires a chemically discriminating nucleation event: studies of an amyloidogenic sequence from the bacterial protein OsmB" *Biochemistry*, 1992; 31:12345-12352.

Jarrett et al., "Seeding "one-dimensional crystallization" of amyloid: a pathogenic mechanism in Alzheimer's disease and scrapie?" *Cell*, 1993; 73:1055-1058.

Jarrett et al., "The carboxy terminus of the beta amyloid protein is critical for the seeding of amyloid formation: implications for the pathogenesis of Alzheimer's disease" *Biochemistry*, 1993; 32:4693-4697.

Jarrett et al., "The C-terminus of the beta protein is critical in amyloidogenesis" *Ann N Y Acad Sci.*, 1993; 695:144-148.

Jax Mice, Mouse Models for Diabetes and Obesity Research, Summer 2004, datasheet. The Jackson Laboratory, Bar Harbor, ME; 39 pages.

Jobin et al., "Curcumin blocks cytokine-mediated NF-kappa B activation and proinflammatory gene expression by inhibiting inhibitory factor I-kappa B kinase activity" *J Immunol.*, Sep. 15, 1999; 163(6):3474-3483.

Jochum et al., "AP-1 in mouse development and tumorigenesis" *Oncogene*, Apr. 30, 2001; 20(19):2401-2412.

Joe et al., "Biological properties of curcumin-cellular and molecular mechanisms of action" *Crit Rev Food Sci Nutr.*, 2004; 44(2):97-111.

Johnson et al., *Concepts and applications of Molecular Similarity*, Wiley; New York, NY; 1990. Title page, copyright page and table of contents only.

Joussen et al., "Nonsteroidal anti-inflammatory drugs prevent early diabetic retinopathy via THF-α suppression" *FASEB J.*, 2002; 16:438-440.

Jovanovic et al., "How curcumin works preferentially with water soluble antioxidants" *J Am Chem Soc.*, Apr. 4, 2001; 123(13):3064-3068.

Kamal et al., "A high-affinity conformation of Hsp90 confers tumour selectivity on Hsp90 Inhibitors" Nature, Sep. 25, 2003; 425(6956):407-410.

Kang et al., "Curcumin supresses lipopolysaccharide-induced cyclooxygenase-2 expression by inhibiting activator protein 1 and nuclear factor kappab bindings in BV2 microglial cells" *J Pharmacol Sci.*, Mar. 2004; 94(3):325-328.

Kang et al., "Inflammation and extracellular matrix degradation mediated by activated transcription factors nuclear factor-kappaB and activator protein-1 in inflammatory acne lesions in vivo" *Am J Pathol.*, Jun. 2005; 166(6):1691-1699.

Kansy et al.,"Physicochemical high-throughput screening: parallel artificial membrane permeation assay in the description of passive processes" *J Med Chem.*, 1998; 41:1007-1010.

Karin et al., "AP-1 function and regulation" *Curr Opin Cell Biol.*, Apr. 1997; 9(2):240-246.

Karin et al., "NF-kappaB in cancer: from innocent bystander to major culprit" *Nat Rev Cancer*, Apr. 2002; 2(4):301-310.

Karin et al., "The IKK NF-kappa B system: a treasure trove for drug development" *Nat Rev Drug Discov.*, Jan. 2004; 3(1):17-26.

Katritzky et al., *Comprehensive organic functional group transformations*, v. 1-6, Pergamon Press, Oxford, England, 1995. Title page, copyright page, table of contents.

Kayed et al., "Common structure of soluble amyloid oligomers implies common mechanism of pathogenesis" *Science*, 2003; 300:486-489.

Kerjaschki et al., "Induction of passive Heymann nephritis with antibodies specific for a synthetic peptide derived from the receptor-associated protein" *J Exp Med.*, 1996; 183:2007-2015.

Khopde et al., "Effect of solvent on the excited-state photophysical properties of curcumin" *Photochem Photobiol.*, 2000; 72:625-631.

Kim et al., "Selective neuronal degeneration induced by soluble oligomeric amyloid beta protein" *FASEB J.*, Jan. 2003; 17(1):118-120. Epub Nov. 1, 2002.

Kitazawa et al., "Microglia as a potential bridge between the amyloid beta-peptide and tau" *Ann NY Acad Sci.*, Dec. 2004; 1035:85-103.

Kleber et al., *Naturwissenschaften*, 1965; 52(18):513-514.

Klunk et al., "Development of small molecule probes for the beta-amyloid protein of Alzheimer's disease" *Neurobiol Aging*, 1994; 15:691-698.

Kohler et al., "Benzalacetophenone (chalcone)" *Organic Synthesis. Collective Volume*; vol. 1, Wiley, New York, NY, 1932. Title page, copyright page, table of contents, and section by Kohler and Chadwell, and pp. 78-80.

Korutla et al., "Inhibition of ligand-induced activation of epidermal growth factor receptor tyrosine phosphorylation by curcumin" *Carcinogenesis*, Aug. 1995; 16(8):1741-1745.

Kowall et al., "In vivo neurotoxicity of beta-amyloid [beta(1-40)] and the beta(25-35) fragment" *Neurobiol Aging.*, 1992; 13:537-542.

Kratzl et al., *Chem Ber.*, 1944; 77B:519-527.

Krunkosky et al., "Effects of TNF alpha on expression of ICAM-1 in human airway epithelial cells in vitro: oxidant-mediated pathways and transcription factors" *Free Radic Biol Med.*, Nov. 1, 2003; 35(9):1158-1167.

Kumar et al., *J Org Chem.*, 1985; 50(16):2818-2825.

Kumar et al., "Curcumin (Diferuloylmethane) inhibition of tumor necrosis factor (TNF)-mediated adhesion of monocytes to endothelial cells by suppression of cell surface expression of adhesion molecules and of nuclear factor-kappaB activation" *Biochem Pharmacol.*, Mar. 15, 1998; 55(6):775-783.

(56) References Cited

OTHER PUBLICATIONS

Kundu et al., "Molecular basis of chemoprevention by resveratrol: NF-kappaB and AP-1 as potential targets" *Mutat Res.*, Nov. 2, 2004; 555(1-2):65-80.
Lambert et al., "Diffusible, nonfibrillar ligands derived from Abeta1-42 are potent central nervous system neurotoxins" *Proc Natl Acad Sci USA*, 1998; 95:6448-6453.
Lansbury et al., "Structural model for the beta-amyloid fibril based on interstrand alignment of an antiparallel-sheet comprising a C-terminal peptide" *Nat Struct Biol.*, 1995; 2:990-998.
Laurin et al., "Midlife dietary intake of antioxidants and risk of late-life incident dementia: the Honolulu-Asia Aging Study" *Am J Epidemiol.*, May 15, 2004; 159(10):959-967.
Leiro, et al., "Effect of cis-resveratrol on genes involved in nuclear factor kappa B signaling" *Int Immunopharmacol.*, 2005; 5:393-406.
Leu et al., "The molecular mechanisms for the antitumorigenic effect of curcumin" *Curr Med Chem Anti-Canc Agents*, 2002; 2:357-370.
LeVine, 3rd, "Quantification of beta-sheet amyloid fibril structures with thioflavin T" *Methods Enzymol.*, 1999; 309:274-284.
Levy et al., "Mutation of the Alzheimer's disease amyloid gene in hereditary cerebral hemorrhage, Dutch type" *Science*, 1990; 248:1124-1126.
Lewis et al., "Computer-Aided Molecular Diversity Analysis and Combinatorial Library Design" *Reviews in Computational Chemistry*, 2000; 16:1-51.
Li et al., "Induced expression of dominant-negative c-jun downregulates NfkappaB and AP-1 target genes and suppresses tumor phenotype in human keratinocytes" *Mol Carcinog.*, Nov. 2000; 29(3):159-169.
Liang et al., "Jesterone dimer, a synthetic derivative of the fungal metabolite jesterone, blocks activation of transcription factor nuclear factor kappaB by inhibiting the inhibitor of kappaB kinase" *Mol Pharmacol.*, Jul. 2003; 64(1):123-131.
Lim et al., "The curry spice curcumin reduces oxidative damage and amyloid pathology in an Alzheimer transgenic mouse" *J Neurosci.*, 2001; 21:8370-8377.
Litwinienko et al., "Abnormal solvent effects on hydrogen atom abstraction. 2. Resolution of the curcumin antioxidant controversy. The role of sequential proton loss electron transfer" *J Org Chem.*, Sep. 3, 2004; 69(18):5888-5896.
Lopez De La Paz et al., "De novo designed peptide-based amyloid fibrils" *Proc Natl Acad Sci USA*, 2002; 99:16052-16057.
Lorenzo et al., "Beta-amyloid neurotoxicity requires fibril formation and is inhibited by congo red" *Proc Natl Acad Sci USA*, 1994; 91:12243-12247.
Lou et al., "GAIP, GIPC and Galphai3 are concentrated in endocytic compartments of proximal tubule cells: putative role in regulating megalin's function" *J Am Soc Nephrol.*, 2002; 13:918-927.
Lue et al., "Inflammatory repertoire of Alzheimer's disease and nondemented elderly microglia in vitro" *Glia*, 2001; 35:72-79.
Lundstrom et al., "Immunocytochemical and biochemical characterization of the Heymann nephritis antigenic complex in rat L2 yolk sac cells" *Am J Pathol.*, 1993; 143:1423-1435.
Luo et al., "Mice deficient in BACE1, the Alzheimer's beta-secretase, have normal phenotype and abolished beta-amyloid generation" *Nat Neurosci.*, 2001; 4:231-232.
Maggio et al., "Zinc and Alzheimer's disease" *Science*, 1995; 268:1920-1921; author reply 1921-1923.
Maiello et al., "Increased expression of tissue plasminogen activator and its inhibitor and reduced fibrinolytic potential of human endothelial cells cultured in elevated glucose" *Diabetes*, 1992; 41:1009-1015.
Makarov, "NF-kappaB as a therapeutic target in chronic inflammation: recent advances" *Mol Med Today*, Nov. 2000; 6(11):441-448.
Mandl-Weber et al., "Early glycated albumin, but not advanced glycated albumin, methylglyoxal, or 3-deoxyglucosone increases the expression of PAI-1 in human peritoneal mesothelial cells" *Perit Dial Int.*, 2001; 21, 487-494.
Manna et al., "Silymarin suppresses TNF-induced activation of NF-kappa B, c-Jun N-terminal kinase, and apoptosis" *J Immunol.*, Dec. 15, 1999; 163(12):6800-6809.
Manna et al., "Resveratrol suppresses TNF-induced activation of nuclear transcription factors NF-kappa B, activator protein-1, and apoptosis: potential role of reactive oxygen intermediates and lipid peroxidation" *J Immunol.*, Jun. 15, 2000;164(12):6509-6519.
Manna et al., "Oleandrin suppresses activation of nuclear transcription factor-kappaB, activator protein-1, and c-Jun NH2-terminal kinase" *Cancer Res.*, Jul. 15, 2000; 60(14):3838-3847.
Markham et al., *Organic Synthesis. Collective Volume*; vol. V, Wiley, New York, NY, 1932. Title page, copyright page, table of contents, and pp. 785-790.
Martin, "Diverse viewpoints on computational aspects of molecular diversity" *J Comb Chem.*, 2001; 3:231-250.
Masuda et al., "Anti-oxidative and anti-inflammatory curcumin-related phenolics from rhizomes of curcuma domestica" *Phytochemistry*, 1993; 32:1557-1560.
Mattson et al., "beta-Amyloid precursor protein metabolites and loss of neuronal Ca2+ homeostasis in Alzheimer's disease" *Trends Neurosci.*, 1993; 16:409-414.
Mattson, "Cellular actions of beta-amyloid precursor protein and its soluble and fibrillogenic derivatives" *Physiol Rev.*, 1997; 77:1081-1132.
Mayeux et al., "Treatment of Alzheimer's disease" *N Engl J Med.*, 1999; 341:1670-1679.
McGeer et al., "The inflammatory response system of brain: implications for therapy of Alzheimer and other neurodegenerative diseases" *Brain Res Brain Res Rev.*, 1995; 21:195-218.
McGeer et al., Inflammatory processes in Alzheimer's disease *Prog Neuropsychopharmacol Biol Psychiatry*, Aug. 2003; 27(5):741-749.
McGovern et al., "A common mechanism underlying promiscuous inhibitors from virtual and high-throughput screening" *J Med Chem.*, 2002; 45:1712-1722.
McLean et al., "Soluble pool of Abeta amyloid as a determinant of severity of neurodegeneration in Alzheimer's disease" *Ann Neurol.*, Dec. 1999; 46(6):860-866.
Meda et al., "Activation of microglial cells by beta-amyloid protein and interferon-gamma" *Nature*, 1995; 374:647-650.
Mehlhorn et al., "Induction of cytokines in glial cells surrounding cortical beta-amyloid plaques in transgenic Tg2576 mice with Alzheimer pathology" *Int J Dev Neurosci.*, 2000; 18:423-431.
Mineur et al., "Genetic mouse models of Alzheimer's disease" *Neural Plast.*, 2005;12(4):299-310.
Mohamed et al., "The role of oxidative stress and NF-κB activation in late diabetic complications" *BioFactors*, 1999; 10:157-167.
Morris et al., "Distributed automated docking of flexible ligands to proteins: parallel application of AutoDock 2.4" *J Comput Aided Mol Des.*, Aug. 1996; 10(4):293-304.
Morris et al., "Automated docking using a Lamarckian genetic algorithm and an empirical binding free energy function" *J Comput Chem.*, 1998; 19(14):1639-1662.
Moynagh, "The NF-κB pathway" *J Cell Sci.*, 2005; 118:4389-4392.
Muller et al., "Tissue and cell type-specific expression.of two human c-onc genes" *Nature*, Aug. 4-10, 1983; 304(5925):454-456.
Muller et al., "Structure of the NF-kappa B p50 homodimer bound to DNA" *Nature*, Jan. 26, 1995; 373(6512):311-317.
Nagar et al., *Planta Med.*, 1979; 37(2):183-185.
Naiki et al., "Fluorometric determination of amyloid fibrils in vitro using the fluorescent dye, thioflavin T1" *Anal Biochem.*, 1989; 177:244-249.
Navarro et al., "Role of inflammation in diabetic complications" *Nephrol Dial Transplant*, 2005; 20:2601-2604.
Neckers, "Hsp90 inhibitors as novel cancer chemotherapeutic agents" *Trends in Molecular Medicine*, 2002; 8(4 Suppl):S55-S61.
Neurath et al., "Role of NF-κB in immune and inflammatory responses in the gut" *Gut*, 1998; 43:856-860.
Nielsen et al., *Bioorgan Med Chem.*, 2004; 12(11):3047-3054.
Nishikawa et al., "Normalizing mitochondrial superoxide production blocks three pathways of hyperglycaemic damage" *Nature*, 2000; 404:787-790.
Nurfina et al., *Eur J Med Chem.*, 1997; 32:321-328.

(56) References Cited

OTHER PUBLICATIONS

Oetari et al., "Effects of Curcumin on Cytochrome P450 and Glutathione S-Transferase Activities in Rat Liver" *Biochem Pharmacol.*, 1996; 51:39-45.

Ohtsu et al., "Antitumor agents. 217. Curcumin analogues as novel androgen receptor antagonists with potential as anti-prostate cancer agents" *J Med Chem*, 2002; 45(23):5037-5042.

Okada et al., "Curcumin and especially tetrahydrocurcumin ameliorate oxidative stress-induced renal injury in mice" *J Nutr.*, 2001; 131:2090-2095.

Olah et al., "An automated PLS search for biologically relevant QSAR descriptors" *J Comput Aided Mol Des.*, 2004; 18:437-449.

O'Neill, "Towards an understanding of the signal transduction pathways for interleukin 1" *Biochim Biophys Acta.*, Apr. 6, 1995; 1266(1):31-44.

O'Neill, "Signal transduction pathways activated by the IL-1 receptor family: ancient signaling machinery in mammals, insects, and plants" *J Leukoc Biol.*, Jun. 1998; 63(6):650-657.

Ono et al., "Curcumin has potent anti-amyloidogenic effects for Alzheimer's beta-amyloid fibrils in vitro" *J Neurosci Res.*, 2004; 75:742-750.

Oprea et al., "Three-dimensional quantitative structure-activity relationships of steroid aromatase inhibitors" *J Comput Aided Mol Des.*, 1996; 10:186-200.

Oprea, "Chemical space navigation in lead discovery" *Curr Opin Chem Biol.*, 2002; 6:384-389.

Oprea et al., "Compound selection for virtual screening" Chapter 4 of *Virtual Screening in Drug Discovery*, Boca Raton, LA, 2005. Title page, copyright page, table of contents and chapter 4 (pp. 89-106?).

Orlando et al., "Identification of a cell line that expresses a cell surface and a soluble form of the gp330/receptor-associated protein (RAP) Heymann nephritis antigenic complex" *Proc Natl Acad Sci USA*, 1993; 90:4082-4086.

Orlowski et al., "NF-kappaB as a therapeutic target in cancer" *Trends Mol Med.*, Aug. 2002; 8(8):385-389.

Oyama et al., "Protective actions of 5'-n-alkylated curcumins on living cells suffering from oxidative stress" *Eur J Pharmacol.*, 1998; 360:65-71.

Ozcan et al., "Endoplasmic reticulum stress links obesity, insulin action, and type 2 diabetes" *Science*, Oct. 15, 2004; 306(5695):457-461.

Pabon, "A synthesis of curcumin and related compounds" *Recueil*, 1964; 83:379-386.

Pahlman et al., "Retinoic acid-induced differentiation of cultured human neuroblastoma cells: a comparison with phorbolester-induced differentiation" *Cell Differ.*, 1984; 14:135-144.

Pain, "Initiation of protein synthesis in eukaryotic cells" *Eur J Biochem.*, Mar. 15, 1996; 236(3):747-771.

Pallister et al., "Lymphocyte content of amyloid precursor protein is increased in Down's syndrome and aging" *Neurobiol Aging*, 1997; 18:97-103.

Pan et al., "Comparative studies on the suppression of nitric oxide synthase by curcumin and its hydrogenated metabolites through down-regulation of IkappaB kinase and NFkappaB activation in macrophages" *Biochem Pharmacol.*, Dec. 1, 2000; 60(11):1665-1676.

Pedersen et al., "Synthesis of naturally occuring curcuminoids and related compounds" *Liebigs Ann. Chem.*, 1985; 8:1557-1569.

Pena et al., "beta-Amyloid regulates gene expression of glial trophic substance S100 beta in C6 glioma and primary astrocyte cultures" *Brain Res Mol Brain Res.*, 1995; 34:118-126.

Periz et al., "Functional reconstitution of gamma-secretase through coordinated expression of presenilin, nicastrin, Aph-1, and Pen-2" *J Neurosci Res.*, 2004; 77:309-322.

Pickup et al., "Is type II diabetes mellitus a disease of the innate immune system?" *Diabetologia*, 1998; 41:1241-1248.

Pieper et al., "Activation of nuclear factor-kappaB in cultured endothelial cells by increased glucose concentrations: prevention by calphostin C" *J Cardiovasc Pharmacol.*, 1997; 30:528-532.

Pillarisetti et al., "Role of oxidative stress and inflammation in the origin of Type 2 diabetes-a paradigm shift" *Expert Opin Ther Targets*, 2004; 8:401-408.

Pinteaux et al., "Expression of interleukin-1 receptors and their role in interleukin-1 actions in murine microglial cells" *J Neurochem.*, Nov. 2002; 83(4):754-763.

Plummer et al., "Inhibition of cyclo-oxygenase 2 expression in colon cells by the chemopreventive agent curcumin involves inhibition of NF-kappaB activation via the NIK/IKK signaling complex" *Oncogene*, Oct. 28, 1999; 18(44):6013-6020.

Polin et al., "Treatment of human prostate tumors PC-3 and TSU-PR1 with standard and investigational agents in SCID mice" *Invest New Drugs*, 1997; 15(2):99-108.

Pomilio et al. "Endothelial dysfunction in children with type 1 diabetes mellitus" *J Pediatr Endocrinol Metab* 2002; 15:343-361.

Prasher et al., "Molecular mapping of Alzheimer-type dementia in Down's syndrome" *Ann Neurol.*, 1998; 43:380-383.

Priyadarsini et al., "Role of phenolic O-H and methylene hydrogen on the free radical reactions and antioxidant activity of curcumin" *Free Radic Biol Med.*, Sep. 1, 2003; 35(5):475-484.

PDB 1YER 1997.

PDB 1YES 1997.

Ramakrishnan et al., "Receptor-specific signaling for both the alternative and the canonical NF-kappaB activation pathways by NF-kappaB-inducing kinase" *Immunity*, Oct. 2004; 21(4):477-489.

Ramanan et al., *Ind J Pharm Sci.*, 1989; 51(5):207-208,.

Ranjan et al., "Curcumin inhibits mitogen stimulated lymphocyte proliferation, NFkappaB activation, and IL-2 signaling" *J Surg Res.*, Oct. 2004; 121(2):171-177.

Ravindranath et al., "Absorption and tissue distribution of curcumin in rats" *Toxicology*, 1980: 16:259-265.

Re et al., "Antioxidant activity applying an improved ABTS radical cation decolorization assay" *Free Radic Biol Med.*, May 1999; 26(9-10):1231-1237.

Reddy et al., "Effect of curcumin and eugenol on iron-induced hepatic toxicity in rats" *Toxicology*, Jan. 22, 1996; 107(1):39-45.

Reddy et al., *Ind J Chem., Section B*, 1999; 38B:1342-1348.

Reisberg et al., "Memantine in moderate-to-severe Alzheimer's disease" *N Engl J Med.*, 2003; 348:1333-1341.

Reuther et al., "Apoptosis promotes a caspase-induced amino-terminal truncation of IκBα that functions as a stable inhibitor of NF-κB" *Journal of Biological Chemistry*, Jul. 16, 1999; 274(29):20664-20670.

Revankar et al., "A transmembrane intracellular estrogen receptor mediates rapid cell signaling" *Science*, 2005; 307:1625-1630.

Ringman et al., "A potential role of the curry spice curcumin in Alzheimer's disease" *Curr Alzheimer Res.*, Apr. 2005; 2(2):131-136.

Rishton, "Reactive compounds and in vitro false positives in HTS" *Drug Discov Today*, 1997; 2:382-338.

Roberds et al., "BACE knockout mice are healthy despite lacking the primary beta-secretase activity in brain: implications for Alzheimer's disease therapeutics" *Hum Mol Genet.*, 2001; 10:1317-1324.

Rogers et al., "Microglia and inflammatory mechanisms in the clearance of amyloid beta peptide" *Glia*, Nov. 2002; 40(2):260-269.

Roher et al., "Oligomerizaiton and fibril assembly of the amyloid-beta protein" *Biochim Biophys Acta*, 2000; 1502:31-43.

Royer et al., "Synthesis and anti-HIV activity of 1,1'-dideoxygossypol and related compounds" *J Med Chem.*, Jun. 23, 1995; 38(13):2427-2432.

Rule et al., *J Org Chem.*, 1995; 60(6):1665-1673.

Rush et al., "Intracerebral beta-amyloid(25-35) produces tissue damage: is it neurotoxic?" *Neurobiol Aging*, 1992; 13:591-594.

Saez et al., "c-fos is required for malignant progression of skin tumors" *Cell*, Sep. 8, 1995; 82(5):721-732.

Sammour et al., *Egypt J Chem.*, 1976;19(40):601-620.

Satoh, "The possible role of tumor necrosis factor-alpha in diabetic polyneuropathy" *Exp Diabesity Res.*, 2003; 4:65-71.

Satoh et al., "NAD(P)H oxidase and uncoupled nitric oxide synthase are major sources of glomerular superoxide in rats with experimental diabetic nephropathy" *Am J Physiol Renal Physiol.*, 2005; 288, F1144-F1152.

(56) References Cited

OTHER PUBLICATIONS

Schalkwijk et al., "Pathophysiological role of Amadori-glycated proteins in diabetic microandiopathy" *Semin Vasc Med.*, 2002; 2:191-197.
Schalkwijk et al., "Vascular complications in diabetes mellitus: the role of endothelial dysfunction" *Clin Sci.*, 2005; 109:143-159.
Schenk et al., "Immunization with amyloid-beta attenuates Alzheimer-disease-like pathology in the PDAPP mouse" *Nature*, 1999; 400:173-177.
Scherrmann, "Drug delivery to brain via the blood-brain barrier" *Vascul Pharmacol.*, 2002; 38:349-354.
Schleicher et al., "Role of the hexosamine biosynthetic pathway in diabetic nephropathy" *Kidney Int Suppl.*, 2000; 77:S13-S18.
Schlesier et al., "Assessment of antioxidant activity by using different in vitro methods" *Free Radic Res.*, Feb. 2002; 36(2):177-187.
Schmitz et al., "Interaction of the COOH-terminal transactivation domain of p65 NF-kappa B with TATA-binding protein, transcription factor IIB, and coactivators" *J Biol Chem.*, Mar. 31, 1995; 270(13):7219-7226.
Schweisguth, "Notch signaling activity" *Curr Biol.*, 2004; 14:R129-138.
Seifert et al., *Tetrahedron*, 1996; 52(41):13167-13180.
Seiffert et al., "Presenilin-1 and -2 are molecular targets for gamma-secretase inhibitors" *J Biol Chem.*, 2000; 275:34086-34091.
Selkoe, "The molecular pathology of Alzheimer's disease" *Neuron*, 1991; 6:487-498.
Selkoe, "Alzheimer's disease: genes, proteins, and therapy" *Physiological Reviews*, 2001; 81:741-766.
Selkoe et al., "Deciphering the genetic basis of Alzheimer's disease" *Annu Rev Genomics Hum Genet.*, 2002; 3:67-99. Epub Apr. 15, 2002.
Selvaraj et al., *Indian Journal of Chemistry, Section B*, 1987; 26B:1104-1105.
Seubert et al., "Isolation and quantification of soluble Alzheimer's beta-peptide from biological fluids" *Nature*, 1992; 359:325-327.
Sharma et al., "Pharmacodynamic and pharmacokinetic study of oral Curcuma extract in patients with colorectal cancer" *Clin Cancer Res.*, 2001; 7:1894-1900.
Sharma et al., "Resveratrol, a polyphenolic phytoalexin, attenuates diabetic nephropathy in rats" *Pharmacology*, 2005; 76:69-75.
Sheu et al., "High glucose induces human endothelial cell apoptosis through a phosphoinositide 3-kinase-regulated cyclooxygenase-2 pathway" *Arterioscler Thromb Vasc Biol.*, 2005; 25:539-545.
Shim et al., "Irreversible inhibition of CD13/aminopeptidase N by the antiangiogenic agent curcumin" *Chem Biol.*, Aug. 2003; 10(8):695-704.
Shimizu et al., "Modulation of signal transduction by tea catechins and related phytochemicals" *Mutat Res.*, 2005; 591, 147-160.
Shinohara et al., "Overexpression of glyoxalase-I in bovine endothelial cells inhibits intracellular advanced glycation endproduct formation and prevents hyperglycemia-induced increases in macromolecular endocytosis" *J Clin Invest.*, 1998; 101:1142-1147.
Shoji et al., "Production of the Alzheimer amyloid beta protein by normal proteolytic processing" *Science*, 1992; 258:126-129.
Singh et al., "Activation of transcription factor NF-kappa B is suppressed by curcumin (diferuloylmethane) [corrected]" *J Biol Chem.*, Oct. 20, 1995; 270(42):24995-25000.
Skrzypczak-Jankun et al., "Curcumin inhibits lipoxygenase by binding to its central cavity: theoretical and X-ray evidence" *Int J Mol Med.*, Nov. 2000; 6(5):521-526.
Soto et al., "Fibrillogenesis of synthetic amyloid-beta peptides is dependent on their initial secondary structure" *Neurosci Lett.*, 1995; 200:105-108.
Soto, "Plaque busters: strategies to inhibit amyloid formation in Alzheimer's disease" *Mol Med Today*, 1999; 5:343-350.
Sovak, "Grape extract, resveratrol, and its analogs: a review" *J Med Food*, 2001 Summer; 4(2):93-105.
Srivastava et al., "Role of aldose reductase and oxidative damage in diabetes and the consequent potential for therapeutic options" *Endocrin Rev.*, 2005; 26:380-392.

Stebbins et al., "Crystal structure of an Hsp90-geldanamycin complex: targeting of a protein chaperone by an antitumor agent" *Cell*, Apr. 18, 1997; 89(2):239-250.
Stenina, "Regulation of vascular genes by glucose" *Curr Pharm Des.*, 2005; 11:2277-2278.
Stopa et al., "Supramolecular ligands: monomer structure and protein ligation capability" *Biochimie*, 1998; 80:963-968.
Stopa et al., "The structure and protein binding of amyloid-specific dye reagents" *Acta Biochim Pol.*, 2003; 50:1213-1227.
Su et al., "Isolation and characterization of murine retinal endothelial cells" *Molec Vision*, 2003; 9:171-178.
Su et al., *Synthesis*, 2003; 4:555-559.
Sugano et al., "High throughput prediction of oral absorption: improvement of the composition of the lipid solution used in parallel artificial membrane permeation assay" *J Biomol Screen.*, 2001; 6:189-196.
Suranarayana et al., "Curcumin and turmeric delay streptozotocin-induced diabetic cataract in rats" *Invest Ophthalmol Vis Sci.*, 2005; 46:2092-2099.
Suresh Babu et al., "Amelioration of renal lesions associated with diabetes by dietary curcumin in streptozotocin diabetic rats" *Mol Cell Biochem.*, 1998; 181:87-96.
Talaga, "Beta-amyloid aggregation inhibitors for the treatment of Alzheimer's disease: dream or reality?" *Mini Rev Med Chem.*, 2001; 1:175-186.
Tanaka et al., *Heterocycles*, 1987; 25(1):463-484.
Tanimoto, *Transactions of the New York Acadamey of Sciences*, 1961; 23:576.
Teplow, "Structural and kinetic features of amyloid beta-protein fibrillogenesis" *Amyloid*, 1998; 5:121-142.
Terry, "Where in the brain does Alzheimer's disease begin?" *Annals of Neurology*, 2000; 47:421.
Thevenin et al., "Inhibition of protein phosphatases by okadaic acid induces AP1 in human T cells" *J Biol Chem.*, May 25, 1991; 266(15):9363-9366.
Thornalley, "Glycation in diabetic neuropathy: characteristics, consequences, causes, and therapeutic options" *Int Rev Neurobiol.*, 2002; 50:37-57.
Tomiyama et al., "Rifampicin prevents the aggregation and neurotoxicity of amyloid beta protein in vitro" *Biochem Biophys Res Commun.*, 1994; 204:76-83.
Trost et al., *Comprehensive organic synthesis: selectivity, strategy & efficiency in modern organic chemistry*, v. 1-8, Pergamon Press, Oxford England, 1991. Title page, copyright page and table of contents.
Tully et al., *J Organomet Chem.*, 2001; 633:162-172.
Turner et al., "Subsite specificity of memapsin 2 (beta-secretase): implications for inhibitor design" *Biochemistry*, 2001; 40:10001-10006.
Tversky, "Features of similarity" *Psychological Review*, Jul. 1977; 84(4):327-352.
Vander Jagt et al., "Methylglyoxal metabolism and diabetic complications: roles of aldose reductase, glyoxalase-I, betaine aldehyde dehydrogenase and 2-oxoaldehyde dehydrogenase" *Chem Biol Interact.*, 2003; 143-144: 341-351.
Van Uden et al., "LDL receptor-related protein (LRP) in Alzheimer's disease: towards a unified theory of pathogenesis" *Microsc Res Tech.*, 2000; 50:268-272.
Van Uden et al., "A protective role of the low density lipoprotein receptor-related protein against amyloid beta-protein toxicity" *J Biol Chem.*, 2000; 275:30525-30530.
Vassar, et al., "Beta-secretase cleavage of Alzheimer's amyloid precursor protein by the transmembrane aspartic protease BACE" *Science*, 1999; 286:735-741.
Venkateswarlu et al., *Asian J. Chem.*, 2000;12(1):141-144.
Viatour et al., "Phosphorylation of NF-kappaB and IkappaB proteins: implications in cancer and inflamation" *Trends Biochem Sci.*, Jan. 2005; 30(1):43-52.
Vitaglione et al., "Bioavailability of trans-resveratrol from red wine in humans" *Mol Nutr Food Res.*, 2005; 49:495-504.

(56) References Cited

OTHER PUBLICATIONS

Waller et al., "Three-dimensional QSAR of human immunodeficiency virus (I) protease inhibitors. 1. A CoMFA study employing experimentally-determined alignment rules" *J Med Chem.*, 1993; 36:4152-4160.
Walsh et al., "Naturally secreted oligomers of amyloid beta protein potently inhibit hippocampal long-term potentiation in vivo" *Nature*, 2002; 416:535-539.
Walsh et al., "Oligomers on the brain: the emerging role of soluble protein aggregates in neurodegeneration" *Protein Pept Lett.*, 2004; 11:213-228.
Walsh et al., "Deciphering the molecular basis of memory failure in Alzheimer's disease" *Neuron*, 2004; 44:181-193.
Wang et al., "The interleukin-1-related cytokine IL-1F8 is expressed in glial cells, but fails to induce IL-1beta signaling responses" *Cytokine*, Mar. 21, 2005; 29(6):245-250.
Watson et al., "Solution structure of methionine-oxidized amyloid beta-peptide (1-40). Does oxidation affect conformational switching?" *Biochemistry*, 1998; 37:12700-12706.
Wautier et al., "Activation of NADPH oxidase by AGE links oxidant stress to altered gene expression via RAGE" *Am J Physiol Endocrinol Metab.*, 2001; 280:E685-E694.
Wautier et al., "Protein glycation: a firm link to endothelial cell dysfunction" *Circ Res.*, 2004; 95, 233-238.
Weber et al., "Anti-oxidant activities of curcumin and related enones" *Bioorg Med Chem.*, Jun. 1, 2005; 13(11):3811-3820.
Weber et al., "Activation of NFkappaB is inhibited by curcumin and related enones" *Bioorg Med Chem.*, Apr. 1, 2006; 14(7):2450-2461. Epub Dec. 7, 2005.
Weber et a., "TPA-induced up-regulation of activator protein-1 can be inhibited or enhanced by analogs of the natural product curcumin" *Biochem Pharmacol.*, Oct. 16, 2006; 72(8):928-940. Epub Aug. 28, 2006.
Weber, Waylon M. (2005) Curcumin and related enones as therapeutics for cancer. PhD dissertation,U. New Mexico United States.
Wellen et al., "Inflammation, stress, and diabetes" *J Clin Invest.*, May 2005; 115(5):1111-1119.
Whiteside et al., "I kappa B proteins: structure, function and regulation" *Semin Cancer Biol.*, Apr. 1997; 8(2):75-82.
Wilkinson et al., "SAPKs and transcription factors do the nucleocytoplasmic tango" *Genes Dev.*, May 15, 1998; 12(10):1391-1397.
Willett, *Similarity and Clustering Techniques in Chemical Information Systems*, Research Studies Press, Letchworth, Hertfordshire, England, 1987. Title page, copyright page and table of contents.
Willett, "Chemoinformatics—similarity and diversity in chemical libraries" *Curr Opin Biotechnol.*, 2000; 11:85-88.
Wimley et al., "Folding of beta-sheet membrane proteins: a hydrophobic hexapeptide model" *Journal of Molecular Biology*, 1998; 277:1091-1110.
Wohnsland et al., "High-throughput permeability pH profile and high-throughput alkane/water log P with artificial membranes" *J Med Chem.*, 2001; 44:923-930.
Xu et al., "Conformational transition of amyloid {beta}-peptide" *Proc Natl Acad Sci USA*, 2005;102:5403-5407.
Yadav et al., "KF adsorbed on alumina effectively promotes the epoxidation of electron deficient alkenes by anhydrous t-BuOOH" *Tetrahedron*, Mar. 4, 1996; 52(10):3659-3668.
Yamagishi et al., "Diabetic vascular complications: pathophysiology, biochemical basis and potential therapeutic strategy" *Curr Pharm Des.*, 2005; 11:2279-2299.
Yamagishi et al., "Angiotensin II augments advanced glycation end product-induced pericyte apoptosis through RAGE overexpression" *FEBS Letters*, 2005; 579:4265-4270.
Yamamoto et al., "Therapeutic potential of inhibition of the NF-kappaB pathway in the treatment of inflammation and cancer" *J Clin Invest.*, Jan. 2001; 107(2):135-142.
Yang et al., "Curcumin inhibits formation of amyloid beta oligomers and fibrils, binds plaques, and reduces amyloid in vivo" *J Biol Chem.*, 2005; 280:5892-5901.
Yasojima et al., "Distribution of cyclooxygenase-1 and cyclooxygenase-2 mRNAs and proteins in human brain and peripheral organs" *Brain Res.*, Jun. 5, 1999; 830(2):226-236.
Yatin et al., "In vitro and in vivo oxidative stress associated with Alzheimer's amyloid beta-peptide (1-42)" *Neurobiol Aging*, 1999; 20:325-330; discussion 339-342.
Yeh et al., "Inhibition of NFkappaB activation with curcumin attenuates plasma inflammatory cytokines surge and cardiomyocytic apoptosis following cardiac ischemia/reperfusion" *J Surg Res.*, May 1, 2005; 125(1):109-116.
Yevdokimova et al., "TGFbeta1 is involved in high glucose-induced accumulation of pericellular chondroitin sulphate in human endothelial cells" *J Diabetes Complications*, 2004; 18:300-308.
Young et al., "Promising molecular targets for cancer prevention: AP-1, NF-kappa B and Pdcd4" *Trends Mol Med.*, Jan. 2003; 9(1):36-41.
Zamora et al., "Surface descriptors for protein-ligand affinity prediction" *J Med Chem.*, 2003; 46:25-33.
Zheng et al., *Org Prep Proced Int.*, 1996; 28(1):117-120.
Zheng et al., "Poly(ADP-ribose) polymerase is involved in the development of diabetic retinopathy via regulation of nuclear factor-kappaB" *Diabetes*, 2004; 53:2960-2967.
Ziegler et al., "Dietary resveratrol does not affect intestinal tumorigenesis in Apc(Min/+) mice" *J Nutr.*, Jan. 2004; 134(1):5-10.

* cited by examiner

Activity of the vectors depending on promoter sequence and presence of a specific transcriptional factor.

Schematic presentation of the packaging procedure for pTR constructs and making of stable cell lines.

Curcumin Analogues

1

2

| Inhibitor | Estimated Ki binding constant |
|---|---|
| Curcumin analogue #1 | 7.66E-7 M |
| Curcumin analogue #2 | 3.33E-8 M |

THERAPEUTIC CURCUMIN DERIVATIVES

This application claims the benefit of U.S. Provisional Application Ser. Nos. 60/695,046, filed Jun. 29, 2005; 60/787,695, filed Mar. 30, 2006; and 60/787,694, filed Mar. 30, 2006; and further, this application is a continuation-in-part of U.S. application Ser. No. 11/373,444, filed Mar. 10, 2006 which, in turn, is a continuation in part of U.S. application Ser. No. 11/057,736, filed Feb. 14, 2005 which, in turn, claims the benefit of U.S. Provisional Application Ser. No. 60/544,424, filed Feb. 12, 2004; all of which are incorporated herein by reference in their entireties.

BACKGROUND

The transcription factor NF-κB is an established regulator of numerous genes important in the inflammatory response. More recently, activation of NF-κB has been shown to have a role in many aspects of oncogenesis including control of apoptosis as well as regulation of cell cycling and cell migration (Yamamoto et al., *J. Clin. Invest*. 2001, 107, 135; Baldwin, A. S. *J. Clin. Invest*. 2001, 107, 241). Activated NF-κB has been observed in many cancers and is especially important in metastasis (Andela et al., *Clin. Orthop. Relat. Res*. 2003, 415 (*suppl*), S75).

NF-κB is a collective name for dimeric transcription factors comprising members of the Rel family of DNA-binding proteins that recognize a common sequence motif. NF-κB is also commonly referred to as, for example, NFκB and NFκB, with the abbreviations being used interchangeably. Five members of the mammalian Rel family are known: RelA (p65), RelB, c-Rel, NF-κB1 (p50) and NF-κB2 (p52) (Baldwin, A. S., Annu. Rev. Immunol. 14, 649 (1996)). The five members to the NFκB family are distinguished by the presence of a Rel homology domain. Each NFκB member is retained in the cytosol as a complex, the most prevalent of which is a dimer consisting of the two subunits, p65 and p50. Any homo- and heterodimer is considered NF-κB, although the most commonly found in activated cells, RelA/NF-κB (p65/p50) heterodimer, is often referred to as "classic" NF-κB. All Rel proteins contain a Rel homology domain (RHD) that is responsible for dimer formation, nuclear translocation, sequence-specific DNA recognition, and interaction with I-κB proteins. RelA, RelB and c-Rel also contain transactivation domains required for the recruitment of transcriptional machinery, and thus represent transcriptionally active components of NF-κB. FIG. 1A provides a pictorial representation of the NF-κB activation cascade.

NF-κB activation is controlled by an interaction with a family of inhibitors proteins known as I-κB. The I-κB family includes I-κBα, I-κBβ, I-κBγ, I-κBε, p100, p102, and Bcl-3 (Whiteside et al., Semin. Cancer Biol. 8, 75 (1997)). All I-κBs share three common structural features: an N-terminal regulatory domain, which is responsible for a signal-dependent I-κB proteolysis, a core domain composed of six or seven ankyrin (ANK) repeats mediating an interaction with Rel proteins, and a C-terminal domain containing a PEST motif implicated in basal I-κB turnover.

In unstimulated cells, NF-κB resides in the cytoplasm as an inactive NF-κB-I-κB complex. I-κB binding hinders recognition of the NF-κB nuclear localization signal by nuclear import machinery, thus retaining NF-κB in the cytoplasm. Stimulation of cells releases active NF-κB, which is now free to enter the nucleus and activate transcription. Release of NF-κB is generally mediated by the degradation of I-κB.

Phosphorylation of IκB by IκB kinase (IKK) in response to an array of signals leads to degradation of IκB and the release of NFκB. Free NFκB is translocated to the nucleus where it binds to promoter regions of DNA resulting in the activation of a battery of genes, including pro-inflammatory genes (cytokines IL1 and TNFα; chemokines; stress response genes; and pro-inflammatory enzymes including iNOS, COX-2 and MMP-9). Compounds inhibiting the activation of NFκB can be directed at IKK or at NFκB. IKK inhibitors will prevent phosphorylation of IκB whereas direct inhibitors of NFκB may block NFκB-DNA interactions. Karin et al., (2004) Nat Rev Drug Discov 3, 17-26. The inducible degradation of I-κB occurs through consecutive steps of phosphorylation, ubiquination, and proteosomal degradation. I-κB processing is controlled by three large multi-protein complexes: IKK or signalsome, I-κB ubiquitin ligase, and 26S proteosome (Makarov, S. S., Mol Med Today. 6, 441-8 (2000)). Whereas the I-κB ubiquin ligase and the 26S proteosome are constitutively active, IKK activity is induced upon stimulation. Various stimuli, including inflammatory cytokines, mitogens, viral proteins, and stress, can activate IKK, thereby inducing phosphorylation of two critical serine residues of I-κB. The phosphorylation of I-κB targets it for rapid ubiquination and proteosomal degradation.

There are two IKK's, designated IKKα and IKKβ, that exist in a complex called the IKK signalsome. Also included in the complex are the IKK-associated protein (IKAP) and NEMO (also called IKKγ). There are many upstream regulators of the IKK signalsome that have been identified and could be useful "targets" for suppression of IKK expression and, ultimately, NFκB expression. Thus, compounds that prevent the phosphorylation of IκB (and therefore prevent the activation of NFκB) may act directly on one or more members of the IKK signalsome or may inhibit upstream kinases, such as SFK or any other such family of kinases. This complicates structure-based design of potential drugs to prevent activation of NFκB, especially because crystal structures of members of the IKK signal some are not available. It is noteworthy that there are also IKK-independent pathways for activation of NFκB.

Most available evidence suggests that IKKβ is the canonical pathway for NFκB activation and that IKKα functions in special circumstances. Karin et al., (2004) Nat Rev Drug Discov 3, 17-26. Whereas binding to IκBβ effectively sequesters NFκB in the cytoplasm, binding to IκBα does not preclude nuclear translocation. In fact, the NFκB-IκBα trimeric complexes shuttle between the cytoplasm and the nucleus. The source of this difference is that binding of IκBβ to a p50/p65 complex blocks NLS located on both NFκB subunits, whereas binding to IκBα blocks only the p65 NLS. Thus, NFκB-IκBα complexes contain both an exposed functional NLS and several nuclear export signals (NES) found in the N-terminal domain of IκBβ and in the activation domain of p65. The functions of both NLS and NES result in this shuttling between the cytoplasm and the nucleus. However, multiple NES seem to dominate, resulting in a primarily cytoplasmic localization of NFκB-IκBα complexes. When nuclear export is blocked with leptomycin B (LMB), the complex accumulates in the nucleus. Since IκBα is the most prevalent IκB isoform, in most resting cells the majority of NFκB protein is located in the cytoplasm bound to IκBα. Inflammatory stimuli, such as IL-1 treatment, leads to activation of IKK activity, phosphorylation of IκBα on serine 32 and 36, recognition of IκBα by the E3 ubiquitin ligase, IκBα ubiquination, degradation of IκBα by the 26S proteasome, and release of NFκB. The two exposed NLS on NFκB subunits then cause nuclear translocation of the transcription complex. However, numerous studies have now documented states where NFκB activation occurs in the absence of IκBα degradation.

For many stimuli, including interleukin-1 (IL-1), and tumor necrosis factor α (TNF-α), I-κB degradation and NF-κB nuclear translocation are necessary, but not sufficient, for the induction of NF-κB dependent transcription. The ability of NF-κB to initiate transcription depends on interactions with different transcriptional co-activators (Schmitz et al., J. Biol. Chem. 270, 7219-7226 (1995). Although regulated independently, the pathways controlling I-κB degradation and NF-κB transcription function act in synergy with the activation of NF-κB mediated transcription.

NF-κB appears to play a pivotal role in both initiation and perpetuation of chronic inflammation. CD4+ T cells are a trigger of immune inflammation, and NF-κB appears to be an important mediator of antigen-induced T-cell activation. Secreted products of activated T cells and direct cell-cell contacts cause activation of macrophages, fibroblasts, and endothelial cells. Once established, autocrine/paracrine loops of inflammatory cytokines and growth factors are capable of maintaining the activation of non-immune cells within the lesion, thereby perpetuating the chronic inflammatory process. Persistent NF-κB activation has been found in many chronic inflammatory diseases, including rheumatoid arthritis, asthma, inflammatory bowel disease, ulcerative colitis, and atherosclerosis (Barnes et al., New Engl. J. Med. 336, 1066-1071 (1997).

Additionally, the evidence that links activation of NF-κB to oncogenesis is compelling. NF-κB is activated by a number of viral transforming proteins (Hiscott et al., *J. Clin. Invest.* 2001, 107, 143), and inhibition of NF-κB activation through expression of a dominant negative IKK can block cell transformation (Arsura et al., *Mol. Cell Biol.* 2000 20, 5381). NF-κB activation protects cells from apoptosis induced by cancer chemo-therapeutics and oncogenes (Barkett et al., *Oncogene* 1999, 18, 6910), and activation of NF-κB promotes expression of metastatic factors (Baldwin, A. S. *J. Clin. Invest.* 2001, 107, 241). NFκB activation results in up-regulation of cyclin D1, a cell cycle regulator that is up-regulated in many tumors. NFκB is constitutively expressed in many cancer cell lines. Additionally, a number of dietary chemopreventive compounds such as flavonoids, curcumin, and reserveratol block activation of NFκB. Further, the expression of interleukin 8 (IL-8) which has been identified as a key factor in both angiogenesis and metastasis is very dependent on NFκB activity.

NF-κB is active in many tumors, and expression of NF-κB-responsive genes provide cancer cells with distinct survival advantages that inhibit cancer treatment. NF-κB is constitutively activated in many cancer cells, and NF-κB may also be conditionally activated in both cancer cells and stromal cells by the tumor microenvironment. Normally, NF-κB activation is prevented by binding to inhibitor (IκB) proteins, the most prevalent being inhibitor of NF-κB alpha (I-κBα). In response to inflammatory cytokines, the release of NF-κB is triggered by phosphorylation of I-κBα on serines 32 and 36, resulting in ubiquination and degradation of I-κBα protein. However, in cancer cells subjected to environmental conditions such as hypoxia, nutrient starvation, or X-rays, NF-κB activation is caused by phosphorylation of I-κBα on a tyrosine residue (Tyr42) by Src family kinases (SFKs). Thus, NF-κB activation via IκBα Tyr42 phosphorylation is expected to occur in solid tumors due to constitutive activation of SFKs such as the Src oncogene in response to the hypoxic and nutrient poor nature of the tumor microenvironment, or due to radiation treatment of the tumor.

NFκB was first identified as the nuclear factor in mature B-lymphocytes that binds to an 11 bp element (GG-GACTTTCC) within the κ-light chain gene enhancer, but it was soon realized that NFκB is not a B-cell-specific transcription factor. A wide variety of environmental stimuli and stresses lead to the formation of active NFκB complexes within almost every cell type, and NFκB activation mediates the transcription of over 180 target genes.

There are several NFκB crystal structures for use in structure-based drug design including a human NFκB-DNA structure. However, compounds that have been reported to inhibit activation of NFκB have generally been suggested to work at the level of IKK, rather than to interfere with NFκB-DNA interactions or with NFκB dimerization to prevent its interaction with DNA. Given the mechanisms of suppression and expression of NFκB, compounds inhibiting the activation of NFκB can be directed at IKK, SFK, or other kinases at NFκB-DNA interactions. Kinase inhibitors will prevent phosphorylation of IκB where direct inhibitors of NFκB may block NFκB-DNA interactions. For example, it has been shown recently that a new class of retinoid-related drug candidates inhibits IKK directly. Bavon et al., (2003) Mol Cell Biol 23, 1061-1074. By comparison, a synthetic derivative of the fungal metabolite jesterone, which blocks activation of NFκB, was shown to inhibit a kinase involved in phosphorylation and activation of IKK (β-subunit). Liang et al., (2003) Mol Pharmacol 64, 123-131. It appears, therefore, that inhibition of one or more of the kinases associated with the IKK signalsome may be a promising route to the development of new therapeutic agents that work through blocking the activation of NFκB. Further, because NFκB responsive genes can promote angiogenesis, cell motility and invasion, and block apoptotic cell death, this mechanism represents a considerable obstacle to cancer treatment. Therefore, there is a greatly felt need for development of small molecule inhibitors of NFκB expression. Particularly, but not exclusively, inhibitors of IκBα Tyr42 phosphorylation have vast potential to serve as adjuvant cancer therapeutics.

Activator Protein-1 (AP-1) is another protein transcription factor found in mammalian cells. AP-1 like NF-κB is a prosurvival and pro-inflammatory protein. AP-1 is an established regulator of numerous genes important in a variety of cellular processes including cell growth regulation, differentiation and proliferation (Angel et al., *Cell* 1987, 49, 729-739). Growth factors, hormones, tumor promoters and oncogenes regulate AP-1 binding to DNA (Bernstein et al., *Science* 1989, 244, 566-569). Activated AP-1 has been shown to play a role in apoptosis, angiogenesis and metastasis (Kang et al., *Am. J. Pathol*. 2005, 166(6), 1691-1699) and is also involved in many diseases including cancer, diabetes and Alzheimer's disease. AP-1 is also associated with the production of metalloproteinases. Collagenases, a class of metalloproteinases, are known to contain AP-1 response elements in their DNA promoters (Kang et al., *Am. J. Pathol*. 2005, 166(6), 1691-1699). The combination of these factors makes AP-1 crucial to many oncogenic processes.

AP-1 consists of 18 dimeric combinations of the families Jun (c-Jun, JunB and JunD) and Fos (c-Fos, FosB, Fra-1 and Fra-2) (Young et al., Trends Mol. Med. 9(1), 36-41 (2003)). Of the dimeric possibilities are Jun-Jun homodimers and Jun-Fos heterodimers. Jun dimers bind tightly to AP-1 DNA recognition elements (Angel et al., Cell 49, 729-739 (1987)). Fos-Fos homodimers are unstable and not readily formed but can bind to DNA by forming heterodimers with Jun proteins (Ziegler et al., *J. Nutr*. 2004, 134, 5-10). The most common dimer is a heterodimer consisting of c-Jun and c-Fos. Also associated with the Jun and Fos families are Jun dimerization partners and activating transcription factors (ATF's) (Angel et al., Biochim. Biophys. Acta 1072, 129-157 (1991)).

In normal tissues, the AP-1 component c-Fos is found only in small concentrations but cytosolic levels are rapidly increased when the cell is induced by mitogenic stimuli (Muller et al., Nature 1983, 304, 454-456). c-Jun, another AP-1 component, plays an important role in the regulation of cellular proliferation (Karin et al., Curr. Opin. Cell Biol. 1997, 9(2), 240-246). When c-Jun and c-Fos become unregulated in the body, abnormal cell proliferation occurs leading to cellular transformations. c-Jun is known to be essential in tumor promotion in several cell lines (Jochum et al., Oncogene 2001, 20(19), 2401-2412; Orlowski et al., Trends Mol. Med. 2002, 8,385-389; Pain, Eur. J. Biochem. 1996, 236, 747-771; Karin et al., Nat. Rev. Cancer 2002, 2(4), 301-310; Dhar et al., Mol. Cell. Biochem. 2002, 234-235, 185-193). c-Fos is also involved in the conversion of cells from benign to malignant (Dong et al., Proc. Natl. Acad. Sci. USA 1994, 91, 609-613; Greenhalgh et al., Cell Growth Differ. 1995, 6, 579-586) and is essential in tumor progression (Saez et al., Cell 1995, 82(5), 721-732). In general, the activation of both NF-κB and AP-1 are required for tumor promotion and progression.

The AP-1 activation cascade can be induced by TNFα, okadaic acid, 12-O-tetradecanoylphorbol-13-acetate (TPA), UV light (Young et al., Trends Mol. Med. 9(1), 36-41 (2003)), cytokines, mitogens, phorbol esters, growth factors, environmental and occupational particles, toxic metals, intracellular stresses, bacterial toxins, viral products and ionizing radiation (Fontecave et al., FEBS Lett. 421, 277-279 (1998)). In general, AP-1 is activated primarily through mitogen-activated protein kinase (MAPK) cascades (Kundu et al., Mutat. Res. 2004, 555, 65-80). MAPK's are composed of MAPK itself and MAPK kinase, also called MAPK-extracellular signal regulated kinase (MEK) (Wilkinson et al., Genes Dev. 1998, 12, 1391-1397). MAPK's are activated by cytokines, hormones and stress-inducing agents (Blenis, Proc. Natl. Acad. Sci. USA 1993, 90(13), 5889-5892). In general, the same factors that stimulate NF-κB also stimulate AP-1.

MAPK or MEK can phosphorylate additional kinases including extracellular regulating kinases (ERK's), c-Jun N-terminal kinase (JNK) and p38 MAPK (Baker et al., Mol. Cell. Biol. 1992, 12(10), 4694-4705; Davis, J. Biol. Chem. 1993, 268(20), 14553-14556). JNK activates the c-Jun protein and ERK activates a protein called Elk-1 both by phosphorylation. c-Jun then binds to DNA along with an ATF to activate genes that produce more of the Jun family in a positive feedback loop (Thevenin et al., J. Biol. Chem. 1991, 266(15), 9363-9366). Elk-1 also binds to DNA with a serum response factor (SRF) to activate genes that produce the Fos family. The Jun and Fos protein families are then activated by JNK and c-Fos-regulating kinase (FRK) respectively. The activated families can now dimerize, bind to DNA and activate gene expression that adversely affects cellular processes. A pictorial representation of AP-1 activation is shown in FIG. 1B.

AP-1 proteins and their activating kinases are related to NF-κB. AP-1 proteins are known to interact with the p65 subunit of NF-κB (Li et al., Mol. Carcinog. 29(3), 159-169 (2000)). MAPK's are known to phosphorylate I-κB (Adler et al., EMBO J. 18, 1321-1334 (1999)). Because AP-1 and NF-κB responsive genes can promote angiogenesis, cell motility and invasion, and block apoptotic cell death, activation of these genes and their products may result in cancerous or precancerous growth. Moreover, AP-1 and NF-κB responsive genes can promote inflammation, activation of these genes and their products may result in greater inflammation in diabetics and others. Therefore, there is a greatly felt need for development of small molecule inhibitors of AP-1 or NF-κB activation.

Alzheimer's Disease

Alzheimer's disease (AD), the most common cause of dementia in elderly populations, currently afflicts almost 5 million people in the U.S., and this number is estimated to increase to 15 million by 2050. Hebert et al., (2003) Arch Neurol 60, 1119-1122. Most AD is sporadic with multiple risk factors, while some 10-15% is familial. It is well accepted that excessive production or diminished clearance of the Aβ peptide derived from the amyloid precursor protein (APP) is an essential factor in the etiology of AD. This is supported by studies of genetic mutations in APP in experimental animal models of AD as well as from studies of the genetics of familial AD. Selkoe et al., (2000) Annu Rev Genomics Hum Genet 3, 67-99.

There are two major neuropathological signatures of AD: extraneuronal amyloid plaques and neurofibrillary tangles. The plaques primarily consist of Aβ aggregates while the tangles consist of hyperphosphorylated tau protein. The exact mechanism by which these aggregates cause neuronal cell death remains to be established. However, considerable recent evidence points towards a major role for oligomeric forms of Aβ which are neurotoxic and can diffuse. Soluble Aβ is found in CSF of AD patients and correlates better with severity of disease than does the quantity of plaques. Kim et al., (2003) FASEB J 17, 118-120; McLean et al., (1999) Ann Neurol 46, 860-866.

There are other common features of AD including the presence of chronic inflammation. The inflammatory response in brain is directed by activated microglia and reactive astrocytes. In normal brain, microglia are not activated. Under these conditions, neither pro-inflammatory signals nor reactive oxygen/nitrogen species (ROS/RNS) are formed. McGeer et al., (2003) Prog Neuropsychopharmacol Biol Psychiatry 2, 741-749. However, when microglia become activated in response to various insults, there is up-regulation of a number of surface receptors that promote phagocytotic activity by microglia. In addition, pro-inflammatory signals are released including interleukin-1β (IL1β) and tumor necrosis factor-α (TNFα) as well as ROS/RNS, thus contributing to the oxidative stress associated with AD. Activated microglia also associate with amyloid plaques. Microglia isolated from AD brain can scavenge Aβ. Rogers et al., (2002) Glia 40, 260-269. The considerable literature on the role of microglia in AD suggests that activation of microglia may contribute initially to clearance of Aβ aggregates, but that the chronic activation of microglia observed in AD leads to the neuropathological changes in the AD brain. Griffin et al., (1998) Brain Pathol 8, 65-72. Activated microglia also contribute to hyperphosphorylation of tau with development of neurofibrillary tangles, as well as to recruitment of activated astrocytes into the Aβ plaques. Kitazawa et al., (2004) Ann NY Acad Sci 1035, 85-103.

It is now recognized that Aβ can increase the inflammatory response by activation of microglia and that the inflammatory response can contribute to Aβ deposition. Consequently there has been interest in hindering microglial activation as an approach to breaking this pathological cycle. Aisen (1997) Gerontology 43, 143-149. Since activation of microglial results in release of ROS/RNS, attention has focused on use of anti-oxidants such as vitamin E. There are conflicting reports of the effects of anti-oxidants on development of AD, some supporting a role for anti-oxidants (Engelhart et al., (2002) JAMA 287, 3223-3229) and others not supporting a role (Laurin et al, (2004) Am J Epidemiol 159, 959-967). Activation of microglia increases the oxidative burden in affected brain regions. However, how significant this increase is in contributing to neurodegeneration is not known. The field of anti-oxidant treatment of AD will need further controlled trials to assess this question.

Another area that has produced conflicting reports is the use of anti-inflammatory drugs, especially non-steroidal anti-inflammatory drugs (NSAIDS), in treatment of AD. COX-2, the inducible form of cyclooxygenase found in neurons and other cells and the source of pro-inflammatory eicosenoids, is up-regulated in AD brains. Yasojima (1999) Brain Res 830, 226-236. Overexpression of human COX-2 in mice results in age-related cognitive decline as well as neuronal apoptosis and astrocyte activation. Andreasson et al., (2001) J Neurosci 21, 8198-8209. The epidemiology studies of use of COX inhibitors (i.e. NSAIDs) by AD patients suggest that NSAID therapy may be useful. McGeer et al., (2003) Prog Neuropsychopharmacol Biol Psychiatry 2, 741-749. However, controlled clinical trials have been disappointing. These conflicting results may reflect the fact that the epidemiology studies begin with normal subjects and then assess risk of developing disease and whether this risk correlates inversely with drug use, whereas the clinical trials begin with subjects who have AD and look for improvement upon treatment. Other studies suggest that only a limited group of NSAIDs are effective and that these NSAIDs influence multiple targets in addition to COX-2. Gasparini et al., (2005) Brain Res Rev 48, 400-408. Animal model studies suggest that the dosing level of NSAID that is clinically feasible may not be sufficient to produce a pharmacological dose at the sites of plaque formation in AD brains. Cole et al., (2004) Ann NY Acad Sci 1035, 68-84.

Another area of interest in AD drug development focuses on signaling pathways that regulate expression of pro-inflammatory genes. Aβ stimulation of microglia results in up-regulation of the expression of TNFα and IL1 that is at least partly NFκB-dependent. Combs et al., (2001) J. Neurosci. 21, 1179-1188. IL1 is known to affect the expression of over 90 genes including those for cytokines, cytokine receptors, tissue remodeling enzymes and adhesion molecules. O'Neill (1995) Biochim Biophys Acta 1266, 31-44. The mechanism for IL1 action involves activation of an IL1 receptor-mediated signal transduction pathway which leads to activation of NFκB. O'Neill et al., (1998) J Leukoc Biol 63, 650-657. Thus NFκB is involved both in up-regulation of IL1 and in expression of the multiple genes regulated by IL1. These observations make inhibition of NFκB an attractive target for control of IL1-responsive genes in brain inflammation.

Diabetes

In 1998, it was suggested that the innate immune system is activated in diabetes, leading to a chronic inflammatory state that contributes to the disease process (Pickup et al., 1998, Diabetologia 41:1241-1248). More recently, there has been considerable support not only for an inflammatory contribution to diabetes but also to diabetic complications (Navarro et al., 2005, Nephrol Dial Transplant 20:2601-2604; Pillarisetti et al., 2004, Expert Opin Ther Targets 8:401-408). Specifically, pro-inflammatory cytokines play a major role in microvascular complications. Endogenous production of TNF-α in vascular tissue is accelerated in diabetes where it contributes to increased vascular permeability in diabetic neuropathy (Satoh et al., 2003, Exp Diabesity Res 4:65-71). Both TNF-α and IL-1 expression are increased in diabetic retina where chronic low-grade inflammation appears to contribute to retinopathy (Joussen et al., 2002, FASEB J 16:438-440). Likewise, diabetic nephropathy is associated with expression of inflammation markers such as CRP, fibrinogen and IL-6, and with increased expression of adhesion molecules such as ICAM-1, which promote inflammation by increasing leukocyte adherence and infiltration (Dalla Vestra et al., 2005, J Am Soc Nephrol 16:S78-S82). The responses to these pro-inflammatory cytokines are especially prominent in endothelial cells (EC). Moreover, the response of EC to these cytokines commonly involves signaling through transcription factor NF-κB (Mohamed et al., 1999, BioFactors 10:157-167).

Oxidative stress has consistently been shown in experimental models of diabetes (Mohamed et al., 1999, BioFactors 10:157-167). Multiple mechanisms are involved that produce oxidative stress in EC in response to hyperglycemia, including: 1) protein glycosylation leading to AGE that trigger ROS production upon binding to the AGE receptor (RAGE) (Wautier et al., 2004, Circ Res 95:233-238); 2) glucose auto-oxidation (Ceriello, 1997, Diabet Med 14:S45-S49); 3) accelerated metabolism of glucose through the aldose reductase/polyol pathway which consumes NADPH (Srivastava et al., 2005, Endocrin Rev 26:380-392); 4) uncoupling of oxidative phosphorylation and of endothelial NO synthase (eNOS) (Satoh et al., 2005, Am J Physiol Renal Physiol 288:F1144-F1152); 5) activation of specific isoforms of PKC (Ahmed et al., 2005, Curr Drug Targets 6:487-494); 6) increased flux through the hexosamine pathway (Schleicher et al., 2000, Kidney Int Suppl 77:S13-S18); and 7) exposure to angiotensin II (Yamagishi et al., 2005, FEBS Letters 579:4265-4270). Activation of NF-κB is often observed in response to these stresses. For example, exposure of EC to AGE generates ROS through activation of NADPH oxidase which then activates NF-κB followed by up-regulation of NF-κB-dependent cytokines and adhesion molecules (Wautier et al., 2001, Am J Physiol Endocrinol Metab 280:E685-E694). Angiotensin II can augment this process through crosstalk with the AGE-RAGE system, again involving NF-κB (Yamagishi et al., 2005, FEBS Letters 579:4265-4270). High glucose can induce EC apoptosis through a PI-3-kinase-regulated expression of COX-2; this was shown to involve ROS and the NF-κB-regulated expression of COX-2 (Sheu et al., 2005, Arterioscler Thromb Vasc Biol 25:539-545). There has been considerable interest in a role for poly(ADP)-ribose polymerase (PARP) in EC dysfunction. PARP directly interacts with both the p50 and p65 subunits of NF-κB, suggesting that the role of PARP activation in diabetic complications is, at least in part, due to its interaction with NF-κB (Zheng et al., 2004, Diabetes 53:2960-2967). Glucose-induced activation of NF-κB in EC is prevented by inhibitors of PKC, suggesting that the role of PKC in triggering the expression of pro-inflammatory cytokines is through downstream activation of NF-κB (Pieper et al., 1997, J Cardiovasc Pharmacol 30:528-532). There has also been considerable interest in mitochondria-derived ROS (specifically superoxide) produced in response to hyperglycemia and the relationship between these ROS and enhanced flux through the polyol pathway and the hexosamine pathway, PKC activation, and intracellular generation of AGE, all of which can be prevented by inhibiting the formation of mitochondria-derived ROS (Nishikawa et al., 2000, Nature 404:787-790). The activation of these biochemical pathways appears to be due to ROS-induced activation of PARP, which results in inactivation of glyceraldehyde-3-phosphate dehydrogenase and subsequent accumulation of glycolytic intermediates that promote these pathways (Araujo et al., 2001, Mem Inst Oswaldo Cruz 96:723-728). It is noteworthy that inhibiting the production of mitochondria-derived ROS also prevents the activation of NF-κB (Du et al., 2003, J Clin Invest 112:1049-1057), which may be related to the activation status of PARP. Clearly, activation of NF-κB appears to be a general feature of EC that are stressed by factors related to diabetic complications, suggesting a central role for NF-κB in EC dysfunction, especially as the key regulator of pro-inflammatory cytokines, adhesion molecules and extracellular matrix components, all of which are major players in diabetic microvascular complications.

The signaling mechanisms involved in inflammation that contributes to diabetes are under investigation, and are described by Wellen et al. (Wellen et al., J. Clin. Invest., 115, 1111-1119). This research indicates that inflammatory signaling pathways can be activated by metabolic stress or extracellular signaling molecules, and that endoplasmic reticulum stress (ER stress) leads to the activation of inflammatory signaling pathways and thus contributes to insulin resistance. Ozcan et al., Science, 306, 457-461 (2004). For example, several serine/threonine kinases are activated by inflammatory or stressful stimuli that contribute to inhibition of insulin signaling, including c-Jun N-terminal kinase (JNK) and I-κB kinase (IKK). The three members of the JNK group of kinases (JNK-1, -2, and -3) belong to the MAPK family and regulate multiple activities, in part through their ability to control transcription by phosphorylating activator protein-1 (AP-1). Loss of JNK1 has been shown to prevent the development of insulin resistance and diabetes in both genetic and dietary models of obesity. Hirosumi et al., Nature, 420, 333-336 (2002).

A model of the overlapping metabolic and inflammatory signaling and sensing pathways in adipocytes and macrophages that influence diabetes and inflammation is provided by FIG. 2. As shown in FIG. 2, signals from various mediators converge on the inflammatory signaling pathways, including the kinases JNK and IKK. These pathways lead to the production of additional inflammatory mediators such as NF-κB and AP-1 through transcriptional regulation as well as to the direct inhibition of insulin signaling. Opposing the inflammatory pathways are transcriptional factors from the PPAR and LXR families, which promote nutrient transport and metabolism and antagonize inflammatory activity.

Glutathione S-Transferase

Glutathione S-transferases (GSTs) are a superfamily of enzymes classified into eight gene families. Many GSTs are also classified as phase II detoxification enzymes that catalyze the conjugation of glutathione to a wide variety of electrophiles as the first step in elimination of xenobiotics. However, GSTs also exhibit numerous family-specific functions, some but not all of which involve glutathione. For example, GSTP1-1, which is the main member of the "pi" family and is the most widely distributed GST, is important as both a detoxification enzyme and in signal regulation through its protein-protein interactions with c-Jun N-terminal kinase (JNK), a kinase that is important in the stress response and apoptosis. Thus, up-regulation of GSTP1-1 serves to protect cells from apoptosis-inducing stress by inhibiting JNK. Notably, the promoter for GSTP1-1 contains NFκB-binding sites. It is important to understand that oxidative stress leads to modification of critical cysteine residues in GSTP1-1, resulting in the release of JNK and initiation of apoptosis. Therefore, it is known that tumors that over-express GSTP1-1 are resistant to stress-induced apoptosis, and the presence of GSTP1-1 assists in the prevention of apoptosis.

Glutathione S-Transferase P1-1 (GSTP1-1) thus has two distinct functions which contribute to the survival of cancer cells. First, GSTP1-1 detoxifies xenobiotic electrophiles, including some cancer drugs, by catalyzing the conjugation of glutathione, thereby contributing to drug resistance. It is involved in eliminating toxic molecules from the cell including drugs that are supposed to be assisting the cell in fighting diseases, and has been implicated in the development of drug resistance in a variety of cancers. Elevated levels of GSTP1-1 are found in numerous cancer cell lines and tumors, including, among others, breast cancers, prostate cancers, and leukemias that are resistant to a range of anti-cancer drugs. It is known in the art that GSTP1-1 positive breast tumors are more aggressive than GSTP1-1 negative tumors and have a poorer prognosis. For example, the MCF7 breast cancer cell line, which is a GSTP1-1 expressing line, was shown to develop resistance to a number of drugs when the cells were transfected with GSTP1-1. It is also known in the art that ovarian cancer cell lines that over-express GSTP1-1 are resistant to taxol and doxorubicin. In fact, GSTP1-1 has also been used as a prognostic tool in invasive breast cancer. Over-expression of GSTP1-1 has been shown to be a marker of poor outcome in breast cancer and advanced non-Hodgkin's lymphoma. And second, because GSTP1-1 also inhibits the pro-apoptotic factor c-Jun N-terminal kinase (JNK), it promotes the pro-survival state.

A number of studies support the idea that inhibitors of GSTP1-1 may have therapeutic potential in the treatment of cancer. If GSTP1-1 can be inhibited, then known cancer therapeutics would not be eliminated from the cell. In one study, inhibition of GSTP1-1 by the glutathione conjugate of doxorubicin induces apoptosis in rat hepatoma cells. Also, ethacrynic acid, a broad-spectrum inhibitor of glutathione S-transferases, provides a therapeutic advantage when combined with other agents. Ethacrynic acid, however, is a potent diuretic; this along with its lack of GST isozyme selectivity precludes the development of ethacrynic acid as an anti-cancer therapeutic. A number of peptidomimetic inhibitors that are selective for GSTP1-1 are in various stages of development, including one in Phase III for non-small cell lung cancer and ovarian cancer.

Curcumin

Nontraditional or alternative medicine is becoming an increasingly attractive approach for the treatment of various inflammatory disorders. Among these alternative approaches is the use of food derivatives, which have the advantage of being relatively nontoxic. A number of dietary compounds such as flavonoids and curcumin block activation of NFkB (Yamamoto et al., J. Clin. Invest., 107, 135 (2001); Bharti et al., Blood 101, 1053 (2003)). Curcumin is a non-nutritive, non-toxic polyphenol natural product found in turmeric, a spice that has been used for centuries in India and elsewhere as an herbal medicinal treatment of wounds, jaundice, and rheumatoid arthritis (Ammon et al., Planta Med., 57, 1 (1991)). Curcumin is the major constituent of turmeric powder extracted from the rhizomes of the plant *Curcuma longa L* found in south and southeast tropical Asia (Govindaraja, V. S., Crit. Rev. Food Sci. Nutri. 12:199 (1980)). In the countries of its origin, turmeric has also been used for centuries as a traditional medicine to treat inflammatory disorders. Scientists have subsequently demonstrated the anti-inflammatory properties of curcumin (Ammon et al., Planta Med. 57:1 (1991). Curcumin also exhibits potent anti-oxidant activity, which depends upon the presence of phenolic groups in the aryl rings (Baldwin, A. S. J. Clin. Invest. 107:241 (2001)). In traditional Indian medicine, curcumin has been used to treat a host of ailments through topical, oral and inhalation administration, and has recently been found safe in six human trials at oral loads up to 8 grams/day for 6 months. Chainani-Wu (2003) J Altern Complement Med 9, 161-168. Most of the clinical trials of curcumin pertain to its anti-tumor activity in colon, skin, stomach, duodenal, soft palate and breast cancers. However, the mechanism of action for curcumin is not well understood.

Curcumin derivatives have been shown to provide antitumor activity. For example, the antitumor activity of curcumin derivatives is described in U.S. patent application Ser. No. 11/057,636, entitled "Method and Compounds for Cancer Treatment Utilizing NFκB as a Direct or Ultimate Target for Small Molecule Inhibitors," filed Feb. 14, 2005, by Vander Jagt et al. and incorporated herein by reference, and U.S. patent application Ser. No. 11/373,444, entitled "Cancer Treatment Using Curcumin Derivatives," filed Mar. 10, 2006, also by Vander Jagt et al. and incorporated herein by reference.

Curcumin is a natural chemoprotective agent that elevates the activities of Phase 2 detoxification enzymes, while inhibiting procarcinogen activating Phase 1 enzymes. It decreases expression of several proto-oncogenes including c-jun, c-fos, and c-myc, and of particular interest, it suppresses the activation of NFκB. Related to this, curcumin has also been shown to induce apoptosis in several tumor cell lines. In addition to the down-regulation of uPA by dominant negative inhibitors of NFκB, numerous other factors, including VEGF, IL-8, and MMP-9 that contribute to angiogenesis, invasion, and metastasis are down-regulated by dominant negative inhibitors of NFκB. Likewise, curcumin inhibits angiogenesis in vivo. Curcumin can be viewed as a lead compound that inhibits metastasis and promotes apoptosis. Other antiangiogenic properties of curcumin are also known. Shim et al. have shown that curcumin causes the irreversible inhibition of CD13/aminopeptidase N, a membrane-bound, zinc-dependent metalloproteinase that plays a key role in tumor invasion and angiogenesis. Shim et al., "Irreversible inhibition of CD13/aminopeptidase N by the antigenic agent curcumin", Chem. Biol. 10(8): 695-704 (August 2003).

Curcumin is known to inhibit the formation of Jun-Fos heterodimers in TPA induced cells and curcumin analogs are known to be up to 90 times more potent than curcumin (Hahm et al., Cancer Lett. 184, 89-96 (2002). It is also known that besides curcumin (turmeric), several natural products including resveratrol (peanuts and grape skins) (Manna et al., J. Immunol. 164, 6509-6519 (2000)), silymarin (artichoke) (Manna et al., J. Immunol. 163(12), 6800-6809 (1999)), oleandrin (Manna et al., Cancer Res. 60, 3838-3847 (2000)) and several compounds isolated from both green and black tea leaves (Chung et al., Cancer Res. 59, 4610-4617 (1999)) inhibit the AP-1 activation cascade. It is possible that curcumin analogs exhibit their activities on JNK since it is known that both silymarin (Manna et al., J. Immunol., 163 (12), 6800-6809 (1999)) and oleandrin (Manna et al., Cancer Res. 60, 3838-3847 (2000)) inhibit JNK activity.

In addition, curcumin exhibits anti-inflammatory activity and is a potent anti-oxidant and free radical scavenger. Leu et al., (2002) Curr Med Chem Anti-Canc Agents 2, 357-370. In APP-overexpressing transgenic mice, curcumin reduced levels of oxidized proteins and inflammatory cytokine IL1 (Lim et al., (2001) J Neurosci 2, 8370-8377), thus offering a potential therapy against microglial activation in patients with Alzheimer's disease. Curcumin has additional activities of interest: it limits the progression of renal lesions in the STZ-diabetic rat model (Suresh Babu et al., (1998) Mol Cell Biochem 181, 87-96), and ameliorates oxidative stress-induced renal injury in mice (Okada et al., (2001) J Nutr 131, 2090-2095). Consequently, there has been extensive interest in the anti-oxidant properties of curcumin and the possibility that many of its biological activities are derived from its anti-oxidant properties. Balasubramanyam et al., (2003) J Biosci 28, 715-721.

Curcumin also inhibits the activation of NFκB (Bharti et al., (2003) Blood 101, 1053-1062), which may explain its anti-inflammatory properties. Curcumin was shown to attenuate the plasma inflammatory cytokine surge and cardiomyocyte apoptosis following cardiac ischemia/reperfusion in experimental animals by inhibiting activation of NFκB. Yeh et al., (2005) J Surg Res 125, 109-110. Curcumin suppressed NOS induction in LPS-stimulated macrophages by inhibiting the activation of NFκB. Pan et al., (2000) Biochem Pharmacol 60, 1655-1676. Likewise, curcumin inhibited mitogen stimulation of lymphocyte proliferation by inhibiting activation of NFκB. Ranjan et al., (2004) J Surg Res 121, 171-177. Of particular interest is the report that curcumin inhibits the activation of NFκB in BV2 microglia cells (Kang et al, (2004) J Pharmacol Sci 94, 325-328). The limited bioavailability of curcumin (Garcea et al., (2004) Br J Cancer 90, 1011-1015) suggests that clinical use of this natural product will be limited and points to the need to develop curcumin analogs with improved properties including improved bioavailability.

It was reported that curcumin inhibits TNF-α-induced NF-κB activation in human myelomonoblastic leukemia cells and phorbol ester-induced c-Jun/AP-1 activation in mouse fibroblast cells (Singh et al., J. Biol. Chem. 270:24995 (1995); Huang et al., Proc. Natl. Acad. Sci. USA 88:5292 (1991). The molecular mechanism for NF-κB inhibition by curcumin was unclear, but involved inhibition of I-κB degradation (Kumar et al., Biochem. Pharmacol. 55:775 (1998). More recent work has demonstrated that curcumin blocks intestinal endothelial cell gene expression by inhibiting the signal leading to IKK activation without directly interfering with NIK or IKK, and that blockade of IKK activation causes inhibition of I-κB phosphorylation/degradation and NF-κB activation (Jobin et al., J. Immunol. 163, 3474-83 (1999)).

The anti-inflammatory properties of curcumin and its ability to inhibit the immune response upon exposure to a variety of external stimuli may, at least in part, result from inhibition of the activation of NF-κB by these external signals, since many of the genes that are implicated in the immune/inflammatory response are up-regulated by NFκB. For example, curcumin inhibits the LPS-induced production of IL-1β and TNFα (Chan, M. M. Biochem. Pharmacol. 49, 1551 (1995)) and the IL-1β-induced expression of IL-2 (Chaudhary, L. R.; Avioli, L. V. J. Biol. Chem. 271, 16591 (1996)), as well as the TNFα-induced expression of ICAM-1, VCAM-1 and E-selectin (Gupta, B.; Ghosh, B. Int. J. Immunopharmacol. 21, 745 (1999)). NF-κB is implicated in these signaling pathways (Wang et al., Cytokine 29, 245 (2005); Krunkosky et al., Free Radical Biol. Med. 35, 1158 (2003)). However, curcumin has also been shown to be a direct inhibitor of enzymes that are important in the inflammatory response, including lipoxygenase and cyclo-oxygenase (Skrzypczak-Jankun et al., J. Int. J. Mol. Med. 6, 521 (2000)).

Further, curcumin has been shown to have possible application in the treatment of cystic fibrosis defects caused by mutations in the gene for the cystic fibrosis transmembrane conductance regulator (CFTR), particularly for A508 mutations. Egan, et al., "Curcumin, A Major Constituent of Turmeric, Corrects Cystic Fibrosis Defects", Science, 304: 600-602 (23 Apr. 2004).

The large consumption of curcumin by the Indian population may help explain their relatively low (4 times less) incidence of Alzheimer's disease compared to the U.S. population. Chandra et al., (2001) Neurology 57, 985-989. Although no systematic trials have been preformed using curcumin in India, recent studies have provided valuable insights on curcumin's role in Alzheimer's disease. Yang et al., (2005) J Biol Chem 280, 5892-5901; Ono et al., (2004) J Neurosci Res 75, 742-750. Curcumin was shown to inhibit the formation of Aβ oligomers and fibrils in vitro and reduce Aβ amyloid burden in vivo. Specifically, Ono et al. have indicated that curcumin inhibits the accumulation of amyloid β-peptide (Aβ) and the formation of β-amyloid fibrils (fAβ) from Aβ and destabilizes preformed fAβ. Ono et al., "Curcumin Has Potent Anti-Amyloidogenic Effects for Alzheimer's β-Amyloid Fibrils In Vitro", J. Neuroscience Res., 75: 742-750 (2004). Importantly, curcumin administered by intravenous (i.v.) injection lowered Aβ deposition in aged APP(Swedish)-transgenic mice (Tg2576), clearly demonstrating its ability to cross the blood-brain barrier in sufficient quantities to reduce amyloid burden. Curcumin is structurally similar to other inhibitors of Aβ aggregation such as Congo Red and Chrysamine G.

Thus, NFκB and its upstream regulators, as well as AP-1 and GSTP1-1, present inviting targets for development of anti-inflammatory drugs, and curcumin represents a promising lead compound. Analogues of curcumin that function as small molecules inhibitors of NFκB, AP-1 and GSTP1-1 activation are highly desirable for the treatment of diseases with inflammatory symptoms or components such as Alzheimer's disease, diabetes, cystic fibrosis and cancer, and also as assistive or adjuvant agents in the chemotherapeutic treatment of cancer.

SUMMARY OF THE INVENTION

In one aspect, the invention provides a method of treating a subject afflicted with a disease, wherein the method includes administering to the subject a therapeutically effective amount of a curcumin derivative.

In one embodiment of the method of the invention, the curcumin derivative is a compound having Formula I ($Ar^1$—L—$Ar^2$), wherein $Ar^1$ and $Ar^2$ are each independently aryl groups, and L represents a divalent linking group.

In one embodiment of the compound of Formula I, $Ar^1$ is a phenyl group according to Formula II:

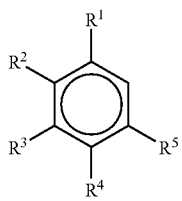

II and/or $Ar^2$ is a phenyl group according to Formula III:

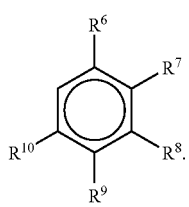

III wherein each of $R^1$-$R^{10}$ is independently selected from the group consisting of hydrogen, hydroxyl, methyl, methoxyl, dimethylamine, trifluoromethyl, chloro, fluoro, acetoxyl, cyano, and carboxymethyl. Alternatively or additionally, either or both of $Ar^1$ and $Ar^2$ are independently heteroaryl groups.

In another embodiment of the method of the invention, the curcumin derivative is a compound having Formula IV ($Ar^1$—L—$R^{11}$), wherein $Ar^1$ is an aryl group, L represents a divalent linking group, and $R^{11}$ is an alkyl group, a heterocyclic group, or a hydrogen. In one embodiment, $Ar^1$ is a phenyl group according to Formula II, wherein each of $R^1$-$R^5$ is independently selected from the group consisting of hydrogen, hydroxyl, methyl, methoxyl, dimethylamine, trifluoromethyl, chloro, fluoro, acetoxyl, cyano, and carboxymethyl.

The divalent linking group L preferably includes an alkylene or an alkenylene including 3, 4, 5, 6, or 7 backbone carbon atoms, wherein one or more of the backbone carbon atoms form part of a carbonyl or secondary alcohol. The linking group L may be saturated or unsaturated; preferably, L contains at least one unsaturated carbon-carbon bond.

In a preferred embodiment, L is an alkylene or an alkenylene selected from the group consisting of: —CH=CH—CHO—, —CH=CH—(CO)—CH=CH—, —CH$_2$—CH$_2$—(CO)—CH$_2$—CH$_2$—, —CH$_2$—CH$_2$—CH(OH)—CH$_2$—CH$_2$—,

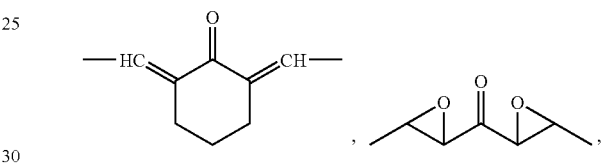

—CH=CH—(CO)—CR—C(OH)—CH=CH—, —CH=CH—(CO)—CR$_2$—(CO)—CH=CH—, and —CH=CH—(CO)—CH—C(OH)—CH=CH—; R is an alkyl or aryl group including 10 carbon atoms or less.

The curcumin derivative of the invention may be administered as a pharmaceutical composition, optionally containing a pharmaceutically acceptable carrier.

The method of the invention is useful for treating any disease or condition characterized by inflammation, including Alzheimer's disease, diabetes (particularly type 2 diabetes), cancer or a precancerous condition (e.g., dysplasia or hyperplasia), cystic fibrosis, rheumatoid arthritis, asthma, inflammatory bowel disease, ulcerative colitis, atherosclerosis and stroke. A subject afflicted with diabetes who is treated in accordance with the invention may exhibit endothelial dysfunction by one or more endothelial cells that express activated NF-κB or AP-1. It should be understood that the method of the invention is generally useful for treating any disease or condition that can be ameliorated by inhibiting the activity of NFκB, AP-1 and/or GSTP1-1.

In some embodiments of the method of treating a subject with Alzheimer's disease, the composition inhibits amyloid plaque formation. In other embodiments, the composition inhibits aggregation of a plurality of Aβ peptides. In additional embodiments, the composition inhibits oligomerization of a plurality of Aβ peptides. In further embodiments, the composition decreases the cytotoxicity of an Aβ peptide aggregate. In yet further embodiments, the composition decreases activation of a glial cell by an Aβ peptide aggregate.

The curcumin derivatives provided herein optionally inhibit the activity of the enzymes AP-1, NF-κB and/or GSTP1-1. Inhibition of enzyme activity may be observed or demonstrated by in vitro assays, in vivo, or both. Inhibition of enzyme activity may decrease inflammation, insulin resistance and/or render a cancer cell more susceptible to a chemotherapeutic agent.

In embodiments of the invention that involve the treatment of cancer or a precancerous condition, the curcumin derivative may be administered to the subject either alone or in combination with one or more other cancer drugs (e.g., chemotherapeutic agents), for example in an assistive or adjuvant capacity. The curcumin derivative may be administered before, concurrent with, or after the administration of the other cancer drug(s).

In another aspect, the present invention provides methods for identifying an therapeutic curcumin derivative that includes contacting a cell containing NF-κB, AP-1 and/or GSTP1-1 with a curcumin derivative, contacting the cell with an activator of NF-κB, AP-1 and/or GSTP1-1, and determining the effect of the curcumin derivative on cell activation by the activator, wherein a curcumin derivative that reduces cell activation is identified as a therapeutic curcumin derivative. Exemplary activators include TNF-α or IL-1. In a further embodiment, the cell is an adipocyte or endothelial cell.

In another aspect, the invention provides a method for identifying a therapeutic curcumin derivative that includes contacting a brain cell comprising an inflammation activator with a curcumin derivative and determining the effect of the curcumin derivative on activation of the brain cell by the inflammation activator. A curcumin derivative that reduces brain cell activation when tested by this method is identified as a therapeutic curcumin derivative. The inflammation activator of this method may include NF-κB or AP-1. In one or more embodiments, the brain cell is a glial cell.

In another aspect, the invention provides a method for identifying a therapeutic curcumin derivative that includes contacting a solution including an Aβ peptide with a curcumin derivative and determining the effect of the curcumin derivative on aggregation by the Aβ peptide. A curcumin derivative that reduces aggregation of the Aβ peptide is identified as a therapeutic curcumin derivative. In one ore more embodiments, effect of the curcumin derivative on aggregation by the Aβ peptide is determined by an immunological assay.

BRIEF DESCRIPTION OF THE FIGURES

The patent or application file contains at least one drawing executed in color. Copies of this patent or patent application with color drawings will be provided by the Office upon request and payment of the necessary fee.

DETAILED DESCRIPTION OF ILLUSTRATIVE EMBODIMENTS

Definitions

Figure 1A:
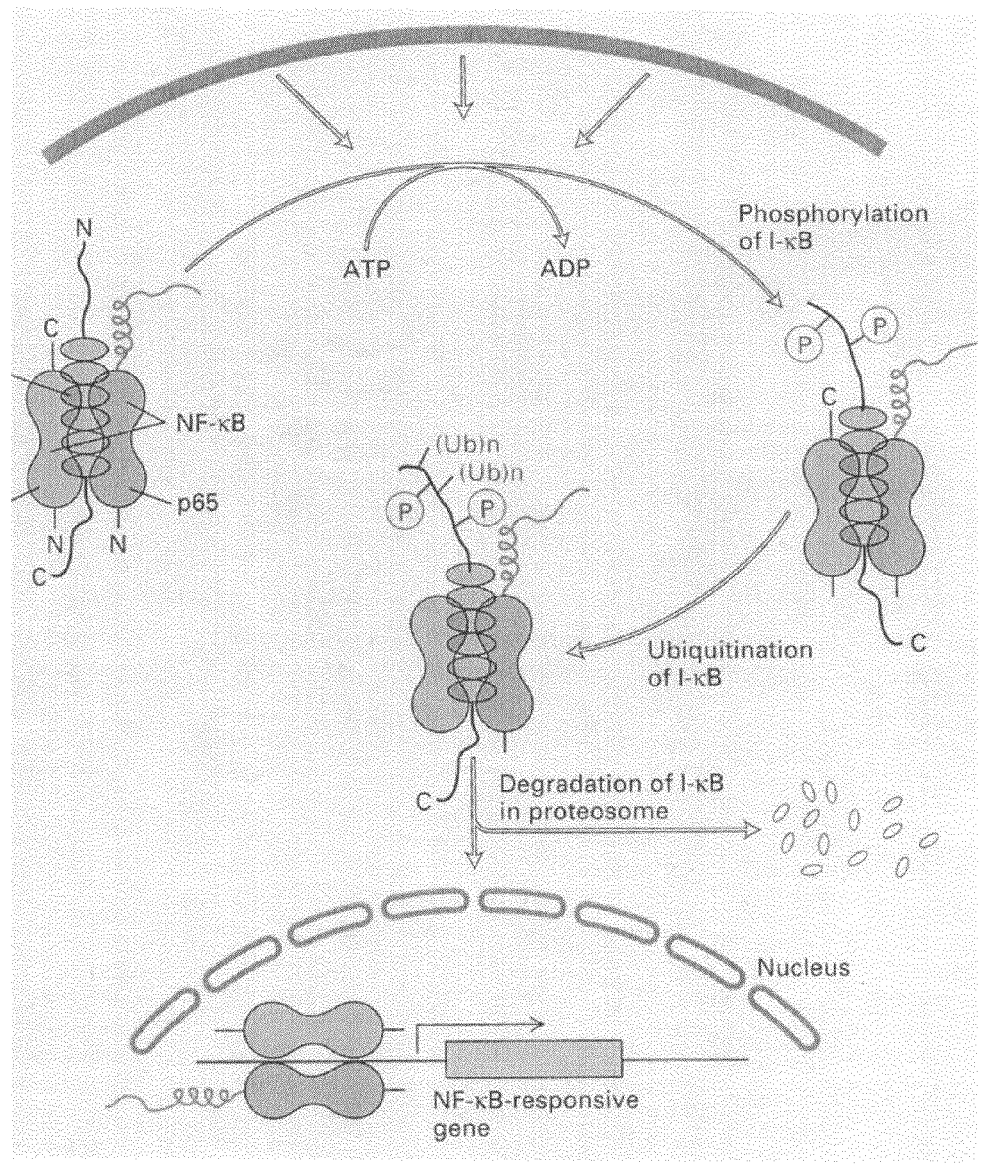
FIG. 1A is a pictorial representation of the NF-κB activation cascade.
Figure 1B:
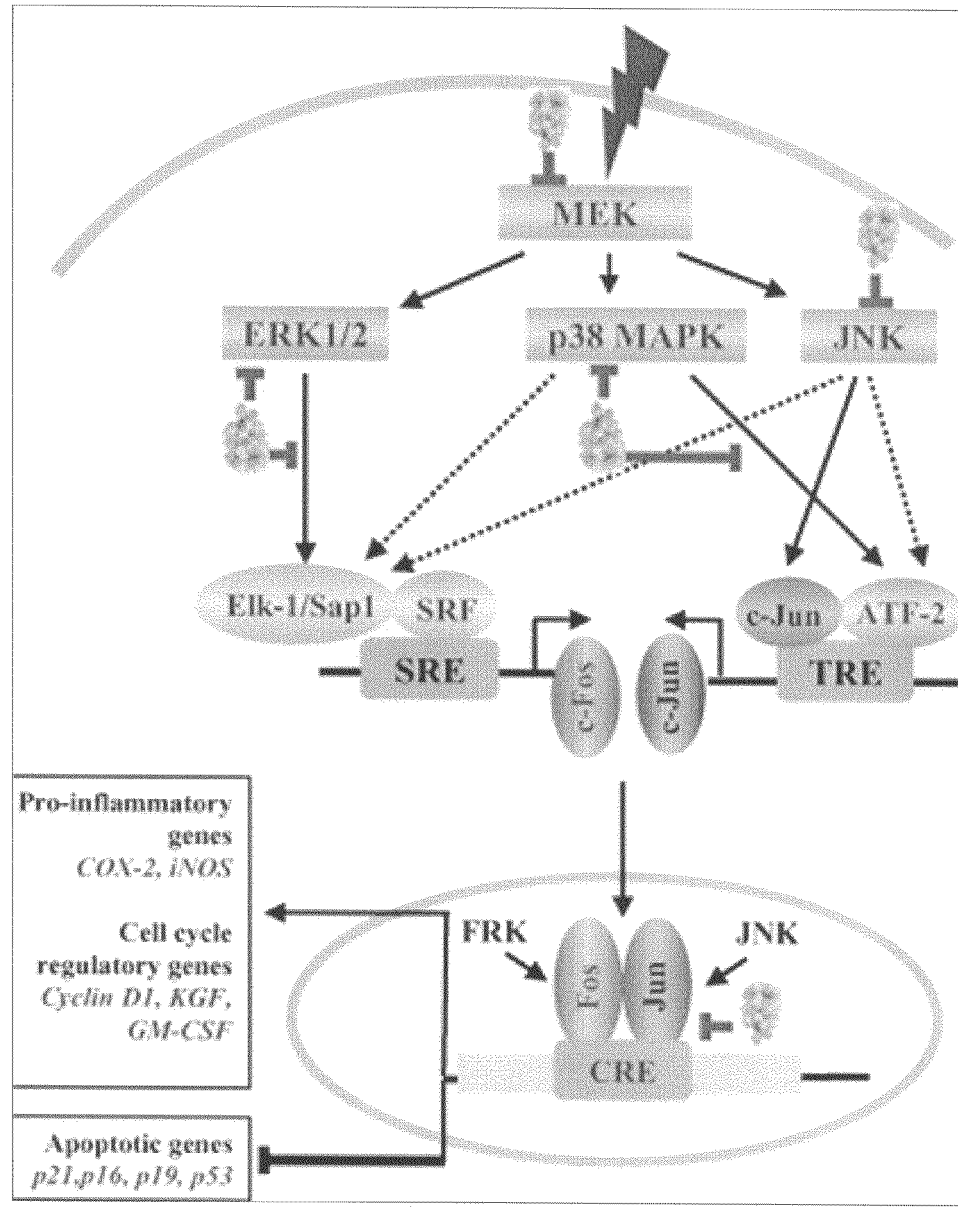
FIG. 1B is a pictorial representation of the AP-1 activation cascade.

The terminology as set forth herein is for description of the embodiments only and should not be construed as limiting of the invention as a whole. Unless otherwise specified, "a," "an," "the," and "at least one" are used interchangeably and mean one or more than one.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for curcumin derivatives of this invention are those that do not interfere with the curcumin derivatives therapeutic activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halogens are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocyclic hydrocarbons. Annulenes have a general formula of $C_nH_n$, where n is an even number, or $C_nH_{n+1}$, where n is an odd number. Examples of annulenes include cyclobutadiene, benzene, and cyclooctatetraene. Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —C(O)—NR$_2$ each of the two R groups is independently selected.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment. Curcumin derivatives of the invention can, for example, be administered prophylactically to a mammal in advance of the occurrence of disease. Prophylactic administration is effective to decrease the likelihood of the subsequent occurrence of disease in the mammal, or decrease the severity of disease that subsequently occurs. Alternatively, curcumin derivatives of the invention can, for example, be administered therapeutically to a mammal that is already afflicted by disease. In one embodiment of therapeutic administration, administration of the curcumin derivatives is effective to eliminate the disease; in another embodiment, administration of the curcumin derivatives is effective to decrease the severity of the disease or lengthen the lifespan of the mammal so afflicted.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein refers to the partial or complete elimination of a potential effect, while inhibitors are compounds that have the ability to inhibit.

The present invention provides methods for the use of curcumin derivatives to treat disease in a subject. The present invention also provides methods for identifying and preparing curcumin derivatives Curcumin (diferuloylmethane, 1,7-bis(4-hydroxy-3-methoxyphenyl)-1,6-heptadiene-3,5-dione) is a symmetrical diphenolic dienone. It exists in solution as an equilibrium mixture of the symmetrical dienone (diketo) and the keto-enol tautomer; the keto-enol form is strongly favored by intramolecular hydrogen bonding.

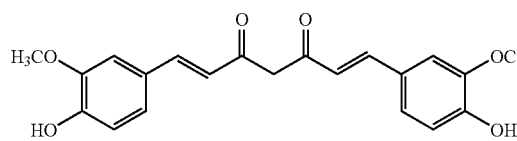 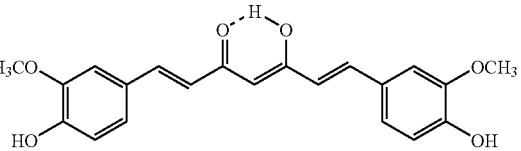

Curcumin contains two aryl rings separated by an unsaturated seven carbon spacer having two carbonyls. The aryl rings of curcumin contain a hydroxyl group in the para position and a methoxy group in the meta position.

Curcumin Derivatives

Curcumin derivatives are expected to be beneficial for use in the treatment methods of the invention. The term "curcumin derivative" is used interchangeably with the term "curcumin analog" and "curcumin analogue" (alternative spelling) and includes, for example, curcumin derivatives, analogs, curcuminoids and chalcones. In one embodiment, the curcumin derivative includes first and second aryl groups covalently attached by way of a spacer, also referred to herein as a linker or a linking group. In another embodiment, the second aryl group is absent, such that the curcumin derivative contains a first aryl group and the spacer but no second aryl group at the distal end of the spacer. Optionally, the first and/or second aryl group is a heteroaryl group. The first and second aryl groups may be independently substituted or unsubstituted.

Representative curcumin derivatives are described herein, and also in Weber et al., 2005, Bioorg. Med. Chem. 13:3811-3820; Weber et al., 2006, Biorg Med Chem 14:2450-2461, and U.S. Pat. Publ. 2001-0051184 A1, published Dec. 13, 2001 (Heng).

Curcumin derivatives that exhibit improved pharmacokinetic properties and/or reduced toxicity are preferred. For example, curcumin derivatives that include heteroaryl groups and/or unsaturated spacers are expected to impart improved pharmacokinetic properties and/or reduced toxicity to the compounds, because they are expected to be less chemically reactive in vivo. One example of preferred curcumin derivatives includes those include one or two carbonyl groups in the spacer region, including those derivatives that preserve the enone functionality of curcumin. Derivatives that include heteroaryl groups and/or unsaturated spacers are expected to be less likely to be degraded and/or form toxic adducts or intermediates under physiological conditions. Additional curcumin derivatives not encompassed by the general definition provided above may also be found in the examples and schemes provided herein.

Curcumin derivatives of the invention are generally encompassed by Formula I:

$$Ar^1—L—Ar^2 \qquad (I)$$

wherein $Ar^2$ is optional; L is a divalent linking group comprising an alkylene or an alkenylene that includes between 3 and 7 backbone carbon atoms, wherein one or more of the backbone carbon atoms include a carbonyl or hydroxyl moiety; and $Ar^1$ and $Ar^2$ (if $Ar^2$ is present) are independently aryl groups. $Ar^1$ and $Ar^2$ (if $Ar^2$ is present) may be unsubstituted or may optionally include one or more substituents selected from the group consisting of hydroxyl, alkyl, alkenyl, haloalkyl, alkoxy, and $NR_2$, where R is hydrogen or alkyl. If $Ar^2$ is absent, it may be replaced by a substituent $R^{11}$, including hydrogen (H). $R^{11}$ can be, for example, a heterocyclic group or an alkyl group, preferably an alkyl group having four or fewer carbon atoms, e.g., a methyl group. $R^{11}$ can alternately be an amine, a hydroxyl, or a hydrogen.

Aryl Groups

Curcumin derivatives of the invention include aryl group $Ar^1$, which is positioned at an end of the linker L. Curcumin derivatives of the invention may optionally include a second aryl group $Ar^2$ that is independently selected from $Ar^1$, which is positioned at the other end of the linker L relative to $Ar^1$ when present.

Preferred aryl groups include phenyl groups, naphthyl groups, thienyl groups, and pyridinium groups.

Aryl groups $Ar^1$ and $Ar^2$ may be substituted or unsubstituted. Preferably, substituents are selected from the group consisting of hydroxyl, halogen, alkyl, alkenyl, haloalkyl, alkoxy, amine, carboxyl, and ester substituents.

For example, in one embodiment of the invention, $Ar^1$ can be a phenyl group according to Formula II:

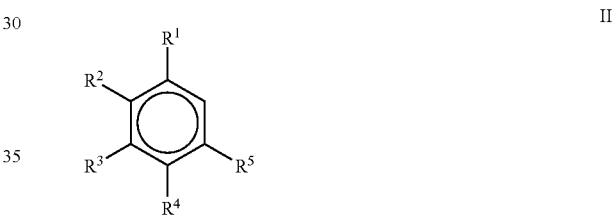

and $Ar^2$ can be a phenyl group according to Formula III:

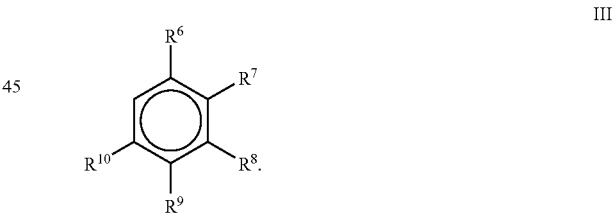

The ring positions may, independently, be unsubstituted (i.e., R=hydrogen) or one or more R groups may be substituents independently selected from a variety of substituents, including hydroxyl, halogen, alkyl, alkenyl, haloalkyl, alkoxy, amine, carboxyl, and ester substituents. In further embodiments, $R^1$-$R^{10}$ are each independently selected from the group including hydrogen (—H), hydroxyl (—OH), methyl (—CH$_3$), methoxyl (—OCH$_3$), dimethylamine (—N(CH$_3$)$_2$), chloro (—Cl), fluoro (—F), trifluoromethyl (—CF$_3$), acetoxyl (—O(CO)CH$_3$) and carboxymethyl (—C(CO)OCH$_3$) moieties.

Divalent Linking Groups

The linker L is a spacer that preferably includes 3, 4, 5, 6 or 7 carbon atoms that form a linear carbon chain connecting the first and second aryl groups. The carbons atoms in the carbon chain that trace out shortest path between the first and optional second aryl groups are referred to herein as the "backbone" carbon atoms. The number of backbone carbon atoms is readily determined in straight chain alkyl groups. In spacers that include a cyclic alkyl group as a constituent of the linear chain (e.g., 38a), the backbone carbon atoms include the least number of ring carbons possible, e.g., 3 ring carbons in 38a. The number of backbone carbon atoms is used herein as a shorthand way to designate the length of the linker being used. For example, a 7-carbon spacer is a divalent spacer that includes 7 backbone carbon atoms. Preferred embodiments of the invention include curcumin derivatives having an odd number of carbon atoms; e.g., 3, 5, and 7-carbon linking groups.

Preferably at least one of the backbone carbon atoms is included in a carbonyl (C=O) moiety. The spacer may be substituted or unsubstituted. The spacer may further be saturated or unsaturated. In a preferred embodiment, the spacer contains an odd number of carbon atoms (i.e., 3, 5, or 7 carbon atoms), and at least one unsaturated carbon-carbon bond. In additional embodiments, the spacer may include a hydroxyl moiety in place of, or in addition to, the at least one carbonyl moiety.

Curcumin derivatives of the invention include a linking group L that is preferably covalently attached at one end to aryl group $Ar^1$. Optionally, the linking group L may also be covalently attached at the other end to a second aryl group, $Ar^2$, which is selected independently from $Ar^1$. The linking group L is a divalent linking group that preferably includes an alkylene or an alkenylene group having between 3 and 7 backbone carbon atoms and preferably at least one carbonyl moiety. The linking group may be substituted or unsubstituted, and may be saturated or unsaturated. Preferably, an unsaturated linking group includes conjugated double bonds. Preferably the linking group also contains an odd number of carbon atoms (i.e., 3, 5, or 7 carbon atoms), and at least one unsaturated carbon-carbon bond. In additional embodiments, the linking group may include a hydroxyl moiety in place of, or in addition to, the at least one carbonyl moiety. Table 1 shows compounds with 7-carbon linkers; Table 2 shows compounds with 5-carbon linkers; and Table 3 shows compounds with 3-carbon linkers.

A divalent linking group includes two carbons with unfilled valencies that provide valence points where a covalent bond can be formed to an adjacent alkyl or aryl group that also includes a carbon with an unfilled valency. Generally, a valence point is represented in a chemical formula by a bond that is shown as not being attached to another group (e.g., $CH_3$—, wherein — represents the valence point). In embodiments wherein the curcumin derivative lacks the second aryl group $Ar^2$, the distal valence point on the linking group can be filled with any substituent of interest, preferably a short chain alkyl group or a hydrogen (H). Compounds lacking a second aryl group may be represented by Formula IV:

$$Ar^1—L—R^{11} \qquad (IV)$$

$R^{11}$ in Formula IV can be, for example, a heterocyclic group or an alkyl group, preferably an alkyl group having four or fewer carbon atoms, e.g., a methyl group. $R^{11}$ can alternately be an amine, a hydroxyl, or a hydrogen.

Curcumin Derivatives Including 7-carbon Linking Groups

In one embodiment of the invention, the curcumin derivatives include one or two aryl groups ($Ar^1$ and optionally $Ar^2$) and a linking group L that is a 7-carbon linking group (i.e., a linking group that includes 7 backbone carbon atoms). Preferably, the 7-carbon linking group includes at least one unsaturated carbon-carbon bond. Examples of 7-carbon linking groups include

—CH=CH—(CO)—CR=C(OH)—CH=CH—,

—CH=CH—(CO)—CR$_2$—(CO)—CH=CH—, and

—CH=CH—(CO)—CH=C(OH)—CH=CH—.

where R includes substituent alkyl or aryl groups comprising 10 carbon atoms or less. In some embodiments, R may be a methyl, ethyl, or benzyl group. These linking groups are the divalent forms of 4-alkyl-1,6 heptadiene-3,5-dione; 4,4-dialkyl-1,6 heptadiene-3,5-dione; and heptane-3,5-dione.

Examples of 7-C Linkers

Table 1 shows a number of examples of curcumin derivatives that include a seven carbon linker. The compounds shown contain two aryl rings separated by a seven carbon spacer having two carbonyls (or the equivalent keto-enol tautomer). In many, but not all, of the compounds, the spacer is unsaturated.

TABLE 1

7-Carbon Linker Analogs.

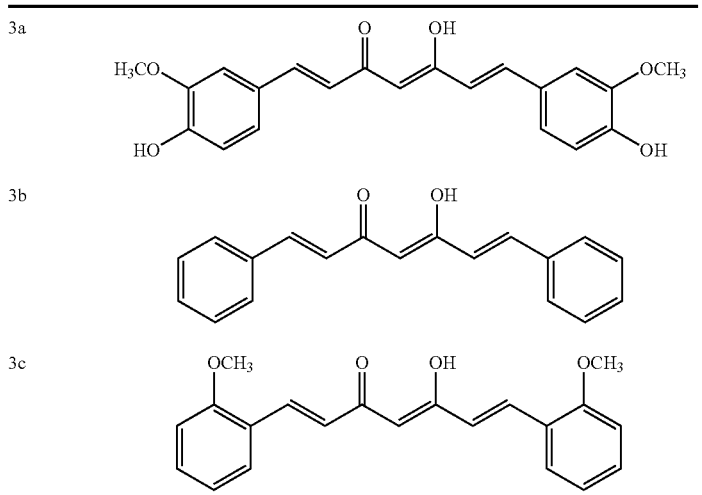

TABLE 1-continued

7-Carbon Linker Analogs.

| | |
|---|---|
| 3d | (2,3-dimethoxyphenyl) curcumin analog |
| 3e | (4-methoxyphenyl) curcumin analog |
| 3f | (4-hydroxyphenyl) curcumin analog |
| 3g | (4-dimethylaminophenyl) curcumin analog |
| 3h | (3-hydroxy-4-methoxyphenyl) curcumin analog |
| 3i | (3,4-dimethoxyphenyl) curcumin analog |
| 6a | 4-methyl curcumin |
| 6b | 4-methyl bisdemethoxycurcumin |
| 9a | 4-benzyl curcumin |
| 9b | 4-benzyl bisdemethoxycurcumin |

TABLE 1-continued
7-Carbon Linker Analogs.
11b 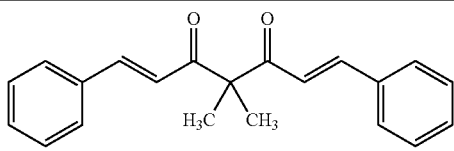
12b 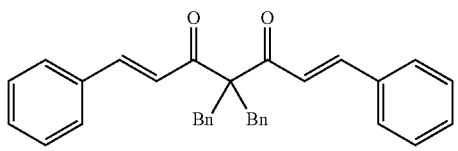 [SMILES: O=C(/C=C/c1ccccc1)C(Cc1ccccc1)(Cc1ccccc1)C(=O)/C=C/c1ccccc1]
13a 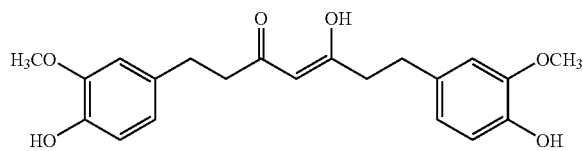 [SMILES: COc1cc(CCC(=O)/C=C(\O)CCc2ccc(O)c(OC)c2)ccc1O]
13b 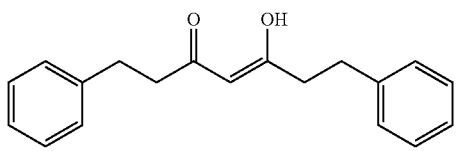 [SMILES: O=C(/C=C(\O)CCc1ccccc1)CCc1ccccc1]
14a 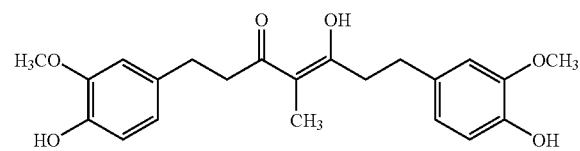 [SMILES: COc1cc(CCC(=O)/C(C)=C(\O)CCc2ccc(O)c(OC)c2)ccc1O]
14b 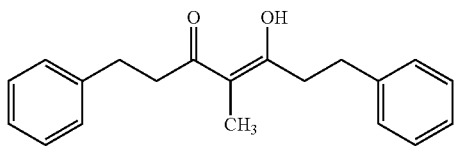 [SMILES: C/C(C(=O)CCc1ccccc1)=C(/O)CCc1ccccc1]
15a 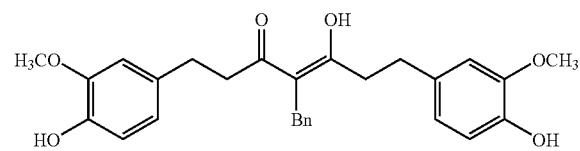 [SMILES: COc1cc(CCC(=O)/C(Cc2ccccc2)=C(\O)CCc2ccc(O)c(OC)c2)ccc1O]
15b 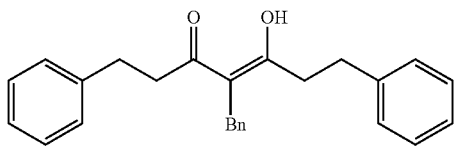 [SMILES: O=C(CCc1ccccc1)/C(Cc1ccccc1)=C(\O)CCc1ccccc1]
16a 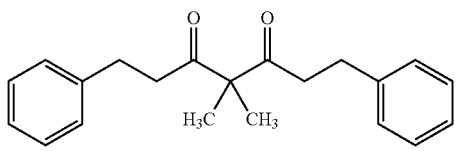 [SMILES: CC(C)(C(=O)CCc1ccccc1)C(=O)CCc1ccccc1]
17b 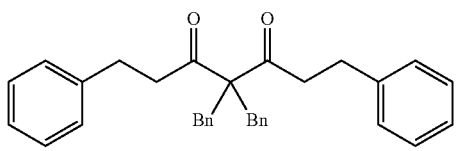 [SMILES: O=C(CCc1ccccc1)C(Cc1ccccc1)(Cc1ccccc1)C(=O)CCc1ccccc1]

Curcumin Derivatives Including 5-carbon Linking Groups

In a further embodiment of the invention, the curcumin derivatives include one or two aryl groups (Ar¹ and optionally Ar²) that are linked by a linking group L that is a 5-carbon linking group (i.e., a linking group that includes 5 backbone carbon atoms). Preferably, the 5-carbon linking group includes at least one unsaturated carbon-carbon bond. Examples of 5-carbon linking groups include:

—CH=CH—(CO)—CH=CH—,

—CH$_2$—CH$_2$—(CO)—CH$_2$—CH$_2$—,

—CH$_2$—CH$_2$—CH(OH)—CH$_2$—CH$_2$—,

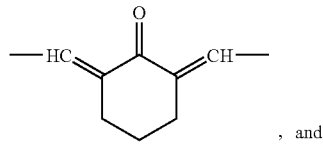

, and

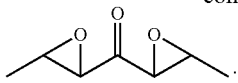

These linking groups are the divalent forms of 1,4-pentadiene-3-one; pentan-3-one; pentan-3-ol, 2,6; bis(methylene) cyclohexanone; and 1,2,4,5-diepoxy pentan-3-one. As noted herein, curcumin derivatives may include a cyclic linking group. For example, compound 31 (1-methyl-2,6-diphenyl-4-piperidone), provided in Example 4 herein, provides a compound with a 5-carbon linking group that is bridged by a tertiary amine to form a cyclic alkylene linking group including the heteroatom nitrogen.

Examples of 5-C Linkers

Table 2 shows a number of examples of curcumin derivatives that include a five carbon linker. The compounds shown contain two aryl rings separated by a five carbon spacer having a single carbonyl or hydroxyl. In many, but not all, of the compounds, the spacer is unsaturated.

TABLE 2

5-Carbon Linker Analogs.

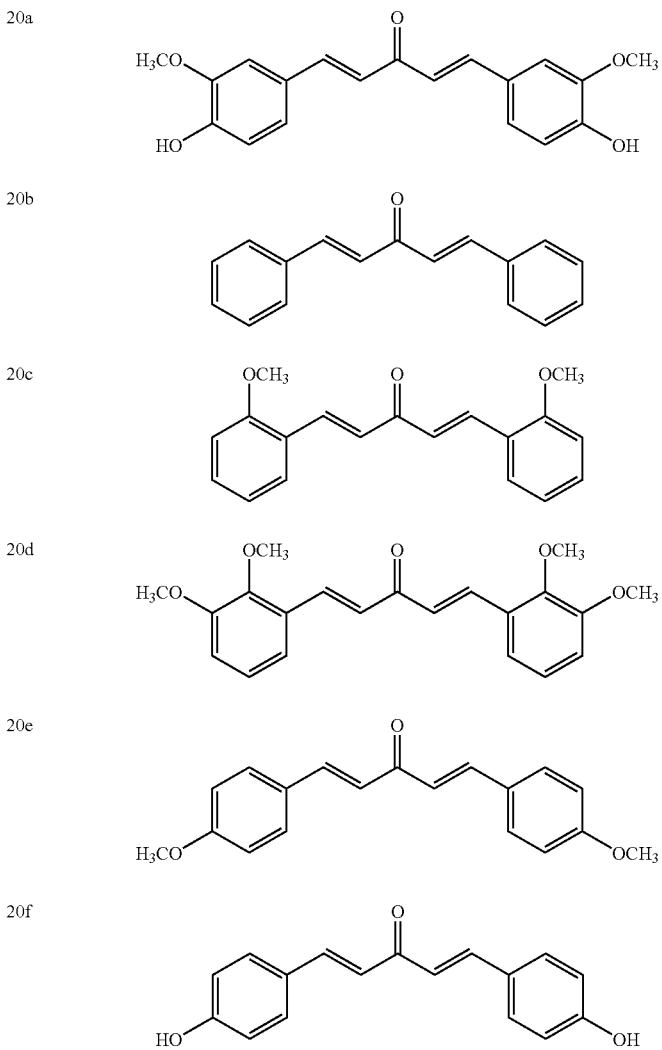

TABLE 2-continued

5-Carbon Linker Analogs.

20g: 1,5-bis(4-dimethylaminophenyl)penta-1,4-dien-3-one

20i: 1,5-bis(3,4-dimethoxyphenyl)penta-1,4-dien-3-one

20k: 1,5-bis(3-methoxyphenyl)penta-1,4-dien-3-one

20l: 1,5-bis(2,6-dimethoxyphenyl)penta-1,4-dien-3-one

20m: 1,5-bis(2,5-dimethoxyphenyl)penta-1,4-dien-3-one

20n: 1,5-bis(2,4-dimethoxyphenyl)penta-1,4-dien-3-one

20o: 1,5-bis(3,5-dimethoxyphenyl)penta-1,4-dien-3-one

20p: 1,5-bis(3-hydroxyphenyl)penta-1,4-dien-3-one

20q: 1,5-bis(2-hydroxyphenyl)penta-1,4-dien-3-one

TABLE 2-continued
5-Carbon Linker Analogs.
20r
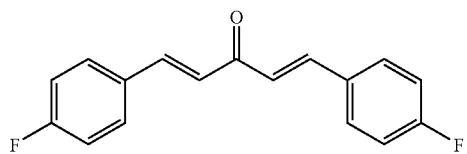 [SMILES: O=C(/C=C/c1ccc(F)cc1)/C=C/c1ccc(F)cc1]
20s
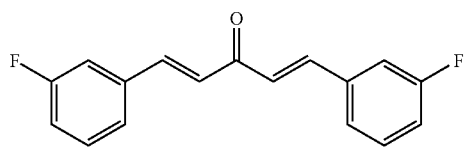 [SMILES: O=C(/C=C/c1cccc(F)c1)/C=C/c1cccc(F)c1]
20t
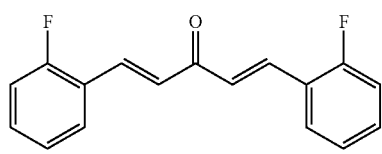 [SMILES: O=C(/C=C/c1ccccc1F)/C=C/c1ccccc1F]
20u
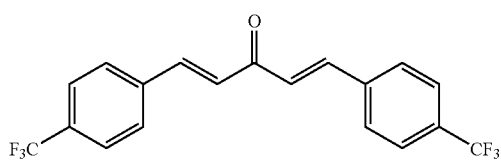 [SMILES: O=C(/C=C/c1ccc(C(F)(F)F)cc1)/C=C/c1ccc(C(F)(F)F)cc1]
20v
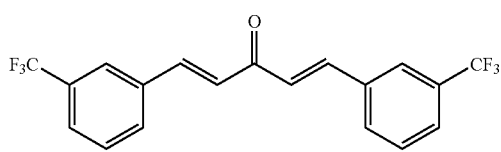 [SMILES: O=C(/C=C/c1cccc(C(F)(F)F)c1)/C=C/c1cccc(C(F)(F)F)c1]
20w
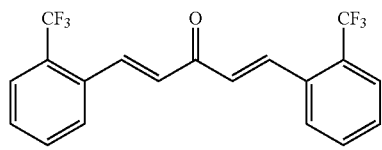 [SMILES: O=C(/C=C/c1ccccc1C(F)(F)F)/C=C/c1ccccc1C(F)(F)F]
20x
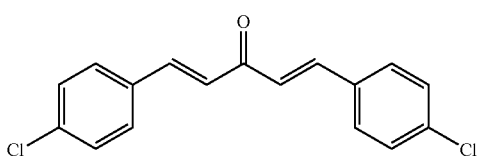 [SMILES: O=C(/C=C/c1ccc(Cl)cc1)/C=C/c1ccc(Cl)cc1]
20y
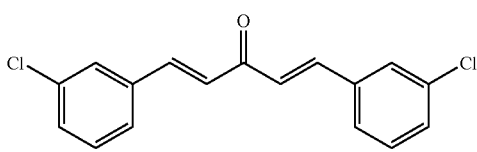 [SMILES: O=C(/C=C/c1cccc(Cl)c1)/C=C/c1cccc(Cl)c1]
20z
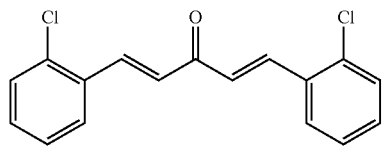
20aa
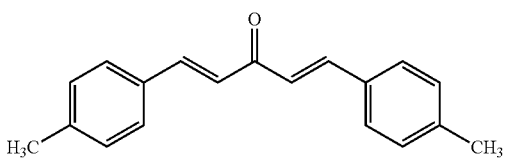

TABLE 2-continued
5-Carbon Linker Analogs.
20ab
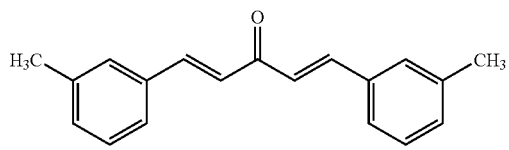
20ac
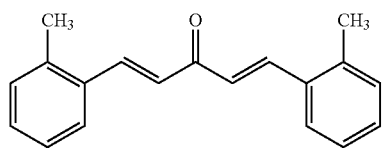 [SMILES: Cc1ccccc1/C=C/C(=O)/C=C/c1ccccc1C]
20ae
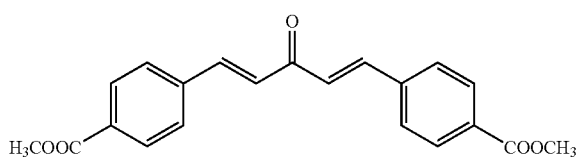
20af
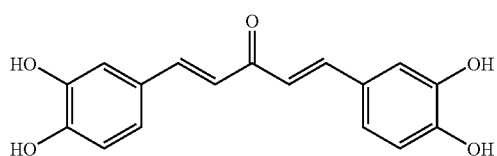 [SMILES: O=C(/C=C/c1ccc(O)c(O)c1)/C=C/c1ccc(O)c(O)c1]
20ag
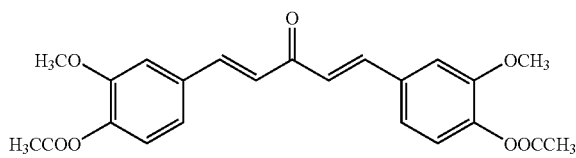
20ah
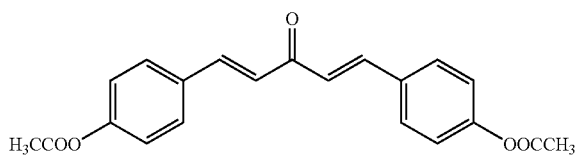
23
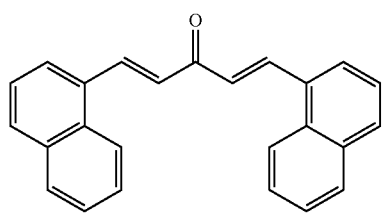 [SMILES: O=C(/C=C/c1cccc2ccccc12)/C=C/c1cccc2ccccc12]
25
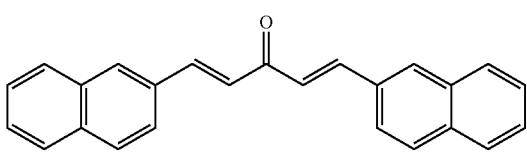 [SMILES: O=C(/C=C/c1ccc2ccccc2c1)/C=C/c1ccc2ccccc2c1]
29
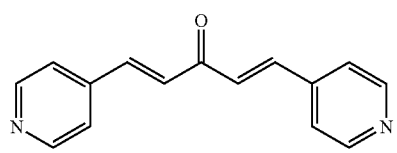 [SMILES: O=C(/C=C/c1ccncc1)/C=C/c1ccncc1]

TABLE 2-continued
5-Carbon Linker Analogs.
| 31 | 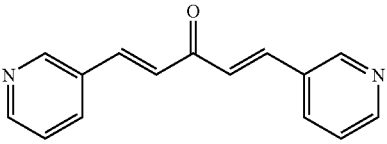 [SMILES: O=C(/C=C/c1cccnc1)/C=C/c1cccnc1] |
| --- | --- |
| 34 | 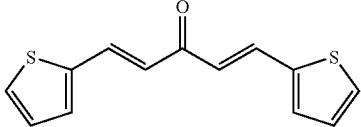 [SMILES: O=C(/C=C/c1cccs1)/C=C/c1cccs1] |
| 36a | 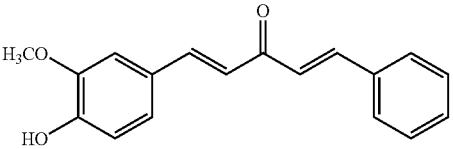 [SMILES: COc1cc(/C=C/C(=O)/C=C/c2ccccc2)ccc1O] |
| 36e | 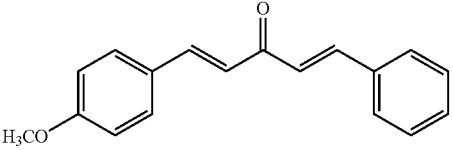 [SMILES: COc1ccc(/C=C/C(=O)/C=C/c2ccccc2)cc1] |
| 38a | 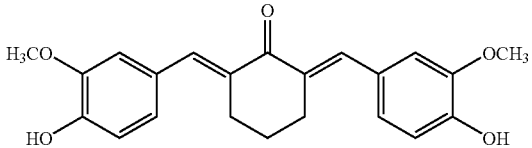 [SMILES: COc1cc(/C=C2\CCC/C(=C\c3ccc(O)c(OC)c3)C2=O)ccc1O] |
| 38b | 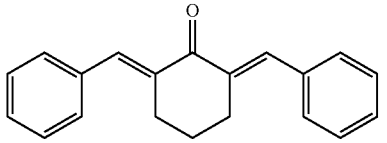 [SMILES: O=C1/C(=C/c2ccccc2)CCC/C1=C\c1ccccc1] |
| 39b | 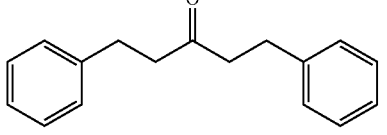 |
| 40b | 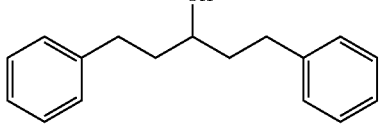 |
| 42b | 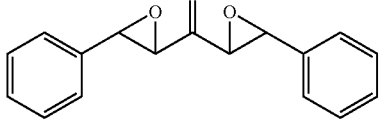 |
| 43b | 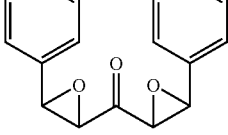 |

Curcumin Derivatives Including 3-carbon Linking Groups

In a further embodiment of the invention, the curcumin derivatives include one or two aryl groups (Ar$^1$ and optionally Ar$^2$) that are linked by a linking group L that is a 3-carbon linking group (i.e., a linking group that includes 3 backbone carbon atoms). Preferably, the 3-carbon linking group includes at least one unsaturated carbon-carbon bond. An example of a 3-carbon linking group is —CH=CH—CH(O)—; i.e., a divalent form of propenone.

Examples of 3-C Linkers

Table 3 shows a number of examples of curcumin derivatives that include a three carbon linker. The compounds shown generally have an unsaturated three-carbon spacer having a single carbonyl. While most of the examples shown have two aryl groups separated by the spacer, several of the embodiments include only a single aryl group. In the examples that include only a single aryl group, a methyl group is provided at the other end of the linking group. Compound 52b includes the heteroatom N in place of one of the backbone carbon atoms; however, this is still considered a 3-C linker in that 3 atoms (C, N, and C) are present along the shortest bridge between the two aryl groups.

TABLE 3

3-Carbon Linker Analogs.

| | |
|---|---|
| 35a | [H$_3$CO, HO-phenyl-CH=CH-C(=O)-CH$_3$] |
| 35e | [H$_3$CO-phenyl-CH=CH-C(=O)-CH$_3$] |
| 35q | [OH-phenyl-CH=CH-C(=O)-CH$_3$] |
| 45a | [H$_3$CO, HO-phenyl-C(=O)-CH=CH-phenyl-OCH$_3$, OH] |
| 45b | [phenyl-C(=O)-CH=CH-phenyl] |
| 46a | [H$_3$CO, HO-phenyl-C(=O)-CH=CH-phenyl] |
| 46ad | [HOOC-phenyl-C(=O)-CH=CH-phenyl] |
| 46ak | [CH$_3$, H$_3$C-phenyl-C(=O)-CH=CH-phenyl] |
| 46al | [NC-phenyl-C(=O)-CH=CH-phenyl] |
| 48a | [phenyl-C(=O)-CH=CH-phenyl-OCH$_3$, OH] |
| 48ad | [phenyl-C(=O)-CH=CH-phenyl-COOH] |
| 50b | [phenyl-C(=O)-CH=C(OH)-phenyl] |
| 52b | [2,6-diphenyl-1-methyl-piperidin-4-one] |

Additional Curcumin Derivatives

Curcumin derivatives of the invention may include a variety of linking groups and Ar groups while retaining biological activity, so long as they provide a structure that will inhibit NK-κB, AP-1 and/or GSTP1-1 activity. Accordingly, additional curcumin analogs are contemplated. Since analogs that contain a central methylene substituent on the 7-carbon spacer have shown significant activity, analogs containing a central group other than methyl or benzyl may also exhibit significant inhibition of NF-κB, AP-1 and/or GSTP1-1 activation. These include curcumin analogs containing central methylene substituents such as ethyl, propyl, butyl, isopropyl and substituted benzyl groups as shown below:

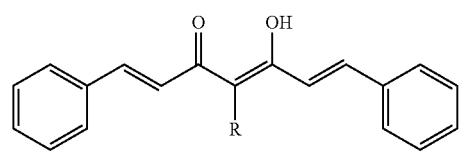

R = CH$_2$CH$_3$, CH(CH$_3$)$_2$, CH$_2$CH$_2$CH$_3$, CH$_2$CH$_2$CH$_2$CH$_3$, CH$_2$C$_6$H$_4$X; X = OH, OCH$_3$, N(CH$_3$)$_2$, CH$_3$

Central methylene substituent analogs

These compounds can be synthesized using the procedures shown in Schemes 1 and Scheme 2. The descriptions and details for these procedures are the same as those described for Schemes 8 and 9.

Scheme 1

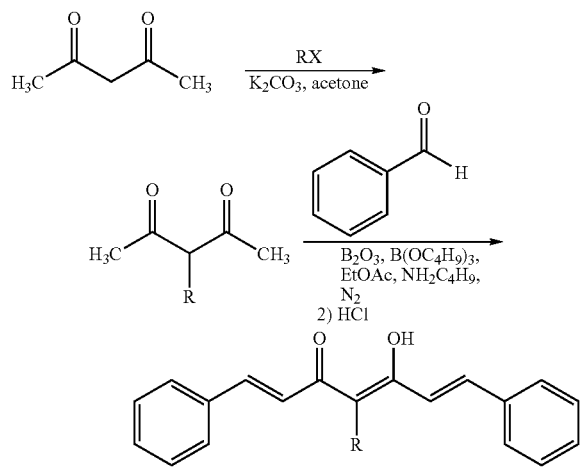

R = CH$_2$CH$_3$, CH(CH$_3$)$_2$, CH$_2$CH$_2$CH$_3$, CH$_2$CH$_2$CH$_2$CH$_3$

Scheme 2

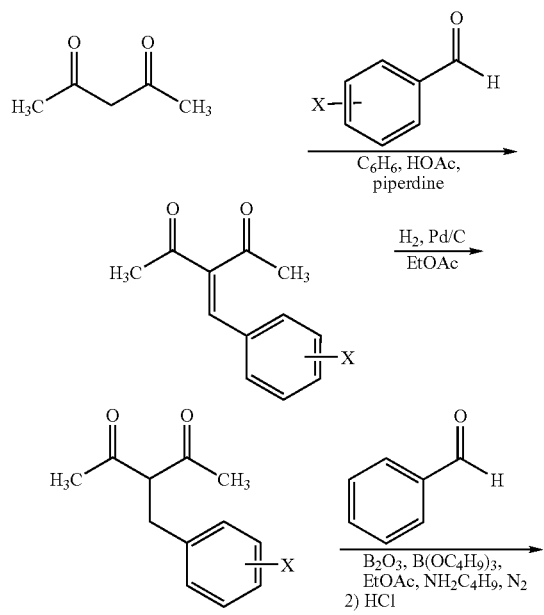

-continued

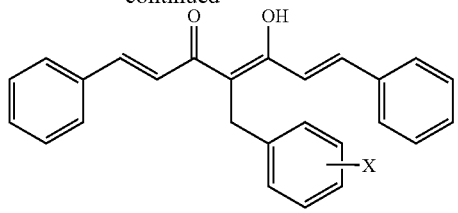

X = OH, OCH$_3$, N(CH$_3$)$_2$, CH$_3$

Additional analogs that are contemplated are those having a pyridine ring with and without a central methylene substituent on the 7-carbon spacer such as those shown below. Analogs without a central methylene substituent can be prepared according to Pabon's method shown in Scheme 3. The descriptions and details for this procedure are the same as described for Scheme 6. The analogs having a pyridine aryl ring with a central methylene substituent on the 7-carbon spacer can be synthesized using a procedure described in Scheme 1 using 2, 3 or 4-pyridine carboxaldehyde.

Pyridine aryl ring analogs.

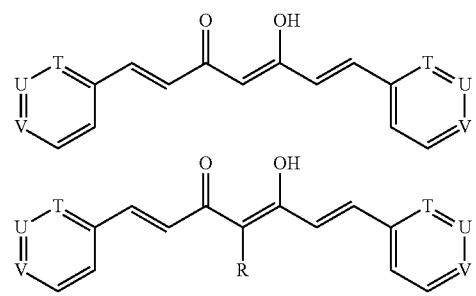

T, U, V = N, R = CH$_2$CH$_3$, CH(CH$_3$)$_2$, CH$_2$CH$_2$CH$_3$, CH$_2$CH$_2$CH$_2$CH$_3$, CH$_2$C$_6$H$_4$X; X = OH, OCH$_3$, N(CH$_3$)$_2$, CH$_3$

Scheme 3

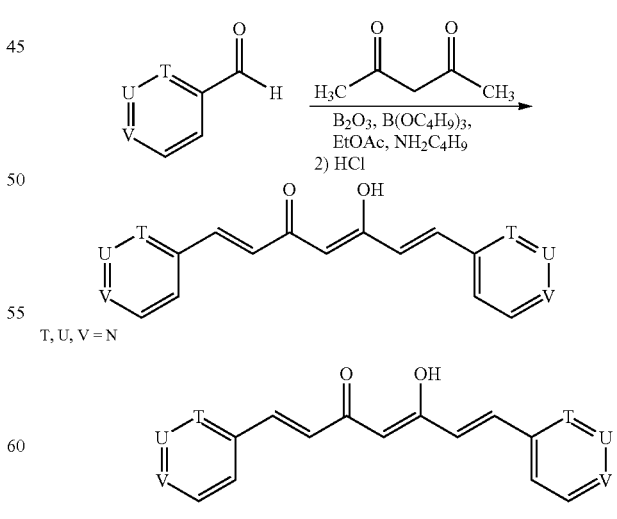

T, U, V = N

Many curcumin analogs which have a 5-carbon spacer possess significant activity. Additional active analogs in this series may contain substituents such as hydroxy and methoxy groups on the aryl rings. Therefore, other substituents and their positions on the aryl rings may also provide significant inhibition of NF-κB, AP-1 and/or GSTP1-1 activation. Examples of these analogs are shown below:

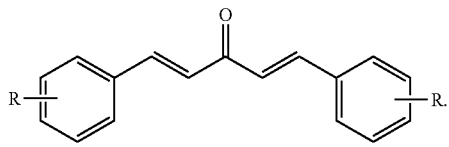

R = CH₂CH₃, CH(CH₃)₂, CH₂CH₂CH₃, CH₂CH₂CH₂CH₃
Aryl substituent analogs

These new analogs can be prepared as shown in Scheme 4. The descriptions and details for this procedure are the same as described for Scheme 13.

Scheme 4

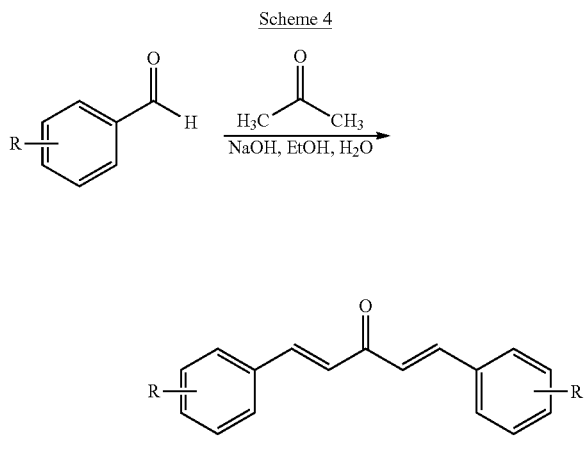

R = CH₂CH₃, CH(CH₃)₂, CH₂CH₂CH₃, CH₂CH₂CH₂CH₃

Although analogs having 3-carbon spacers were generally not as active as analogs having 7-carbon or 5-carbon spacers, additional analogs may provide significant inhibition of NF-κB, AP-1 and/or GSTP1-1 activation. Relatively few analogs in this series containing a heterocyclic ring on the spacer have been synthesized. Analogs having different substituents on the aryl rings may provide significant inhibition of NF-κB, AP-1, and/or GSTP1-1 activation. In addition, analogs that contain different substituents on the nitrogen of the heterocyclic ring may provide significant inhibition of NF-κB, AP-1, and/or GSTP1-1 activation. Examples of these series 3 analogs are shown below:

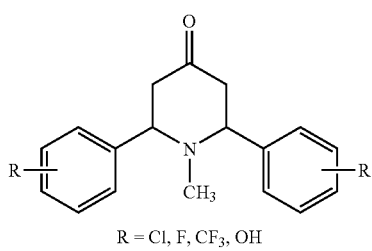

R = Cl, F, CF₃, OH

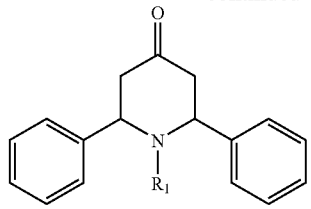 [SMILES: CN1C(c2ccccc2)CC(=O)CC1c1ccccc1]

R₁ = Ph, CH₂CH₃
Heterocyclic analogs

These analogs can be synthesized as shown in Scheme 5. The descriptions and details for this procedure are the same as those described for Scheme 36.

Scheme 5

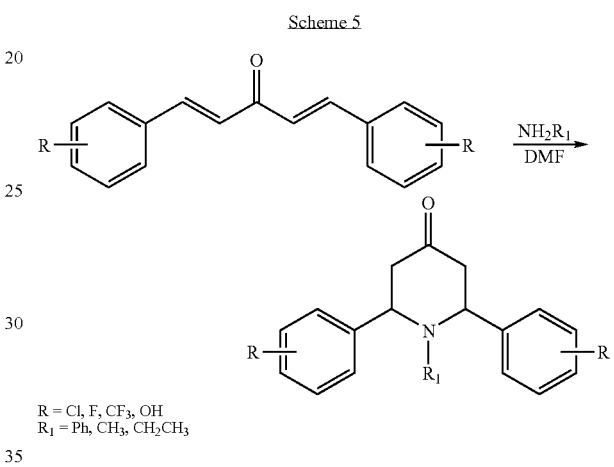

R = Cl, F, CF₃, OH
R₁ = Ph, CH₃, CH₂CH₃

Additional curcumin derivatives of the invention that are not encompassed by the embodiments provided above may also be found in the examples and schemes provided herein.

Disease Treatment Using Curcumin Derivatives

Treatment, as defined herein, is the amelioration of the symptoms associated with disease. Symptoms may be reduced either by decreasing the level of the disease itself, or by decreasing the symptoms associated with the disease. The subject of the treatment is preferably a mammal, such as a domesticated farm animal (e.g., cow, horse, pig) or pet (e.g., dog, cat). More preferably, the subject is a human.

As noted herein, and without being bound by any particular theory, one mechanism by which administration of curcumin derivatives may treat disease is through inhibition of the activity of AP-1, NF-κB and/or GSTP1-1. Inhibition of NF-κB results in a decrease in NF-κB activity, and includes direct inhibition and indirect inhibition. Direct inhibition is the direct effect of a curcumin derivative on NF-κB and its activity. For example, one type of direct inhibition of NF-κB is a block of NF-κB DNA interactions. Indirect inhibition, on the other hand, involves the effect of a curcumin derivative on other compounds involved in the regulation of NF-κB that leads to a decrease in NF-κB activity. For example, as phosphorylation of the NF-κB regulator IκB by IκB kinases (IKK) or Src family kinases (SFK) results in a dysregulation of NF-κB, and an according increase in NF-κB activity, inhibition of IKK or SFK by curcumin derivatives provides an example of indirect inhibition.

Inhibition of AP-1 results in a decrease in AP-1 activity, and includes direct inhibition and indirect inhibition. Direct inhibition is the direct effect of a curcumin derivative on AP-1

(or its subunits) and its activity. Indirect inhibition, on the other hand, involves the effect of a curcumin derivative on other compounds involved in the regulation of AP-1 that leads to a decrease in AP-1 activity. For example, indirect inhibition of AP-1 activity may occur as a result of an affect on AP-1 activating proteins such as mitogen-activated protein kinases (MAPK) or c-Fos-regulating kinase (FRK).

Inhibition of GSTP1-1 results in a decrease GSTP1-1 activity, and includes direct inhibition and indirect inhibition. Direct inhibition is the direct effect of a curcumin derivative on GSTP1-1 (or its subunits) and its activity. Indirect inhibition, on the other hand, involves the effect of a curcumin derivative on other compounds involved in the regulation of GSTP1-1 that leads to a decrease in GSTP1-1 activity. Various methods for inhibiting of GSTP1-1 are exemplified in Examples 12 and 13.

Alzheimer's Disease

In one aspect, the present invention provides a method of using curcumin derivatives to treat a subject with Alzheimer's disease. The present invention also provides a method of using curcumin derivatives to treat symptoms of Alzheimer's disease in a subject with Alzheimer's disease. Curcumin derivatives treat Alzheimer's disease through one or more biochemical mechanisms. For example, without being bound by theory, administration of curcumin derivatives may treat Alzheimer's disease by inhibiting the activity of AP-1 and/or NF-κB. Decreasing the activity of AP-1 and/or NF-κB may, in turn, lead to a decrease in inflammation.

As another example, again without being bound by theory, administration of curcumin derivatives may treat Alzheimer's disease through an effect on the Aβ peptide, for example by inhibiting the formation of Aβ oligomers and fibrils, reducing Aβ peptide aggregation, or by reducing the Aβ amyloid burden of subjects with Alzheimer's disease. The effects of curcumin derivatives on Aβ peptide aggregation may include binding to Aβ peptide aggregates and/or effects on Aβ peptide conformation. Effects on Aβ peptide conformation include destabilization of the β-sheet conformation of Aβ peptide aggregates, and/or the stabilization of non-aggregated Aβ peptide α-helical/random coil conformation. The effects of curcumin derivatives may further include a decrease in the cytotoxicity of Aβ peptide aggregates, or a decrease in glial cell activation by Aβ peptide aggregates.

Symptoms of Alzheimer's disease include, for example, formation of amyloid plaques and neurofibrillary tangles, chronic brain inflammation, glial cell activation, and cognitive decline. A number of other symptoms are known and can be readily identified by one skilled in the art.

Type 2 Diabetes

In another aspect, the present invention provides a method of using curcumin derivatives to treat a subject with type 2 diabetes. The present invention also provides a method of using curcumin derivatives to treat symptoms of diabetes in a subject with type 2 diabetes such as inflammation or insulin resistance.

Symptoms of type 2 diabetes include, for example, insulin resistance and inflammation. A number of other symptoms are known and can be readily identified by one skilled in the art.

Other Inflammatory Diseases or Conditions

In should be understood that the present invention provides a method of using curcumin derivatives to treat a subject with any disease or condition characterized by inflammation, including Alzheimer's disease, diabetes (particularly type 2 diabetes), cancer, cystic fibrosis, rheumatoid arthritis, asthma, inflammatory bowel disease, ulcerative colitis, atherosclerosis and stroke.

Assistive or Adjuvant Treatment for Cancer

In another aspect, the present invention pertains generally to treatment of cancer or a precancerous condition such as dysplasia or hyperplasia, by administering a curcumin derivative of the invention. Administration of the curcumin derivative may advantageously inhibit the activity Glutathione S-transferase P1-1 (GSTP1-1), NFκB and/or AP-1. Inhibition of GSTP1-1 may occur by affecting gene transcription and/or by direct effects on enzyme activity.

In a preferred embodiment, administration of the curcumin derivative is effected in combination with the administration of another chemotherapeutic agent. The curcumin derivative can be administered before, during of after the administration of the chemotherapeutic agent. Administration of the curcumin derivative is especially advantageous in cases where the cancer cells may develop or have developed resistance to the chemotherapeutic agent; and/or when the cancer cells overexpress GSTP1-1. Expression of GSTP1-1 may allow the cancer cell to pump out the chemotherapeutic agent, and by inhibiting the activity of GSTP1-1, the curcumin derivative may preserve or prolong the cytostatic or cytotoxic effects of the chemotherapeutic agent. The present invention is particularly useful for improving the effectiveness of chemotherapeutic agents by preventing GSTP1-1's inhibition of pro-apoptotic factors, particularly c-Jun N-terminal kinase (JNK).

Curcumin was shown recently to inhibit apoptosis in cancer cells in part through its ability to inhibit the expression of GSTP1-1 mRNA and protein, which was demonstrated to be the result of inhibition of the activation of NFκB. This observation that compounds such as curcumin can block activation of NFκB raises the possibility that synthetic drugs can be developed that are more potent than curcumin, and that these drugs will promote apoptosis in cancer cells. These drugs could sensitize cancer cells to conventional adjuvant chemotherapy by blocking the NFκB-dependent development of the anti-apoptotic pro-survival state, and inhibit the expression of GSTP1-1. In addition, curcumin inhibits the GSTP1-1 catalyzed conjugation of glutathione with electrophiles. Furthermore, curcumin inhibits the proliferation of a variety of tumor cells and has anti-metastatic activity, possibly owing to its ability to induce apoptosis by inhibiting NFκB.

Curcumin contains two alpha, beta-unsaturated carbonyl groups, one of which exists as the enol tautomer. Curcumin reacts with glutathione; this reaction is accelerated by GSTP1-1, indicating that curcumin is a substrate of GSTP1-1, albeit a poor substrate. Curcumin also inhibits GSTP1-1 in its conjugation of glutathione with other electrophiles, suggesting that curcumin is both a substrate and an inhibitor of GSTP1-1. This is consistent with the known inhibition of GSTP1-1 by the flavonoid quercetin, which, like curcumin, is also a polyphenol. Curcumin itself has low bioavailability and therefore is not a promising drug.

In view of the reports that suggest a role for curcumin in cancer therapy as a direct inhibitor of GSTP1-1, as well as a down-regulator of GSTP1-1 through inhibition of NFκB, analogues of curcumin with good bioavailability can be developed as new anti-cancer drugs that may inhibit the catalytic activity of GSTP1-1, thereby sensitizing cancer cells to conventional chemotherapy by drugs that normally are metabolized through GSTP1-1 catalyzed conjugation with glutathione; and/or, through inhibition of GSTP1-1 and/or NFκB the curcumin derivatives, contribute to improved chemotherapeutic drug sensitivity of cancer cells by promoting the pro-apoptotic state. These analogs thus may have a dual mechanism of action—both the inhibition of the catalytic activity of GSTP1-1 and the down-regulation of GSTP1-1 transcription through inhibition of NFκB. GSTP1-1 inhibitors may limit the ability of GSTP1-1 to inactivate other cancer drugs and may prove to be synergistic when combined with important chemotherapeutic drugs including platinums, taxanes and anthracyclines. The invention is not limited to the types of cancer that can be treated. Cancers that can be treated include breast cancer, ovarian cancer, prostate cancer, non-Hodgkin's lymphoma, and leukemia.

Identification of Agents

Another aspect of the invention includes methods for identifying therapeutic curcumin derivatives that may be used to treat a subject afflicted with a disease. Potential agents suitable for testing are referred to herein as "candidate" agents. In one embodiment, the method involves exposing AP-1, NF-κB or GSTP1-1 to the candidate agent and determining whether or not its activation by an AP-1, NF-κB or GSTP1-1 activator is inhibited. As AP-1 and NF-κB are transcription factors, their activation is most readily evaluated in a cell assay. However, AP-1 or NF-κB activation can also be evaluated in cell-free systems using techniques readily known by those skilled in the art. Sources for candidate agents include, for instance, chemical compound libraries, and extracts of plants and other vegetations.

For example, in one embodiment, the method for identifying a therapeutic curcumin derivative involves contacting a cell containing NF-κB with a candidate curcumin derivative, contacting the cell with an NF-κB activator (e.g., TNF-α or IL-1) and determining the effect on NF-κB activation by the curcumin derivative. Preferably, the cell contains "activatable" NF-κB; that is, the cell has or retains the capacity for NF-κB activation. A candidate agent that results in a decrease of NF-κB activation is accordingly identified by this method as a therapeutic curcumin derivative. Cells that may be used to test for a decrease of NF-κB activation include, for example, adipose and endothelial cells. For example, a cell assay suitable for identifying curcumin derivatives that are useful for treating a subject with type 2 diabetes is provided by Example 3, herein.

In a further exemplary embodiment, the method for identifying a therapeutic curcumin derivative involves contacting a cell containing AP-1 with a candidate curcumin derivative, contacting the cell with an AP-1 activator (e.g., TNF-α or phorbol 12-myristate 13-acetate) and determining the extent of the effect on AP-1 activation by the curcumin derivative. Preferably, the cell contains "activatable" AP-1; that is, the cell has or retains the capacity for AP-1 activation. A candidate agent that results in a decrease of AP-1 activation is accordingly identified by this method as a therapeutic curcumin derivative. Cells that may be used to test for a decrease of AP-1 activation include, for example, adipose and endothelial cells. For example, a cell assay suitable for identifying curcumin derivatives that are useful for treating a subject with type 2 diabetes is provided by Example 5, herein.

In another exemplary embodiment, the method for identifying a therapeutic curcumin derivative involves contacting a cell containing GSTP1-1 with a candidate curcumin derivative, contacting the cell with a GSTP1-1 activator (e.g., TNF-α) and determining the extent of the effect on GSTP1-1 activation by the curcumin derivative. Preferably, the cell contains "activatable" GSTP1-1; that is, the cell has or retains the capacity for GSTP1-1 activation. A candidate agent that results in a decrease of AP-1 activation is accordingly identified by this method as a therapeutic curcumin derivative. A cell assay suitable for identifying curcumin derivatives that are useful for assistive or adjuvant chemotherapeutic treatment, for example, is provided by Examples 12 and 13.

As another example, therapeutic curcumin derivatives can be identified by observing the effect of curcumin derivatives on cell activation by inflammation activators. Inflammation activators, as defined herein, include compounds that stimulate cells to result in an increase in inflammation. Activated cells may, for example, release higher levels of cytokines (e.g., IL-1 or IL-6) than unactivated cells. Examples of inflammation activators include AP-1 and NF-κB. As AP-1 and NF-κB are transcription factors, their activation is most readily evaluated in a cell assay. However, AP-1 or NF-κB activation can also be evaluated in cell-free systems using techniques readily known by those skilled in the art.

A therapeutic curcumin derivative that is useful as an anti-Alzheimer's agent can be identified by evaluating the effect of the candidate agent on symptoms or biochemicals associated with Alzheimer's disease neuropathology. For example, in one embodiment, a therapeutic curcumin derivative can be identified by contacting a brain cell that includes an inflammation activator with a curcumin derivative and determining the effect of the curcumin derivative on brain cell activation by the inflammation activator. A candidate agent that reduces brain cell activation is accordingly identified by this method as a curcumin derivative that may be used to treat a subject with Alzheimer's disease. Brain cells, as defined herein, include neurons and glial cells. Glial cells further include microglia, which are a specialized form of macrophage cells. Cell activation may be evaluated, for example, by determining the level of cytokines (e.g., IL-1 or IL-6) released or expressed by the cells.

Curcumin derivatives effective to treat Alzheimer's disease may be identified by directly determining their effect on the activity of NF-κB or AP-1, as detailed elsewhere herein. Evaluation of the effect on NF-κB or AP-1 can be carried out in a variety of different types of cells. For example, a cell assay involving activation of NF-κB that is suitable for identifying curcumin derivatives that are useful for treating a subject with Alzheimer's disease is provided by Example 3. An example of a cell assay involving activation of AP-1 that is suitable for identifying curcumin derivatives that are useful for treating Alzheimer's disease is provided by Example 5. Therapeutic curcumin derivatives may also be identified using high-throughput screening (HTS), as described in Example 9.

Another method for identifying therapeutic curcumin derivatives effective to treat Alzheimer's disease includes observing the effects of curcumin derivatives on the Aβ peptide. These effects may include inhibition of the formation of Aβ oligomers and fibrils, a decrease in Aβ peptide aggregation, or a decrease in the Aβ amyloid burden of subjects with Alzheimer's disease. More specifically, the effects of curcumin derivatives on Aβ peptide aggregation may include binding to Aβ peptide aggregates and/or effects on Aβ peptide conformation. Effects on Aβ peptide conformation may include destabilization of the β-sheet conformation of Aβ peptide aggregates, and/or the stabilization of non-aggregated Aβ peptide α-helical/random coil conformation. The effects of curcumin derivatives may further include a decrease in the cytotoxicity of Aβ peptide aggregates, or a decrease in glial cell activation by Aβ peptide aggregates. These effects may be determined using a number of different assays, such as those described in Example 10.

For example, one method for identifying antiAlzheimer curcumin derivatives includes contacting a solution that includes an Aβ peptide with a curcumin derivative and determining the effect of the curcumin derivative on aggregation by the Aβ peptide. A curcumin derivative that reduces aggregation of the Aβ peptide is thus identified as an antiAlzheimer curcumin derivative. The Aβ peptide may include derivatives of the Aβ peptide such as N-terminal biotinylated A(1-40) peptide. The effect of the curcumin derivative on aggregation by the Aβ peptide can be determined using a variety of different techniques known to those skilled in the art, such as use of an immunological assay to determine the amount of aggregated Aβ peptide formed.

Candidate agents may also be tested in animal models. In one embodiment, the animal model is selected for the study of diabetes. The study of diabetes in animal models (for instance, mice) is a commonly accepted practice by those skilled in the art. Examples of mouse models for type 2 diabetes include C57BLKs, CBA/CaJ, NON/LtJ, and B6.HRS(BKS)-Cpe$^{fat}$/J mouse strains. Further strains may be obtained from JAX Mice Diabetes & Obesity Research Models, The Jackson Laboratory (Bar Harbour, Me.). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the diabetes such as inflammation or insulin resistance.

In another embodiment, the animal model is one developed by those skilled in the art for use in studies of Alzheimer's disease. For example, rat and mouse models of Alzheimer's disease have been developed that overexpress the Aβ peptide. See, for example, the review of genetic mouse models of Alzheimer's disease by Mineur et al., Neural Plast. (2005) 12(4), 299-310. Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with Alzheimer's disease, such as inflammation or Aβ peptide aggregation.

Administration and Formulation of Curcumin Derivatives

The present invention provides a method for using a composition that includes one or more small molecule inhibitors of the invention to treat a subject afflicted with a disease by administering curcumin derivatives alone, or along with one or more pharmaceutically acceptable carriers. One or more curcumin derivatives with demonstrated biological activity can be administered to a subject in an amount alone or together with other active agents and with a pharmaceutically acceptable buffer. The a composition that includes one or more small molecule inhibitors of the invention can be combined with a variety of physiological acceptable carriers for delivery to a patient including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

Methods of administering small molecule therapeutic agents are well-known in the art. Reference is made, for example, to U.S. Pat. Publ. 2001-0051184 A1, published Dec. 13, 2001 (Heng) concerning illustrative modes of administration of curcumin analogs as well as dosage amounts and protocols.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The curcumin derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations suitable for parenteral administration conveniently include a sterile aqueous preparation of the active agent, or dispersions of sterile powders of the active agent, which are preferably isotonic with the blood of the recipient. Parenteral administration of curcumin derivatives (e.g., through an I.V. drip) is an additional form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the curcumin derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of curcumin derivatives (i.e., active agent) is such that the dosage level will be effective to produce the desired result in the patient.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

The curcumin derivatives of the invention can be incorporated directly into the food of the mammal's diet, as an additive, supplement, or the like. Thus, the invention further provides a food product containing a curcumin derivative of the invention. Any food is suitable for this purpose, although processed foods already in use as sources of nutritional supplementation or fortification, such as breads, cereals, milk, and the like, may be more convenient to use for this purpose.

Small molecule inhibitors such as curcumin derivatives are well-suited for inhibiting AP-1 or NF-κB activity, as they are usually easily synthesized and readily taken up by mammalian cells. In some embodiments, the small molecule inhibitor is derivatized or conjugated with a carrier molecule according to methods well known in the art, so as to increase targeting efficiency and/or the rate of cellular uptake, for example by being covalently linked to a ligand that binds to a cell surface receptor.

Preparation of Curcumin Derivatives

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Generally, compounds of the present invention are prepared by reacting a pair of aryl aldehydes using an aldol reaction. For example, curcumin derivatives including a 7-carbon linker may be prepared by reacting 2,4-pentanedione with a substituted arylaldehyde in an aldol-type reaction according to the procedure described by Pabon (Pabon, H. J. J. Recueil 83, 379 (1964)). In a further example, curcumin derivatives including a 5-carbon linker may be prepared by reaction of acetone with substituted arylaldehydes in a base catalyzed aldol reaction, as described by Masuda et al. (Masuda et al., Phytochemistry 32, 1557 (1993)), and curcumin derivatives including a 3-carbon linker (also referred to as chalcones) can be prepared by reaction of a substituted arylaldehyde with a substituted aceto-aryl compound (e.g., acetophenone) in a base catalyzed aldol reaction as described by Kohler and Chadwell (Kohler, E. P.; Chadwell, H. M. Org. Synth., Coll. 1, 78 (1932)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope of the invention as set forth herein.

EXAMPLES

Example 1

Chemical Synthesis of Curcumin Derivatives

Several derivatives were synthesized that have some structural similarity to curcumin. The following is a discussion of the analogs that were synthesized and the methods used to accomplish the structural changes. Spectral data were useful in characterizing structural changes in the molecules. Proton and carbon nuclear magnetic resonance spectroscopies (NMR) were used to detect functional groups in the curcumin analogs. The following schemes summarize the procedures used to prepare the three series of curcumin analogs. Analogs in series 1, which retain the 7-carbon spacer contained in curcumin, were prepared as shown in Schemes 6-11. Analogs in series 2, which contain a 5-carbon spacer, were prepared as shown in Schemes 12-27. Analogs in series 3, which contain a 3-carbon spacer, were prepared as shown in Schemes 28-37.

Synthesis of 7-Carbon Spacer Analogs

Analogs 3a-3i, contain two aryl rings separated by an unsaturated 7-carbon spacer having two carbonyls (Schemes 1 and 2). The aryl rings contain different substituents in various positions on the ring. These analogs were designed to test the importance of the type of substituent and its location on the aryl ring. Analogs 3a-3h, as shown in Scheme 6, were prepared following the procedure described by Pabon (Pabon, Recueil, 83, 379-386 (1964)). 2,4-Pentanedione (2) was reacted with boric anhydride to give the boron/pentanedione complex. The complex was then reacted with the appropriately substituted benzaldehyde (1a-1h), tributyl borate, and butylamine in dry ethyl acetate in an aldol type reaction followed by hydrolysis with warm dilute hydrochloric acid to give curcumin (3a) or one of its analogs 3b-3h.

The formation of the products was verified by proton NMR by the appearance of a pair of doublets in the aromatic region with J values of 15.5-16.5 Hz for the alkene protons present in the spacer. Also observed in the proton NMR was the loss of a signal at ~10 ppm for the aldehyde proton in the starting benzaldehyde and the loss of signals at 1.89 ppm and 2.08 ppm for the methyl protons on 2,4-pentanedione (2). The structures were also verified by carbon NMR by the appearance of a signal at ~182 ppm for the keto-enol carbonyl carbon and the loss of a signal at ~195 ppm for the aldehyde carbon in the starting benzaldehyde (1a-1h). Also absent from the carbon NMR were signals at 24.1 ppm and 30.2 ppm for the methyl carbons on 2,4-pentanedione (2).

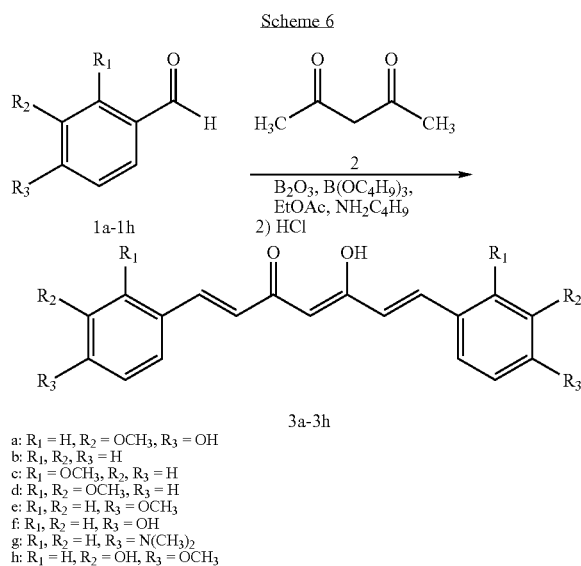

Scheme 6

3a-3h a: $R_1$ = H, $R_2$ = $OCH_3$, $R_3$ = OH
b: $R_1$, $R_2$, $R_3$ = H
c: $R_1$ = $OCH_3$, $R_2$, $R_3$ = H
d: $R_1$, $R_2$ = $OCH_3$, $R_3$ = H
e: $R_1$, $R_2$ = H, $R_3$ = $OCH_3$
f: $R_1$, $R_2$ = H, $R_3$ = OH
g: $R_1$, $R_2$ = H, $R_3$ = $N(CH_3)_2$
h: $R_1$ = H, $R_2$ = OH, $R_3$ = $OCH_3$

Analog 3d, which is not in the literature, was verified by elemental analysis.

Scheme 7 describes the synthesis of analog 3i. Analog 3i was also prepared following the procedure described by Pabon (Pabon, Recueil, 83, 379-386 (1964)). 2,4-Pentanedione (2) was reacted with boric anhydride in dry ethyl acetate at 40° C. to give the boron/pentanedione complex. The complex was then reacted with 3,4-dimethoxybenzaldehyde (1i), tributyl borate, and butylamine in dry ethyl acetate at 40° C. in an aldol type reaction followed by hydrolysis with warm dilute hydrochloric acid to give analog 3i. The formation of the product was verified by proton NMR by the appearance of a pair of doublets in the aromatic region with J values of 15.9 Hz for the alkene protons present in the spacer. Also observed in the proton NMR was the loss of a signal at 9.85 ppm for the aldehyde proton in the starting benzaldehyde (1i) and the loss of signals at 1.89 ppm and 2.08 ppm for the methyl protons on 2,4-pentanedione (2). The structure was also verified by carbon NMR by the appearance of a signal at 183.0 ppm for the keto-enol carbonyl carbon and the loss of a signal at 190.9 ppm for the aldehyde carbon in the starting benzaldehyde (1i). Also absent from the carbon NMR were signals at 24.1 ppm and 30.2 ppm for the methyl carbons on 2,4-pentanedione (2).

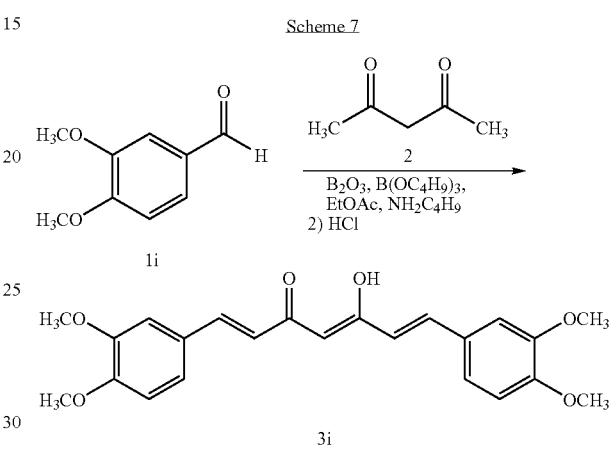

Scheme 7

Two additional curcumin analogs, 6a and 6b, were prepared as shown in Scheme 8. Analogs 6a and 6b contain two aryl rings separated by an unsaturated 7-carbon spacer having two carbonyls and a single methyl substituent attached to the central methylene carbon. These analogs were designed to test the importance of a methyl substituent on the central methylene carbon. 3-Methyl-2,4-pentanedione (5) was first synthesized by reaction of 2,4-pentanedione (2) with potassium carbonate and methyl iodide (4) in acetone at 56° C. in a substitution reaction following the procedure described by Markham and Price (Markham et al., Org. Synth. Coll. Vol. V. 785-790). This reaction gave the monomethyl substituted product as the major product along with small amounts of both unreacted 2,4-pentanedione (2) and of the dimethyl substituted product. The formation of the product was verified by proton NMR by the appearance of a doublet at 1.12 ppm for the methyl protons and a quartet at 3.52 ppm for the remaining methylene proton. Analogs 6a and 6b were then prepared from compound 5, following the procedure described by Pabon (Pabon, Recueil, 83, 379-386 (1964)), by reaction with boric anhydride under a nitrogen atmosphere to give the boron/pentanedione complex. The complex was then reacted with 4-hydroxy-3-methoxybenzaldehyde (1a) or benzaldehyde (1b), tributyl borate, and butylamine in an aldol type reaction followed by hydrolysis with warm dilute hydrochloric acid to give 6a and 6b respectively. The formation of products was verified by proton NMR by the appearance of a pair of doublets in the aromatic region with J values of 15.5 Hz for the alkene protons in the spacer and the loss of signals at 1.92 ppm and 2.00 ppm for the terminal methyl protons on 3-methyl-2,4-pentanedione (5). The structures were also verified by carbon NMR by the appearance of a signal at ~182.2 ppm for the keto-enol carbonyl carbon. The carbon NMR also showed the loss of signals at 23.0 ppm and 28.4 ppm for the terminal methyl carbons on 3-methyl-2,4-pentanedione (5). The carbon NMR of analog 6b also showed the loss of a signal at 192.1 ppm for the aldehyde carbon in the starting benzaldehyde (1b), whereas in analog 6a, a signal is present at 196.0 ppm due to the carbonyl carbon of the diketo form and not the aldehyde carbon of the starting benzaldehyde (1b). Both analogs 6a and 6b, which are not in the literature, were verified by elemental analysis.

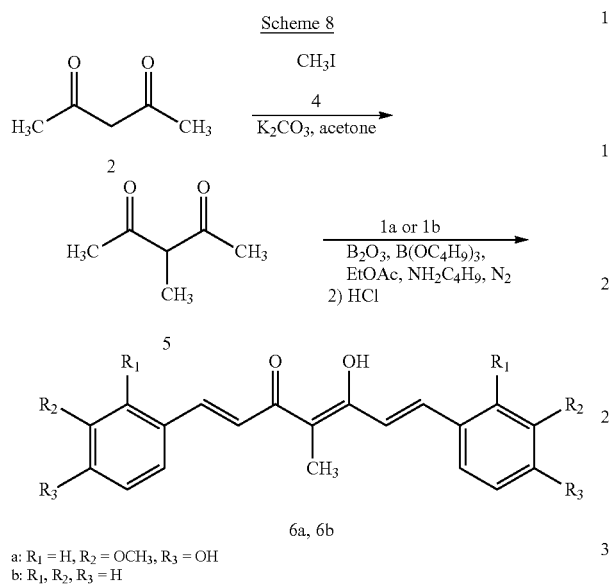

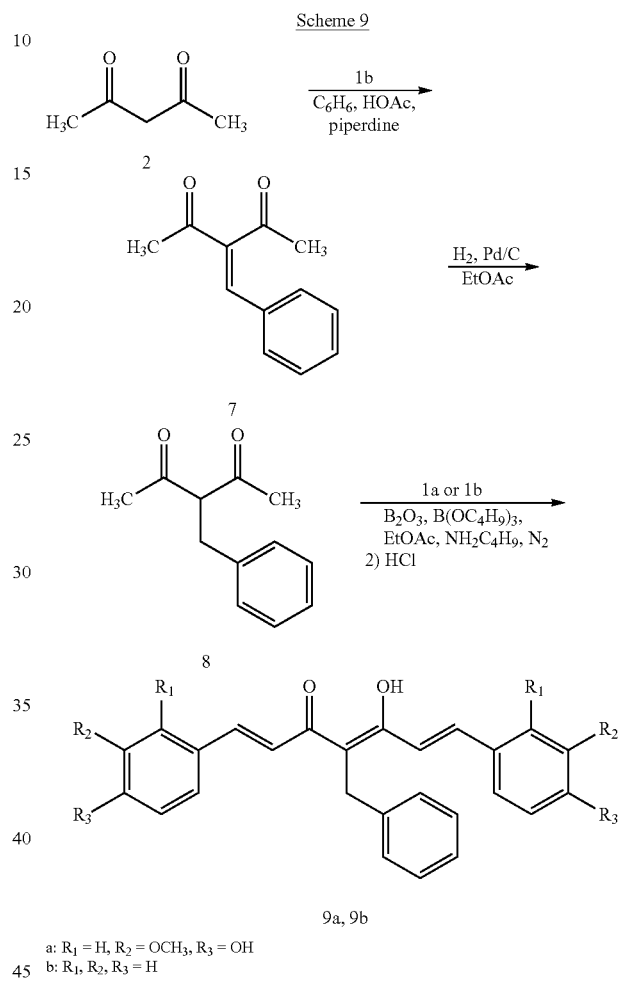

Two additional curcumin analogs, 9a and 9b, were prepared as shown in Scheme 9. Analogs 9a and 9b contain two aryl rings separated by an unsaturated 7-carbon spacer having two carbonyls and a single benzyl substituent attached to the central methylene carbon. These analogs were designed to test the importance of a benzyl substituent on the central methylene carbon. The starting material 3-benzylidene-2,4-pentanedione (7), was prepared by a Knoevenagel condensation reaction of 2,4-pentanedione (2) with benzaldehyde (1b), glacial acetic acid and piperdine in benzene at 65° C. following the procedure described by Antonioletti (Antonioletti et al., Tetrahedron 58(3), 589-596 (2002)). The formation of the product was verified by proton NMR by the appearance of a signal at 7.45 ppm for the alkene proton and the loss of a signal at 5.37 ppm for the central methylene proton on compound 2. 3-Benzyl-2,4-pentanedione (8) was prepared by reaction of compound 7 with palladium on activated carbon under a hydrogen atmosphere on a Parr apparatus in a reduction reaction following the procedure described by Venkateswarlu (Venkateswarlu et al., Asian J. Chem. 12(1), 141-144 (2000)). The formation of the product was verified by proton NMR by the appearance of triplet at 4.01 ppm for the central methylene proton and a doublet at 3.11 ppm for the benzylic protons of the diketo form of compound 8. Also observed in the proton NMR is a singlet at 3.62 ppm for the benzylic protons of the keto-enol form of compound 8. The proton NMR also shows the loss of a signal at 7.45 ppm for the alkene proton in compound 7. Analogs 9a and 9b were then prepared from compound 8, following the procedure described by Pabon (Pabon, Recueil, 83, 379-386 (1964)), by reaction with boric anhydride under a nitrogen atmosphere to give the boron/pentanedione complex. The complex was then reacted with 4-hydroxy-3-methoxybenzaldehyde (1a) or benzaldehyde (1b), tributyl borate, and butylamine in an aldol type reaction followed by hydrolysis with warm dilute hydrochloric acid to give 9a and 9b respectively. The formation of the products was verified by proton NMR by the appearance of a pair of doublets in the aromatic region with J values of 15.1-15.6 Hz for the alkene protons in the spacer and the loss of signals at ~2.05 ppm for the methyl protons of 3-benzyl-2,4-pentanedione (8). The structures were also verified by carbon NMR by the appearance of a signal at 183.3 ppm for the keto-enol carbonyl carbon. Also observed in the carbon NMR was the loss of signals at 22.9 ppm and 29.4 ppm for the methyl carbons of 3-benzyl-2,4-pentanedione (8). The carbon NMR of analog 9b also showed the loss of a signal at 192.1 ppm for the aldehyde carbon in the starting benzaldehyde (1b); whereas in analog 9a, a signal was present at 194.0 ppm for the carbonyl carbon of the diketo form of the analog. Analog 9a, which is not in the literature, was verified by elemental analysis.

Two additional curcumin analogs, 11b and 12b, were prepared as shown in Scheme 10. Analogs 11b and 12b contain two aryl rings separated by an unsaturated 7-carbon spacer having two carbonyls. Analog 11b contains two methyl substituents attached to the central methylene carbon, whereas analog 12b contains two benzyl substituents attached to the central methylene carbon. These analogs were designed to test the importance of two substituents on the central methylene carbon. Analogs 11b and 12b were prepared by reaction of analog 3b with sodium hydroxide, tetrabutylammonium chloride and either methyl iodide (4) or benzyl bromide (10) in dichloromethane at 40° C. in a substitution reaction following the procedure described by Pedersen (Pedersen et al., Liebigs Ann. Chem. 8, 1557-1569 (1985)). The formation of the products was verified by proton NMR by the appearance of a signal at 1.48 ppm for the methyl protons in analog 11b and a signal at 3.39 ppm for the benzylic protons in analog 12b. Also observed in the proton NMR was the loss of a signal at 5.84 ppm for the central methylene proton in analog 3b. Pedersen (Pedersen et al., Liebigs Ann. Chem. 8, 1557-1569 (1985)) observed the monosubstituted product, analog 9b. However, we observed only the disubstituted product, analog 12b. To verify the formation of analogs 11b and 12b, integration of the proton NMR was examined. The signal for the benzylic protons at 3.39 ppm was integrated and compared to each of the alkene signals in the aromatic region. The benzylic singlet at 3.39 ppm in analog 12b integrates for four protons and the two alkene signals in the aromatic region integrate for four protons which is to be expected if the product is disubstituted. The same observation was made in analog 11b. The methyl singlet at 1.48 ppm integrates for six protons compared to four protons for the alkene signals indicating the presence of the disubstituted product. The structures were also verified by carbon NMR by the shift of the methylene signal from ~101.6 ppm to ~66 ppm and the appearance of signals at 21.1 ppm (11b) for the methyl carbons and 37.0 ppm (12b) for the benzylic carbons. Analog 11b, which is not in the literature, was verified by elemental analysis.

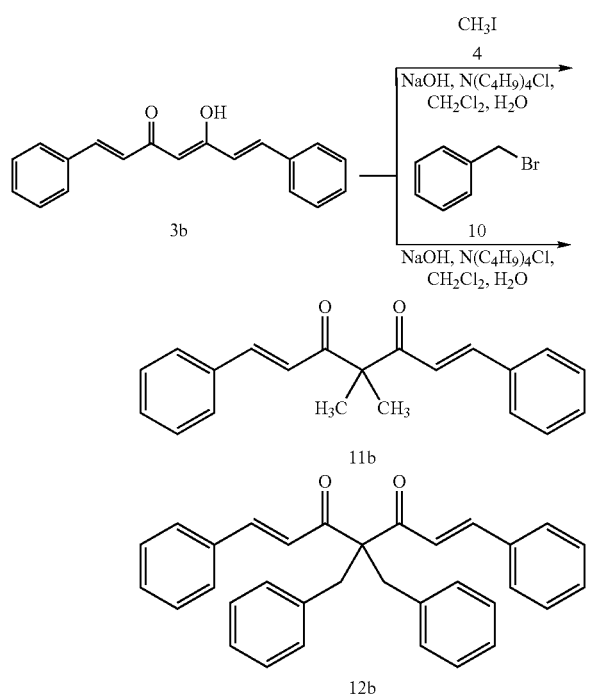

Eight additional curcumin analogs, 13a, 13b, 14a, 14b, 15a, 15b, 16b, and 17b, were prepared as shown in Scheme 11. These analogs contain two identical aryl rings separated by a saturated 7-carbon spacer containing two carbonyls. The analogs were designed to test the importance of saturation in the spacer. Analogs 13a, 13b, 14a, 14b, 15a, 15b, 16b, and 17b were prepared from analogs 3a, 3b, 6a, 6b, 9a, 9b, 11b, and 12b respectively by reduction with palladium on activated carbon under a hydrogen atmosphere on a Parr apparatus following the procedure described by Venkateswarlu (Venkateswarlu et al., Asian J. Chem. 12(1), 141-144 (2000)). The formation of the products was verified by proton NMR by the appearance of two multiplets at ~2.75 ppm for the alkane protons in the spacer. Also observed in the proton NMR was the loss of two doublets in the aromatic region for the alkene protons. The structures were also verified by carbon NMR by the appearance of signals at ~30.5 ppm and ~42.5 ppm for the alkane carbons. The carbon NMR also showed the loss of two signals in the aromatic region for the alkene carbons. Analogs 14a, 14b, 15a, 15b, and 17b, which are not in the literature, were verified by high resolution mass spectroscopy. Analog 16b, which is not in the literature, was verified by elemental analysis.

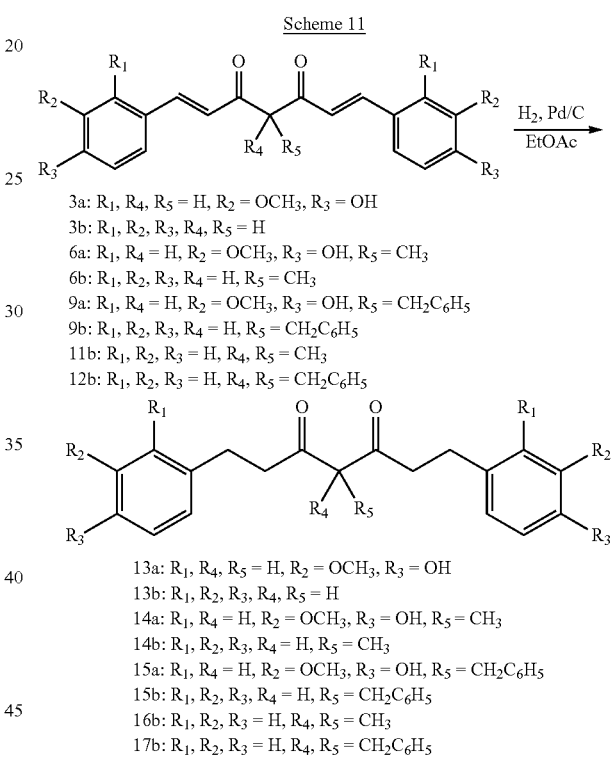

Synthesis of 5-Carbon Spacer Analogs

Analogs in series 2, which contain a shorter 5-carbon spacer than in curcumin, were prepared as shown in Schemes 12-27. Analogs 20a-20g, 20i, 20k-20ac and 20ae-20ah, as shown in Schemes 12-16, all contain two identical aryl rings separated by an unsaturated 5-carbon spacer having a single carbonyl. These analogs were designed to test the importance of the length of the spacer and the type of functional group and location of the substituent on the aryl ring. Analog 20a, which contains the same aryl substituents as curcumin was prepared as shown in Scheme 12 following the procedure as described by Masuda (Masuda et al., Phytochemistry 32(6), 1557-1560 (1993)). 4-Methoxymethyloxy-3-methoxybenzaldehyde (1j) was prepared by reaction of 4-hydroxy-3-methoxybenzaldehyde (1a) with potassium carbonate and chloromethyl methyl ether (18) in a substitution reaction to protect the phenol. Protection was necessary because the aldol reaction on the phenol did not proceed, even upon heating to reflux. The formation of compound 1j was verified by proton NMR by the appearance of signals at 5.21 ppm for the methylene protons and 3.40 ppm for the methyl protons of the protecting group. 1,5-Bis(4-methoxymethyloxy-3-methoxyphenyl)-1,4-pentadien-3-one (20j) was prepared by reaction of compound 1j with acetone (19) and sodium hydroxide in an aldol reaction. The formation of the product was verified by proton NMR by the appearance of a pair of doublets at 7.69 ppm and 6.97 ppm with J values of 15.9 Hz for the alkene protons in the spacer. The final step in the preparation of analog 20a was the removal of the groups protecting the phenols. The removal of the protecting groups was accomplished by reaction of compound 20j with a catalytic amount of concentrated hydrochloric acid in methanol at 65° C. to give the phenol, analog 20a. The formation of 20a was verified by proton NMR by the loss of signals at 3.40 ppm and 5.21 ppm for the protons of the protecting group on compound 20j. The structure was also verified by carbon NMR by the loss of signals at 56.4 ppm and 95.2 ppm for the carbons of the protecting groups on compound 20j.

Scheme 13

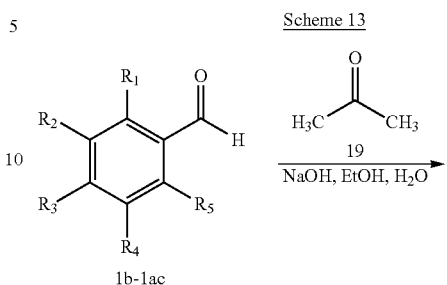

Scheme 12

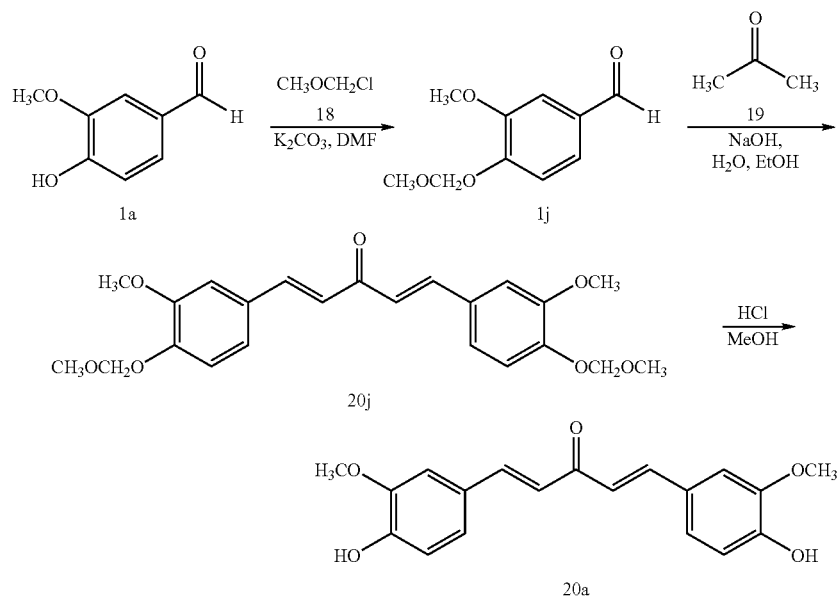

Scheme 13 describes the synthesis of analogs 20b-20g, 20i, and 20k-20ac. Analogs 20b-20g, 20i, and 20k-20ac were prepared following the procedure described by Masuda (Masuda et al., Phytochemistry 32(6), 1557-1560 (1993)). A substituted benzaldehyde (1b-1g, 1i, and 1k-1ac) was reacted with acetone (19) and sodium hydroxide in an aldol reaction to give analogs 20b-20g, 20i, and 20k-20ac. The formation of the products was verified by proton NMR by the appearance of a pair of doublets in the aromatic region with J values between 15.6-16.1 Hz for the alkene protons present in the spacer. Also observed in the proton NMR was the absence of a signal at ~10 ppm for the aldehyde proton of the starting benzaldehyde (1b-1g, 1i, and 1k-1ac) and a signal at 2.04 ppm for the methyl protons of acetone (19). The structures were also verified by carbon NMR by the appearance of two signals in the aromatic region for the alkene carbons in the spacer. Absent from the carbon NMR was a signal at 30.6 ppm for methyl carbons in acetone (19). Analogs 20s and 20v, which are not in the literature, were verified by elemental analysis.

-continued

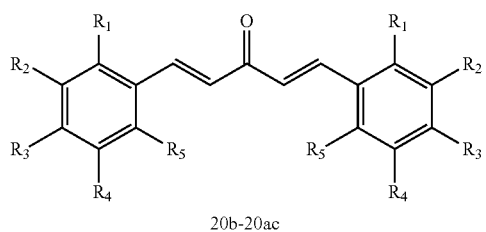

-continued b: R$_1$, R$_2$, R$_3$, R$_4$, R$_5$ = H
c: R$_1$ = OCH$_3$, R$_2$, R$_3$, R$_4$, R$_5$ = H
d: R$_1$, R$_2$ = OCH$_3$, R$_3$, R$_4$, R$_5$ = H
e: R$_1$, R$_2$, R$_4$, R$_5$ = H, R$_3$ = OCH$_3$
f: R$_1$, R$_2$, R$_4$, R$_5$ = H, R$_3$ = OH
g: R$_1$, R$_2$, R$_4$, R$_5$ = H, R$_3$ = N(CH$_3$)$_2$
i: R$_1$, R$_4$, R$_5$ = H, R$_2$, R$_3$ = OCH$_3$
k: R$_1$, R$_3$, R$_4$, R$_5$ = H, R$_2$ = OCH$_3$
l: R$_1$, R$_5$ = OCH$_3$, R$_2$, R$_3$, R$_4$ = H
m: R$_1$, R$_4$ = OCH$_3$, R$_2$, R$_3$, R$_5$ = H
n: R$_1$, R$_3$ = OCH$_3$, R$_2$, R$_4$, R$_5$ = H
o: R$_1$, R$_3$, R$_5$ = H, R$_2$, R$_4$ = OCH$_3$
p: R$_1$, R$_3$, R$_4$, R$_5$ = H, R$_2$ = OH q: R$_1$ = OH, R$_2$, R$_3$, R$_4$, R$_5$ = H
r: R$_1$, R$_2$, R$_4$, R$_5$ = H, R$_3$ = F
s: R$_1$, R$_3$, R$_4$, R$_5$ = H, R$_2$ = F
t: R$_1$ = F, R$_2$, R$_3$, R$_4$, R$_5$ = H
u: R$_1$, R$_2$, R$_4$, R$_5$ = H, R$_3$ = CF$_3$
v: R$_1$, R$_3$, R$_4$, R$_5$ = H, R$_2$ = CF$_3$
w: R$_1$ = CF$_3$, R$_2$, R$_3$, R$_4$, R$_5$ = H
x: R$_1$, R$_2$, R$_4$, R$_5$ = H, R$_3$ = Cl
y: R$_1$, R$_3$, R$_4$, R$_5$ = H, R$_2$ = Cl
z: R$_1$ = Cl, R$_2$, R$_3$, R$_4$, R$_5$ = H
aa: R$_1$, R$_2$, R$_4$, R$_5$ = H, R$_3$ = CH$_3$
ab: R$_1$, R$_3$, R$_4$, R$_5$ = H, R$_2$ = CH$_3$
ac: R$_1$ = CH$_3$, R$_2$, R$_3$, R$_4$, R$_5$ = H Scheme 14 describes the synthesis of analog 20ae. Analog 20ae was prepared following the procedure described by White and Zoeller (White et al., U.S. Pat. No. 5,395,692 (1995); Chem. Abstr., 123, P84361n (1995)). 4-Formylbenzoic acid (1ad) was reacted with methanol and thionyl chloride in an esterification reaction to give compound 1ae. The formation of the product was verified by proton NMR by the appearance of a signal at 3.87 ppm for the methyl ester protons. Compound 1ae was then reacted with acetone (19) and sodium hydroxide in an aldol reaction to give analog 20ae. The formation of the product was verified by proton NMR by the appearance of a pair of doublets in the aromatic region with J values of 15.9 Hz and 16.1 Hz for the alkene protons present in the spacer. Also observed in the proton NMR was the loss of a signal at 10.12 ppm for the aldehyde proton of the starting benzaldehyde (1ae) and a signal at 2.04 ppm for the methyl protons of acetone (19). The structure was also verified by carbon NMR by the appearance of two signals in the aromatic region for the alkene carbons. The carbon NMR also showed the loss of a signal at 30.6 ppm for the loss of the methyl carbons of acetone (19).

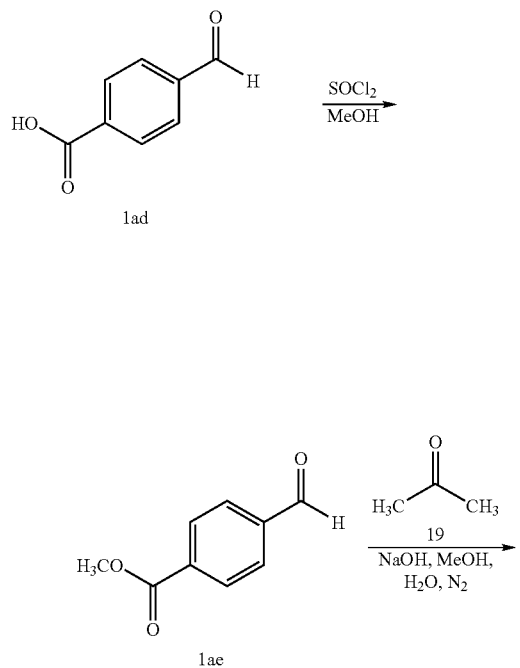

Scheme 14

1ad

1ae

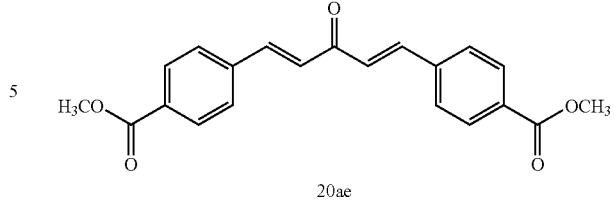

20ae

Scheme 15 describes the synthesis of analog 20af. Analog 20af was prepared following the procedure described by Royer (Royer et al., J. Med. Chem. 38(13), 2427-2432 (1995)). Analog 20i was demethylated with boron tribromide to give analog 20af. The same reaction was also attempted on analogs 20d and 20l-20o with the anticipation of forming the corresponding tetrahydroxy analogs, however pure stable products could not be obtained. Immediately following chromatography there was a single spot on tlc, indicating pure product, however after approximately 24 hours, tlc showed a large spot at the origin. In order to verify these results, the tetramethoxymethyl ether analogs of 20d and 20l were deprotected using methods described in Scheme 12 (Masuda et al., Phytochemistry 32(6), 1557-1560 (1993)) to give the corresponding tetrahydroxy analogs. The same results were obtained, thus confirming the analogs were decomposing. Analog 20af appeared to be stable and was tested immediately. The formation of analog 20af was verified by proton NMR by the appearance of signals at 9.63 ppm and 9.15 ppm for the phenolic protons. Also observed in the proton NMR was the loss of signals at 3.94 ppm and 3.92 ppm for the methyl protons on analog 20i. The structure was also verified by carbon NMR by the loss of a signal at 55.9 ppm for the methyl carbons on analog 20i.

Scheme 15

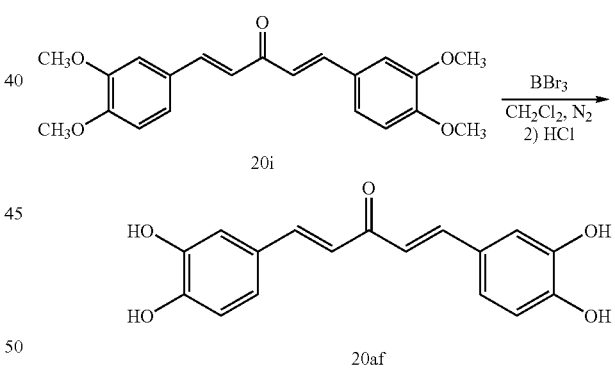

20i

20af

Scheme 16 describes the synthesis of analogs 20ag and 20ah. Analogs 20ag and 20ah were prepared following the procedure described by Suarez (Suarez et al., World Patent 2004,047,716 (2004); Chem. Abstr., 141, 38433 (2004)). Analog 20a or 20f was reacted with acetic anhydride in the presence of pyridine in an esterification reaction to give analogs 20ag and 20ah respectively. The formation of the products was verified by proton NMR by the appeerence of a signal at 2.31 ppm for the methyl protons of the acetyl groups. The structures were also verified by carbon NMR by the appearance of a signal at ~20.9 ppm for the methyl carbons of the acetyl groups and a signal at ~168.7 ppm for the carbonyls of the acetyl groups. Analog 20ag and 20ah, which are not in the literature, were verified by high resolution mass spectroscopy.

Scheme 16

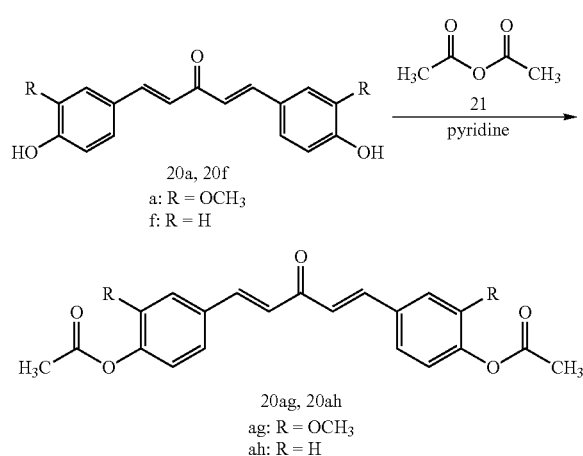

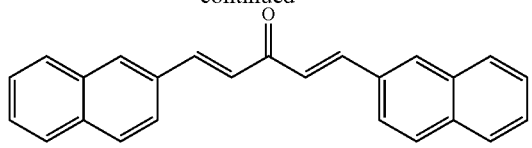

Two additional 5-carbon spacer analogs, 23 and 25, were prepared as shown in Scheme 17. Analogs 23 and 25 contain two naphthalene rings separated by an unsaturated 5-carbon spacer having a single carbonyl. These analogs were designed to test the importance of naphthalene rings. Compound 22 or 24 was reacted with acetone (19) and sodium hydroxide in an aldol reaction following the procedure described by Masuda (Masuda et al., Phytochemistry 32(6), 1557-1560 (1993)) to give analogs 23 and 25. The formation of the products was verified by proton NMR by the appearance of a pair of doublets in the aromatic region with J values between 15.7-15.9 Hz for the alkene protons present in the spacer. Also observed in the proton NMR was the loss of a signal at ~10.25 ppm for the aldehyde proton of the starting naphthaldehydes (22 and 24) and a signal at 2.04 ppm for the methyl protons of acetone (19). The structures were also verified by carbon NMR by the appearance of two signals in the aromatic region for the alkene carbons on the spacer. The carbon NMR also showed the loss of a signal at 30.6 ppm for the methyl carbons in acetone (19).

Four additional 5-carbon spacer analogs, 28, 29, 31 and 32, were prepared as shown in Scheme 18. Analogs 28, 29, 31 and 32 contain two nitrogen containing aryl rings separated by an unsaturated 5-carbon spacer having a single carbonyl. These analogs were designed to test the importance of nitrogen containing aryl rings. Analogs 28 and 31 were prepared following the procedure described by Zelle and Su (Zelle et al., World Patent 9,820,891 (1998); Chem. Abstr., 129, P23452v (1998)). 4-Pyridinecarboxaldehyde (26) or 3-pyridinecarboxaldehyde (30) was reacted with 1,3-acetonedicarboxylic acid (27) in an aldol type reaction followed by addition of concentrated hydrochloric acid to give analogs 28 and 31 as hydrochloride salts. Analogs 29 and 32, the free bases, were then prepared by shaking analogs 28 and 31 respectively in sodium hydroxide. The formation of analogs 28, 29, 31 and 32 were verified by proton NMR by the appearance of a pair of doublets in the aromatic region with J values between 15.9-16.3 Hz for the alkene protons present in the spacer. Also observed in the proton NMR was the loss of a signal at ~10.11 ppm for the aldehyde proton in the starting pyridinecarboxaldehydes (26 and 30) and a signal at 3.55 ppm for the methylene protons of 1,3-acetonedicarboxylic acid (27). The structures were also verified by carbon NMR by the appearance of two signals in the aromatic region for the alkene carbons and the loss of a signal at ~191.3 ppm for the aldehyde carbon of the starting pyridinecarboxaldehyde (26 and 30). Also observed in the carbon NMR was the loss of a signal at 170.3 ppm for the two carboxylic acid carbons and a signal at 50.1 ppm for the methylene carbons in 1,3-acetonedicarboxylic acid (27). The NMR spectra for the uncharged analogs, 29 and 32 were taken in $CDCl_3$, whereas the charged analogs 28 and 31 were taken in $D_2O$.

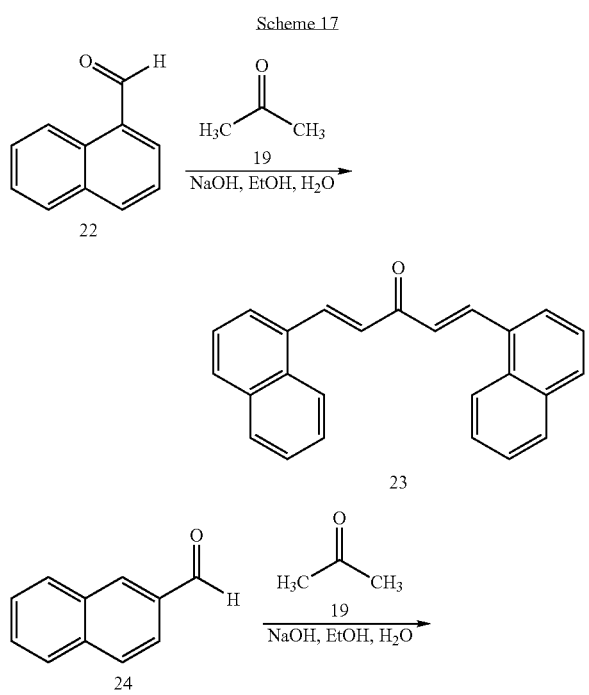

Scheme 18

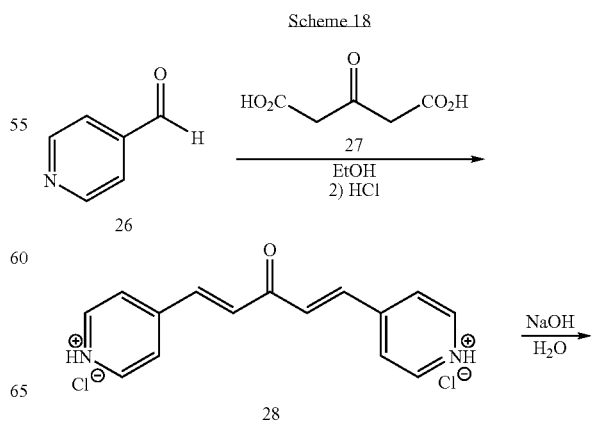

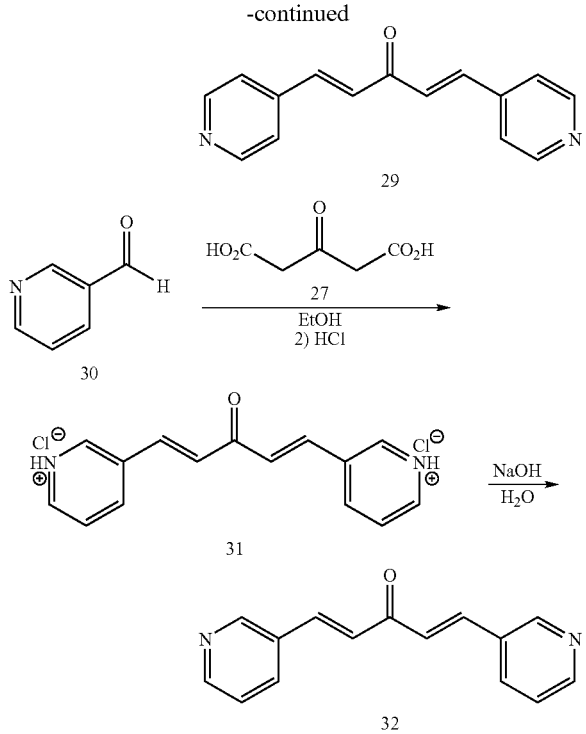

An additional 5-carbon spacer analog, 34, was prepared as shown in Scheme 19. Analog 34 contains two sulfur containing aryl rings separated by an unsaturated 5-carbon spacer having a single carbonyl. This analog was designed to test the importance of thiophene rings. 2-Thiophenecarboxaldehyde (33) was reacted with acetone (19) and sodium hydroxide in an aldol reaction to give analog 34 following the procedure described by Masuda (Masuda et al., Phytochemistry 32(6), 1557-1560 (1993)). The formation of analog 34 was verified by proton NMR by the appearance of a pair of doublets in the aromatic region with J values of 15.5 Hz for the alkene protons present in the spacer. Also observed in the proton NMR was the loss of a signal at 9.79 ppm for the aldehyde proton in the starting 2-thiophenecarboxaldehyde (33) and a signal at 2.04 ppm for the methyl protons in acetone (19). The structure was also verified by carbon NMR by the appearance of two signals in the aromatic region for the alkene carbons in the spacer. The carbon NMR also showed

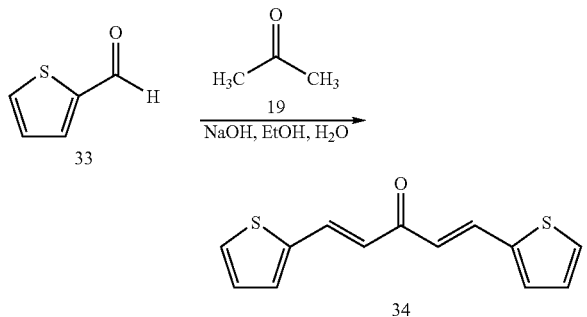

the loss of a signal at 30.6 ppm for the loss of the methyl carbons in acetone (19).

Three additional analogs, 35a, 35e and 35q, were prepared as shown in Schemes 20 and 21. These analogs contain a single aryl ring with an unsaturated 4-carbon tether and a single carbonyl and were designed to test the necessity of two aryl rings. Analog 35a was prepared as shown in Scheme 20 following the procedure described by Masuda (Masuda et al., Phytochemistry 32(6), 1557-1560 (1993)). Compound 1j, prepared as previously reported in Scheme 12, was reacted with excess acetone (19) and sodium hydroxide in an aldol reaction to give compound 35j. Protection was necessary because the aldol reaction on the phenol did not proceed, even upon heating to reflux. The formation of compound 35j was verified by proton NMR by the appearance of a pair of doublets in the aromatic region with J values of 16.1 Hz for the alkene protons present on the tether and a signal at 2.34 ppm for the methyl protons present on the tether. Also observed in the proton NMR was the loss of a signal at 9.75 ppm for the aldehyde proton in the starting benzaldehyde (1j). Compound 35j was then reacted with a catalytic amount of concentrated hydrochloric acid to give the phenol, analog 35a. The formation of analog 35a was verified by proton NMR by the loss of signals at 3.48 ppm and 5.24 ppm for the protons of the protecting group in compound 35j. The structure was also verified by carbon NMR by the loss of signals at

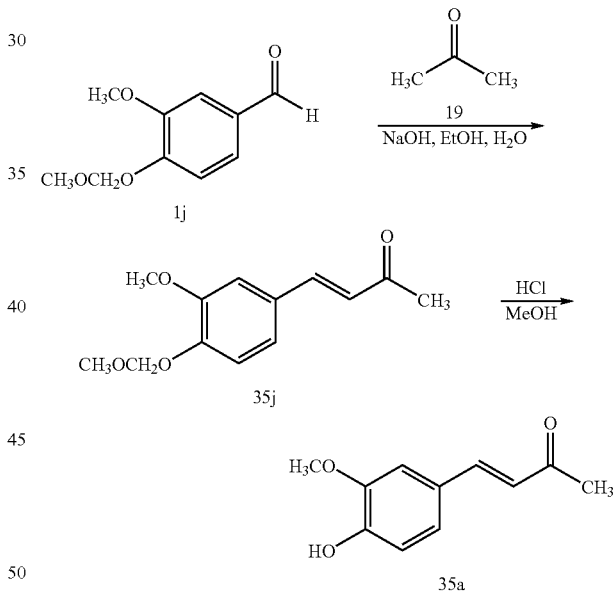

56.2 ppm and 94.8 ppm for the carbons of the protecting group in compound 35j.

Scheme 21 describes the synthesis of analogs 35e and 35q following the procedure described by Masuda (Masuda et al., Phytochemistry 1993, 32(6), 1557-1560). Compound 1e or 1q was reacted with excess acetone (19) and sodium hydroxide in an aldol reaction to give analogs 35e and 35q. The formation of the products was verified by proton NMR by the appearance of a pair of doublets in the aromatic region with J values of 16.3-16.5 Hz for the alkene protons present on the tether and the appearance of a signal at ~2.37 ppm for the methyl protons on the tether. Also observed in the proton NMR was the loss of a signal at ~9.94 ppm for the aldehyde proton in the starting benzaldehyde (1e or 1q) and the loss of a signal at 2.04 ppm for the methyl protons of acetone (19).

The structures were also verified by carbon NMR by the appearance of two signals in the aromatic region for the alkene carbons present on the tether.

Scheme 21

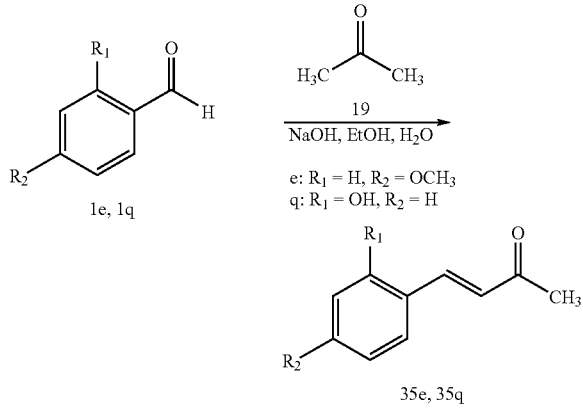

Two additional 5-carbon spacer analogs, 36a and 36e, were prepared as shown in Schemes 22 and 23. These analogs contain two different aryl rings separated by a 5-carbon unsaturated spacer containing a single carbonyl and were designed to test the importance of symmetry in analogs with a 5-carbon spacer. Analog 36a was prepared as shown in Scheme 22 following the procedure described by Masuda (Masuda et al., Phytochemistry 32(6), 1557-1560 (1993)). Compound 35j, prepared as shown in Scheme 21, was reacted with benzaldehyde (1b) in an aldol reaction to give compound 36j. The formation of compound 36j was verified by proton NMR by the appearance of a second pair of doublets in the aromatic region for the new alkene in the spacer and the loss of a signal at 2.34 ppm for the methyl protons on the tether in compound 35j. Compound 36j was then reacted with a catalytic amount of concentrated hydrochloric acid to give the phenol, analog 36a. The formation of analog 36a was verified by proton NMR by the loss of signals at 3.5 ppm and 5.2 ppm for the protons of the protecting group in compound 36j. The structure was also verified by carbon NMR by the loss of signals at 56.2 ppm and 94.8 ppm for the carbons of the protecting group in compound 36j.

Scheme 22

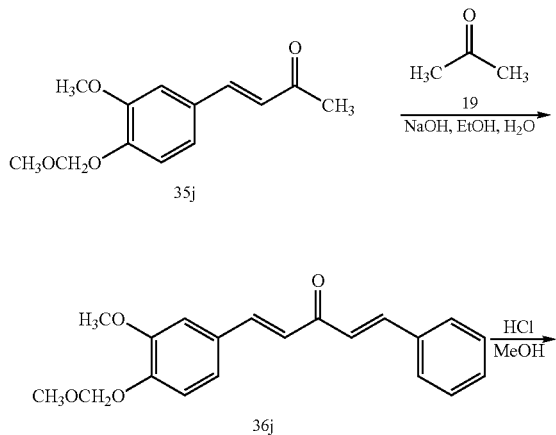

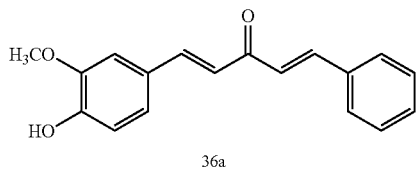

Scheme 23 describes the synthesis of analog 36e. Analog 35e, prepared as shown in Scheme 21, was reacted with benzaldehyde (1b) and sodium hydroxide in an aldol reaction following the procedure described by Masuda (Masuda et al., Phytochemistry 32(6), 1557-1560 (1993)) to give analog 36e. The formation of the product was verified by proton NMR by the appearance of a second pair of doublets in the aromatic region with J values of 15.9-16.1 Hz for the new alkene protons present in the spacer and the loss of a signal at 2.34 ppm for the methyl protons on the tether in analog 35e. The structure was also verified by carbon NMR by the appearance of two signals in the aromatic region for the new alkene carbons and the loss of a signal at 27.5 ppm for the methyl carbon on the tether in analog 35e.

Scheme 23

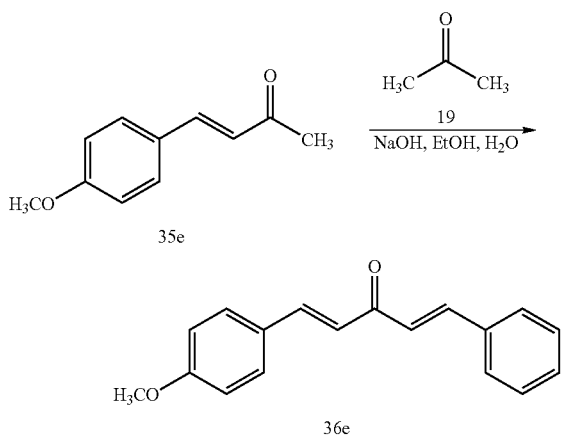

Two additional 5-carbon spacer analogs, 38a and 38b, were prepared as shown in Schemes 24 and 25. These analogs contain two identical aryl rings separated by an unsaturated 5-carbon spacer having a single carbonyl and a saturated ring. Analogs 38a and 38b were designed to test the importance of a ring in the spacer. Analog 38a was prepared as shown in Scheme 24 following the procedure described by Masuda (Masuda et al., Phytochemistry 32(6), 1557-1560 (1993)). Compound 1j, prepared as shown in Scheme 12, was reacted with cyclohexanone (37) and sodium hydroxide in an aldol reaction to give compound 38j. The formation of compound 38j was verified by proton NMR by the appearance of a signal at 7.74 ppm for the alkene protons on the spacer and the loss of a signal at 9.75 ppm for the aldehyde proton in the starting benzaldehyde (1j). Compound 38j was then reacted with a catalytic amount of concentrated hydrochloric acid to give the phenol, analog 38a. The formation of the product was verified by proton NMR by appearance of a signal at 5.88 ppm for the phenolic protons and the loss of signals at 3.52 ppm and 5.26 ppm for the

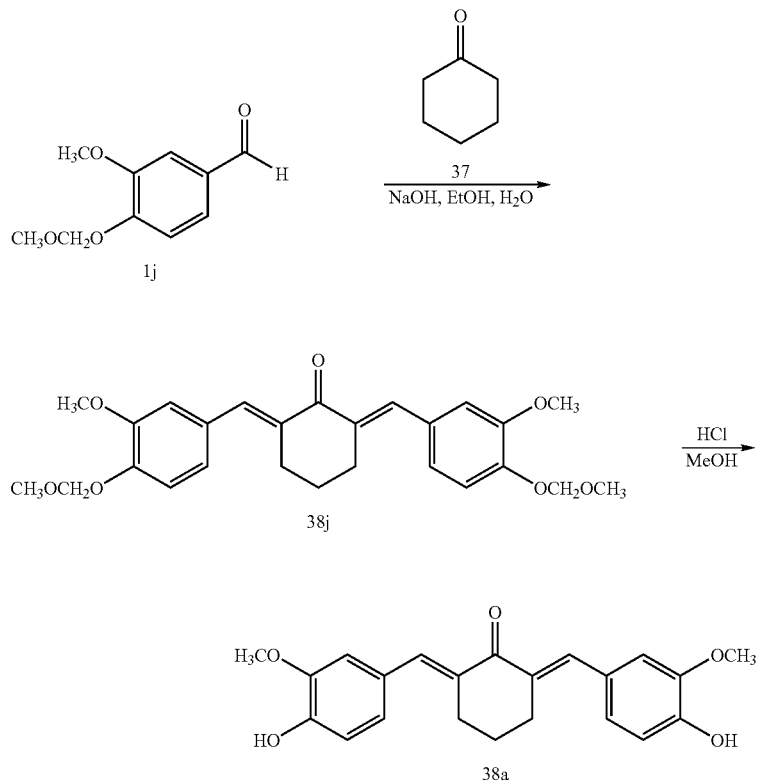

protons of the protecting group in compound 38j. The structure was also verified by carbon NMR by the loss of signals at 55.8 ppm and 95.1 ppm for the carbons of the protecting group in compound 38j.

Scheme 25 describes the synthesis of analog 38b following the procedure described by Masuda (Masuda et al., Phytochemistry 32(6), 1557-1560 (1993)). Benzaldehyde (1b) was reacted with cyclohexanone (37) and sodium hydroxide in an aldol reaction to give analog 38b. The formation of the product was verified by proton NMR by the appearance of a signal at 7.80 ppm for the alkene protons on the spacer and the loss of a signal at 9.94 ppm for the aldehyde proton on the starting benzaldehyde (1b). The structure of the product was also verified by carbon NMR by the appearance of two signals in the aromatic region for the alkene carbons on the spacer.

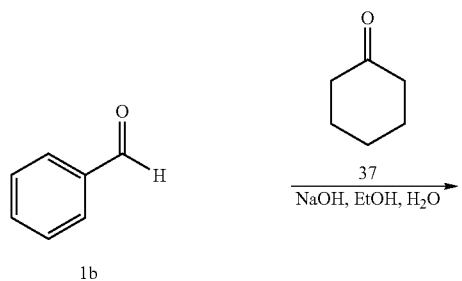

-continued

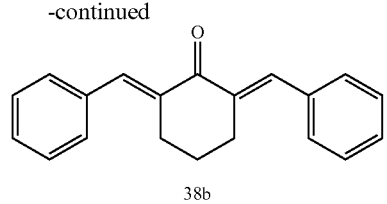

Two additional 5-carbon spacer analogs, 39b and 40b, were prepared as shown in Scheme 26 following the procedure described by Venkateswarlu (Venkateswarlu et al., Asian J. Chem. 12(1), 141-144 (2000)). Analog 39b contains two identical aryl rings separated by a saturated 5-carbon spacer and was designed to test the importance of unsaturation in the spacer of series 2 analogs. Analog 40b was designed to test the importance of a carbonyl in the spacer. Analogs 39b and 40b were prepared by reduction of analog 20b with palladium on activated carbon under a hydrogen atmosphere on a Parr apparatus. A mixture containing analogs 39b and 40b was obtained and separated by chromatography. The formation of analog 39b was verified by proton NMR by the appearance of triplets at 2.76 ppm and 2.97 ppm for the methylene protons on the spacer. The proton NMR also showed the loss of a pair of doublets in the aromatic region for the alkene protons. The structure was also verified by carbon NMR by the appearance of signals at 29.6 ppm and 44.2 ppm for the methylene carbons on the spacer and the loss of two signals in the aromatic region for the alkene carbons on the spacer in analog 20b. The formation of analog 40b was verified by proton NMR by the appearance of a pentet for the proton on the carbon bearing the hydroxyl group and multiplets at 1.85 ppm and 2.77 ppm for the methylene protons on the spacer. The structure was also verified by carbon NMR by the appearance of signals at 32.1 ppm, 39.2 ppm and 70.8 ppm for the carbon bearing the hydroxyl group and for the methylene carbons on the spacer. The carbon NMR also shows the loss of two signals in the aromatic region for the alkene carbons on the spacer and the loss of a signal at 188.7 ppm for the carbonyl carbon in analog 20b.

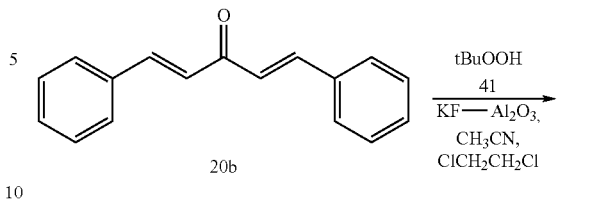

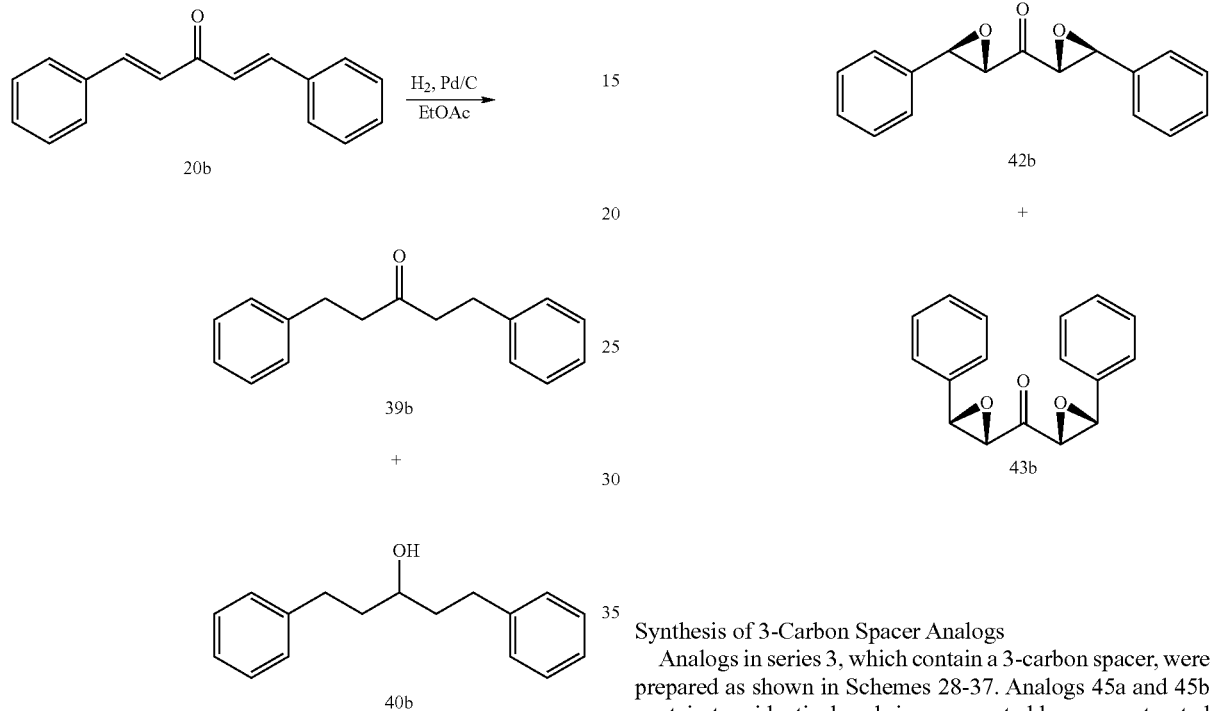

Two additional 5-carbon spacer analogs, 42b and 43b, were prepared as shown in Scheme 27 following the procedure described by Yadav and Kapoor (Yadav et al., Tetrahedron 52(10), 3659-3668 (1996)). These analogs contain two identical aryl rings separated by a saturated 5-carbon spacer containing both a carbonyl and two epoxide rings. These analogs were designed to test the importance of epoxide rings on the spacer. Analogs 42b and 43b were prepared by reaction of analog 20b with t-butyl hydroperoxide and aluminum oxide-potassium fluoride in an epoxidation reaction. A mixture containing analog 42b and analog 43b was formed and the trans/trans isomer, analog 42b, was separated from the cis/cis isomer, analog 43b, through recrystallization from ethanol as described by Yadav and Kapoor (Yadav et al., Tetrahedron 52(10), 3659-3668 (1996)). The formation of the products was verified by proton NMR by the appearance of a pair of doublets at 3.30 ppm and 4.09 ppm for the alkane protons on the spacer in analog 42b. Analog 43b has a pair of doublets at 3.72 ppm and 4.18 ppm for the alkane protons on the spacer. Also observed in the proton NMR was the loss of two signals in the aromatic region for the alkene protons on the spacer in analog 20b. The structures were also verified by carbon NMR by the appearance of a two signals at ~59.9 ppm for the alkane carbons on the spacer. The carbon NMR also showed the loss of two signals in the aromatic region for the alkene carbons on the spacer in analog 20b.

Synthesis of 3-Carbon Spacer Analogs

Analogs in series 3, which contain a 3-carbon spacer, were prepared as shown in Schemes 28-37. Analogs 45a and 45b contain two identical aryl rings separated by an unsaturated 3-carbon spacer having a single carbonyl and were designed to test the importance of the length of the spacer. Analog 45a was prepared as shown in Scheme 28 following the procedures described by Masuda (Masuda et al., Phytochemistry 32(6), 1557-1560 (1993)) and by Kohler and Chadwell (Kohler et al., Org. Synth., Coll. Vol. 178-80 (1932)). 4-Hydroxy-3-methoxyacetophenone (44a) was reacted with potassium carbonate and chloromethyl methyl ether (18) in a substitution reaction to give compound 44j. The formation of the product was verified by proton NMR by the appearance of signals at 3.33 ppm and 5.12 ppm for the protons of the protecting group. Compound 1j, prepared as shown in Scheme 12, was reacted with compound 44j and barium hydroxide in an aldol reaction to give compound 45j. The formation of the product was verified by proton NMR by the appearance of a pair of doublets in the aromatic region with J values of 15.5 Hz for the alkene protons on the spacer. Also observed in the proton NMR was the loss of a signal at 2.38 ppm for the methyl protons of the starting acetophenone (44j) and the loss of a signal at 9.75 ppm for the aldehyde proton of the starting benzaldehyde (1j). Compound 45j was then reacted with a catalytic amount of concentrated hydrochloric acid to give the phenol, analog 45a. The formation of the product was verified by proton NMR by the appearance of signals at 6.00 ppm and 6.19 ppm for the phenolic protons. Also observed in the proton NMR was the loss of signals at 3.50 ppm, 5.25 ppm

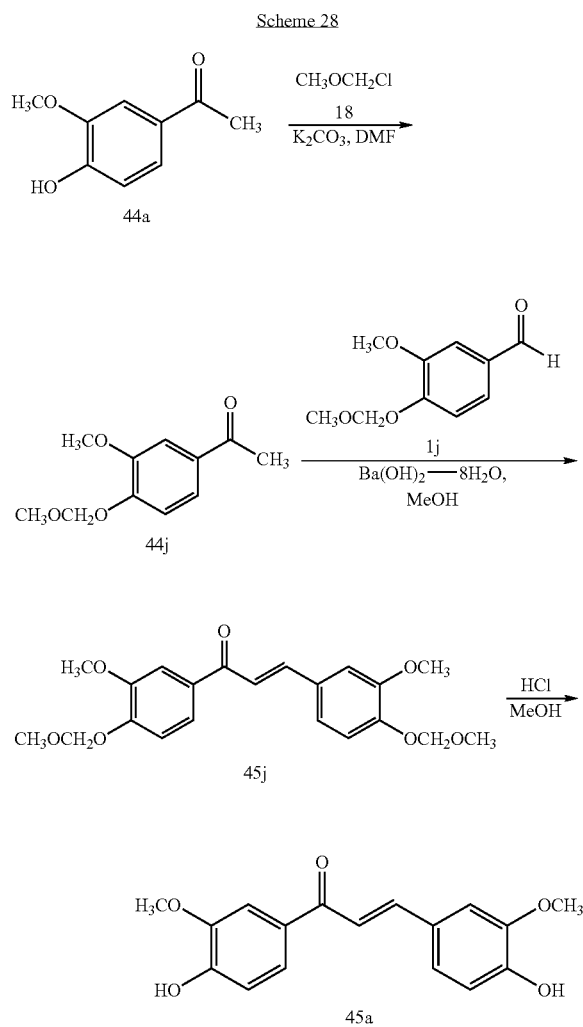

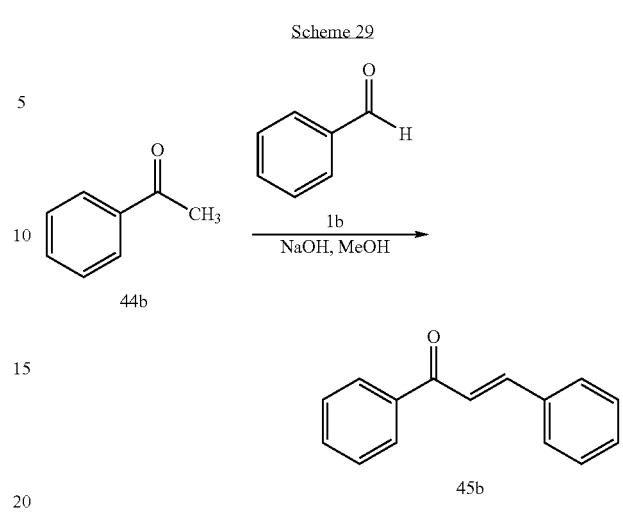

and 5.30 ppm for the protons in the protecting groups in compound 45j. The structure was also verified by carbon NMR by the loss of signals at ~57 ppm and ~95 ppm for the carbons of the protecting groups in compound 45j.

Scheme 29 describes the synthesis of analog 45b following the procedure described by Kohler and Chadwell (Kohler et al., Org. Synth., Coll. Vol. 178-80 (1932)). Acetophenone (44b) was reacted with benzaldehyde (1b) and sodium hydroxide in an aldol reaction to give analog 45b. The formation of the product was verified by proton NMR by the appearance of a pair of doublets in the aromatic region with J values of 15.7 Hz for the alkene protons on the spacer. Also observed in the proton NMR was the loss of a signal at 9.74 ppm for the aldehyde proton on the starting benzaldehyde (1b) and a signal at 2.51 ppm for the methyl protons in the starting acetophenone (44b). The structure was also verified by carbon NMR by the appearance of two signals in the aromatic region for the alkene carbons on the spacer and the loss of a signal at 26.0 ppm for the methyl carbon on the starting acetophenone (44b).

Six additional 3-carbon spacer analogs, 46a, 46ak-46am, 48a and 48ad, were prepared as shown in Schemes 30-34. Analogs 46a, 46ak-46am, 48a and 48ad contain two different aryl rings separated by an unsaturated 3-carbon spacer having a single carbonyl. These analogs were designed to test the importance of the length of the spacer and the importance of ring symmetry in series 3 analogs. Analog 46a was prepared as shown in Scheme 30 following the procedures described by Masuda (Masuda et al., Phytochemistry 32(6), 1557-1560 (1993)) and by Kohler and Chadwell (Kohler et al., Org. Synth., Coll. Vol. 178-80 (1932)). Compound 44j, prepared as shown in Scheme 28, was reacted with benzaldehyde (1b) and barium hydroxide in an aldol reaction to give compound 46j. The formation of the product was verified by proton NMR by the appearance of a pair of doublets in the aromatic region with J values of 15.7 Hz for the alkene protons on the spacer. Also observed in the proton NMR was the loss of a signal at 2.38 ppm for the methyl protons on the starting acetophenone (44j) and a signal at 9.74 ppm for the aldehyde proton in the starting benzaldehyde (1b). Compound 46j was then reacted with a catalytic amount of concentrated hydrochloric acid to give the phenol, analog 46a. The formation of the product was verified by proton NMR by the appearance of a signal at 6.29 ppm for the phenolic proton. Also observed in the proton NMR was the loss of signals at 3.48 ppm and 5.28 ppm for the protons of the protecting group in compound 46j. The structure was also verified by carbon NMR by the loss of signals at ~57 ppm and ~95 ppm for the carbons of the protecting group in compound 46j.

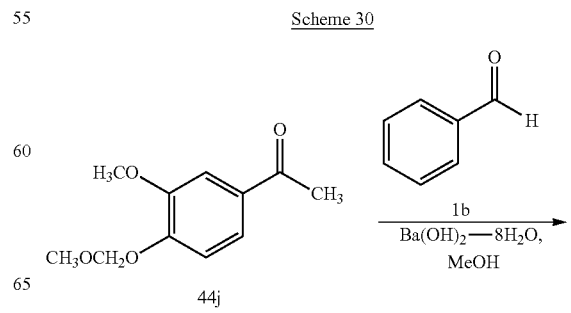

-continued

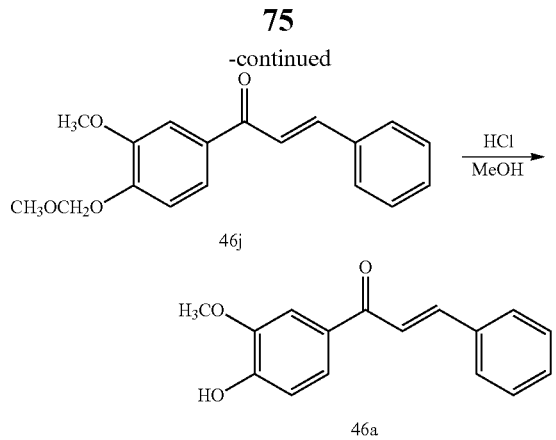

Scheme 31 describes the synthesis of analogs 46ak and 46al following the procedure described by Kohler and Chadwell (Kohler et al., Org. Synth., Coll. Vol. 178-80 (1932)). Acetophenone 44ak or 44al was reacted with benzaldehyde (1b) and barium hydroxide in an aldol reaction to give analogs 46ak or 46al respectively. The formation of the products was verified by proton NMR by the appearance of a pair of doublets in the aromatic region with J values of 15.9-16.1 Hz for the alkene protons on the spacer. Also observed in the proton NMR was the loss of a signal at 9.74 ppm for the aldehyde proton in the starting benzaldehyde (1b) and a signal at ~2.49 ppm for the methyl protons of the starting acetophenones (44ak and 44al). The structure of the product was also verified by carbon NMR by the appearance of two signals in the aromatic region for the alkene carbons on the spacer. Also observed in the carbon NMR was the loss of a signal at 26.7 ppm for the methyl carbon on the starting acetophenones (44ak and 44al).

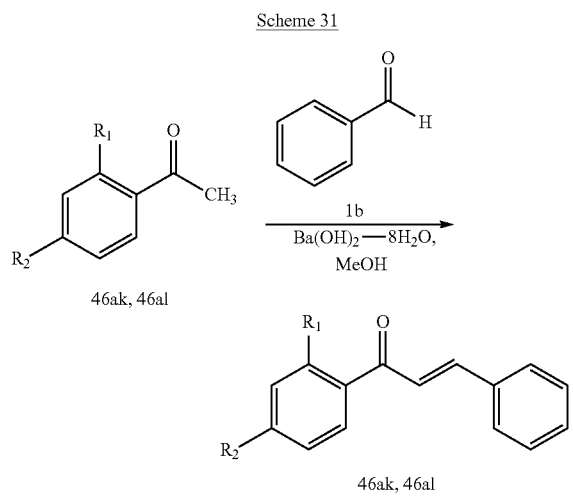

ak: $R_1, R_2 = CH_3$
al: $R_1 = H, R_2 = CN$

Scheme 32 describes the synthesis of analog 46ad following the procedure described by Cleeland (Cleeland et al., U.S. Pat. No. 4,045,487 (1977); Chem. Abstr., 87, P167872u (1977)). Compound 44al was reacted with concentrated sulfuric acid in a hydrolysis reaction to give compound 44ad. The formation of the product was verified by proton NMR by the appearance of a signal at 13.34 ppm for the carboxylic acid proton. Compound 44ad was then reacted with benzaldehyde (1b) and sodium hydroxide in an aldol reaction followed by acidification with dilute hydrochloric acid to give analog 46ad. The formation of the product was verified by proton NMR by the appearance of a pair of doublets in the aromatic region with J values of 15.5-16.1 Hz for the alkene protons on the spacer. Also observed in the proton NMR was the loss of a signal at 2.43 ppm for the methyl protons on the starting acetophenone (44ad) and a signal at 9.74 ppm for the aldehyde proton in the starting benzaldehyde (1b). The structure of the product was also verified by carbon NMR by the appearance of two signals in the aromatic region for the alkene carbons on the spacer. Also seen in the carbon NMR was the loss of a signal at 23.7 ppm for the methyl carbon in the starting acetophenone (44ad).

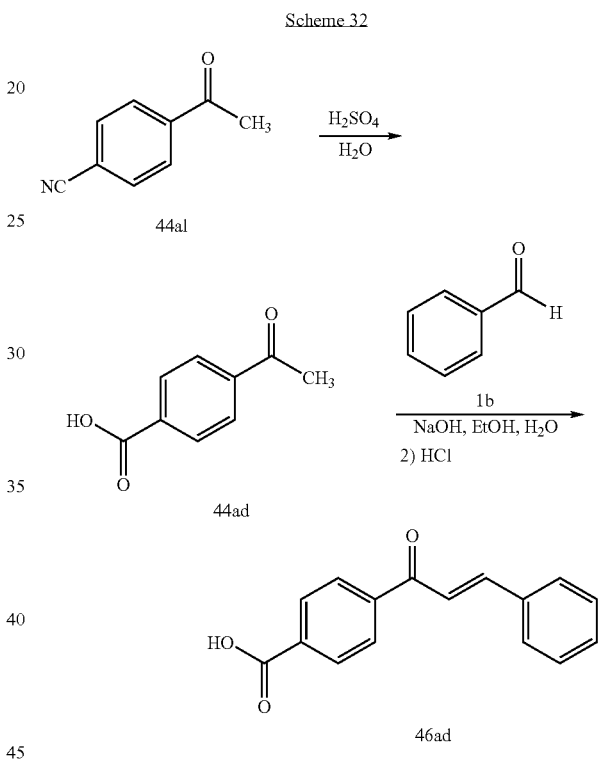

Scheme 33 describes the synthesis of analog 48a following the procedure described by Takagaki (Takagaki et al., European Patent 370,461 (1990); Chem. Abstr., 113, P230963x (1990)). Compound 1a was reacted with 3,4-dihydropyran and pyridiniump-toluenesulfonate in a substitution reaction to give compound 1am. The formation of the product was verified by proton NMR by the appearance of multiplets in the aliphatic region for the protecting group protons. Compound 1am was then reacted with acetophenone (44b) and barium hydroxide in an aldol reaction to give compound 48am. The formation of the product was verified by proton NMR by the appearance of a pair of doublets in the aromatic region with J values of 15.5-15.9 Hz for the alkene protons on the spacer. Also observed in the proton NMR was the loss of a signal at 2.38 ppm for the methyl protons on the starting acetophenone (44b) and a signal at 9.87 ppm for the aldehyde proton in the starting benzaldehyde (1am). Compound 48am was then reacted with p-toluenesulfonic acid to give the phenol, analog 48a. The formation of the product was verified by proton NMR by the appearance of a signal at 5.96 ppm for the phenolic proton. Also observed in the proton NMR was the loss of multiplets in the aliphatic region for the protons of the protecting group in compound 48am. The structure was also verified by carbon NMR by the loss of five signals in the aliphatic region for the carbons of the protecting group in compound 48am.

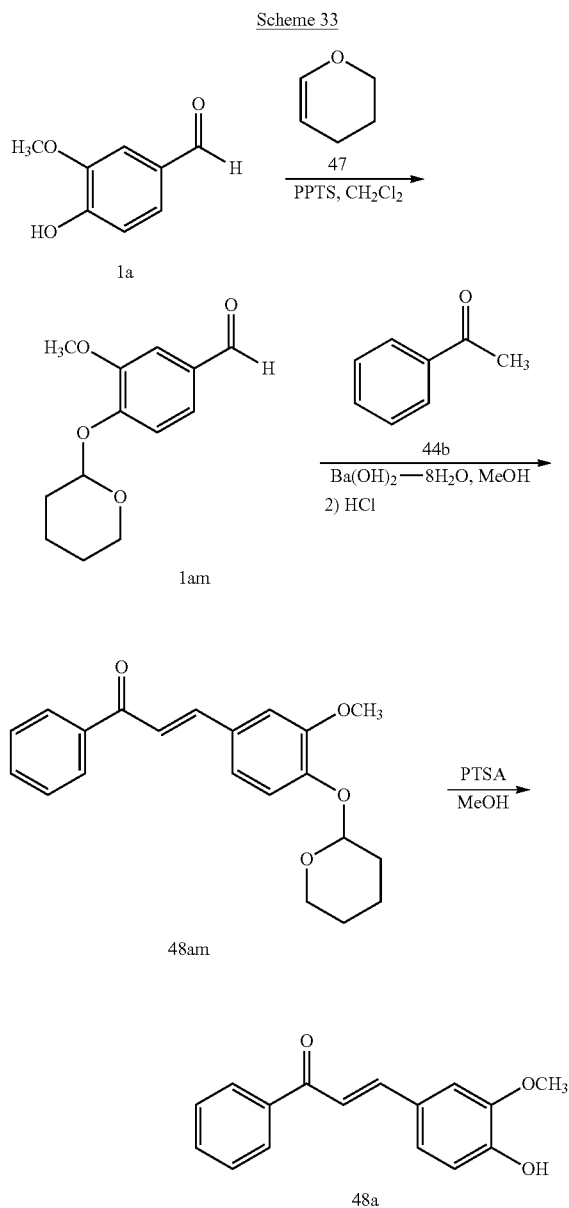

Scheme 34 describes the synthesis of analog 48ad following the procedure described by Cleeland (Cleeland et al., U.S. Pat. No. 4,045,487 (1977); Chem. Abstr., 87, P167872u (1977)). Compound 1ad was reacted with compound 44b and sodium hydroxide in an aldol reaction followed by acidification with dilute hydrochloric acid to give analog 48ad. The formation of the product was verified by proton NMR by the appearance of a pair of doublets in the aromatic region for the alkene protons on the spacer. Also observed in the proton NMR was the loss of a signal at 2.38 ppm for the methyl protons on the starting acetophenone (44b) and a signal at 10.12 ppm for the

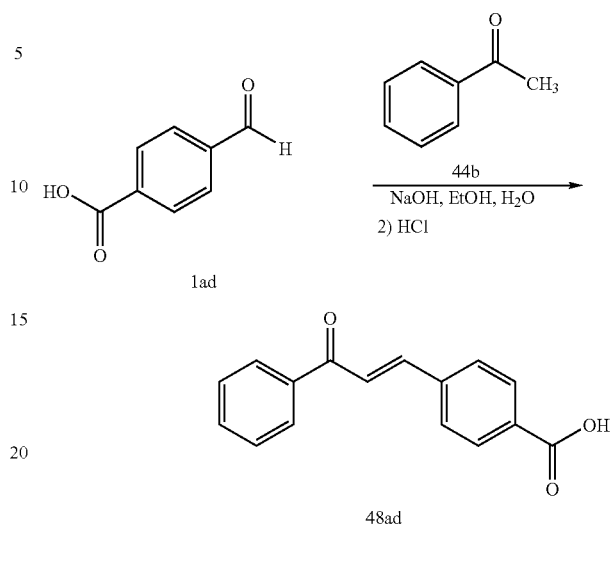

aldehyde proton in the starting benzaldehyde (1ad). The structure of the product was also verified by carbon NMR by the appearance of two signals in the aromatic region for the alkene carbons on the spacer. Also seen in the carbon NMR was the loss of a signal at 26.0 ppm for the methyl carbon in the starting acetophenone (44b).

An additional 3-carbon spacer analog, 50b, was prepared as shown in Scheme 35 following the procedure described by Chisolm (Chisolm et al., Patent 050,713 (1992); Chem. Abstr., 115, P207660d (1992)). Analog 50b contains two aryl rings separated by a 3-carbon spacer having two carbonyls. This analog was designed to test the importance of two carbonyls in a 3-carbon spacer. Acetophenone (44b) was reacted with methyl benzoate (49) and sodium methoxide in a condensation reaction to give analog 50b. The formation of the product was verified by proton NMR by the appearance of a signal at 6.85 ppm for the enol proton on the spacer and the loss of a signal at 2.38 for the methyl protons on acetophenone (44b) and a signal at 3.88 ppm for the methyl ester protons of methyl benzoate (49). The structure was also verified by carbon NMR by the appearance of signals at 93.1 ppm for the enol carbon and 185.6 ppm for the carbonyl carbons on the spacer. Also observed in the carbon NMR was the loss of signals at 166.2 ppm for the carbonyl carbon and 51.4 ppm for the methyl carbon on methyl benzoate (49) and signals at 197.3 ppm for the carbonyl carbon and 26.0 for the methyl carbon on acetophenone (44b).

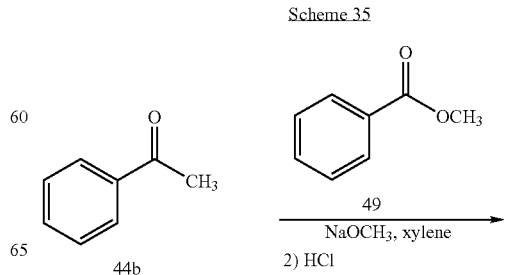

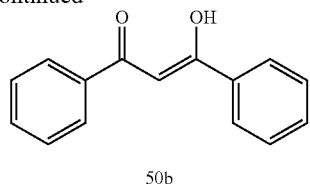

50b

Six additional analogs, 52b, 52c, 52e, 52aa, 52ac and 53 were prepared as shown in Schemes 36 and 37 following the procedure described by Selvaraj (Selvaraj et al., Ind. J. Chem., Sect. B 26B, 1104-1105 (1987)). Analogs 52b, 52c, 52e, 52aa, 52ac and 53 contain two identical aryl rings separated by a 3-carbon spacer having both a carbonyl and a saturated heterocyclic ring and were designed to test the importance of a heterocyclic ring in the spacer. Analogs 52b, 52c, 52e, 52aa and 52ac were prepared as shown is Scheme 36 by reaction of analogs 20b, 20c, 20e, 20aa and 20ac with methylamine (51) in a Michael addition reaction. The formation of the products was verified by proton NMR by the appearance of a pair of doublets at ~2.50 ppm and ~3.45 ppm for the protons alpha to the carbonyl and a triplet at ~2.82 ppm for the protons alpha to the amine. The structures were also verified by carbon NMR by the appearance of signals at ~50.8 ppm and ~70.2 ppm for the alkane carbons in the nitrogen containing heterocyclic ring and by the loss of two signals in the aromatic region for the alkene carbons. Analogs 52c and 52ac, which are not in the literature, were verified by high resolution mass spectroscopy.

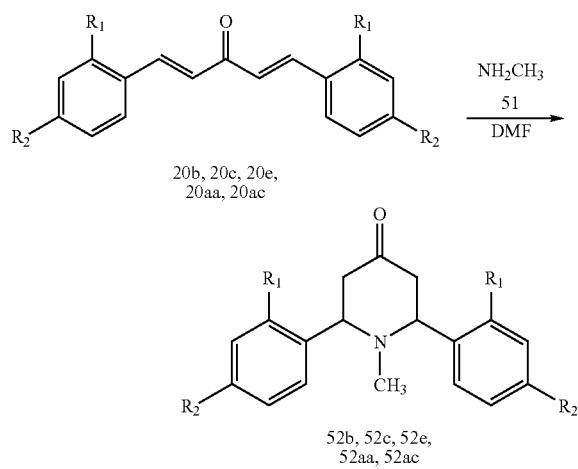

Scheme 37 describes the synthesis of analog 53 following the procedure described by Selvaraj (Selvaraj et al., Ind. J. Chem., Sect. B 26B, 1104-1105 (1987)). Analog 25 was reacted with methylamine (51) in a Michael addition reaction to give analog 53. The formation of the products was verified by proton NMR by the appearance of a pair of doublets at 2.59 ppm and 3.66 ppm for the protons alpha to the carbonyl and a triplet at 2.97 ppm for the protons alpha to the amine. The structures were also verified by carbon NMR by the appearance of signals at 50.7 ppm and 70.3 ppm for the alkane carbons in the nitrogen containing heterocyclic ring and by the loss of two signals in the aromatic region for the alkene carbons. Analog 53, which is not in the literature, was verified by high resolution mass spectroscopy.

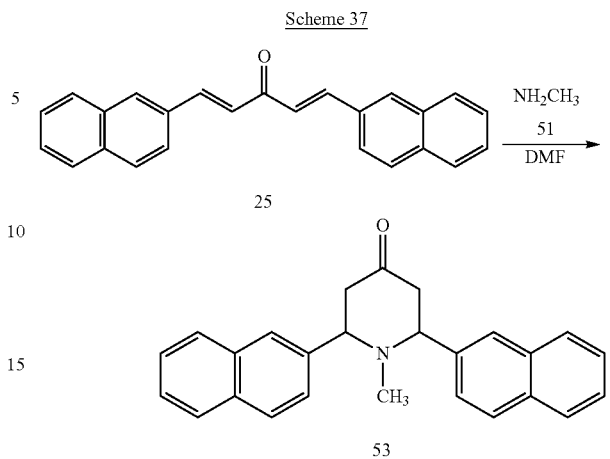

Experimental

Reagent quality solvents were used without purification with the exception of ethyl acetate which was distilled from magnesium sulfate before use. Liquid benzaldehydes, acetone and acetyl acetone were distilled before use. All other reagents were obtained from commercial sources and used without further purification. All compounds isolated were greater than 95% pure by proton and carbon NMR. Column chromatographic separations were performed using EM Science type 60 silica gel (230-400 mesh). Melting points were determined on a Thomas Hoover capillary melting point apparatus and are uncorrected. NMR spectra were recorded on a Bruker AC250 (250 MHz) NMR spectrometer in $CDCl_3$ unless otherwise noted. Chemical shifts are reported in ppm (δ) relative to $CDCl_3$ at 7.24 ppm for proton NMR and 77.0 for carbon NMR or DMSO at 2.49 ppm for proton NMR and 39.5 ppm for carbon NMR. Proton NMR peaks are reported as follows: chemical shift, multiplicity (s=singlet, d=doublet, t=triplet, q=quartet, m=multiplet, dd=doublet of doublets and dt=doublet of triplets), integration, and coupling constants (J in Hz). High resolution mass spectra were performed at the UNM Mass Spectrometry Facility, University of New Mexico, Albuquerque N.Mex. Analytical data was obtained from Galbraith Laboratories, Knoxville Tenn.

4-Methoxymethyloxy-3-methoxybenzaldehyde (1j). 4-Hydroxy-3-methoxybenzaldehyde (1a, 2.00 g, 13.1 mmol) and potassium carbonate (9.00 g, 65.1 mmol) were combined in dimethyl formamide (30 ml) and stirred for 15 min at room temperature. Chloromethyl methyl ether (1.60 ml, 21.1 mmol) was added and stirring was continued for 6 hr at room temperature. The resulting mixture was filtered and the filtrate extracted into ethyl acetate, washed with saturated sodium chloride, dried over magnesium sulfate, filtered and evaporated to give 2.55 g (99%) of a white solid: mp 39-40° C. [expected mp 41° C.]; $^1$H NMR: δ 3.40 (s, 3H), 3.83 (s, 3H), 5.21 (s, 2H), 7.15 (d, 1H, J=8.7 Hz), 7.30 (dd, 1H, J=6.0, 2.0 Hz), 7.32 (s, 1H), 9.75 (s, 1H); $^{13}$C NMR: δ 55.8, 56.2, 94.8, 109.4, 114.6, 125.9, 130.9, 149.8, 151.7, 190.4.

4-Carbmethoxybenzaldehyde (1ae). 4-Formylbenzoic acid (1ad, 1.00 g, 6.7 mmol) was dissolved in dry methanol (200 ml) and stirred for 10 min at 0° C. Thionyl chloride (6 ml, 82.3 mmol) was added dropwise and the mixture stirred for 90 min at 0° C. and 3 hr at room temperature. The methanol was evaporated and the resulting residue extracted into dichloromethane, washed with saturated sodium chloride, dried over magnesium sulfate, filtered and evaporated to afford a solid. The crude solid was recrystallized from hexane to give 1.07 g (98%) of a white solid: mp 60-62° C. [expected mp 61° C.]; $^1$H NMR: δ 3.87 (s, 3H), 8.01 (d, 2H, J=7.9 Hz), 8.13 (d, 2H, J=7.6 Hz), 10.08 (s, 1H); $^{13}$C NMR: δ 52.7, 129.7, 129.9, 134.4, 139.1, 165.6, 192.9.

1,7-Bis(4-hydroxy-3-methoxyphenyl)-1,6-heptadiene-3,5-dione (3a). Boric anhydride (0.49 g, 7.0 mmol) was combined with 2,4-pentanedione (2, 1.05 ml, 10.0 mmol) and stirred for 18 hr at room temperature under a nitrogen atmosphere. A solution of dry ethyl acetate (10 ml), 4-hydroxy-3-methoxybenzaldehyde (1a, 3.04 g, 20.0 mmol) and tributyl borate (11.00 ml, 40.5 mmol) was added and the mixture stirred for 15 min at room temperature. Butylamine (0.20 ml, 2.0 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a solid. The crude solid was triturated with methanol to give 2.82 g (77%) of an orange-yellow solid: mp 182-184° C. [expected mp 182-183° C.]; $^1$H NMR: (DMSO) δ 3.83 (s, 6H), 6.05 (s, 1H), 6.74 (d, 2H, J=15.9 Hz), 6.82 (d, 2H, J=8.1 Hz), 7.14 (d, 2H, J=8.0 Hz), 7.31 (s, 2H), 7.54 (d, 2H, J=15.7 Hz), 9.63 (s, 2H), 16.29 (s, 1H); $^{13}$C NMR: (DMSO) δ 55.6, 100.5, 111.3, 115.5, 120.9, 122.8, 126.2, 140.4, 147.8, 149.1, 182.8.

1,7-Diphenyl-1,6-heptadiene-3,5-dione (3b). Boric anhydride (0.49 g, 7.0 mmol) was combined with 2,4-pentanedione (2, 1.05 ml, 10.0 mmol) and stirred for 18 hr at room temperature under a nitrogen atmosphere. A solution of dry ethyl acetate (10 ml), benzaldehyde (1b, 2.05 g, 20.2 mmol) and tributyl borate (11.00 ml, 40.5 mmol) was added and the mixture stirred for 15 min at room temperature. Butylamine (0.20 ml, 2.0 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a solid. The crude solid was triturated with methanol to give 0.90 g (33%) of a yellow solid: mp 140-142° C. [expected mp 139-140° C.]; $^1$H NMR: δ 5.84 (s, 1H), 6.62 (d, 2H, J=15.7 Hz), 7.39 (m, 6H), 7.54 (dd, 4H, J=7.4, 4.0 Hz), 7.66 (d, 2H, J=15.9 Hz), 15.85 (s, 1H); $^{13}$C NMR: δ 101.6, 124.1, 128.0, 128.9, 130.0, 135.0, 140.5, 183.2.

1,7-Bis(2-methoxyphenyl)-1,6-heptadiene-3,5-dione (3c). Boric anhydride (0.33 g, 4.7 mmol) was combined with 2,4-pentanedione (2, 0.70 ml, 6.7 mmol) and stirred for 18 hr at room temperature. A solution of dry ethyl acetate (15 ml), 2-methoxybenzaldehyde (1c, 1.81 g, 13.3 mmol) and tributyl borate (7.25 ml, 26.7 mmol) was added and the mixture stirred for 15 min at room temperature. Butylamine (1.00 ml, 10.1 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a semi-solid. The crude semi-solid was chromatographed on silica gel with ethyl acetate/hexane to give 0.48 g (21%) of a yellow crystals: mp 121-123° C. [expected mp 121-122° C.]; $^1$H NMR: δ 3.89 (s, 6H), 5.86 (s, 1H), 6.71 (d, 2H, J=16.1 Hz), 6.94 (d, 4H), 7.33 (dt, 2H, J=8.1, 1.4 Hz), 7.54 (dd, 2H, J=7.8, 1.4 Hz), 7.97 (d, 2H, J=16.1 Hz), 16.00 (s, 1H); $^{13}$C NMR: δ 55.5, 101.4, 111.1, 120.6, 124.0, 124.7, 128.5, 131.1, 135.6, 158.3, 183.6.

1,7-Bis(2,3-dimethoxyphenyl)-1,6-heptadiene-3,5-dione (3d). Boric anhydride (0.49 g, 7.0 mmol) was combined with 2,4-pentanedione (2, 1.05 ml, 10.0 mmol) and stirred for 18 hr at room temperature under a nitrogen atmosphere. A solution of dry ethyl acetate (10 ml), 2,3-dimethoxybenzaldehyde (1d, 3.32 g, 20.0 mmol) and tributyl borate (11.00 ml, 40.5 mmol) was added and the mixture stirred for 15 min at room temperature. Butylamine (0.20 ml, 2.0 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a semi-solid. The crude semi-solid was triturated with methanol to give 2.01 g (51%) of a yellow solid: mp 117-120° C. [expected mp 117-120° C.]; $^1$H NMR: δ 3.87 (s, 12H), 5.87 (s, 1H), 6.68 (d, 2H, J=16.1 Hz), 6.92 (d, 2H, J=8.2 Hz), 7.05 (t, 2H, J=8.0 Hz), 7.18 (d, 2H, J=6.8 Hz), 7.95 (d, 2H, J=16.1 Hz), 15.88 (s, 1H); $^{13}$C NMR: (DMSO) δ 55.7, 60.7, 101.9, 114.6, 118.7, 124.1, 125.1, 128.0, 134.2, 147.7, 152.6, 182.9; Anal. Calcd for $C_{23}H_{24}O_6$: C, 69.68; H, 6.10. Found: C, 69.43; H, 6.16.

1,7-Bis(4-methoxyphenyl)-1,6-heptadiene-3,5-dione (3e). Boric anhydride (0.49 g, 7.0 mmol) was combined with 2,4-pentanedione (2, 1.05 ml, 10.0 mmol) and stirred for 18 hr at room temperature under a nitrogen atmosphere. A solution of dry ethyl acetate (10 ml), 4-methoxybenzaldehyde (1e, 2.43 ml, 20.0 mmol) and tributyl borate (11.00 ml, 40.5 mmol) was added and the mixture stirred for 15 min at room temperature. Butylamine (0.20 ml, 2.0 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a solid. The crude solid was triturated with methanol to give 2.83 g (84%) of a yellow solid: mp 157-159° C. [expected mp 154-155° C.]; $^1$H NMR: δ 3.82 (s, 6H), 5.75 (s, 1H), 6.48 (d, 2H, J=15.9 Hz), 6.90 (d, 4H, J=8.7 Hz), 7.49 (d, 4H, J=8.7 Hz), 7.60 (d, 2H, J=15.9 Hz), 16.04 (s, 1H); $^{13}$C NMR: δ 55.4, 101.2, 114.4, 121.9, 127.9, 129.7, 140.0, 161.2, 183.2.

1,7-Bis(4-hydroxyphenyl)-1,6-heptadiene-3,5-dione (3f). Boric anhydride (0.33 g, 4.7 mmol) was combined with 2,4-pentanedione (2, 0.70 ml, 6.7 mmol) and stirred for 18 hr at room temperature. A solution of dry ethyl acetate (15 ml), 4-hydroxybenzaldehyde (1f, 1.62 g, 13.3 mmol) and tributyl borate (7.25 ml, 26.7 mmol) was added and the mixture stirred for 15 min at room temperature. Butylamine (1.0 ml, 10.1 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a solid. The crude solid was recrystallized from methanol to give 0.40 g (19%) of red-orange crystals: mp 226-228° C. [expected mp 223-224° C.]; $^1$H NMR: (DMSO) δ 6.03 (s, 1H), 6.67 (d, 2H, J=15.9 Hz), 6.81 (d, 4H, J=7.7 Hz), 7.55 (m, 6H), 10.03 (s, 2H), 16.37 (s, 1H); $^{13}$C NMR: (DMSO) δ 100.7, 115.8, 120.7, 125.7, 130.1, 140.1, 159.5, 182.9.

1,7-Bis(4-dimethylaminophenyl)-1,6-heptadiene-3,5-dione (3g). Boric anhydride (0.33 g, 4.7 mmol) was combined with 2,4-pentanedione (2, 0.70 ml, 6.7 mmol) and stirred for 18 hr at room temperature. A solution of dry ethyl acetate (15 ml), 4-dimethylaminobenzaldehyde (1g, 2.00 g, 13.4 mmol)

and tributyl borate (7.25 ml, 26.7 mmol) was added and the mixture stirred for 15 min at room temperature. Butylamine (1.0 ml, 10.1 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a solid. The crude solid was triturated with methanol to give 0.57 g (23%) of a purple solid: mp 207-208° C. [expected mp 210-212° C.]; $^1$H NMR: (DMSO) δ 3.01 (s, 12H), 5.71 (s, 1H), 6.41 (d, 2H, J=15.61 Hz), 6.67 (d, 4H, J=8.02 Hz), 7.44 (d, 4H, J=8.11 Hz), 7.58 (d, 2H, J=15.65 Hz), 16.56 (s, 1H); $^{13}$C NMR: (DMSO) δ 39.6, 100.3, 111.7, 118.5, 122.0, 129.7, 140.3, 151.4, 182.6.

1,7-Bis(3-hydroxy-4-methoxyphenyl)-1,6-heptadiene-3,5-dione (3h). Boric anhydride (0.49 g, 7.0 mmol) was combined with 2,4-pentanedione (2, 1.05 ml, 10.0 mmol) and stirred for 18 hr at room temperature under a nitrogen atmosphere. A solution of dry ethyl acetate (10 ml), 3-hydroxy-4-methoxybenzaldehyde (1h, 3.04 g, 20.0 mmol) and tributyl borate (1.0 ml, 40.5 mmol) was added and the mixture stirred for 15 min at room temperature. Butylamine (0.20 ml, 2.0 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was filtered to afford a solid. The crude solid was triturated with methanol to give 2.60 g (71%) of a orange-yellow solid: mp 190-192° C. [expected mp 189-190° C.]; $^1$H NMR: (DMSO) δ 3.78 (s, 6H), 6.09, (s, 1H), 6.60 (d, 2H, J=15.9 Hz), 6.49 (d, 2H, J=8.9 Hz), 7.11 (m, 4H), 7.47 (d, 2H, J=15.9 Hz), 9.19 (s, 2H); $^{13}$C NMR: (DMSO) δ 55.6, 100.9, 112.0, 114.0, 121.2, 121.5, 127.5, 140.2, 146.6, 149.8, 182.8.

1,7-Bis(3,4-dimethoxyphenyl)-1,6-heptadiene-3,5-dione (3i). Boric anhydride (0.49 g, 7.0 mmol) and 2,4-pentanedione (2, 1.05 ml, 10.0 mmol) were combined in dry ethyl acetate (10 ml) and stirred for 30 min at 40° C. 3,4-Dimethoxybenzaldehyde (1i, 3.32 g, 20.0 mmol) and tributyl borate (7.90 ml, 29.1 mmol) were added and stirring was continued for 30 min at 40° C. A solution of butylamine (1.5 ml, 15.2 mmol) in dry ethyl acetate (10 ml) was added dropwise over 15 min and stirring was continued for 18 hr at 40° C. Hydrochloric acid (10 ml, 2 N) was added and the mixture stirred for 1 hr at 60° C. The resulting mixture was cooled to room temperature, extracted with ethyl acetate, washed with saturated sodium chloride, dried over magnesium sulfate, filtered and evaporated to afford a semi-solid. The crude semi-solid was chromatographed on silica gel with ethyl acetate/hexane to give a solid. The crude solid was recrystallized from methanol to give 1.16 g (29%) of an orange solid: mp 129-131° C. [expected mp 128-130° C.]; $^1$H NMR: (DMSO) δ 3.79 (s, 6H), 3.81 (s, 6H), 6.10 (s, 1H), 6.82 (d, 2H, J=15.9 Hz), 7.00 (d, 2H, J=8.3 Hz), 7.25 (d, 2H, J=6.8 Hz), 7.33 (s, 2H), 7.57 (d, 2H, J=15.7 Hz), 16.32 (s, 1H); $^{13}$C NMR: (DMSO) δ 55.6, 100.8, 110.5, 111.7, 122.0, 122.7, 127.5, 140.2, 148.9, 150.9, 183.0.

3-Methyl-2,4-pentanedione (5). 2,4-Pentanedione (2, 6.3 ml, 60.2 mmol) and potassium carbonate (7.75 g, 56.1 mmol) were combined in acetone (12 ml) and stirred for 15 min at room temperature. Methyl iodide (4, 4.6 ml, 73.9 mmol) was added and the resulting mixture refluxed with a calcium chloride drying tube for 18 hr. An additional amount of methyl iodide (1.5 ml, 24.1 mmol) was added and reflux was continued for 2 hr. The resulting mixture was filtered and the solvent evaporated to afford a liquid. The crude liquid was distilled to give 5.33 g (78%) of a clear liquid: bp 164-170° C.; $^1$H NMR: δ enol form: 1.65 (s, 6H), 1.92 (s, 3H); keto form: 1.12 (d, 3H, J=7.0 Hz), 2.00 (s, 6H), 3.52 (q, 1H, J=7.0 Hz); $^{13}$C NMR: δ 12.2, 12.6, 23.0, 28.4, 61.3, 104.4, 189.9, 204.5.

4-Methyl-1,7-bis(4-hydroxy-3-methoxyphenyl)-1,6-heptadiene-3,5-dione (6a). Boric anhydride (0.49 g, 7.0 mmol) was combined with 3-methyl-2,4-pentanedione (5, 1.14 g, 10 mmol) and stirred for 24 hr at room temperature under a nitrogen atmosphere. A solution of dry ethyl acetate (10 ml), 4-hydroxy-3-methoxybenzaldehyde (1a, 3.04 g, 20.0 mmol) and tributyl borate (11.0 ml, 40.5 mmol) was added and the mixture stirred for 30 min at room temperature. Butylamine (0.2 ml, 2.0 mmol) was added dropwise over 40 min and stirring was continued for 24 hr at room temperature. Hydrochloric acid (15 ml, 0.4 N) was warmed to 60° C., added to the mixture and stirring was continued for 4 hr. The resulting mixture was filtered through celite and silica gel. The filtrate was washed with saturated sodium chloride, dried over magnesium sulfate, filtered and evaporated to afford a solid. The crude solid was recrystallized three times from methanol to give 0.86 g (22%) of an orange solid: mp 180-183° C. [expected mp 180-183° C.]; $^1$H NMR: δ 2.16 (s, 3H), 3.94 (s, 6H), 5.83 (s, 2H), 6.94 (m, 4H), 7.04 (d, 2H, J=1.6 Hz), 7.16 (d, 2H, J=8.0 Hz), 7.66 (d, 2H, J=15.5 Hz); $^{13}$C NMR: δ 11.5, 13.1, 55.2, 55.6, 55.8, 105.6, 111.4, 111.6, 115.5, 117.7, 122.1, 123.2, 123.5, 125.6, 126.6, 141.4, 143.7, 147.8, 149.1, 149.6, 182.1, 196.0; Anal. Calcd for $C_{22}H_{22}O_6$: C, 69.10; H, 5.80. Found: C, 69.19; H, 5.89.

4-Methyl-1,7-diphenyl-1,6-heptadiene-3,5-dione (6b). Boric anhydride (0.49 g, 7.0 mmol) was combined with 3-methyl-2,4-pentanedione (5, 1.14 g, 10.0 mmol) and stirred for 24 hr at room temperature under a nitrogen atmosphere. A solution of ethyl acetate (10 ml), benzaldehyde (1b, 2.05 ml, 20.2 mmol) and tributyl borate (11.0 ml, 40.5 mmol) was added and the mixture stirred for 15 min at room temperature. Butylamine (0.20 ml, 2.0 mmol) was added dropwise over 30 min and stirring was continued for 24 hr at room temperature. The resulting mixture was filtered to afford a solid. The crude solid was triturated with methanol to give 1.80 g (62%) of an orange solid: mp 154-157° C. [expected mp 154-157° C.]; $^1$H NMR: δ 2.17 (s, 3H), 7.12 (d, 2H, J=15.5 Hz), 7.38 (m, 6H), 7.58 (m, 4H), 7.74 (d, 2H, J=15.5 Hz); $^{13}$C NMR: δ 12.1, 106.2, 120.8, 182.1, 128.8, 129.9, 135.4, 141.3, 182.4. Anal. Calcd for $C_{20}H_{18}O_2$: C, 82.73; H, 6.25. Found: C, 82.69; H, 6.36.

3-Benzylidene-2,4-pentanedione (7). 2,4-Pentanedione (2, 4.10 ml, 39.2 mmol) and benzaldehyde (1b, 4.06 ml, 40.0 mmol) were stirred in benzene (10 ml). Piperdine (3 drops) and glacial acetic acid (6 drops) were added and the mixture refluxed with a Dean-Stark water trap for 3 hr. The resulting mixture was cooled to room temperature, extracted into ethyl ether, washed with hydrochloric acid (1 N), saturated sodium bicarbonate, hydrochloric acid (1 N) and twice with water. The organic layer was dried over magnesium sulfate, filtered and evaporated to afford an oil. The crude oil was distilled bulb to bulb to give 7.03 g (95%) of a yellow oil; [expected mp 165-167° C.]; $^1$H NMR: δ 2.24 (s, 3H), 2.38 (s, 3H), 7.35 (s, 5H), 7.45 (s, 1H); $^{13}$C NMR: δ 26.5, 31.6, 128.9, 129.6, 130.5, 132.8, 139.6, 142.7, 196.2, 205.3.

3-Benzyl-2,4-pentanedione (8). 3-Benzylidene-2,4-pentanedione (7, 6.50 g, 34.5 mmol) and palladium on activated carbon (0.25 g, 10%) were combined in ethyl acetate (50 ml). The mixture was placed under a hydrogen atmosphere (60 psi) on a Parr apparatus for 4 hr at room temperature. The resulting mixture was filtered through celite and the solvent evaporated to afford an oil. The crude oil was distilled bulb to bulb to give 6.52 g (99%) of a clear oil; $^1$H NMR: δ enol form: 2.02 (s, 6H), 3.62 (s, 2H), 7.24 (m, 5H); keto form: 2.07 (s, 6H), 3.11 (d, 2H, J=7.4 Hz), 4.01 (t, 1H, J=7.7 Hz), 7.24 (m, 5H); $^{13}$C NMR: δ 22.9, 29.4, 32.5, 33.8, 69.2, 107.9, 125.9, 126.3, 127.0, 128.1, 128.2, 137.7, 139.3, 191.4, 202.9.

4-Benzyl-1,7-bis(4-hydroxy-3-methoxyphenyl)-1,6-heptadiene-3,5-dione (9a). Boric anhydride (0.49 g, 7.0 mmol) was combined with 3-benzyl-2,4-pentanedione (8, 1.90 g, 10 mmol) and stirred for 18 hr at room temperature under a nitrogen atmosphere. A solution of dry ethyl acetate (15 ml), 4-hydroxy-3-methoxybenzaldehyde (1a, 3.04 ml, 20.0 mmol) and tributyl borate (11.0 ml, 40.5 mmol) was added and the mixture stirred for 30 min at room temperature. Butylamine (0.2 ml, 2.0 mmol) was added dropwise over 40 min and stirring was continued for 48 hr at room temperature. Hydrochloric acid (15 ml, 0.5 N) was warmed to 60° C., added to the mixture and stirring was continued for 1 hr. The resulting mixture was extracted into ethyl acetate, washed with saturated sodium chloride, dried over magnesium sulfate, filtered and evaporated to afford a solid. The crude solid was recrystallized three times from methanol to give 2.73 g (59%) of a orange-yellow solid: mp 144-146° C. [expected mp 139-141° C.]; $^{1}$H NMR: (DMSO) δ 3.81 (s, 6H), 4.11 (s, 2H), 6.78 (d, 2H, J=8.1 Hz), 7.20 (m, 11H), 7.58 (d, 2H, J=15.1 Hz), 9.66 (s, 2H); $^{13}$C NMR: (DMSO) δ 30.2, 33.7, 55.6, 55.7, 63.0, 109.9, 111.3, 115.5, 117.9, 122.4, 123.2, 123.7, 125.5, 125.7, 126.0, 126.5, 127.7, 128.1, 128.3, 128.7, 139.1, 141.7, 142.3, 144.1, 147.8, 149.2, 149.7, 183.0, 194.0; Exact mass calcd for $C_{28}H_{26}O_6$: 458.1729, observed (M+H) 459.1798.

4-Benzyl-1,7-diphenyl-1,6-heptadiene-3,5-dione (9b). Boric anhydride (0.49 g, 7.0 mmol) was combined with 3-benzyl-2,4-pentanedione (8, 1.90 g, 10.0 mmol) and stirred for 48 hr at room temperature under a nitrogen atmosphere. A solution of dry ethyl acetate (10 ml), benzaldehyde (1b, 2.05 ml, 20.2 mmol) and tributyl borate (11.0 ml, 40.5 mmol) was added and the mixture stirred for 15 min at room temperature. Butylamine (0.20 ml, 2.0 mmol) was added dropwise over 30 min and stirring was continued for 18 hr at room temperature. Hydrochloric acid (15 ml, 0.4 N) was warmed to 60° C., added to the mixture and stirring was continued for 1 hr. The resulting mixture was filtered to afford a solid. The crude solid was triturated with methanol to give 2.30 g (63%) of a yellow solid: mp 162-164° C. [expected mp 156-158° C.]; $^{1}$H NMR: δ 3.99 (s, 2H), 6.99 (d, 2H, J=15.6 Hz), 7.34 (m, 15H), 7.77 (d, 2H, J=15.2 Hz); $^{13}$C NMR: δ 31.8, 109.3, 120.8, 126.5, 127.8, 128.1, 128.8, 130.0, 135.3, 140.5, 141.9, 183.6.

4,4-Dimethyl-1,7-diphenyl-1,6-heptadiene-3,5-dione (11b). 1,7-Diphenyl-1,6-heptadiene-3,5-dione (3b, 0.30 g, 1.1 mmol) was stirred in dichloromethane (10 ml) for 5 min at room temperature. A solution of sodium hydroxide (0.10 g, 2.5 mmol), tetrabutylammonium chloride (0.42 g, 1.5 mmol) and water (3 ml) was added and the mixture stirred for 10 min at room temperature. Methyl iodide (4, 0.21 ml, 3.4 mmol) was added and the mixture stirred for 1 hr at 40° C. The mixture was cooled to room temperature, washed with saturated sodium chloride, dried over magnesium sulfate, filtered and evaporated to afford an oil. The crude oil was distilled bulb to bulb to give 0.25 g (76%) of a yellow oil; $^{1}$H NMR: δ 1.46 (s, 6H), 6.77 (d, 2H, J=15.7 Hz), 7.33 (m, 6H), 7.49 (m, 4H), 7.72 (d, 2H, J=15.6 Hz); $^{13}$C NMR: δ 21.1, 60.9, 121.4, 128.5, 128.7, 130.6, 134.1, 144.1, 197.9; Anal. Calcd for $C_{20}H_{18}O_2$: C, 82.86; H, 6.62. Found: C, 82.54; H, 6.72.

4,4-Dibenzyl-1,7-diphenyl-1,6-heptadiene-3,5-dione (12b). 1,7-Diphenyl-1,6-heptadiene-3,5-dione (3b, 0.25 g, 0.9 mmol) was stirred in dichloromethane (4 ml) for 5 min at room temperature. A solution of sodium hydroxide (80.0 mg, 2.0 mmol), tetrabutylammonium chloride (0.29 g, 1.0 mmol) and water (2 ml) was added and the mixture stirred for 10 min at room temperature. Benzyl bromide (10, 0.22 ml, 1.8 mmol) was added and the mixture stirred for 1 hr at 40° C. The resulting mixture was cooled to room temperature, washed with saturated sodium chloride, dried over magnesium sulfate, filtered and evaporated to afford a solid. The crude solid was chromatographed on silica gel with ethyl acetate/hexane to give a solid. The solid was recrystallized from methanol to give 0.25 g (61%) of a white solid: mp 182-183° C. [expected mp 181° C.]; $^{1}$H NMR: δ 3.39 (s, 4H), 6.70 (d, 2H, J=15.5 Hz), 7.09-7.44 (m, 20H), 7.73 (d, 2H, J=15.5 Hz); $^{13}$C NMR: δ 37.7, 70.3, 123.1, 126.7, 128.1, 128.6, 128.8, 130.3, 130.7, 134.2, 136.3, 142.7, 196.8.

1,7-Bis(4-hydroxy-3-methoxyphenyl)heptane-3,5-dione (13a). 1,7-Bis(4-hydroxy-3-methoxyphenyl)-1,6-heptadiene-3,5-dione (3a, 0.55 g, 1.5 mmol) and palladium on activated carbon (0.25 g, 5%) were combined in ethyl acetate (30 ml). The mixture was placed under a hydrogen atmosphere (60 psi) on a Parr apparatus for 4 hr at room temperature. The resulting mixture was filtered through celite and the solvent evaporated to afford a solid. The crude solid was recrystallized from ethyl acetate/hexane to give 0.30 g (54%) of white crystals: mp 92-94° C. [expected mp 92-93° C.]; $^{1}$H NMR: δ 2.53 (t, 4H, J=7.9 Hz), 2.83 (m, 4H), 3.84 (s, 6H), 5.40 (s, 1H), 5.48 (s, 2H), 6.64 (m, 4H), 6.81 (d, 2H, J=8.3 Hz), 15.44 (s, 1H); $^{13}$C NMR: δ 29.2, 31.3, 40.4, 45.5, 55.9, 99.7, 110.9, 111.0, 114.3, 120.7, 132.4, 143.9, 146.3, 193.0.

1,7-Diphenylheptane-3,5-dione (13b). 1,7-Diphenyl-1,6-heptadiene-3,5-dione (3b, 0.56 g, 2.0 mmol) and palladium on activated carbon (0.25 g, 5%) were combined in ethyl acetate (40 ml). The mixture was placed under a hydrogen atmosphere (60 psi) on a Parr apparatus for 4 hr at room temperature. The resulting mixture was filtered through celite and the solvent evaporated to afford an oil. The crude oil was purified by preparative thin layer chromatography with ethyl acetate/hexane to give 0.40 g (70%) of an orange-yellow oil; $^{1}$H NMR: δ enol form: 2.53 (m, 4H), 2.83 (m, 4H), 5.47 (s, 1H), 7.30 (m, 10H); keto form: 2.53 (m, 4H), 2.83 (m, 4H), 3.54 (s, 2H), 7.30 (m, 10H); $^{13}$C NMR: δ 29.4, 31.5, 39.9, 45.0, 99.5, 126.1, 128.3, 128.5, 140.5, 170.4, 172.0, 192.8.

4-Methyl-1,7-bis(4-hydroxy-3-methoxyphenyl)heptane-3,5-dione (14a). 4-Methyl-1,7-bis(4-hydroxy-3-methoxyphenyl)-1,6-heptadiene-3,5-dione (6a, 0.20 g, 0.5 mmol) and palladium on activated carbon (0.25 g, 10%) were combined in ethyl acetate (100 ml). The mixture was placed under a hydrogen atmosphere (60 psi) on a Parr apparatus for 2 hr at room temperature. The resulting mixture was filtered through celite and the solvent evaporated to afford an oil. The crude oil was twice chromatographed on silica gel with ethyl acetate/hexane to give a semi-solid. The crude semi-solid was distilled bulb to bulb to give 80 mg (38%) of a pale yellow oil; $^{1}$H NMR: δ enol form: 1.69 (s, 3H), 2.72 (m, 8H), 3.83 (s, 6H), 5.48 (s, 2H), 6.69 (m, 4H), 6.79 (d, 2H, J=7.5 Hz); keto for: 1.23 (d, 3H, J=7.2 Hz), 2.72 (m, 8H), 3.57 (q, 1H, J=7.0 Hz), 3.83 (s, 6H), 5.48 (s, 2H), 6.69 (m, 4H), 6.79 (d, 2H, J=7.5 Hz); $^{13}$C NMR: δ 12.5, 29.2, 43.3, 55.9, 61.4, 111.0, 114.2, 120.7, 132.4, 143.9, 146.3, 206.1; Exact mass calcd for $C_{22}H_{26}O_6$: 386.1729, observed (M+H) 387.1783.

4-Methyl-1,7-diphenylheptane-3,5-dione (14b). 4-Methyl-1,7-diphenyl-1,6-hetpadiene-3,5-dione (6b, 0.96 g, 3.3 mmol) and palladium on activated carbon (0.25 g, 10%) were combined in ethyl acetate (50 ml). The mixture was placed under a hydrogen atmosphere (60 psi) on a Parr apparatus for 2 hr at room temperature. The resulting mixture was filtered through celite and the filtrate was washed with saturated sodium chloride, dried over magnesium sulfate, filtered and evaporated to afford an oil. The crude oil was twice chromatographed on silica gel with ethyl acetate/hexane to give an oil. The oil was distilled bulb to bulb to give 0.71 g (73%) of a clear oil; ¹H NMR: δ enol form: 1.66 (s, 3H), 2.73 (m, 8H), 7.17 (m, 10H); keto form: 1.20 (d, 3H, J=7.2 Hz), 2.73 (m, 8H), 3.55 (q, 1H, J=7.0 Hz), 7.17 (m, 10H); ¹³C NMR: δ 12.3, 29.3, 31.0, 37.6, 42.8, 60.9, 104.2, 125.9, 128.1, 128.2, 140.4, 140.8, 174.6, 191.5, 205.6; Exact mass calcd for $C_{20}H_{22}O_2$: 294.1620, observed (M+H) 295.1693.

4-Benzyl-1,7-bis(4-hydroxy-3-methoxyphenyl)heptane-3,5-dione (15a). 4-Benzyl-1,7-bis(4-hydroxy-3-methoxyphenyl)-1,6-heptadiene-3,5-dione (9a, 0.25 g, 0.5 mmol) and palladium on activated carbon (0.20 g, 10%) were combined in ethyl acetate (45 ml). The mixture was placed under a hydrogen atmosphere (60 psi) on a Parr apparatus for 2 hr at room temperature. The resulting mixture was filtered through celite and the filtrate was washed with saturated sodium chloride, dried over magnesium sulfate, filtered and evaporated to afford an oil. The crude oil was twice chromatographed on silica gel with ethyl acetate/hexane to give 0.12 g (48%) of a pale yellow oil; ¹H NMR: δ enol form: 2.66 (m, 8H), 3.53 (s, 2H), 3.77 (s, 6H), 5.55 (s, 2H), 6.56 (m, 4H), 6.77 (d, 2H, J=7.6 Hz), 7.06 (m, 6H), 7.20 (m, 2H); keto form: 2.66 (m, 8H), 3.08 (d, 2H, J=7.3 Hz), 3.82 (s, 6H), 3.92 (t, 1H, J=8.3 Hz), 5.55 (s, 2H), 6.56 (m, 4H), 6.77 (d, 2H, J=7.6 Hz), 7.06 (m, 6H), 7.20 (m, 2H); ¹³C NMR: δ 29.0, 31.1, 31.8, 34.3, 37.7, 44.6, 55.8, 69.2, 111.0, 114.2, 120.7, 120.8, 126.6, 127.4, 128.5, 128.6, 132.3, 132.6, 137.9, 143.8, 146.3, 193.4, 204.5; Exact mass calcd for $C_{28}H_{30}O_6$: 462.2042, observed (M+H) 463.2073.

4-Benzyl-1,7-diphenylheptane-3,5-dione (15b). 4-Benzyl-1,7-diphenyl-1,6-heptadiene-3,5-dione (9b, 0.26 g, 0.7 mmol) and palladium on activated carbon (0.25 g, 10%) were combined in ethyl acetate (50 ml). The mixture was placed under a hydrogen atmosphere (60 psi) on a Parr apparatus for 2 hr at room temperature. The resulting mixture was filtered through celite and the filtrate was washed with saturated sodium chloride, dried over magnesium sulfate, filtered and evaporated to afford an oil. Hexane was added to the crude oil and the resulting precipitate was filtered. The crude solid was recrystallized twice from hexane to give 0.18 g (69%) of white needles: mp 74-75° C.; ¹H NMR: δ enol form: 2.61 (m, 10H), 7.14 (m, 15H); keto form: 2.61 (m, 8H), 3.07 (d, 2H, J=7.2 Hz), 3.90 (t, 1H, J=7.6 Hz), 7.14 (m, 15H); ¹³C NMR: δ 29.3, 34.3, 44.3, 69.2, 126.1, 126.7, 128.3, 128.4, 128.6, 128.7, 137.9, 140.4, 204.3; Exact mass calcd for $C_{26}H_{26}O_2$: 370.1933, observed (M+H) 371.2014.

4,4-Dimethyl-1,7-diphenylheptane-3,5-dione (16b). 4,4-Dimethyl-1,7-diphenyl-1,6-heptadiene-3,5-dione (11b, 0.15 g, 0.5 mmol) and palladium on activated carbon (0.20 g, 10%) were combined in ethyl acetate (25 ml). The mixture was placed under a hydrogen atmosphere (60 psi) on a Parr apparatus for 1 hr at room temperature. The resulting mixture was filtered through celite and the filtrate was washed with saturated sodium chloride, dried over magnesium sulfate, filtered and evaporated to afford an oil. The crude oil was chromatographed on silica gel with ethyl acetate/hexane to give 0.12 g (80%) of a pale yellow oil; ¹H NMR: δ 1.25 (s, 6H), 2.60 (t, 4H, J=7.4 Hz), 2.80 (t, 4H, J=7.0 Hz), 7.18 (m, 10H); ¹³C NMR: δ 21.1, 29.8, 40.2, 62.4, 126.1, 128.3, 140.7, 208.4; Exact mass calcd for $C_{21}H_{24}O_2$: 308.1776, observed (M+H) 309.1843.

4,4-Dibenzyl-1,7-diphenylheptane-3,5-dione (17b). 4,4-Dibenzyl-1,7-diphenyl-1,6-heptadiene-3,5-dione (12b, 70 mg, 0.2 mmol) and palladium on activated carbon (0.10 g, 10%) were combined in ethyl acetate (25 ml). The mixture was placed under a hydrogen atmosphere (60 psi) on a Parr apparatus for 5 hr at room temperature. The resulting mixture was filtered through celite and the filtrate was washed with saturated sodium chloride, dried over magnesium sulfate, filtered and evaporated to afford a solid. The crude solid was chromatographed on silica gel with ethyl acetate/hexane to give a solid. The solid was recrystallized from hexane to give 60 mg (86%) of a white solid: mp 101-102° C. [expected mp 100.5-101.5° C.]; ¹H NMR: δ 2.56 (t, 4H, J=7.4 Hz), 2.74 (t, 4H, J=6.8 Hz), 3.29 (s, 4H), 7.04 (m, 20H); ¹³C NMR: δ 29.6, 37.3, 42.5, 71.1, 126.1, 126.8, 128.4, 129.6, 136.0, 140.6, 207.8; Anal. Calcd for $C_{33}H_{32}O_2$: C, 86.05; H, 7.00. Found: C, 86.28; H, 7.11.

1,5-Bis(4-hydroxy-3-methoxyphenyl)-1,4-pentadien-3-one (20a). 1,5-Bis(4-methoxymethoxy-3-methoxyphenyl)-1,4-pentadien-3-one (20j, 0.41 g, 10.0 mmol) was stirred in methanol (50 ml) for 15 min at 50° C. Concentrated hydrochloric acid (1 drop) was added and the solution stirred for 3 hr at 50° C. The methanol was evaporated and the resulting residue extracted into ethyl acetate, washed with saturated sodium chloride, dried over magnesium sulfate, filtered and evaporated to afford a semi-solid. The crude semi-solid was purified by preparative thin layer chromatography with ethyl acetate/hexane to give 0.31 g (96%) of a yellow solid: mp 84-86° C. [expected mp 82-83° C.]; ¹H NMR: δ 3.89 (s, 6H), 6.87 (d, 2H, J=8.4 Hz), 6.88 (d, 2H, J=15.9 Hz), 7.10 (m, 4H), 7.62 (d, 2H, J=15.9 Hz); ¹³C NMR: δ 56.1, 109.8, 114.8, 123.3, 123.4, 127.5, 143.0, 146.8, 148.1, 188.6.

1,5-Diphenyl-1,4-pentadien-3-one (20b). Benzaldehyde (1b, 2.54 ml, 25.0 mmol) and acetone (19, 0.90 ml, 12.2 mmol) were combined in ethanol (20 ml) and stirred for 15 min at room temperature. A solution of sodium hydroxide (2.50 g, 62.5 mmol) and water (25 ml) was added and the solution stirred for 3 hr at room temperature. The resulting precipitate was filtered and recrystallized from ethanol to afford 2.35 g (82%) of yellow crystals: mp 110-112° C. [expected mp 112-114° C.]; ¹H NMR: δ 7.07 (d, 2H, J=15.9 Hz), 7.40 (m, 8H), 7.61 (m, 2H), 7.73 (d, 2H, J=15.9 Hz); ¹³C NMR: δ 125.4, 128.3, 12.9, 130.4, 134.7, 143.2, 188.7.

1,5-Bis(2-methoxyphenyl)-1,4-pentadien-3-one (20c). 2-Methoxybenzaldehyde (1c, 1.50 ml, 12.4 mmol) and acetone (19, 0.46 ml, 6.2 mmol) were combined in ethanol (10 ml) and stirred for 15 min at room temperature. A solution of sodium hydroxide (0.50 g, 12.5 mmol) and water (10 ml) was added and the mixture stirred for 18 hr at room temperature. The resulting precipitate was filtered and recrystallized from ethanol to give 1.56 g (85%) of a yellow solid: mp 123-124° C. [expected mp 124° C.]; ¹H NMR: δ 3.87 (s, 6H), 6.91 (m, 4H), 7.15 (d, 2H, J=16.1 Hz), 7.33 (dt, 2H, J=7.2, 1.4 Hz), 7.59 (d, 2H, J=7.5 Hz), 8.06 (d, 2H, J=16.3 Hz); ¹³C NMR: δ 55.4, 111.1, 120.6, 123.8, 126.1, 128.5, 131.4, 138.0, 158.4, 189.6.

1,5-Bis(2,3-dimethoxyphenyl)-1,4-pentadien-3-one (20d). 2,3-Dimethoxybenzaldehyde (1d, 4.50 g, 27.1 mmol) and acetone (19, 1.00 ml, 13.5 mmol) were combined in ethanol (25 ml) and stirred for 15 min at room temperature. A solution of sodium hydroxide (2.20 g, 55.0 mmol) and water (25 ml) was added and the mixture stirred for 6 hr at room temperature. The resulting precipitate was filtered and recrystallized from ethanol to give 4.15 g (87%) of a yellow solid: mp 106-108° C. [expected mp 108° C.]; ¹H NMR: δ 3.89 (s, 6H), 3.90 (s, 6H), 6.96 (d, 2H, J=8.1 Hz), 7.09 (t, 2H, J=8.1 Hz), 7.16 (d, 2H, J=16.3 Hz), 7.25 (d, 2H, J=7.4 Hz), 8.05 (d, 2H, J=16.1 Hz); ¹³C NMR: δ 55.9, 61.3, 114.1, 119.3, 124.1, 126.8, 129.0, 137.8, 148.7, 153.0, 189.5.

1,5-Bis(4-methoxyphenyl)-1,4-pentadien-3-one (20e). 4-Methoxybenzaldehyde (1e, 1.50 ml, 12.3 mmol) and acetone (19, 0.45 ml, 6.2 mmol) were combined in ethanol (20 ml) and stirred for 15 min at room temperature. A solution of sodium hydroxide (2.53 g, 63.3 mmol) and water (25 ml) was added and the mixture stirred for 3 hr at room temperature. The resulting precipitate was filtered and recrystallized from ethanol to give 1.00 g (55%) of a yellow solid: mp 128-130° C. [expected mp 133-134° C.]; $^1$H NMR: δ 3.82 (s, 6H), 6.90 (d, 4H, J=8.5 Hz), 6.93 (d, 2H, J=15.9 Hz), 7.54 (d, 4H, J=8.5 Hz), 7.68 (d, 2H, J=15.9 Hz); $^{13}$C NMR: δ 55.4, 114.4, 123.5, 127.6, 129.9, 142.5, 161.4, 188.6.

1,5-Bis(4-hydroxyphenyl)-1,4-pentadien-3-one (20f). 4-Hydroxybenzaldehyde (1f, 2.00 g, 16.4 mmol) and acetone (19, 0.61 ml, 8.3 mmol) were combined in ethanol (30 ml) and stirred for 15 min at room temperature. A solution of sodium hydroxide (1.00 g, 25.0 mmol) and water (30 ml) was added and the mixture stirred for 4 hr at room temperature. The resulting mixture was extracted into ethyl acetate, washed with saturated sodium chloride, dried over magnesium sulfate, filtered and evaporated to afford a solid. The crude solid was recrystallized from ethyl acetate/hexane to give 0.85 g (39%) of a yellow solid: mp 235-237° C. [expected mp 238-239° C.]; $^1$H NMR: (DMSO) δ 6.82 (d, 4H, J=8.5 Hz), 7.08 (d, 2H, J=16.1 Hz), 7.61 (d, 4H, J=8.5 Hz), 7.64 (d, 2H, J=15.7 Hz), 10.08 (s, 2H); $^{13}$C NMR: (DMSO) δ 115.8, 122.6, 125.7, 130.3, 142.3, 159.7, 187.9.

1,5-Bis(4-dimethylaminophenyl)-1,4-pentadien-3-one (20g). 4-Dimethylaminobenzaldehyde (1g, 1.00 g, 6.7 mmol) and acetone (19, 0.24 ml, 3.2 mmol) were combined in ethanol (10 ml) and stirred for 15 min at room temperature. A solution of sodium hydroxide (0.40 g, 10 mmol) and water (10 ml) was added and the mixture stirred for 18 hr at room temperature. The resulting mixture was extracted into ethyl acetate, washed with saturated sodium chloride, dried over magnesium sulfate, filtered and evaporated to afford a solid. The crude solid was recrystallized from ethanol to give 0.53 g (51%) of an orange solid: mp 179-181° C. [expected mp 174-176° C.]; $^1$H NMR: δ 3.01 (s, 12H), 6.69 (d, 4H, J=8.7 Hz), 6.87 (d, 2H, J=15.7 Hz), 7.50 (d, 4H, J=8.7 Hz), 7.67 (d, 2H, J=15.7 Hz); $^{13}$C NMR: δ 40.2, 98.9, 111.8, 121.2, 122.9, 129.9, 142.8, 151.6.

1,5-Bis(3,4-dimethoxyphenyl)-1,4-pentadien-3-one (20i). 3,4-Dimethoxybenzaldehyde (1i, 2.25 g, 13.5 mmol) and acetone (19, 0.50 ml, 6.8 mmol) were combined in ethanol (15 ml) and stirred for 15 min at room temperature. A solution of sodium hydroxide (1.10 g, 27.5 mmol) and water (10 ml) was added and the mixture stirred for 2 hr at room temperature. The resulting precipitate was filtered and recrystallized from ethanol to give 1.80 g (75%) of a yellow solid: mp 72-75° C. [expected mp 68-70° C.]; $^1$H NMR: δ 3.92 (s, 6H), 3.94 (s, 6H), 6.89 (d, 2H, J=8.3 Hz), 6.96 (d, 2H, J=15.9 Hz), 7.14 (s, 2H), 7.20 (d, 2H, J=8.1 Hz), 7.69 (d, 2H, J=15.9 Hz); $^{13}$C NMR: δ 55.9, 109.9, 111.0, 122.9, 123.5, 127.7, 142.8, 149.1, 151.2, 188.4.

1,5-Bis(4-methoxymethyloxy-3-methoxyphenyl)-1,4-pentadien-3-one (20j). 4-Methoxymethyloxy-3-methoxybenzaldehyde (1j, 1.95 g, 10.0 mmol) and acetone (19, 0.37 ml, 5.0 mmol) were combined in ethanol (25 ml) and stirred for 15 min at room temperature. A solution of sodium hydroxide (0.65 g, 16.3 mmol) and water (25 ml) was added and the solution stirred for 18 hr at room temperature. The resulting mixture was extracted into dichloromethane, washed with saturated sodium chloride, dried over magnesium sulfate, filtered and evaporated to afford an oil. The crude oil was chromatographed on silica gel with ethyl acetate/hexane to give 1.40 g (67%) of a yellow solid: mp 81-82° C.; $^1$H NMR: δ 3.53 (s, 6H), 3.95 (s, 6H), 5.29 (s, 4H), 6.97 (d, 2H, J=15.9 Hz), 7.17 (m, 6H), 7.69 (d, 2H, J=15.9 Hz); $^{13}$C NMR: δ 56.0, 56.4, 95.2, 110.8, 115.9, 122.5, 124.0, 124.6, 129.2, 142.8, 148.7, 149.8, 188.5.

1,5-Bis(3-methoxyphenyl)-1,4-pentadien-3-one (20k). 3-Methoxybenzaldehyde (1k, 3.09 ml, 25.4 mmol) and acetone (19, 0.94 ml, 12.7 mmol) were combined in ethanol (20 ml) and stirred for 15 min at room temperature. A solution of sodium hydroxide (1.50 g, 37.5 mmol) and water (20 ml) was added and the mixture stirred for 18 hr at room temperature. The resulting mixture was extracted into ethyl acetate, washed with saturated sodium chloride, dried over magnesium sulfate, filtered and evaporated to afford an oil. The crude oil was chromatographed on silica gel with ethyl acetate/hexane to yield a solid. The solid was recrystallized from ethanol to give 2.06 g (62%) of a yellow solid: mp 64-65° C. [expected mp 52-54° C.]; $^1$H NMR: δ 3.83 (s, 6H), 6.94 (dd, 2H, J=8.1, 2.4 Hz), 7.04 (d, 2H, J=15.9 Hz), 7.15 (m, 4H), 7.32 (t, 2H, J=8.0 Hz), 7.68 (d, 2H, J=16.1 Hz); $^{13}$C NMR: δ 55.2, 113.2, 116.2, 120.9, 125.5, 129.8, 136.0, 143.0, 159.8, 188.6.

1,5-Bis(2,6-dimethoxyphenyl)-1,4-pentadien-3-one (20l). 2,6-Dimethoxybenzaldehyde (20l, 1.00 g, 6.0 mmol) and acetone (19, 0.44 ml, 3.0 mmol) were combined in ethanol (10 ml) and stirred for 10 min at room temperature. A solution of sodium hydroxide (0.72 g, 9.0 mmol) and water (15 ml) was added and the mixture stirred for 18 hr at room temperature. The resulting precipitate was filtered and recrystallized from ethanol to give 0.66 g (63%) of a yellow solid: mp 152-154° C. [expected mp 152-154° C.]; $^1$H NMR: δ 3.90 (s, 12H), 6.57 (d, 4H, J=8.5 Hz), 7.26 (t, 2H, J=8.5 Hz), 7.59 (d, 2H, J=16.3 Hz), 8.17 (d, 2H, J=16.3 Hz); $^{13}$C NMR: δ 55.8, 103.7, 113.1, 129.0, 130.9, 133.3, 160.0, 192.4.

1,5-Bis(2,5-dimethoxyphenyl)-1,4-pentadien-3-one (20m). 2,5-Dimethoxybenzaldehyde (1m, 2.00 g, 12.0 mmol) and acetone (19, 0.44 ml, 6.0 mmol) were combined in ethanol (15 ml) and stirred for 15 min at room temperature. A solution of sodium hydroxide (0.72 g, 18.0 mmol) and water (15 ml) was added and the mixture stirred for 18 hr at room temperature. The resulting precipitate was filtered and recrystallized from ethanol to give 1.46 g (69%) of a yellow solid: mp 105-106° C. [expected mp 105-106° C.]; $^1$H NMR: δ 3.79 (s, 6H), 3.85 (s, 6H), 6.88 (m, 4H), 7.11 (d, 2H, J=2.8 Hz), 7.12 (d, 2H, J=16.1 Hz), 8.01 (d, 2H, J=16.1 Hz); $^{13}$C NMR: δ 55.8, 56.1, 112.4, 113.1, 117.1, 124.5, 126.3, 137.9, 153.0, 153.4, 189.6.

1,5-Bis(2,4-dimethoxyphenyl)-1,4-pentadien-3-one (20n). 2,4-Dimethoxybenzaldehyde (1n, 2.00 g, 12.0 mmol) and acetone (19, 0.44 ml, 6.0 mmol) were combined in ethanol (15 ml) and stirred for 15 min at room temperature. A solution of sodium hydroxide (0.72 g, 18.0 mmol) and water (15 ml) was added and the mixture stirred for 18 hr at room temperature. The resulting precipitate was filtered and recrystallized from ethanol to give 1.71 g (81%) of a yellow solid: mp 138-140° C. [expected mp 138-139° C.]; $^1$H NMR: δ 3.81 (s, 6H), 3.85 (s, 6H), 6.43 (d, 2H, J=2.2 Hz), 6.48 (dd, 2H, J=8.5, 2.2 Hz), 7.04 (d, 2H, J=16.1 Hz), 7.52 (d, 2H, J=8.5 Hz), 7.96 (d, 2H, J=16.1 Hz); $^{13}$C NMR: δ 55.4, 55.5, 98.3, 105.3, 117.1, 124.1, 130.0, 137.6, 159.9, 162.6, 189.7.

1,5-Bis(3,5-dimethoxyphenyl)-1,4-pentadien-3-one (20o). 3,5-Dimethoxybenzaldehyde (1o, 2.00 g, 12.0 mmol) and acetone (19, 0.44 ml, 6.0 mmol) were combined in ethanol (15 ml) and stirred for 15 min at room temperature. A solution of sodium hydroxide (0.72 g, 18.0 mmol) and water (15 ml) was added and the mixture stirred for 18 hr at room temperature. The resulting precipitate was filtered and recrystallized from ethanol to give 1.32 g (63%) of a yellow solid: mp 126-128° C. [expected mp 124.5-125.5° C.]; $^1$H NMR: δ 3.80 (s, 12H), 6.49 (s, 2H), 6.73 (d, 4H, J=2.0 Hz), 7.00 (d, 2H, J=15.9 Hz), 7.62 (d, 2H, J=15.7 Hz); $^{13}$C NMR: δ 55.4, 102.7, 106.2, 125.7, 136.8, 143.2, 160.9, 188.6.

1,5-Bis(3-hydroxyphenyl)-1,4-pentadien-3-one (20p). 3-Hydroxybenzaldehyde (1p, 2.07 g, 17.0) and acetone (19, 0.62 ml, 8.4 mmol) were combined in ethanol (15 ml) and stirred for 15 min at room temperature. A solution of sodium hydroxide (1.00 g, 25.0 mmol) and water (4 ml) was added and the solution stirred for 48 hr at room temperature. The resulting mixture was neutralized with hydrochloric acid (1 N), extracted with ethyl acetate, washed with saturated sodium chloride, dried over magnesium sulfate, filtered and evaporated to afford a solid. The crude solid was recrystallized from ethyl acetate to give 0.42 g (19%) of a brown solid: mp 190-195° C. [expected mp 198-200° C.]; $^1$H NMR: (DMSO) δ 6.83 (d, 2H, J=7.0 Hz), 7.22 (m, 8H), 7.68 (d, 2H, J=16.1 Hz), 9.63 (s, 2H); $^{13}$C NMR: (DMSO) δ 114.7, 117.5, 119.4, 125.4, 129.7, 135.8, 142.7, 157.5, 168.2.

1,5-Bis(2-hydroxyphenyl)-1,4-pentadien-3-one (20q). 2-Hydroxybenzaldehyde (1q, 1.81 ml, 17.0 mmol) and acetone (19, 0.62 ml, 8.4 mmol) were combined in ethanol (15 ml) and stirred for 15 min at room temperature. A solution of sodium hydroxide (1.00 g, 25.0 mmol) and water (4 ml) was added and the solution stirred for 1 week at room temperature. The mixture was neutralized with hydrochloric acid (1 N) and the resulting precipitate filtered and recrystallized from ethyl acetate/hexane to give 1.79 g (80%) of a yellow solid: mp 154-157° C. [expected mp 155° C.]; $^1$H NMR: (DMSO) δ 6.89 (m, 4H), 7.27 (m, 4H), 7.68 (d, 2H, J=7.4 Hz), 7.93 (d, 2H, J=16.1 Hz), 10.22 (s, 2H); $^{13}$C NMR: (DMSO) δ 116.1, 119.3, 121.3, 125.3, 128.5, 131.5, 137.6, 156.9, 188.5.

1,5-Bis(4-fluorophenyl)-1,4-pentadien-3-one (20r). 4-Fluorobenzaldehyde (1r, 0.75 ml, 7.0 mmol) and acetone (19, 0.26 ml, 3.5 mmol) were combined in ethanol (30 ml) and stirred for 10 min at room temperature. A solution of sodium hydroxide (0.50 g, 12.5 mmol) and water (20 ml) was added and the mixture stirred for 18 hr at room temperature. The resulting precipitate was filtered and recrystallized from ethanol to afford 0.82 g (86%) of a yellow solid: mp 150-152° C. [expected mp 152-154° C.]; $^1$H NMR: δ 6.97 (d, 2H, J=15.9 Hz), 7.09 (m, 4H), 7.58 (m, 4H), 7.68 (d, 2H, J=15.9 Hz); $^{13}$C NMR: δ 116.1, 1125.1, 130.2, 130.9, 142.0, 164.0, 188.3.

1,5-Bis(3-fluorophenyl)-1,4-pentadien-3-one (20s). 3-Fluorobenzaldehyde (1s, 0.5 ml, 4.7 mmol) and acetone (19, 0.18 ml, 2.3 mmol) were combined in ethanol (20 ml) and stirred for 10 min at room temperature. A solution of sodium hydroxide (0.29 g, 7.3 mmol) and water (15 ml) was added and the mixture stirred for 18 hr at room temperature. The resulting mixture was filtered and chromatographed on silica gel with ethyl acetate/hexane to give a solid. The crude was recrystallized from ethanol to afford 0.26 g (42%) of yellow crystals: mp 96-97° C. [expected mp 96-97° C.]; $^1$H NMR: δ 7.03 (d, 2H, J=16.1 Hz), 7.09 (m, 2H), 7.35 (m, 6H), 7.67 (d, 2H, J=15.9 Hz); $^{13}$C NMR: δ 114.4, 117.5, 124.4, 126.3, 130.4, 136.9, 142.0, 162.9, 188.1; Anal. Calcd for $C_{17}H_{12}OF_2$: C, 75.55; H, 4.48. Found: C, 75.26; H, 4.65.

1,5-Bis(2-fluorophenyl)-1,4-pentadien-3-one (20t). 2-Fluorobenzaldehyde (1t, 0.5 ml, 4.7 mmol) and acetone (19, 0.18 ml, 2.4 mmol) were combined in ethanol (20 ml) and stirred for 10 min at room temperature. A solution of sodium hydroxide (0.29 g, 7.3 mmol) and water (15 ml) was added and the mixture stirred for 18 hr at room temperature. The resulting mixture was filtered and chromatographed on silica gel with ethyl acetate/hexane to give a solid. The crude solid was recrystallized from ethanol to afford 0.27 g (41%) of yellow crystals: mp 68-72° C. [expected mp 68-70° C.]; $^1$H NMR: δ 7.13 (m, 6H), 7.36 (m, 2H), 7.61 (dt, 2H, J=7.6 Hz, 1.4 Hz), 7.84 (d, 2H, J=16.3 Hz); $^{13}$C NMR: δ 116.2, 122.8, 124.4, 127.6, 129.3, 131.8, 135.9, 161.5, 188.7.

1,5-Bis(4-trifluoromethyl)-1,4-pentadien-3-one (20u). 4-(Trifluoromethyl)benzaldehyde (1u, 0.50 ml, 3.7 mmol) and acetone (19, 0.13 ml, 1.8 mmol) were combined in ethanol (15 ml) and stirred for 10 min at room temperature. A solution of sodium hydroxide (0.22 g, 5.5 mmol) and water (15 ml) was added and the mixture stirred for 18 hr at room temperature. The resulting precipitate was filtered and recrystallized from ethanol to afford 0.57 g (87%) of a yellow solid: mp 151-154° C. [expected mp 156-157° C.]; $^1$H NMR: δ 7.12 (d, 2H, J=15.9 Hz), 7.69 (m, 8H), 7.73 (d, 2H, J=15.9 Hz); $^{13}$C NMR: δ 121.6, 125.9, 127.2, 128.5, 132.1, 138.0, 141.8, 187.9.

1,5-Bis(3-trifluoromethyl)-1,4-pentadien-3-one (20v). 3-(Trifluoromethyl)benzaldehyde (1v, 0.5 ml, 3.7 mmol) and acetone (19, 0.14 ml, 1.9 mmol) were combined in ethanol (15 ml) and stirred for 10 min at room temperature. A solution of sodium hydroxide (0.23 g, 5.8 mmol) and water (15 ml) was added and the mixture stirred for 18 hr at room temperature. The resulting mixture was filtered and chromatographed on silica gel with ethyl acetate/hexane to give a solid. The crude solid was recrystallized from ethanol to give 0.25 g (36%) of yellow crystals: mp 116-117° C. [expected mp 116-117° C.]; $^1$H NMR: δ 7.12 (d, 2H, J=15.9 Hz), 7.53 (t, 2H, J=7.6 Hz), 7.66 (d, 2H, J=8.0 Hz), 7.73 (d, 2H, J=7.2 Hz), 7.82 (m, 4H); $^{13}$C NMR: δ 123.7, 124.7, 126.7, 126.8, 129.5, 131.5, 131.6, 135.4, 141.8, 187.8; Anal. Calcd for $C_{19}H_{12}OF_6$: C, 61.63; H, 3.27. Found: C, 61.82; H, 3.28.

1,5-Bis(2-trifluoromethylphenyl)-1,4-pentadien-3-one (20w). 2-(Trifluoromethyl)-benzaldehyde (1w, 0.75 ml, 5.7 mmol) and acetone (19, 0.21 ml, 2.8 mmol) were combined in ethanol (20 ml) and stirred for 10 min at room temperature. A solution of sodium hydroxide (0.34 g, 8.5 mmol) and water (15 ml) was added and the mixture stirred for 18 hr at room temperature. The resulting precipitate was filtered and recrystallized from ethanol to afford 0.92 g (87%) of a yellow solid: mp 131-133° C. [expected mp 131° C.]; $^1$H NMR: δ 6.99 (d, 2H, J=15.9 Hz), 7.48 (t, 2H, J=7.6 Hz), 7.56 (t, 2H, J=7.0 Hz), 7.70 (d, 2H, J=7.7 Hz), 7.77 (d, 2H, J=7.6 Hz), 8.07 (d, 2H, J=15.7 Hz); $^{13}$C NMR: δ 123.9, 126.2, 127.9, 128.8, 129.4, 129.7, 132.1, 133.7, 139.1, 188.0.

1,5-Bis(4-chlorophenyl)-1,4-pentadien-3-one (20x). 4-Chlorobenzaldehyde (1x, 1.00 g, 7.1 mmol) and acetone (19, 0.26 ml, 3.5 mmol) were combined in ethanol (10 ml) and stirred for 15 min at room temperature. A solution of sodium hydroxide (0.40 g, 10.0 mmol) and water (10 ml) was added and the mixture stirred for 3 hr at room temperature. The resulting precipitate was filtered and recrystallized from ethyl acetate to give 0.75 g (70%) of yellow crystals: mp 187-189° C. [expected mp 191-193° C.]; $^1$H NMR: δ 7.00 (d, 2H, J=15.9 Hz), 7.37 (d, 4H, J=8.5 Hz), 7.52 (d, 4H, J=8.5 Hz), 7.66 (d, 2H, J=15.9 Hz); $^{13}$C NMR: δ 125.7, 129.2, 129.5, 133.2, 136.4, 141.9, 188.1.

1,5-Bis(3-chlorophenyl)-1,4-pentadien-3-one (20y). 3-Chlorobenzaldehyde (1y, 2.00 ml, 17.7 mmol) and acetone (19, 0.65 ml, 8.8 mmol) were combined in ethanol (20 ml) and stirred for 15 min at room temperature. A solution of sodium hydroxide (1.00 g, 25.0 mmol) and water (20 ml) was added and the mixture stirred for 2 hr at room temperature. The resulting precipitate was filtered and recrystallized from ethyl acetate to give 2.41 g (90%) of a yellow solid: mp 125-127° C. [expected mp 120-121° C.]; $^1$H NMR: δ 7.03 (d, 2H, J=15.9 Hz), 7.33 (m, 4H), 7.45 (d, 2H, J=6.6 Hz), 7.58 (m, 2H), 7.64 (d, 2H, J=15.9 Hz); $^{13}$C NMR: δ 126.3, 126.6, 127.9, 130.1, 130.3, 134.9, 136.5, 141.8, 188.0.

1,5-Bis(2-chlorophenyl)-1,4-pentadien-3-one (20z). 2-Chlorobenzaldehyde (1z, 2.00 ml, 17.8 mmol) and acetone (19, 0.65 ml, 8.8 mmol) were combined in ethanol (20 ml) and stirred for 15 min at room temperature. A solution of sodium hydroxide (1.00 g, 25.0 mmol) and water (20 ml) was added and the mixture stirred for 18 hr at room temperature. The resulting precipitate was filtered and recrystallized from ethyl acetate to give 1.80 g (67%) of a yellow solid: mp 119-121° C. [expected mp 110° C.]; $^1$H NMR: δ 7.04 (d, 2H, J=16.1 Hz), 7.29 (m, 4H), 7.41 (m, 2H), 7.67 (m, 2H), 8.11 (d, 2H, J=16.1 Hz); $^{13}$C NMR: δ 127.0, 127.5, 127.6, 130.1, 131.1, 132.9, 135.3, 139.2, 188.4.

1,5-Bis(4-methylphenyl)-1,4-pentadien-3-one (20aa). 4-Methylbenzaldehyde (1aa, 1.50 ml, 12.7 mmol) and acetone (19, 0.47 ml, 6.4 mmol) were combined in ethanol (10 ml) and stirred for 15 min at room temperature. A solution of sodium hydroxide (0.52 g, 13.0 mmol) and water (10 ml) was added and the mixture stirred for 1 hr at room temperature. The resulting precipitate was filtered and recrystallized from ethanol to give 1.30 g (78%) of a yellow solid: mp 174-176° C. [expected mp 171-172° C.]; $^1$H NMR: δ 2.37 (s, 6H), 7.02 (d, 2H, J=15.9 Hz), 7.20 (d, 4H, J=8.0 Hz), 7.50 (d, 4H, J=7.9 Hz), 7.70 (d, 2H, J=15.9 Hz); $^{13}$C NMR: δ 21.6, 124.6, 128.3, 129.6, 132.1, 140.8, 143.0, 188.9.

1,5-Bis(3-methylphenyl)-1,4-pentadien-3-one (20ab). 3-Methylbenzaldehyde (1ab, 3.00 ml, 25.4 mmol) and acetone (19, 0.94 ml, 12.7 mmol) were combined in ethanol (20 ml) and stirred for 15 min at room temperature. A solution of sodium hydroxide (1.50 g, 37.5 mmol) and water (20 ml) was added and the mixture stirred for 18 hr at room temperature. The resulting mixture was extracted into ethyl acetate, washed with saturated sodium chloride, dried over magnesium sulfate, filtered and evaporated to afford a solid. The crude solid was recrystallized from ethanol to give 2.39 g (72%) of a yellow solid: mp 68-72° C. [expected mp 68-72° C.]; $^1$H NMR: δ 2.38 (s, 6H), 7.06 (d, 2H, J=15.9 Hz), 7.26 (m, 4H), 7.40 (m, 4H), 7.70 (d, 2H, J=15.9 Hz); $^{13}$C NMR: δ 21.3, 125.1, 125.4, 128.6, 128.8, 131.1, 134.6, 138.4, 143.1, 188.6.

1,5-Bis(2-methylphenyl)-1,4-pentadien-3-one (20ac). 2-Methylbenzaldehyde (1ac, 1.45 ml, 12.5 mmol) and acetone (19, 0.46 ml, 6.3 mmol) were combined in ethanol (20 ml) and stirred for 15 min at room temperature. A solution of sodium hydroxide (2.61 g, 65.3 mmol) and water (25 ml) was added and the mixture stirred for 3 hr at room temperature. The resulting mixture was extracted into ethyl acetate, washed with saturated sodium chloride, dried over magnesium sulfate, filtered and evaporated to afford a solid. The crude solid was recrystallized from ethanol to give 0.71 g (43%) of a yellow solid: mp 98-100° C. [expected mp 94-96° C.]; $^1$H NMR: δ 2.47 (s, 6H), 6.98 (d, 2H, J=15.9 Hz), 7.24 (m, 6H), 7.64 (d, 2H, J=7.2 Hz), 8.03 (d, 2H, J=15.9 Hz); $^{13}$C NMR: δ 19.7, 126.1, 126.2, 126.5, 129.9, 130.7, 133.6, 137.9, 140.5, 188.5.

1,5-Bis(4-carbmethoxyphenyl)-1,4-pentadien-3-one (20ae). 4-Carbmethoxybenzaldehyde (1ae, 0.62 g, 3.8 mmol) and acetone (19, 0.14 ml, 1.9 mmol) were combined in methanol (20 ml) and stirred under a nitrogen atmosphere for 15 min at room temperature. A solution of sodium hydroxide (0.15 g, 3.8 mmol) in water (5 ml) was added the mixture stirred for 18 hr at room temperature under a nitrogen atmosphere. The resulting precipitate was filtered and recrystallized from xylene to give 0.29 g (44%) of a yellow solid: mp 206-210° C. [expected mp 221-223° C.]; $^1$H NMR: δ 3.92 (s, 6H), 7.12 (d, 2H, J=16.1 Hz), 7.65 (d, 4H, J=8.1 Hz), 7.73 (d, 2H, J=15.9 Hz), 8.06 (d, 4H, J=8.0 Hz); $^{13}$C NMR: δ 52.3, 127.1, 128.1, 130.1, 131.6, 138.8, 142.1, 166.2, 188.0.

1,5-Bis(3,4-dihydroxyphenyl)-1,4-pentadien-3-one (20af). 1,5-Bis(3,4-dimethoxyphenyl)-1,4-pentadien-3-one (20i, 0.56 g, 1.6 mmol) was dissolved in dichloromethane (10 ml) and stirred under a nitrogen atmosphere at −78° C. for 5 min. Boron tribromide (0.90 ml, 9.5 mmol) was added and stirring continued for 60 min at −78° C., 60 min at 0° C. and 60 min at room temperature. The mixture was poured into hydrochloric acid (30 ml, 1 N) and stirring was continued for 18 hr at room temperature. The resulting mixture was extracted into ethyl acetate, washed with water and saturated sodium chloride, dried over magnesium sulfate, filtered and evaporated to afford a solid. The crude solid was chromatographed on silica gel with ethyl acetate/hexane to give 0.36 g (76%) of an orange solid: mp>250° C. [expected mp 221-223° C.]; $^1$H NMR: (DMSO) δ 6.78 (d, 2H, J=8.1 Hz), 6.99 (d, 2H, J=15.9 Hz), 7.06 (d, 2H, J=7.9 Hz), 7.14 (s, 2H), 7.55 (d, 2H, J=15.7 Hz), 9.15 (s, 2H), 9.63 (s, 2H); $^{13}$C NMR: (DMSO) δ 114.9, 115.6, 121.5, 122.5, 126.2, 142.5, 145.4, 148.2, 187.6.

1,5-Bis(4-acetoxy-3-methoxyphenyl)-1,4-pentadien-3-one (20ag). 1,5-Bis(4-hydroxy-3-methoxyphenyl)-1,4-pentadien-3-one (20a, 0.32 g, 1.0 mmol) was dissolved in acetic anhydride (21, 7.00 ml, 74.1 mmol) and stirred for 5 min at room temperature. Pyridine (0.70 ml, 8.7 mmol) was added and the mixture stirred for 30 min at 100° C. The resulting mixture was poured into water, extracted with ethyl acetate, washed with saturated sodium chloride, dried over magnesium sulfate, filtered and evaporated to afford a solid. The crude solid was recrystallized from tetrahydrofuran/hexane to give 0.36 g (88%) of a yellow solid: mp 179-180° C. [expected mp 150° C.]; $^1$H NMR: δ 2.31 (s, 6H), 3.87 (s, 6H), 6.98 (d, 2H, J=15.9 Hz), 7.06 (d, 2H, J=8.1 Hz), 7.18 (m, 4H), 7.67 (d, 2H, J=15.9 Hz); $^{13}$C NMR: δ 20.7, 56.0, 111.7, 121.4, 123.3, 125.5, 133.7, 141.6, 142.6, 151.4, 168.5, 188.3; Exact mass calcd for $C_{23}H_{22}O_7$: 410.1366, observed (M+H) 411.1444.

1,5-Bis(4-acetoxyphenyl)-1,4-pentadien-3-one (20ah). 1,5-Bis(4-hydroxyphenyl)-1,4-pentadien-3-one (20f, 0.26 g, 1.0 mmol) was dissolved in acetic anhydride (21, 7.00 ml, 74.1 mmol) and stirred for 5 min at room temperature. Pyridine (0.70 ml, 8.7 mmol) was added and the mixture stirred for 30 min at 100° C. The resulting mixture was poured into water, extracted with ethyl acetate, washed with saturated sodium chloride, dried over magnesium sulfate, filtered and evaporated to afford a solid. The crude solid was recrystallized from tetrahydrofuran/hexane to give 0.28 g (82%) of a yellow solid: mp 167-168° C. [expected mp 167-168° C.]; $^1$H NMR: δ 2.30 (s, 6H), 7.00 (d, 2H, J=15.9 Hz), 7.13 (d, 4H, J=8.3 Hz), 7.60 (d, 4H, J=8.2 Hz), 7.69 (d, 2H, J=15.9 Hz); $^{13}$C NMR: δ 21.1, 122.1, 125.4, 129.4, 132.4, 142.1, 152.2, 168.9, 188.3; Exact mass calcd for $C_{21}H_{18}O_5$: 350.1154, observed (M+H) 351.1232.

1,5-Bis(1-naphthyl)-1,4-pentadien-3-one (23). 1-Naphthaldehyde (22, 1.36 ml, 10.0 mmol) and acetone (19, 0.37 ml, 5.0 mmol) were combined in ethanol (10 ml) and stirred for 15 min at room temperature. A solution of sodium hydroxide (0.40 g, 10.0 mmol) and water (10 ml) was added and the mixture stirred for 18 hr at room temperature. The resulting mixture was extracted into ethyl acetate, washed with saturated sodium chloride, filtered and evaporated to afford a solid. The crude solid was recrystallized from ethyl acetate to give 0.63 g (38%) of a yellow solid: mp 132-133° C. [expected mp 128° C.]; $^1$H NMR: δ 7.24 (d, 2H, J=15.7 Hz), 7.57 (m, 6H), 7.92 (m, 6H), 8.28 (d, 2H, J=8.0 Hz), 8.65 (d, 2H, J=15.5 Hz); $^{13}$C NMR: δ 123.4, 125.1, 125.4, 126.2, 126.9, 128.1, 128.7, 130.7, 131.7, 132.2, 133.7, 140.3, 188.5.

1,5-Bis(2-naphthyl)-1,4-pentadien-3-one (25). 2-Naphthaldehyde (24, 1.56 g, 10.0 mmol) and acetone (19, 0.37 ml, 5.0 mmol) were combined in ethanol (10 ml) and stirred for 15 min at room temperature. A solution of sodium hydroxide (0.60 g, 15.0 mmol) and water (10 ml) was added and the mixture stirred for 18 hr at room temperature. The resulting precipitate was filtered and recrystallized from ethanol to give 1.16 g (69%) of a yellow solid: mp 244-246° C. [expected mp 243-244° C.]; $^1$H NMR: δ 7.23 (d, 2H, J=15.9 Hz), 7.52 (m, 4H), 7.83 (m, 8H), 7.93 (d, 2H, J=15.9 Hz), 8.03 (s, 2H); $^{13}$C NMR: δ 123.6, 125.7, 126.7, 127.3, 127.8, 128.6, 128.7, 130.5, 132.3, 133.3, 134.3, 143.1, 190.0.

1,5-Bis(4-pyridinium chloride)-1,4-pentadien-3-one (28). 1,3-Acetonedicarboxylic acid (27, 1.05 g, 7.2 mmol) was dissolved in ethanol (10 ml) and stirred for 15 min at room temperature. 4-Pyridinecarboxaldehyde (26, 1.37 ml, 14.4 mmol) was added dropwise and the mixture stirred for 2 hr at room temperature. Hydrochloric acid (5 ml) was added and the mixture stirred for 1 hr at 80° C. The resulting precipitate was filtered and recrystallized from water/acetone to give 0.59 g (27%) of a yellow solid: mp 247-249° C. [expected mp 247-249° C.]; $^1$H NMR: (D$_2$O) δ 7.54 (d, 2H, J=16.3 Hz), 7.78 (d, 2H, J=15.9 Hz), 8.15 (d, 4H, J=6.6 Hz), 8.70 (d, 4H, J=6.6 Hz); $^{13}$C NMR: (D$_2$O) δ 128.2, 136.2, 141.3, 144.2, 154.4, 193.0.

1,5-Bis(4-pyridyl)-1,4-pentadien-3-one (29). 1,5-Bis(4-pyridinium chloride)-1,4-pentadien-3-one (28, 0.25 g, 0.8 mmol) and sodium hydroxide (0.80 g, 20 mmol) were combined in water (20 ml) and stirred for 15 min at room temperature. The resulting mixture was extracted with ethyl acetate, washed with saturated sodium chloride, dried over magnesium sulfate, filtered and evaporated to afford a solid. The crude solid was recrystallized from ethyl acetate/hexane to give 0.16 g (84%) of a yellow solid: mp 145-146° C. [expected mp 149° C.]; $^1$H NMR: δ 7.17 (d, 2H, J=15.9 Hz), 7.42 (d, 4H, J=5.6 Hz), 7.63 (d, 2H, J=15.9 Hz), 8.67 (d, 4H, J=5.6 Hz); $^{13}$C NMR: δ 121.9, 128.6, 141.0, 141.6, 150.6, 172.5.

1,5-Bis(3-pyridinium chloride)-1,4-pentadien-3-one (31). 1,3-Acetonedicarboxylic acid (27, 1.05 g, 7.2 mmol) was dissolved in ethanol (10 ml) and stirred for 15 min at room temperature. 3-Pyridinecarboxaldehyde (30, 1.36 ml, 14.4 mmol) was added dropwise and the mixture stirred for 2 hr at room temperature. Hydrochloric acid (5 ml) was added and the mixture stirred for 1 hr at 80° C. The resulting mixture was filtered to afford a solid. The crude solid was recrystallized from water/acetone to give 1.57 g (71%) of a yellow solid: mp>250° C. [expected mp>250° C.]; $^1$H NMR: (D$_2$O) δ 7.40 (d, 2H, J=16.3 Hz), 7.78 (d, 2H, J=16.1 Hz), 8.02 (t, 2H, J=7.9 Hz), 8.70 (d, 2H, J=5.6 Hz), 8.79 (d, 2H, J=7.9 Hz), 8.98 (s, 2H); $^{13}$C NMR: (D$_2$O) δ 130.1, 132.8, 136.9, 139.9, 143.7, 144.3, 147.3, 193.0.

1,5-Bis(3-pyridyl)-1,4-pentadien-3-one (32). 1,5-Bis(3-pyridinium chloride)-1,4-pentadien-3-one (31, 0.50 g, 1.6 mmol) and sodium hydroxide (1.6 g, 40 mmol) were combined in water (40 ml) and stirred for 15 min at room temperature. The resulting mixture was extracted with ethyl acetate, washed with saturated sodium chloride, dried over magnesium sulfate, filtered and evaporated to afford a solid. The crude solid was recrystallized from ethyl acetate/hexane to give 0.31 g (81%) of a yellow solid: mp 148-149° C. [expected mp 150° C.]; $^1$H NMR: δ 7.11 (d, 2H, J=16.1 Hz), 7.32 (m, 2H), 7.71 (d, 2H, J=15.9 Hz), 7.90 (d, 2H, J=6.2 Hz), 8.61 (d, 2H, J=4.6 Hz), 8.81 (s, 2H); $^{13}$C NMR: δ 123.7, 126.7, 130.3, 134.4, 139.9, 149.9, 151.1, 198.6.

1,5-Bis(2-thienyl)-1,4-pentadien-3-one (34). 2-Thiophenecarboxaldehyde (33, 0.50 ml, 5.3 mmol) and acetone (19, 0.20 ml, 2.7 mmol) were combined in ethanol (10 ml) and stirred for 10 min at room temperature. A solution of sodium hydroxide (0.30 g, 7.5 mmol) and water (10 ml) was added and the mixture stirred for 18 hr at room temperature. The resulting precipitate was filtered and recrystallized from ethanol/water to give 0.55 g (82%) of a yellow solid: mp 115-117° C. [expected mp 115-117° C.]; $^1$H NMR: δ 6.80 (d, 2H, J=15.5 Hz), 7.06 (dt, 2H, J=3.6, 1.4 Hz), 7.31 (d, 2H, J=3.4 Hz), 7.39 (d, 2H, J=5.0 Hz), 7.82 (d, 2H, J=15.5 Hz); $^{13}$C NMR: δ 124.4, 128.2, 128.7, 131.7, 135.5, 140.2, 187.5.

1-(4-Hydroxy-3-methoxyphenyl)-1-buten-3-one (35a). 1-(4-Methoxymethyloxy-3-methoxyphenyl)-1-buten-3-one (35j, 0.40 g, 1.7 mmol) was dissolved in methanol (40 ml) and stirred for 15 min at 50° C. Hydrochloric acid (3 drops) was added and the mixture stirred for 18 hr at 65° C. The methanol was evaporated and the resulting residue extracted into ethyl acetate, washed with saturated sodium chloride, dried over magnesium sulfate, filtered and evaporated to afford a solid. The crude solid was chromatographed on silica gel with ethyl acetate/hexane to give 0.24 g (74%) of an orange-yellow solid: mp 120-122° C. [expected mp 128-129° C.]; $^1$H NMR: δ 2.34 (s, 3H), 3.91 (s, 3H), 5.98 (s, 1H), 6.56 (d, 1H, J=16.1 Hz), 6.91 (d, 1H, J=8.2 Hz), 7.04 (m, 2H), 7.43 (d, 1H, J=16.3 Hz); $^{13}$C NMR: δ 27.3, 56.0, 109.3, 114.8, 123.4, 124.9, 126.9, 143.6, 146.8, 148.2, 198.2.

1-(4-Methoxyphenyl)-1-buten-3-one (35e). 4-Methoxybenzaldehyde (1e, 0.63 ml, 5.2 mmol) and acetone (19, 4.00 ml, 54.0 mmol) were combined in ethanol (4 ml) and stirred for 15 min at room temperature. A solution of sodium hydroxide (0.40 g, 10.0 mmol) and water (4 ml) was added dropwise and the mixture stirred for 1 hr at room temperature. The resulting mixture was extracted into ethyl acetate, washed with saturated sodium chloride, dried over magnesium sulfate, filtered and evaporated to afford a solid. The crude solid was recrystallized from ether/hexane to give 0.57 g (62%) of a yellow solid: mp 71-73° C. [expected mp 68° C.]; $^1$H NMR: δ 2.34 (s, 3H), 3.83 (s, 3H), 6.59 (d, 1H, J=16.3 Hz), 6.90 (d, 2H, J=8.7 Hz), 7.46 (d, 1H, J=16.3 Hz), 7.48 (d, 2H, J=8.7 Hz); $^{13}$C NMR: δ 27.5, 55.4, 114.4, 125.0, 127.1, 129.9, 143.1, 161.5, 198.1.

1-(4-Methoxymethyloxy-3-methoxyphenyl)-1-buten-3-one (35j). 4-Methoxymethyloxy-3-methoxybenzaldehyde (1j, 2.30 g, 11.7 mmol) and acetone (19, 8.75 ml, 118.4 mmol) were combined in ethanol (20 ml) and stirred for 15 min at room temperature. A solution of sodium hydroxide (0.80 g, 20.0 mmol) and water (20 ml) was added and the mixture stirred for 1 hr at room temperature. The resulting mixture was extracted into ethyl acetate, washed with saturated sodium chloride, dried over magnesium sulfate, filtered and evaporated to afford a solid. The crude solid was recrystallized from hexane to give 2.70 g (97%) of a white solid: mp 73-75° C.; $^1$H NMR: δ 2.34 (s, 3H), 3.48 (s, 3H), 3.89 (s, 3H), 5.24 (s, 2H), 6.58 (d, 1H, J=16.1 Hz), 7.07 (m, 2H), 7.13 (d, 1H, J=8.7 Hz), 7.43 (d, 1H, J=16.1 Hz); $^{13}$C NMR: δ 27.4, 55.9, 56.3, 95.2, 110.4, 115.9, 122.5, 125.7, 128.7, 143.1, 148.7, 149.8, 198.0.

1-(2-Hydroxyphenyl)-1-buten-3-one (35q). 2-Hydroxybenzaldehyde (1q, 0.90 ml, 8.4 mmol) and acetone (19, 1.24 ml, 16.8 mmol) were combined in ethanol (7 ml) and stirred for 15 min at room temperature. A solution of sodium hydroxide (0.5 g, 12.5 mmol) and water (2 ml) was added dropwise and the mixture stirred for 48 hr at room temperature. The mixture was neutralized with hydrochloric acid (1 N), extracted with ethyl acetate, washed with saturated sodium chloride, dried over magnesium sulfate, filtered and evaporated to afford a solid. The crude solid was recrystallized from tetrahydrofuran/hexane to give 0.36 g (26%) of a yellow solid: mp 136-137° C. [expected mp 139-140° C.]; $^1$H NMR: δ 2.42 (s, 3H), 6.92 (m, 2H), 7.03 (d, 1H, J=16.5 Hz), 7.24 (dt, 1H, J=7.0, 1.4 Hz), 7.45 (d, 1H, J=7.7 Hz), 7.88 (d, 1H, J=16.3 Hz), 8.00 (s, 1H); $^{13}$C NMR: δ 26.8, 116.6, 120.5, 127.5, 129.5, 131.9, 141.0, 156.1, 156.1, 201.3.

1-(4-Hydroxy-3-methoxyphenyl)-5-phenyl-1,4-pentadien-3-one (36a). 1-(4-Methoxymethyloxy-3-methoxyphenyl)-1-buten-3-one (35j, 1.00 g, 4.2 mmol) and benzaldehyde (1b, 0.46 ml, 4.5 mmol) were combined in ethanol (10 ml) and stirred for 15 min at room temperature. A solution of sodium hydroxide (0.30 g, 7.5 mmol) and water (10 ml) was added and the mixture stirred for 18 hr at room temperature. The resulting mixture was extracted into ethyl acetate, washed with saturated sodium chloride, dried over magnesium sulfate, filtered and evaporated to give 1.35 g (99%) of an oil which was used without purification. The oil (36j, 1.30 g, 4.0 mmol) was stirred in methanol (50 ml) for 15 min at 60° C. Concentrated hydrochloric acid (3 drops) was added and the solution stirred for 18 hr at 60° C. The methanol was evaporated and the resulting residue extracted into ethyl acetate, washed with saturated sodium chloride, dried over magnesium sulfate, filtered and evaporated to afford a semi-solid. The crude semi-solid was chromatographed on silica gel with ethyl acetate/hexane to give 0.41 g (36%) of a yellow oil; $^1$H NMR δ 3.92 (s, 3H), 6.08 (s, 1H), 6.91 (d, 1H, J=16.1 Hz), 6.93 (d, 1H, J=8.2 Hz), 7.07 (d, 1H, J=15.9 Hz), 7.10 (s, 1H), 7.15 (d, 1H, J=8.0 Hz), 7.38 (m, 3H), 7.59 (m, 2H), 7.67 (d, 1H, J=15.9 Hz), 7.71 (d, 1H, J=15.9 Hz); $^{13}$C NMR: δ 56.0, 109.8, 114.9, 123.4, 125.3, 127.3, 128.3, 128.8, 130.3, 134.9, 142.8, 143.5, 146.8, 148.3, 188.7.

1-(4-Methoxyphenyl)-5-phenyl-1,4-pentadien-3-one (36e). 1-(4-Methoxyphenyl)-1-buten-3-one (35e, 0.29 g, 1.6 mmol) was dissolved in methanol (5 ml) and stirred for 5 min at room temperature. A solution of sodium hydroxide (0.14 g, 3.5 mmol) and water (5 ml) was added and the mixture stirred for 30 min at room temperature. Benzaldehyde (1b, 0.17 ml, 1.7 mmol) was added dropwise and the mixture stirred for 18 hr at room temperature. The resulting precipitate was filtered and recrystallized from ethanol to give 0.41 g (94%) of a yellow solid: mp 85-89° C. [expected mp 118-119° C.]; $^1$H NMR: δ 3.82 (s, 3H), 6.91 (d, 2H, J=8.5 Hz), 6.94 (d, 1H, J=15.9 Hz), 7.06 (d, 1H, J=16.1 Hz), 7.38 (m, 4H), 7.57 (m, 3H), 7.71 (dd, 2H, J=15.9, 2.0 Hz); $^{13}$C NMR: δ 55.4, 114.4, 123.3, 125.5, 127.4, 128.2, 128.8, 130.0, 130.2, 134.8, 142.6, 143.0, 161.5, 188.6.

2,6-Bis(4-hydroxy-3-methoxybenzylidene)cyclohexanone (38a). 2,6-Bis(4-methoxymethyloxy-3-methoxybenzylidene)cyclohexanone (38j, 0.49 g, 1.1 mmol) was dissolved in methanol (100 ml) and stirred for 15 min at room temperature. Concentrated hydrochloric acid (3 drops) was added and the mixture stirred for 3 hr at 60° C. The methanol was evaporated and the resulting residue extracted into ethyl acetate, washed with saturated sodium chloride, dried over magnesium sulfate, filtered and evaporated to afford a solid. The crude solid was recrystallized from ethanol to give 0.26 g (66%) of a yellow solid: mp 177-178° C. [expected mp 179-181° C.]; $^1$H NMR: δ 1.79 (m, 2H), 2.90 (t, 4H, J=5.4 Hz), 3.89 (s, 6H), 5.88 (s, 2H), 6.91 (s, 2H), 6.96 (d, 2H, J=4.8 Hz), 7.06 (d, 2H, J=8.0 Hz), 7.72 (s, 2H); $^{13}$C NMR: δ 23.1, 28.5, 56.0, 113.2, 114.4, 124.4, 128.5, 134.2, 136.9, 146.2, 146.4, 172.8.

2,6-Bis(benzylidene)cyclohexanone (38b). Benzaldehyde (1b, 1.00 ml, 9.8 mmol) and cyclohexanone (37, 0.51 ml, 4.9 mmol) were combined in ethanol (10 ml) and stirred for 15 min at room temperature. A solution of sodium hydroxide (0.40 g, 10 mmol) and water (10 ml) was added and the mixture stirred for 18 hr at room temperature. The resulting precipitate was filtered and recrystallized from ethyl acetate to give 0.99 g (73%) of yellow crystals: mp 118-119° C. [expected mp 117° C.]; $^1$H NMR: δ 1.77 (m, 2H), 2.92 (t, 4H, J=5.2 Hz), 7.39 (m, 10H), 7.80 (s, 2H); $^{13}$C NMR: δ 23.1, 28.5, 128.3, 128.5, 130.2, 135.9, 136.1, 136.8, 190.1.

2,6-Bis(4-methoxymethyloxy-3-methoxybenzylidene)cyclohexanone (38j). 4-Methoxymethyloxy-3-methoxybenzaldehyde (1j, 2.08, 10.1 mmol) and cyclohexanone (37, 0.55 ml, 5.3 mmol) were combined in ethanol (10 ml) and stirred for 15 min at room temperature. A solution of sodium hydroxide (0.40 g, 10.0 mmol) and water (10 ml) was added and the mixture stirred for 18 hr at room temperature. The resulting precipitate was filtered and recrystallized from ethyl acetate to give 1.66 g (69%) of a yellow solid: mp 73-75° C.; $^1$H NMR: δ 1.81 (m, 2H), 2.90 (t, 4H, J=5.2 Hz), 3.52 (s, 6H), 3.91 (s, 6H), 5.26 (s, 4H), 7.05 (m, 4H), 7.17 (d, 2H, J=7.9 Hz), 7.74 (s, 2H); $^{13}$C NMR: δ 22.9, 28.4, 55.8, 56.1, 95.1, 114.1, 115.6, 123.4, 130.2, 134.7, 136.4, 146.8, 149.1, 190.3.

1,5-Diphenylpentan-3-one (39b). 1,5-Diphenyl-1,4-pentadien-3-one (20b, 1.00 g, 4.3 mmol) and palladium on activated carbon (0.25 g, 5%) were combined in ethyl acetate (50 ml). The mixture was placed under a hydrogen atmosphere (60 psi) on a Parr apparatus for 2 hr at room temperature. The resulting mixture was filtered through celite and the solvent evaporated to afford an oil. The crude oil was chromatographed on silica gel with ethyl acetate/hexane to give 0.82 g (80%) of a clear oil; $^1$H NMR: δ 2.76 (t, 4H, J=7.6 Hz), 2.97 (t, 4H, J=7.4 Hz), 7.30 (m, 10H); $^{13}$C NMR: δ 29.6, 44.2, 125.8, 128.0, 128.2, 140.7, 208.4.

1,5-Diphenylpentan-3-ol (40b). 1,5-Diphenyl-1,4-pentadien-3-one (20b, 1.00 g, 4.3 mmol) and palladium on activated carbon (0.25 g, 5%) were combined in ethyl acetate (50 ml). The mixture was placed under a hydrogen atmosphere (60 psi) on a Parr apparatus for 2 hr at room temperature. The resulting mixture was filtered through celite and the solvent evaporated to afford an oil. The crude oil was chromatographed on silica gel with ethyl acetate/hexane to give 0.12 g (12%) of a white solid: mp 47-49° C. [expected mp 45-46° C.]; $^1$H NMR: δ 1.86 (m, 4H), 2.77 (m, 4H), 3.70 (m, 1H), 7.31 (m, 10H); $^{13}$C NMR: δ 32.1, 39.2, 70.8, 125.6, 128.3, 142.0.

trans,trans-1,2,4,5-Diepoxy-1,5-diphenylpentan-3-one (42b) and cis,cis-1,2,4,5-diepoxy-1,5-diphenylpentan-3-one (43b). Potassium fluoride dihydrate (9.40 g, 0.1 mol) and neutral aluminum oxide (10.0 g, 98.1 mmol) were combined in water (100 ml) and stirred for 30 min at room temperature. The water was evaporated and the resulting material placed in an oven for 5 days at 125° C. A suspension of potassium fluoride-aluminum oxide (0.48 g, 3.0 mmol) in acetonitrile (6 ml) was added to a solution of 1,5-diphenyl-1,4-pentadien-3-one (20b, 0.47 g, 2.0 mmol) in acetonitrile (1.0 ml) and the mixture stirred for 15 min at room temperature. t-Butyl hydroperoxide (41, 1.7 ml, 17.7 mmol, 70% solution in water) was extracted with dichloroethane (6 ml), dried over magnesium sulfate, filtered, added to the suspension and stirred for 30 min at room temperature. The resulting mixture was filtered and the solvent evaporated to afford a solid. The crude solid was chromatographed on silica gel with ethyl acetate/hexane to give a mixture of isomers 42b and 43b. The crude solid was recrystallized twice from ethanol to give 0.21 g (39%) of 42b as white crystals: mp 117-119° C. [expected mp 118-118.5° C.]; $^1$H NMR: δ 3.80 (d, 2H, J=1.4 Hz), 4.09 (d, 2H, J=1.4 Hz), 7.30 (m, 10H); $^{13}$C NMR: δ 59.0, 60.9, 125.7, 128.7, 129.2, 134.5, 199.0. The filtrate was evaporated to give 0.25 g (47%) of 43b as a yellow oil; $^1$H NMR: δ 3.72 (d, 2H, J=1.6 Hz), 4.18 (d, 2H, J=1.6 Hz), 7.33 (m, 10H); $^{13}$C NMR: δ 58.9, 60.3, 125.8, 128.7, 129.2, 134.5, 199.0.

4-Methoxymethyloxy-3-methoxyacetophenone (44j). 4-Hydroxy-3-methoxyacetophenone (44a, 2.5 g, 15 mmol) and potassium carbonate (15.0 g, 108.5 mmol) were combined in dimethyl formamide (50 ml) and stirred for 15 min at room temperature. Chloromethyl methyl ether (18, 1.25 ml, 16.5 mmol) was added and stirring was continued for 4 hr at room temperature. Potassium carbonate was filtered and the filtrate extracted into ethyl acetate, washed with saturated sodium chloride, dried over magnesium sulfate, filtered and evaporated to 3.09 g (98%) of an oil; $^1$H NMR: δ 2.38 (s, 3H), 3.33 (s, 3H), 3.75 (s, 3H), 5.12 (s, 2H), 6.99 (d, 1H, J=8.9 Hz), 7.35 (dd, 1H, J=6.6, 2.0 Hz), 7.82 (s, 1H).

1,3-Bis(4-hydroxy-3-methoxyphenyl)-2-propen-1-one (45a). 4-Methoxymethyloxy-3-methoxyacetophenone (44j, 2.14 g, 10.2 mmol) and barium hydroxide octahydrate (3.25 g, 10.3 mmol) were combined in methanol (50 ml) and stirred for 15 min at 50° C. 4-Methoxymethyloxy-3-methoxybenzaldehyde (1j, 2.00 g, 10.2 mmol) was added and the mixture stirred for 18 hr at 50° C. The methanol was evaporated and the resulting residue extracted into ethyl acetate, washed with saturated sodium chloride, dried over magnesium sulfate, filtered and evaporated to give 3.90 g (99%) of an oil which was used without purification: $^1$H NMR: δ 3.50 (s, 6H), 3.92 (s, 3H), 3.94 (s, 3H), 5.25 (s, 2H), 5.30 (s, 2H), 7.18 (m, 4H), 7.39 (d, 1H, J=15.5 Hz), 6.61 (m, 2H), 7.73 (d, 1H, J=15.5 Hz). The oil (45j, 1.10 g, 2.8 mmol) was stirred in methanol (50 ml) for 5 min at 60° C. Concentrated hydrochloric acid (3 drops) was added and the mixture stirred for 3 hr at 60° C. The methanol was evaporated and the resulting residue was extracted into ethyl acetate, washed with saturated sodium chloride, dried over magnesium sulfate, filtered and evaporated to afford an oil. The crude oil was chromatographed on silica gel to give 0.47 g (55%) of a yellow solid: mp 111-114° C. [expected mp 126-128° C.]; $^1$H δ 3.94 (s, 3H), 3.95 (s, 3H), 6.00 (s, 1H), 6.19 (s, 1H), 6.95 (m, 2H), 7.11 (d, 1H, J=1.6 Hz), 7.20 (dd, 1H, J=8.3, 1.6 Hz), 7.38 (d, 1H, J=15.5 Hz), 7.61 (m, 2H), 7.73 (d, 1H, J=15.7 Hz); $^{13}$C NMR: δ 56.0, 56.1, 110.0, 110.5, 113.6, 114.8, 119.2, 123.0, 123.4, 127.6, 131.1, 144.2, 146.7, 146.8, 148.0, 150.1, 188.4.

1,3-Diphenyl-propenone (45b). Acetophenone (44b, 1.20 ml, 10.3 mmol) and sodium hydroxide (0.40 g, 10.0 mmol) were combined in methanol (10 ml) and stirred for 30 min at room temperature. A solution of benzaldehyde (1b, 1.02 ml, 10.0 mmol) and methanol (10 ml) was added dropwise and the mixture stirred for 21 hr at room temperature. Water (25 ml) was added and the mixture neutralized with hydrochloric acid (1 N). The mixture was extracted into ethyl acetate, washed with saturated sodium chloride, dried over magnesium sulfate, filtered and evaporated to afford a semi-solid. The crude semi-solid was chromatographed on silica gel with ethyl acetate/hexane to give a solid. The solid was recrystallized from hexane to give 1.11 g (53%) of a pale yellow solid: mp 52-54° C. [expected mp 55-58° C.]; $^1$H NMR: δ 7.40 (m, 3H), 7.46 (t, 1H, J=1.6 Hz), 7.63 (m, 5H), 7.81 (d, 1H, J=15.7 Hz), 8.02 (dd, 2H, J=8.0, 1.2 Hz); $^{13}$C NMR: δ 122.1, 128.3, 128.4, 128.5, 128.8, 130.4, 132.6, 134.8, 138.2, 144.7, 190.3.

1-(4-Hydroxy-3-methoxyphenyl)-3-phenyl-2-propen-1-one (46a). 4-Methoxymethyloxy-3-methoxyacetophenone (44j, 2.66 g, 12.7 mmol) and barium hydroxide octahydrate (4.00 g, 12.7 mmol) were combined in methanol (50 ml) and stirred for 5 min at 50° C. Benzaldehyde (1b, 1.30 ml, 12.8 mmol) was added and the mixture stirred for 8 hr at 50° C. The methanol was evaporated and the resulting residue was extracted into ethyl acetate, washed with saturated sodium chloride, dried over magnesium sulfate, filtered and evaporated to give 3.38 g (90%) of an oil which was used without purification; $^1$H NMR: δ 3.48 (s, 3H), 3.92 (s, 3H), 5.28 (s, 2H), 7.18 (d, 2H, J=8.9 Hz), 7.36 (m, 3H), 7.51 (d, 1H, J=15.7 Hz), 7.60 (m, 3H), 7.77 (d, 1H, J=15.7 Hz). The oil (46j, 3.35 g, 11.2 mmol) was stirred in methanol (75 ml) for 10 min at 50° C. Concentrated hydrochloric acid (3 drops) was added and the mixture stirred for 3 hr at 50° C. The methanol was evaporated and the resulting residue was extracted into ethyl acetate, washed with saturated sodium chloride, dried over magnesium sulfate, filtered and evaporated to afford an oil. The crude oil was distilled bulb to bulb to give 2.12 (74%) of a yellow solid: mp 61-64° C. [expected mp 63-66° C.]; $^1$H NMR δ 3.95 (s, 3H), 6.29 (s, 1H), 6.98 (d, 1H, J=8.3 Hz), 7.38 (m, 2H), 7.53 (d, 1H, J=15.5 Hz), 7.62 (m, 5H), 7.79 (d, 1H, J=15.5 Hz); $^{13}$C NMR: δ 56.1, 110.5, 113.8, 121.6, 123.6, 128.3, 128.8, 130.2, 130.9, 135.0, 143.8, 146.8, 150.4, 188.4.

1-(4-Carboxyphenyl)-3-phenyl-2-propen-1-one (46ad). 4-Acetylbenzonitrile (44al, 1.00 g, 6.9 mmol) and sulfuric acid (4 ml) were combined in water (4 ml) and the mixture stirred for 2.5 hr at reflux. The resulting mixture was extracted into ethyl acetate, washed with saturated sodium chloride, dried over magnesium sulfate, filtered and evaporated to give 0.98 g (87%) of compound 44ad as a white solid: mp 204° C.; $^1$H NMR: (DMSO) δ 2.61 (s, 3H), 8.04 (s, 4H), 13.23 (s, 1H). The solid (44ad, 0.50 g, 3.0 mmol) and sodium hydroxide (0.29 g, 7.3 mmol) were combined in water (4 ml) and ethanol (4 ml) and stirred for 30 min at room temperature. Benzaldehyde (1b, 0.31 ml, 3.1 mmol) was added and the mixture stirred for 48 hr at room temperature. The resulting mixture was acidified with hydrochloric acid (1 N), extracted into ethyl acetate, washed with saturated sodium chloride, dried over magnesium sulfate, filtered and evaporated to afford a solid. The crude solid was recrystallized from ethyl acetate to give 0.54 g (70%) of a yellow solid: mp 217-220° C. [expected mp 217-220° C.]; $^1$H NMR: (DMSO) δ 7.45 (m, 5H), 7.76 (d, 1H, J=16.1 Hz), 7.93 (d, 1H, J=15.5 Hz), 8.09 (d, 2H, J=7.9 Hz), 8.23 (d, 2H, J=7.6 Hz) 13.34 (s, 1H); $^{13}$C NMR: (DMSO) δ 121.9, 128.5, 128.8, 128.9, 129.4, 130.6, 134.3, 134.4, 140.6, 144.6, 166.4, 188.8.

1-(2,4-Dimethylphenyl)-3-phenyl-2-propen-1-one (46ak). 2,4-Dimethylacetophenone (44ak, 1.48 g, 10.0 mmol) and sodium hydroxide (0.54 g, 13.5 mmol) were combined in methanol (30 ml) and stirred for 30 min at room temperature. A solution of benzaldehyde (1b, 1.02 ml, 10.0 mmol) and methanol (30 ml) was added dropwise and the mixture stirred for 18 hr at room temperature. Water (25 ml) was added and the mixture neutralized with hydrochloric acid (1 N). The mixture was extracted into ethyl acetate, washed with saturated sodium chloride, dried over magnesium sulfate, filtered and evaporated to afford an oil. The crude oil was distilled bulb to bulb to give 1.98 g (84%) of a yellow oil: [expected mp 68° C.]; $^1$H NMR δ 2.37 (s, 3H), 2.44 (s, 3H), 7.05 (m, 2H), 7.16 (d, 1H, J=16.1 Hz), 7.38 (m, 3H), 7.49 (d, 1H, J=15.9 Hz), 7.54 (m, 3H); $^{13}$C NMR: δ 20.4, 21.4, 126.0, 126.6, 128.2, 128.5, 128.8, 130.4, 132.2, 134.7, 136.1, 137.4, 140.8, 145.0, 195.6.

1-(4-Cyanophenyl)-3-phenyl-2-propen-1-one (46al). 4-Acetylbenzonitrile (44al, 1.00 g, 6.9 mmol), sodium hydroxide (0.40 g, 10.0 mmol) and water (20 ml) were combined in ethanol (20 ml) and stirred for 15 min at room temperature. Benzaldehyde (1b, 0.70 ml, 6.9 mmol) was added and the mixture stirred for 2 hr at room temperature. The resulting mixture was filtered and recrystallized from ethanol to give 1.46 g (91%) of a yellow solid: mp 120° C. [expected mp 119-120° C.]; $^1$H NMR: δ 7.34 (m, 3H), 7.62 (m, 2H), 7.80 (m, 4H), 8.06 (d, 2H, J=8.1 Hz); $^{13}$C NMR: δ 115.9, 117.9, 121.1, 128.6, 128.8, 129.0, 131.0, 132.4, 134.3, 141.4, 146.4, 188.9.

3-(4-Hydroxy-3-methoxyphenyl)-1-phenyl-2-propen-1-one (48a). 4-Hydroxy-3-methoxybenzaldehyde (1a, 2.02 g, 13.3 mmol) and pyridiniump-toluenesulfonate (90 mg, 0.4 mmol) were combined in dichloromethane (60 ml) and stirred for 5 min at room temperature. A solution of 3,4-dihydropyran (47, 3.6 ml, 39.5 mmol) in dichloromethane (20 ml) was added dropwise and the mixture stirred for 5 hr at room temperature. The resulting mixture was washed with saturated sodium chloride, dried over magnesium sulfate, filtered and evaporated to afford an oil. The crude oil was chromatographed on silica gel with ethyl acetate/hexane to give 2.61 g (85%) of a clear oil. The oil (1am, 1.01 g, 4.3 mmol) and barium hydroxide octahydrate (1.03 g, 3.3 mmol) were combined in methanol (26 ml) and stirred for 15 min at room temperature. Acetophenone (44b, 0.30 ml, 2.6 mmol) was added and the mixture stirred for 16 hr at 50° C. The methanol was evaporated, water was added and the mixture acidified with hydrochloric acid (6 N). The resulting mixture was extracted into ethyl acetate, washed with saturated sodium chloride, dried over magnesium sulfate, filtered and evaporated to afford an oil. The crude oil was triturated with hexane to give a solid. The crude solid was recrystallized from ethyl acetate/hexane to give 0.39 g (45%) of a yellow solid: mp 87-88° C. The solid (48am, 0.39 g, 1.2 mmol) and dp-toluenesulfonic acid (0.10 g, 0.6 mmol) were combined in methanol (50 ml) and stirred for 4 hr at room temperature. The methanol was evaporated and water was added. The mixture was neutralized with saturated sodium bicarbonate and extracted into ethyl acetate. The ethyl acetate was washed with water, dried over magnesium sulfate, filtered and evaporated to afford an oil. The crude oil was chromatographed on silica gel with ethyl acetate/hexane to afford a solid. The crude solid was recrystallized from hexane to give 0.18 g (62%) of a yellow solid: mp 81-84° C. [expected mp 85-90° C.]; $^1$H NMR: δ 3.92 (s, 3H), 5.96 (s, 1H), 6.94 (d, 2H, J=8.1 Hz), 7.11 (s, 1H), 7.21 (d, 1H, J=7.6 Hz), 7.35 (d, 1H, J=15.9 Hz), 7.51 (m, 2H), 7.73 (d, 1H, J=15.5 Hz), 7.99 (d, 1H, J=7.0 Hz); $^{13}$C NMR: δ 56.1, 110.0, 114.8, 119.8, 123.3, 127.4, 128.4, 128.5, 132.5, 138.5, 145.1, 146.7, 148.2, 190.5.

3-(4-Carboxyphenyl)-1-phenyl-2-propen-1-one (48ad). Acetophenone (44b, 0.50 ml, 4.3 mmol) and sodium hydroxide (0.50 g, 12.5 mmol) were combined in ethanol (2 ml) and water (2 ml) and stirred for 30 min at room temperature. 4-Formylbenzoic acid (1ad, 0.71 g, 4.7 mmol) was added and the mixture stirred for 48 hr at room temperature. Water (25 ml) was added, the mixture acidified with hydrochloric acid (1 N) and the resulting precipitate was filtered and recrystallized from ethyl acetate to give 0.65 g (60%) of a white solid: mp 222-224° C. [expected mp 227-229° C.]; $^1$H NMR: (DMSO) δ 7.67 (m, 4H), 7.99 (m, 4H), 8.18 (m, 3H), 13.14 (s, 1H); $^{13}$C NMR: (DMSO) δ 124.2, 128.5, 128.7, 128.8, 129.6, 132.1, 133.2, 137.3, 138.7, 142.4, 166.7, 189.0.

1,3-Diphenylpropane-1,3-dione (50b). Methanol (0.26 ml, 6.4 mmol) and sodium (0.14 g, 6.1 mmol) were combined in xylene (60 ml) and stirred for 20 min at room temperature. Methyl benzoate (49, 2.47 ml, 19.7 mmol) and acetophenone (0.58 ml, 5.0 mmol) were added and the mixture stirred for 6 hr at 140° C. The mixture was cooled to room temperature and hydrochloric acid (10 ml, 6 N) was added and stirred for 15 min. The resulting mixture was extracted into ethyl acetate, washed twice with water, twice with saturated sodium bicarbonate and twice with water. The ethyl acetate was dried over magnesium sulfate, filtered and evaporated to afford an oil. The crude oil was chromatographed on silica gel with ethyl acetate/hexane to give a solid. The solid was recrystallized from methanol to give 0.71 g (63%) of a pink-orange solid: mp 70-71° C. [expected mp 77-78° C.]; $^1$H NMR: δ 6.85 (s, 1H), 7.51 (m, 6H), 7.98 (d, 4H, J=6.8 Hz); $^{13}$C NMR: δ 93.1, 127.1, 128.6, 132.4, 135.5, 185.6.

2,6-Diphenyl-1-methyl-4-piperidone (52b). 1,5-Diphenyl-1,4-pentadien-3-one (20b, 4.00 g, 17.1 mmol) was dissolved in dimethyl formamide (60 ml). Methylamine (51, 6.0 ml, 70.0 mmol, 40% in water) was added and the mixture stirred for 96 hr at room temperature. The mixture was poured into water (250 ml) and stirred for 1 hr at room temperature. The resulting mixture was extracted into ethyl ether, washed with saturated sodium chloride, dried over magnesium sulfate, filtered and evaporated to afford a solid. The crude solid was recrystallized from ethanol to give 2.74 g (60%) of a white solid: mp 147-149° C. [expected mp 148-150° C.]; $^1$H NMR δ 1.82 (s, 3H), 2.50, (dd, 2H, J=12.3, 2.5 Hz), 2.82 (t, 2H, J=13.3 Hz), 3.45 (dd, 2H, J=12.9, 2.4 Hz), 7.34, (m, 10H); $^{13}$C NMR: δ 40.8, 50.8, 70.2, 127.0, 127.6, 128.8, 143.1, 206.8.

2,6-Bis(2-methoxyphenyl)-1-methyl-4-piperidone (52c). 1,5-Bis(2-methoxyphenyl)-1,4-pentadien-3-one (20c, 0.26 g, 0.9 mmol) was dissolved in dimethyl formamide (5 ml). Methylamine (51, 0.40 ml, 4.6 mmol, 40% in water) was added and the mixture stirred for 24 hr at room temperature. The mixture was poured into water (50 ml) and stirred for 24 hr at room temperature. The resulting mixture was extracted into ethyl acetate, washed with saturated sodium chloride, dried over magnesium sulfate, filtered and evaporated to afford a solid. The solid was recrystallized twice from ethanol to give 0.16 g (55%) of a white solid: mp 146-148° C.; $^1$H NMR δ 1.89 (s, 3H), 2.50 (d, 2H, J=13.7 Hz), 2.65 (t, 2H, J=11.9 Hz), 3.82 (s, 6H), 4.11 (d, 2H, J=11.5 Hz), 6.87 (d, 2H, J=8.3 Hz), 7.03 (t, 2H, J=7.2 Hz), 7.23 (t, 2H, J=5.8 Hz), 7.72 (d, 2H, J=7.6 Hz); $^{13}$C NMR: δ 40.3, 49.2, 55.4, 61.2, 110.7, 121.0, 127.6, 127.8, 131.5, 156.3, 208.1; Exact mass calcd for $C_{20}H_{23}NO_3$: 325.1678, observed (M+H) 326.1754.

2,6-Bis(4-methoxyphenyl)-1-methyl-4-piperidone (52e). 1,5-Bis(4-methoxyphenyl)-1,4-pentadien-3-one (20e, 0.40 g, 1.4 mmol) was dissolved in dimethyl formamide (10 ml). Methylamine (51, 0.75 ml, 8.7 mmol, 40% in water) was added and the mixture stirred for 24 hr at room temperature. The mixture was poured into water (50 ml) and stirred for 2 hr at room temperature. The resulting mixture was extracted into ethyl acetate, washed with saturated sodium chloride, dried over magnesium sulfate, filtered and evaporated to afford a solid. The crude solid was chromatographed on silica gel with ethyl acetate/hexane to afford a solid that was recrystallized from ethanol to give 0.30 g (68%) of a white solid: mp 141-143° C. [expected mp 129-130° C.]; $^1$H NMR δ 1.77, (s, 3H), 2.45 (d, 2H, J=14.5 Hz), 2.78 (t, 2H, J=12.9 Hz), 3.33 (d, 2H, J=11.9 Hz), 3.79 (s, 6H), 6.88 (d, 4H, J=8.5 Hz), 7.32 (d, 4H, J=8.5 Hz); $^{13}$C NMR: δ 40.6, 50.9, 55.3, 69.5, 114.1, 128.0, 135.3, 158.9, 207.1.

2,6-Bis(4-methylphenyl)-1-methyl-4-piperidone (52aa). 1,5-Bis(4-methylphenyl)-1,4-pentadien-3-one (20aa, 0.32 g, 1.2 mmol) was dissolved in dimethyl formamide (9 ml). Methylamine (51, 0.5 ml, 5.8 mmol, 40% in water) was added and the mixture stirred for 72 hr at room temperature. The mixture was poured into water (50 ml) and stirred for 2 hr at room temperature. The resulting mixture was extracted into ethyl acetate, washed with saturated sodium chloride, dried over magnesium sulfate, filtered and evaporated to afford a solid. The crude solid was chromatographed on silica gel with ethyl acetate/hexane to afford a solid that was recrystallized from ethanol to give 0.26 g (75%) of a white solid: mp 120-121° C. [expected mp 105-107° C.]; $^1$H NMR δ 1.79 (s, 3H), 2.36 (s, 6H), 3.10 (d, 2H, J=14.9 Hz), 2.79 (t, 2H, J=13.1 Hz), 3.35 (dd, 2H, J=11.9, 2.4 Hz), 7.15 (d, 4H, J=8.0 Hz), 7.21 (d, 4H, J=7.9 Hz); $^{13}$C NMR: δ 21.2, 40.7, 50.9, 70.0, 126.9, 129.4 137.2, 140.2, 207.1.

2,6-Bis(2-methylphenyl)-1-methyl-4-piperidone (52ac). 1,5-Bis(2-methylphenyl)-1,4-pentadien-3-one (20ac, 0.50 g, 1.9 mmol) was dissolved in dimethyl formamide (10 ml). Methylamine (51, 1.0 ml, 11.6 mmol, 40% in water) was added and the mixture stirred for 24 hr at room temperature. The mixture was poured into water (50 ml) and stirred for 2 hr at room temperature. The resulting mixture was extracted into ethyl acetate, washed with saturated sodium chloride, dried over magnesium sulfate, filtered and evaporated to afford a solid. The crude solid was chromatographed on silica gel with ethyl acetate/hexane to afford a solid that was recrystallized from ethanol to give 0.29 g (52%) of a white solid: mp 155-157° C.; $^1$H NMR δ 1.82, (s, 3H), 2.40, (s, 6H), 2.44 (d, 2H, J=11.9 Hz), 2.77 (t, 2H, J=13.3 Hz), 3.74 (d, 2H, J=11.9 Hz), 7.16 (m, 6H), 7.67, (d, 2H, J=7.0 Hz); $^{13}$C NMR: δ 19.5, 39.9, 49.3, 65.8, 126.7, 126.9, 130.6, 134.8, 140.9, 207.2; Exact mass calcd for $C_{20}H_{23}NO$: 293.1779, observed (M+H) 294.1856.

2,6-Bis(2-naphthyl)-1-methyl-4-piperidone (53). 1,5-Bis(2-naphthyl)-1,4-pentadien-3-one (25, 0.82 g, 2.5 mmol) was dissolved in dimethyl formamide (15 ml). Methylamine (51, 1.30 ml, 15.1 mmol, 40% in water) was added and the mixture stirred for 72 hr at room temperature. The mixture was poured into water (100 ml) and stirred for 24 hr at room temperature. The resulting mixture was extracted into ethyl acetate, washed with saturated sodium chloride, dried over magnesium sulfate, filtered and evaporated to afford a solid. The crude solid was chromatographed on silica gel with ethyl acetate/hexane to afford a solid that was recrystallized twice from ethanol to give 0.20 g (22%) of a white solid: mp 209-212° C.; $^1$H NMR δ 1.89 (s, 3H), 2.59 (d, 2H, J=13.9 Hz), 2.97 (t, 2H, J=11.3 Hz), 3.66 (d, 2H, J=11.7 Hz), 7.49 (m, 4H), 7.81 (m, 10H); $^{13}$C NMR: δ 41.1, 50.7, 70.3, 124.6, 125.9, 126.0, 126.2, 127.6, 127.7, 128.9, 133.0, 133.4, 140.4, 206.6; Exact mass calcd for $C_{26}H_{23}NO$: 365.1780, observed (M+H) 366.1852.

Example 2

Antioxidant Activity of Curcumin Derivatives

It has been suggested that the antioxidant activity of curcumin depends on the phenolic groups (Barclay et al., Organic Lett. 2(18), 2841-2843 (2000); Priyadarsini et al., Free Radical Biol. Med. 35(5), 475-484 (2003)). However, other studies support the conclusion that the central methylene hydrogens of curcumin are important for antioxidant activity (Jovanovic et al., J. Am. Chem. Soc. 123(13), 3064-3068 (2001)). More recently it has been demonstrated that both the central methylene hydrogens and the phenolic hydrogens may be involved in the mechanism of formation of the phenoxy radical, depending upon reaction conditions (Litwinienko et al., J. Org. Chem. 69(18), 5888-5896 (2004)). The library consisting of three series of analogs examined the role of the enone functionality in aryl systems where the spacer is 7-carbons (as in curcumin), 5-carbons or 3-carbons in length. In addition, the importance of aryl ring substituents including phenolic groups was assessed as well as the importance of the central methylene hydrogens of curcumin. The antioxidant activities of the curcumin analogs were determined in two standard assays. There are multiple standardized methods to determine antioxidant activities, and it is recommended that at least two different procedures be used (Barclay et al., Organic Lett. 2(18), 2841-2843 (2000)). The first assay was the Total Radical-trapping Anti-oxidant Parameter assay (TRAP assay) and the second assay was the Ferric Reducing/Anti-oxidant Power assay (FRAP assay).

TRAP Assay

The first procedure called for antioxidant activity to be measured as the ability of the analogs to react with the preformed radical monocation of 2,2'-azinobis-(3-ethylbenzothiazoline)-6-sulfonic acid ($ABTS^+$). This assay is also known as the Total radical-trapping anti-oxidant parameter assay (TRAP assay). For the TRAP assay (Re et al., Free Rad. Biol. Med. 26, 1231-1237 (1999)), 2,2'-azino-bis(3-ethylbenzthiazoline)-6-sulfonic acid (ABTS, 1.8 mM) was reacted with potassium persulfate (0.63 mM) in double distilled water, at room temperature in the dark, overnight, to generate the dark blue colored $ABTS^+$ radical cation, which has a maximum absorption at 734 nm. Just before the experiment, $ABTS^+$ was diluted with absolute ethanol to an absorbance of approximately 0.7 at 734 nm. $ABTS^+$ (1 ml) was added to curcumin or its analogs (10 μM in ethanol) and mixed by vortexing. The turquoise colored reaction was allowed to stabilize for 5 min and the absorbance monitored on a Perkin Elmer UV/Vis Lambda 2S. The activities of curcumin and its analogs were determined by their abilities to quench the color of the radical cation. The synthetic analog of α-tocopherol (vitamin E), Trolox, was used as a reference standard (10 μM in ethanol).

Figure 2:
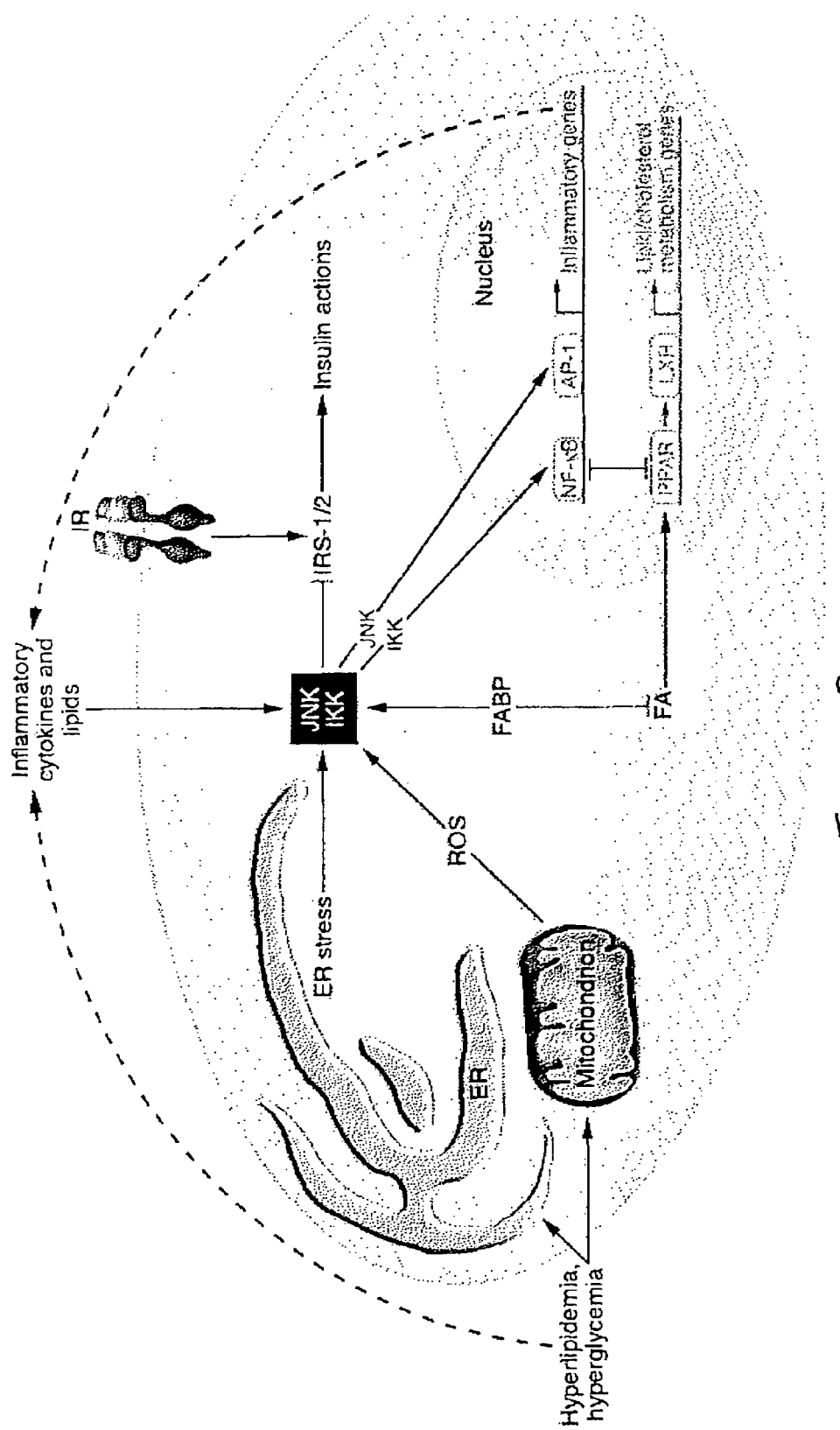
FIG. 2 is a pictorial representation of the inflammatory and metabolic pathways affecting insulin resistance and diabetes.

The first assay, the TRAP assay, determines the analogs abilities to reduce a radical cation generated from 2,2'-azino-bis(3-ethylbenzthiazoline)-6-sulfonic acid (ABTS). The following FIGS. (2A-2C) show the analogs active in the TRAP assay. The active analogs in FIGS. 2A-2C are arranged from highly active on the left to slightly active on the right.

Figure 3A:
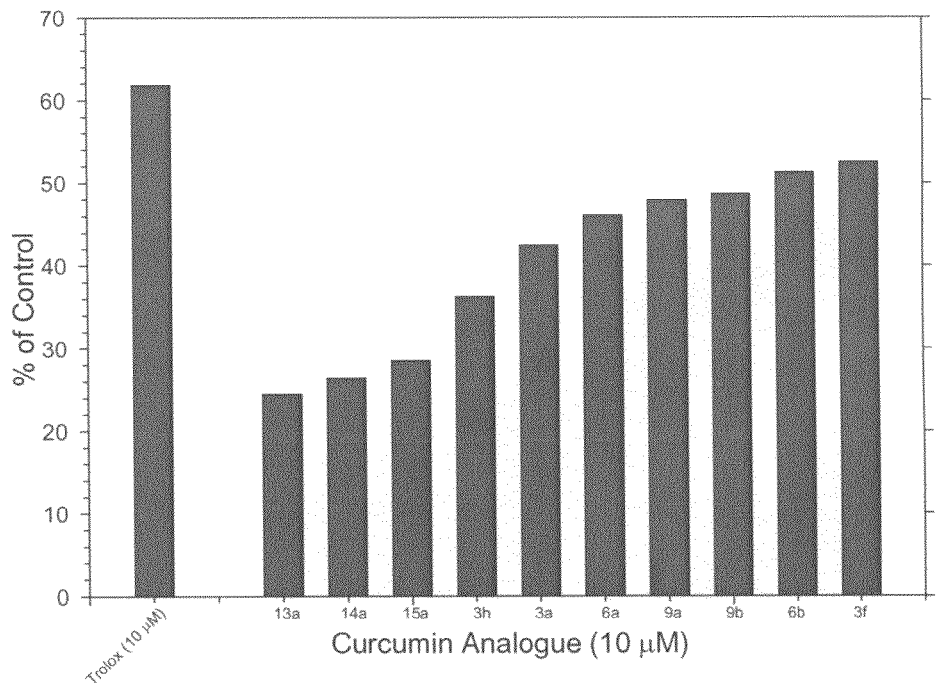
FIG. 3A is a bar graph showing the activities of curcumin analogs including 7-carbon linker groups in the TRAP assay.

Active analogs retaining a 7-carbon spacer as in curcumin are shown in FIG. 3A. Four analogs, 13a, 14a, 15a and 3h, in this series were found to be more active than curcumin (3a). Of the ten active analogs in this series, eight retain phenolic groups as in curcumin. The three best analogs, 13a, 14a and 15a, not only contained phenolic groups but also contained a saturated spacer between the aryl rings. It is also evident that a central methylene substituent is favorable in analogs displaying antioxidant activity as six of the ten analogs in FIG. 3A contain a central methylene substituent.

Figure 3B:
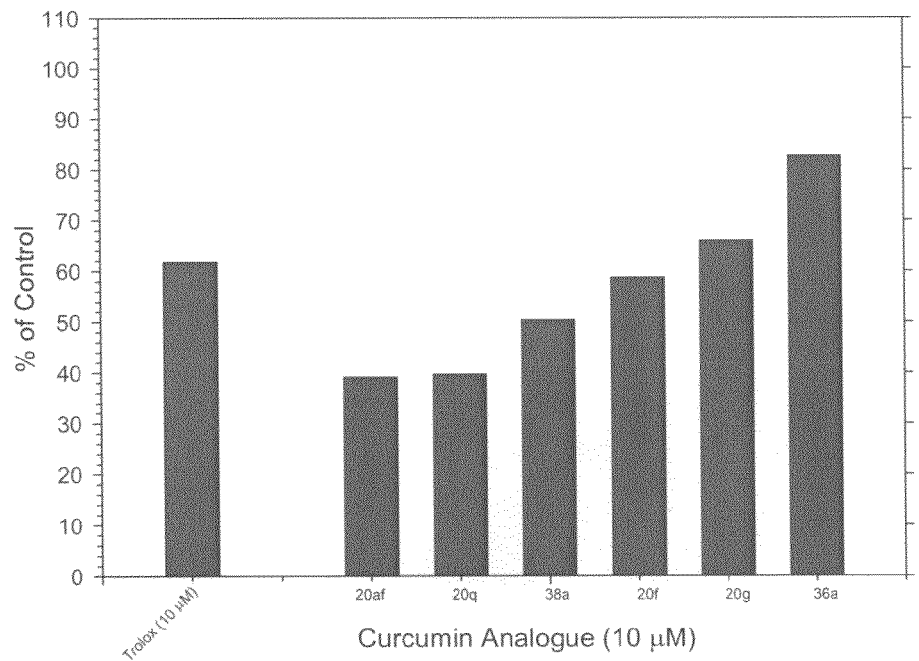
FIG. 3B is a bar graph showing the activities of curcumin analogs including 5-carbon linker groups in the TRAP assay.

Active analogs in series 2, which have a 5-carbon spacer, are shown in FIG. 3B. Two analogs, 20af and 20q, in this series were found to be more active than curcumin. Of the six active analogs in this series, five contain phenolic groups. The best analog, 20af, is a tetraphenol.

Figure 3C:
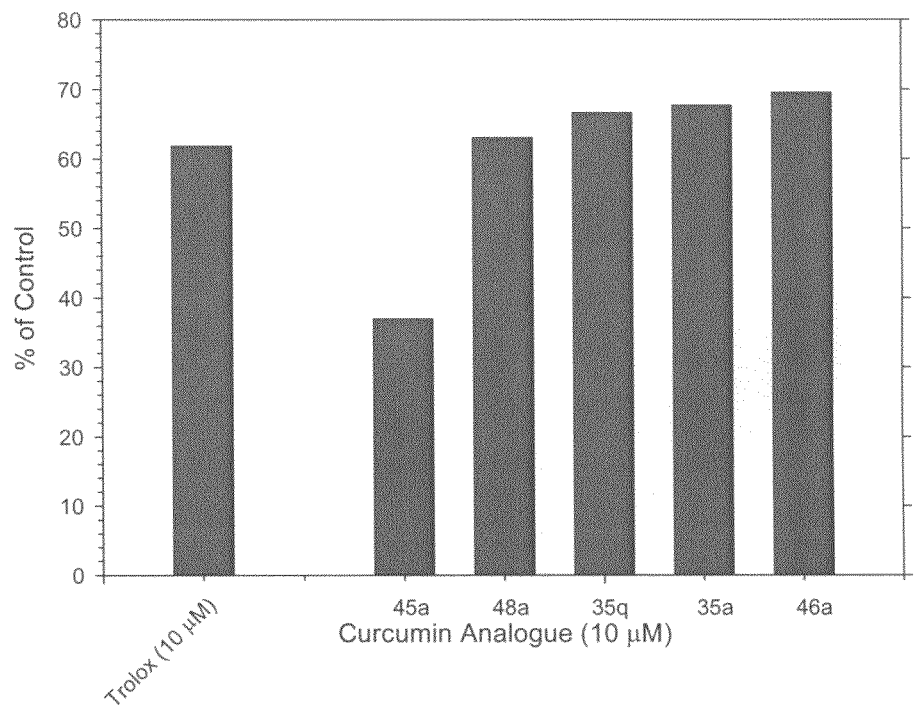
FIG. 3C is a bar graph showing the activities of curcumin analogs including 3-carbon linker groups in the TRAP assay.

Active analogs in series 3, which have a 3-carbon spacer, are shown in FIG. 3C. Only one analog, 45a, in this series was found to be more active than curcumin. All five of the active analogs in this series contain phenolic groups.

FRAP Assay

Anti-oxidant activity was also measured in the Ferric reducing/anti-oxidant power assay (FRAP assay) in which the analogs are reacted with a ferric tripyridyltriazine complex. For the FRAP assay (Benzie et al., Meth. Enzymol. 1999, 299, 15-27), the ferric complex was prepared at room temperature by reaction of ferric chloride (16.7 mM) and 2,4,6-tripyridyl-s-triazine (8.33 mM) in acetate buffer (0.25 M) to pH 3.6. The FRAP reagent was used immediately after preparation. The ferric complex (1 ml) was added to curcumin or its analogs (10 μM in ethanol). The reaction was mixed by vortexing, allowed to stabilize for 5 min and the absorbance recorded on a Perkin Elmer UV/Vis Lambda 2S. The activities of curcumin and its analogs were determined by their abilities to reduce the ferric complex to a ferrous complex, monitored by the formation of the purple colored ferrous complex at 593 nm. The synthetic analog of α-tocopherol (vitamin E), Trolox, was used as a reference standard (10 μM in ethanol).

The second assay used, the FRAP assay, determines the analogs abilities to reduce a Fe(III) tripyridyltriazine complex to a Fe(II) tripyridyltriazine complex. The following FIGS. (3A-3C) show analogs active in the FRAP assay. The active analogs in FIGS. 3A-3C are arranged from highly active on the left to slightly active on the right.

Figure 4A:
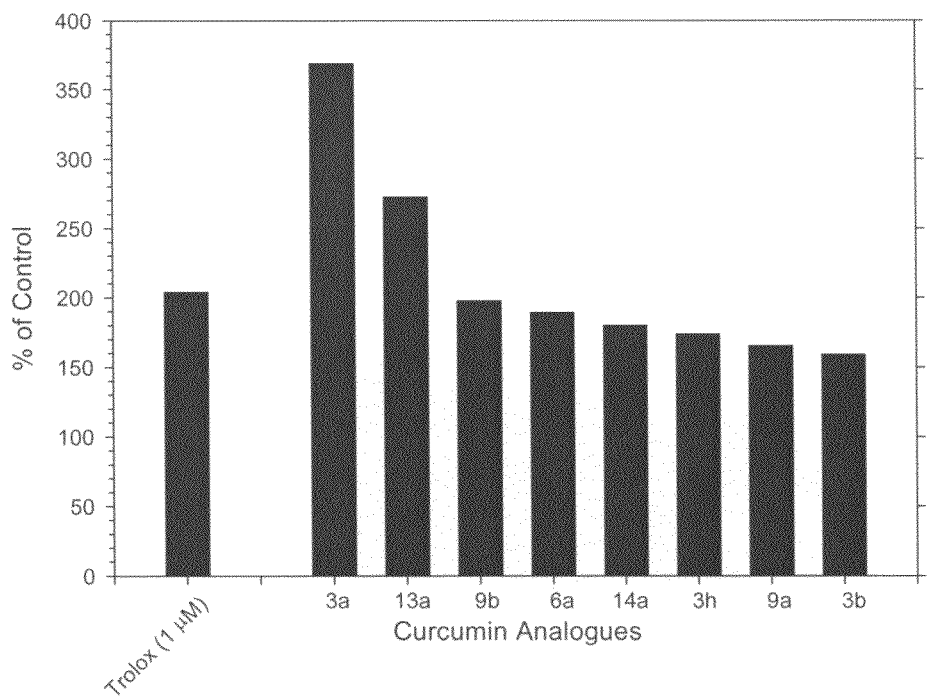
FIG. 4A is a bar graph showing the activities of curcumin analogs including 7-carbon linker groups in the FRAP assay.

Active analogs retaining a 7-carbon spacer as in curcumin are shown in FIG. 4A. Curcumin (3a) displayed the most antioxidant activity in this series. Analog 13a, the reduced form of curcumin, also displayed potent antioxidant activity. Six of the eight active analogs in this series contain phenolic groups as in curcumin and four analogs contain substituents on the central methylene carbon.

Figure 4B:
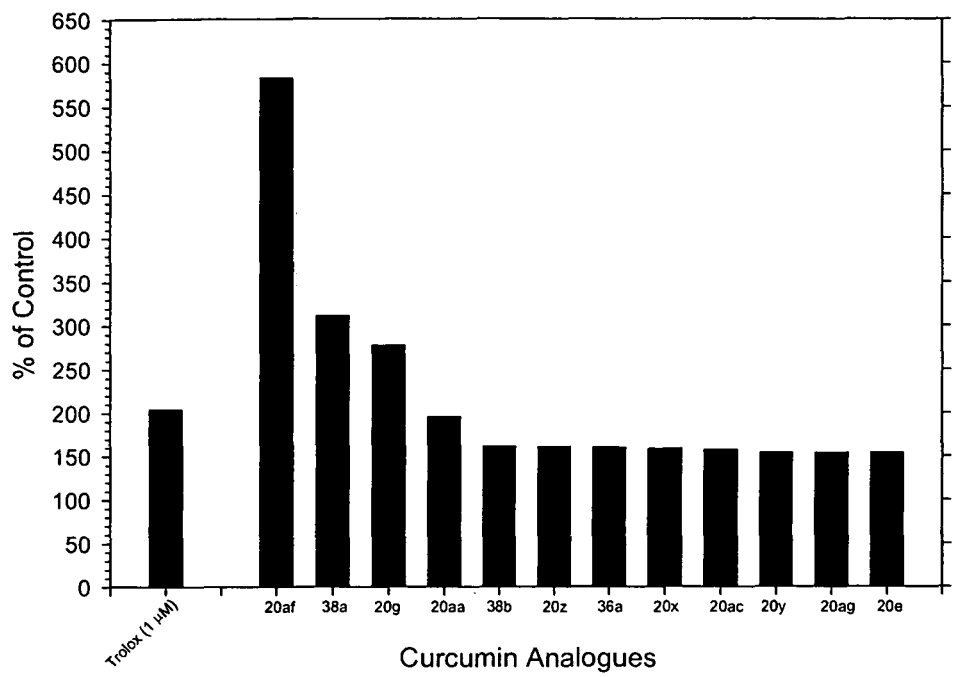
FIG. 4B is a bar graph showing the activities of curcumin analogs including 5-carbon linker groups in the FRAP assay.

Active analogs in series 2 are shown in FIG. 4B. Only one analog, 20af, in this series was found to be more active than curcumin. The two best analogs, 20af and 38a, in this series contain phenolic groups. However, contrary to any of the previous antioxidant results, only three of the twelve most active analogs in this series contain phenolic groups. There is currently no explanation as to why nine of the top twelve analogs in this series contain no phenolic groups and further investigation is necessary.

Figure 4C:
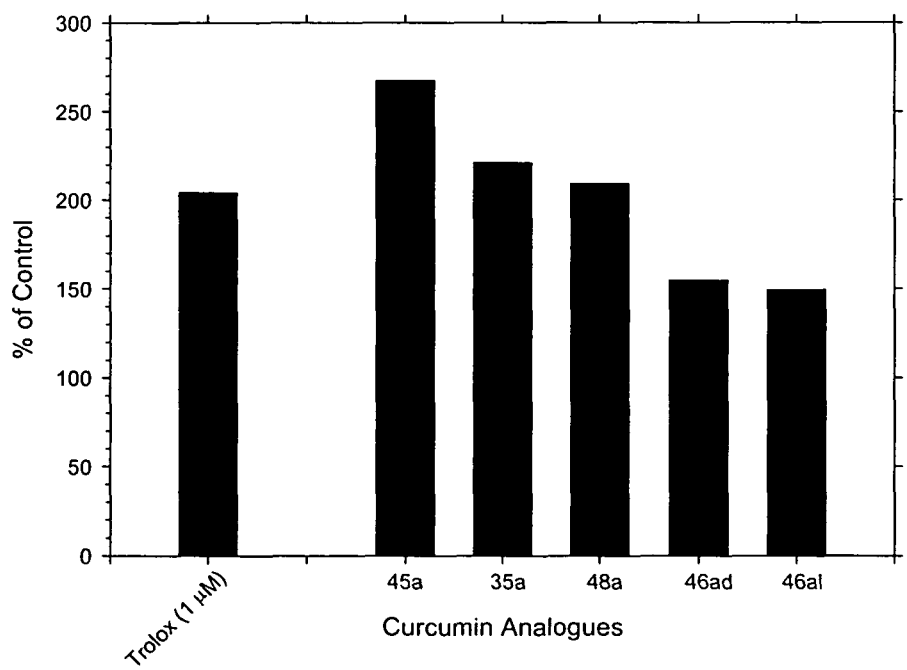
FIG. 4C is a bar graph showing the activities of curcumin analogs including 3-carbon linker groups in the FRAP assay.

Active analogs in series 3 are shown in FIG. 4C. No analog in this series was more active than curcumin. Three of the five active analogs, 45a, 35a and 48a, in this series contain phenolic groups and a fourth, 46ad, contains an acidic carboxylic acid proton.

Most analogs that display antioxidant activity retain phenolic groups. Eighteen of the twenty one active analogs in the TRAP assay and twelve of the seventeen active analogs (minus the eight least active in the 5-carbon series) contain phenolic groups. This indicates that a phenolic substituent is desirable for antioxidant activity but not essential. Analogs in all three series were found to contain antioxidant activity with seven analogs in the 7-carbon series, three in the 5-carbon series and four in the 3-carbon series displaying activity in both the TRAP and FRAP assays.

Example 3

Inhibition of NF-κB Activity by Curcumin Derivatives

Curcumin and its analogs were screened for activity against NF-κB by a cellular assay using the NF-κB stable cell line (293T/NF-κB-luc). The cell line is derived from human 293T embryonic kidney cells expressing the large T antigen containing a chromosomal integration of a luciferase reporter construct regulated by 6 copies of the NF-κB response element (Panomics, Inc.). This stable clonal cell line is obtained by co-transfection of pNF-κB-luc and pTK-hyg containing plasmids followed by the addition of hygromycin (200 µg/ml) to maintain cell selection.

The cell line was grown in a humidified atmosphere at 37° C. in 5% $CO_2$/95% air and maintained in Dulbecco's Modified Eagle's Medium (DMEM-high glucose containing 4 mM glutamine) containing fetal bovine serum (FBS, 10%), sodium pyruvate (1 mM), penicillin (100 units/ml), streptomycin (100 µg/ml) and hygromycin (100 µg/ml) to maintain cell selection (Gibco/Invitrogen).

The 293T/NF-κB-luc cells were re-plated 24 hr prior to treatment, into 24-well cell culture plates in media without hygromycin, to prevent it from interfering with the assay. The cells were then allowed to grow and attach, to the wells, for 24 hr in a humidified atmosphere at 37° C. in 5% $CO_2$/95% air. After 24 hr, the cells had reached approximately 70% confluency and were given fresh media (1 ml) 1 hr prior to treatment with curcumin and its analogs. The cells were then re-given media (1 ml) with or without recombinant tumor necrosis factor alpha (TNFα, 20 ng/ml in phosphate buffered saline (PBS) at pH 7.4 containing 0.1% human serum albumin, R&D Biosciences/Clontech) followed by immediate treatment with curcumin or its analog (10 µM in DMSO). The cells then were placed again in a humidified atmosphere at 37° C. in 5% $CO_2$/95% air for 7 hr. Plate wells were gently washed with PBS, pH 7.4, and lysed with passive lysis buffer (1x, 100 µl, Promega). The subsequent chemiluminescent lysates were analyzed with the Luciferase Assay System (Promega) utilizing a TD-20/20 luminometer. The relative light units (photons) were determined by the addition of firefly luciferase substrate (75 µl) to cell lysate (10 µl). The light units were then normalized to the amount of protein in the well (mg/ml) with BCA Protein Assay Kit (Pierce) and standardized to percent of control (TNFα).

To determine cell viability, cells were treated as above but with 15 µM analog. After gently washing to remove any dead cells, they were given media (100 µl) and CellTiter 96® AQueous One Solution reagent (20 µl) for 1 hour and read at 490 nm with a Spectromax plate reader.

Curcumin is a known inhibitor of the NF-κB activation cascade. Therefore, modification of the structure of curcumin could lead to enhanced activity. The library consisting of three series of curcumin analogs were used to examine the role of the enone functionality in aryl systems where the spacer is 7-carbons (as in curcumin), 5-carbons or 3-carbons in length. In addition, the importance of aryl ring substituents was assessed. The NF-κB activities of curcumin and analogs were determined by a cellular firefly luciferase assay. This assay utilized a commercially available cell line (Panomics 293T-luc cellular assay) developed for screening inhibitors of NF-κB. This cell line is stably transfected with a luciferase reporter controlled by an NF-κB dependent promoter. The cell is stimulated with tumor necrosis factor alpha (TNFα) which activates NF-κB. NF-κB then binds to one of six promoter regions on the cell's DNA leading to the production of a luciferase enzyme. Luciferin is added to the cell lysates and the luciferase enzyme catalyzes a cleavage of luciferin leading to the emission of light.

The following FIGS. (4A-4C) show analogs active in the NF-κB cellular assay. The active analogs in FIGS. 4A-4C are arranged from highly active on the left to slightly active on the right.

Figure 5A:
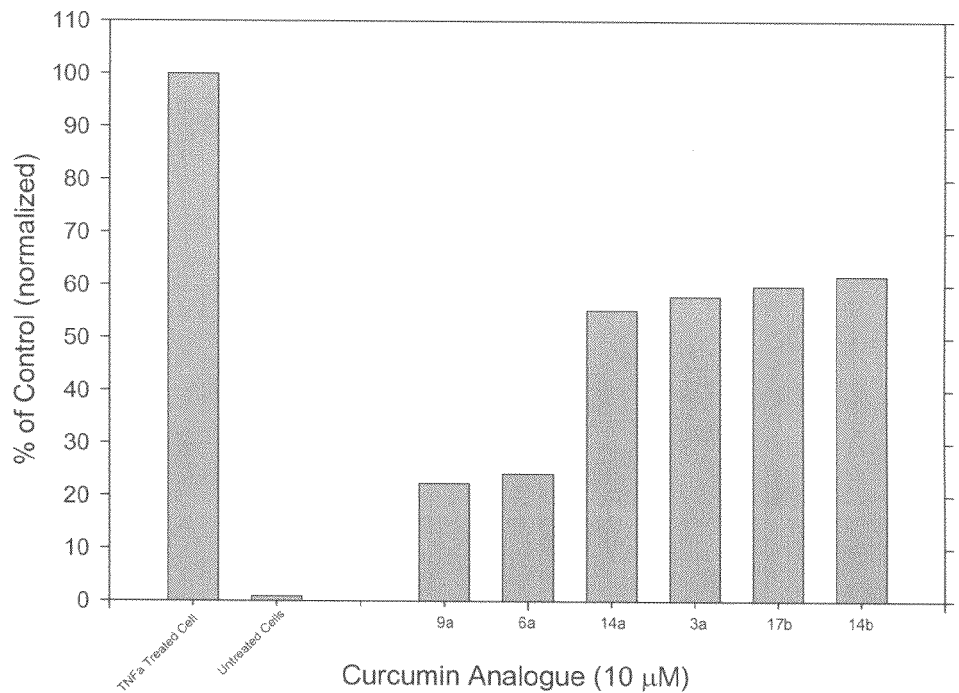
FIG. 5A is a bar graph showing the activities of curcumin analogs including 7-carbon linker groups as inhibitors of the activation of NF-κB by TNFα.

Active analogs in series 1, which contain a 7-carbon spacer, are shown in FIG. 5A. Three analogs, 9a, 6a and 14a in this series were more active than curcumin (3a). These three analogs all contain the same aryl substituents as in curcumin. In addition, five of the six best analogs in this series contain a substituent on the central methylene carbon, indicating this position may be important to enhance activity. Three analogs also contain a saturated 7-carbon spacer indicating that saturation may be important in this series. Four of the six active analogs in this series have antioxidant activity. It is important to note that two analogs were active against NF-κB activation independent of antioxidant activity.

Figure 5B:
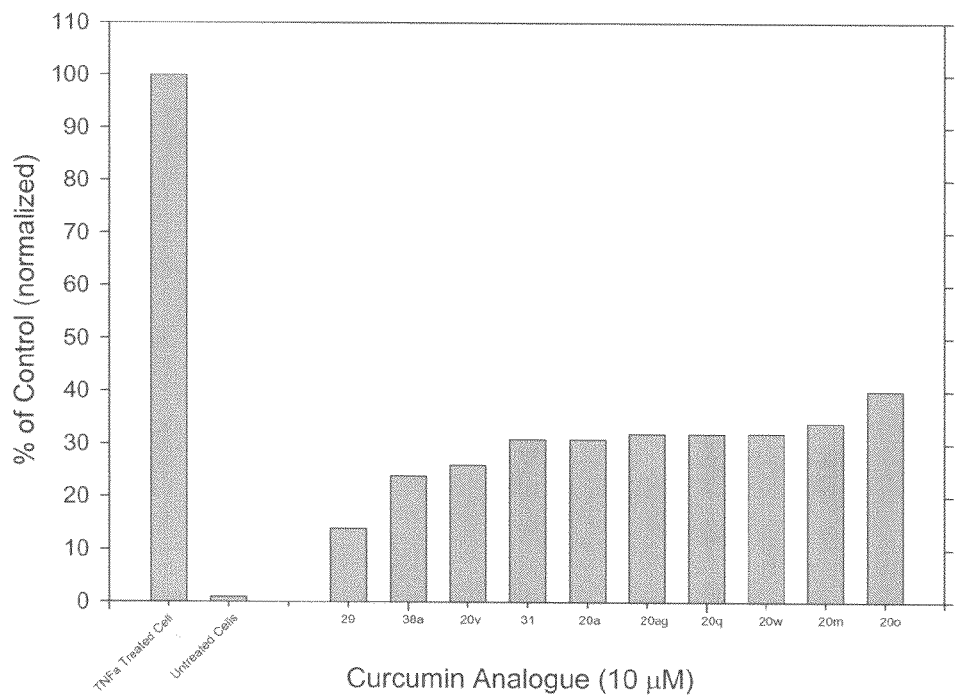
FIG. 5B is a bar graph showing the activities of curcumin analogs including 5-carbon linker groups as inhibitors of the activation of NF-κB by TNFα.

Active analogs in series 2, which contain a 5-carbon spacer, are shown in FIG. 5B. Ten analogs, 29, 38a, 20v, 31, 20a, 20ag, 20q, 20w, 20m and 20o in this series were more active than curcumin. Eight of the ten active analogs in this series contain aryl substituents. Six analogs contain substituents meta to the spacer on the aryl group, indicating this position may be important for NF-κB activity. Analogs 29 and 31 contain pyridine rings with no substituents on the ring. These two active analogs indicate that if the analogs in this series have a specific target, the target may contain a hydrogen bond donor in the area of binding. Only one of the ten active analogs in this series displays antioxidant activity. Therefore, it can then be concluded that these analogs are targeting a specific protein.

Figure 5C:
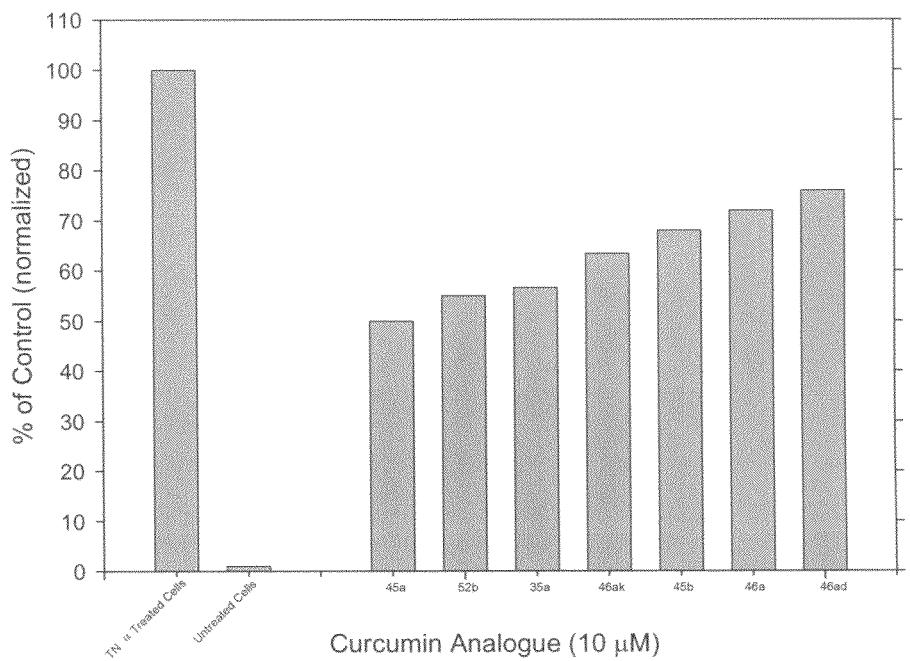
FIG. 5C is a bar graph showing the activities of curcumin analogs including 3-carbon linker groups as inhibitors of the activation of NF-κB by TNFα.

Active analogs in series 3, which contain a 3-carbon spacer, are shown in FIG. 5C. Three analogs, 45a, 52b and 35a, in this series were more active than curcumin. Three of the seven active analogs in this series retain the same aryl substituents as in curcumin. Analog 52b contains a piperidone ring on the spacer, indicating this type of spacer may be important for activity. Two of the seven active analogs were active as antioxidants. It is important to note that five analogs were active against NF-κB independent of antioxidant activity.

Figure 6A:
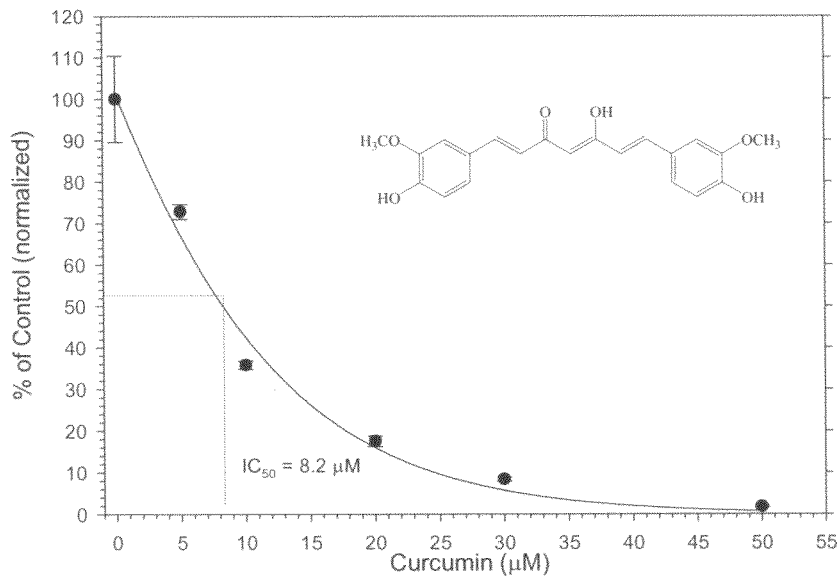
FIG. 6A is a graph showing an $IC_{50}$ plot of varying doses of curcumin against inhibition of NF-κB activity.
Figure 6B:
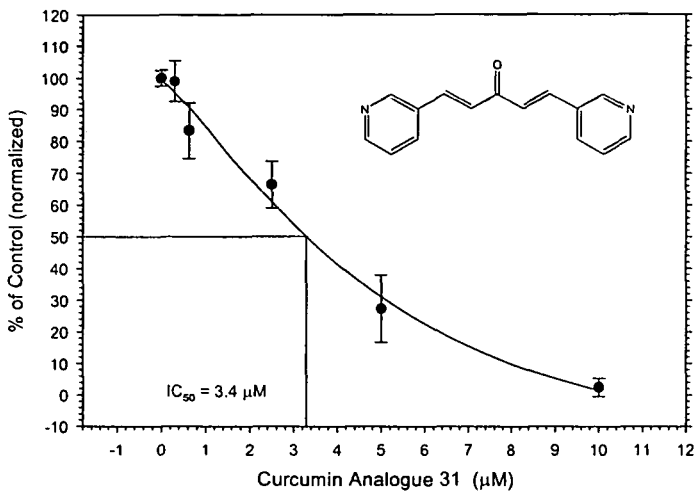
FIG. 6B is a graph showing an $IC_{50}$ plot of varying doses of analog 31 against inhibition of NF-κB activity.
Figure 6C:
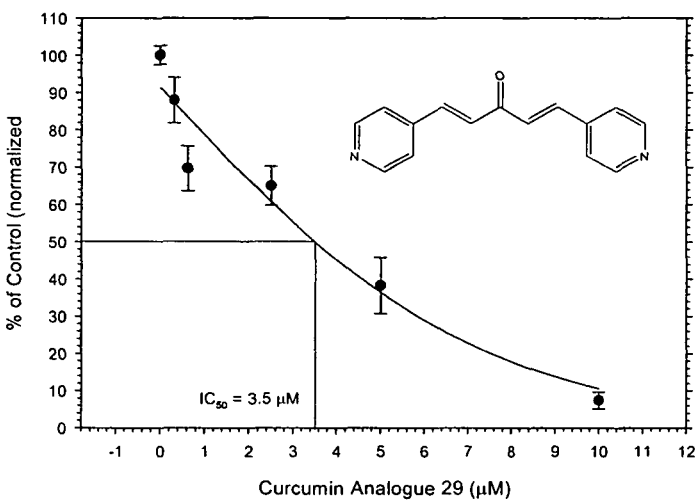
FIG. 6C is a graph showing an $IC_{50}$ plot of varying doses of analog 29 against inhibition of NF-κB activity.
Figure 6D:
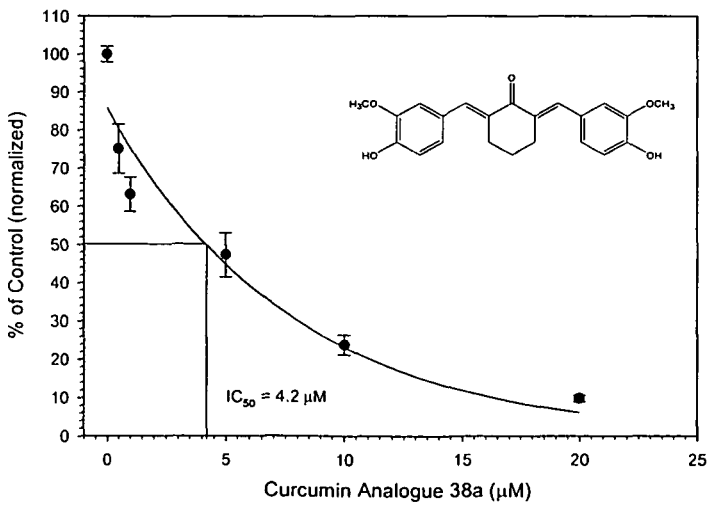
FIG. 6D is a graph showing an $IC_{50}$ plot of varying doses of analog 38a against inhibition of NF-κB activity.
Figure 6E:
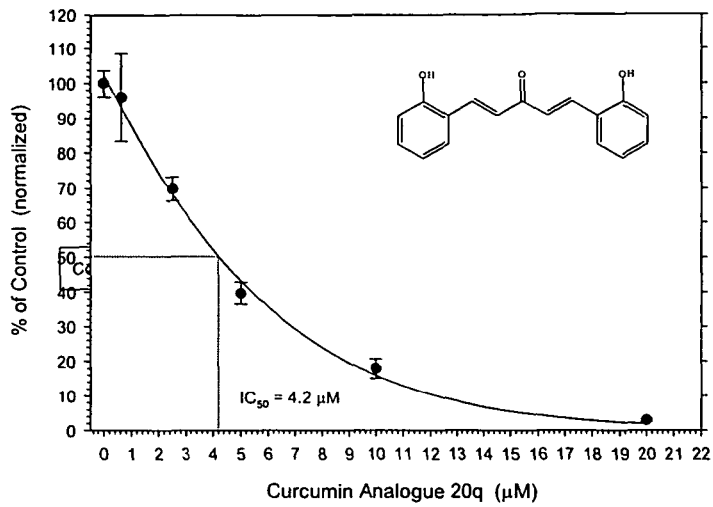
FIG. 6E is a graph showing an $IC_{50}$ plot of varying doses of analog 20q against inhibition of NF-κB activity.
Figure 6F:
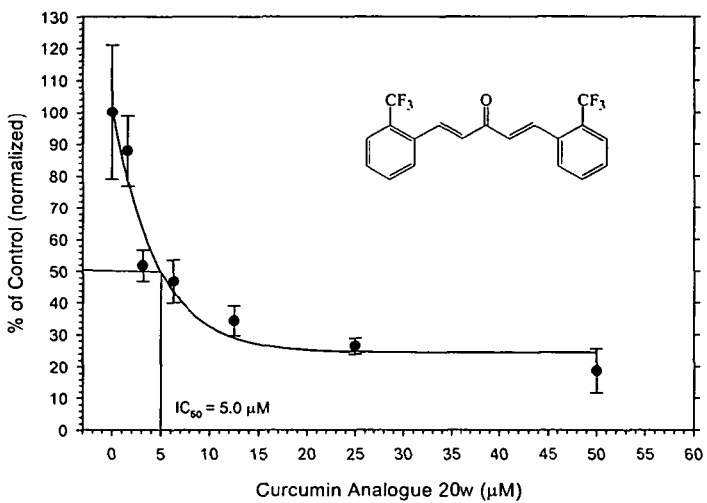
FIG. 6F is a graph showing an $IC_{50}$ plot of varying doses of analog 20w against inhibition of NF-κB activity.
Figure 6G:
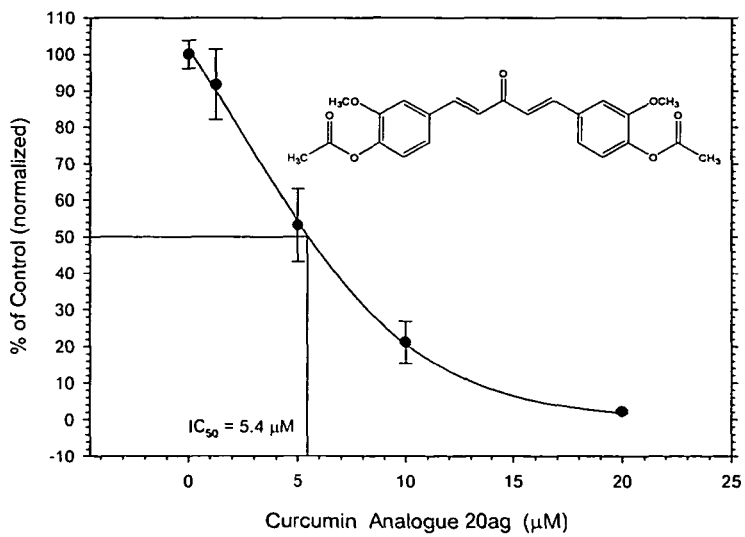
FIG. 6G is a graph showing an $IC_{50}$ plot of varying doses of analog 20ag against inhibition of NF-κB activity.
Figure 6H:
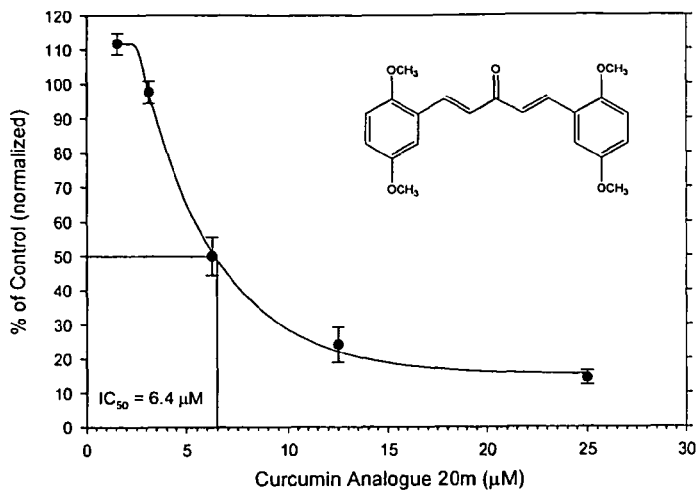
FIG. 6H is a graph showing an $IC_{50}$ plot of varying doses of analog 20m against inhibition of NF-κB activity.
Figure 6I:
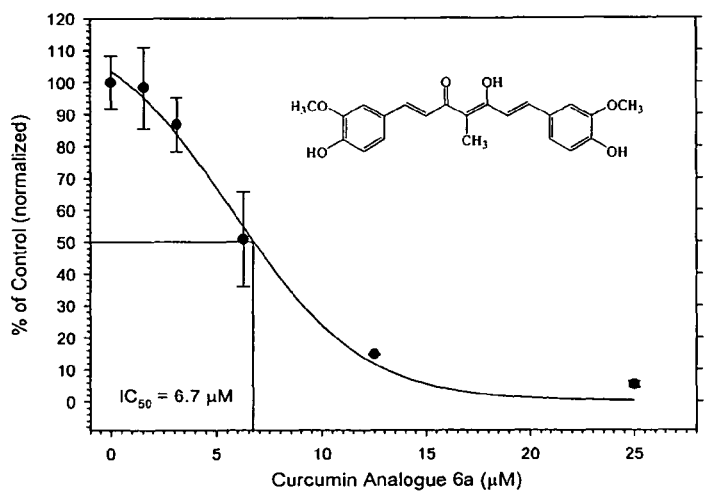
FIG. 6I is a graph showing an $IC_{50}$ plot of varying doses of analog 6a against inhibition of NF-κB activity.
Figure 6J:
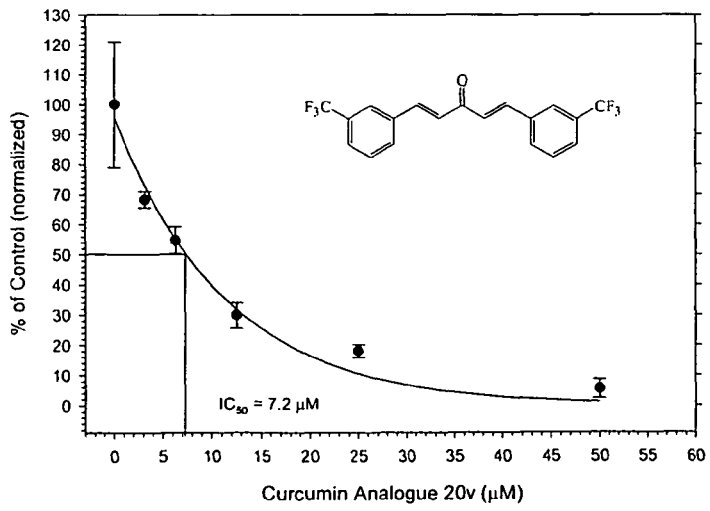
FIG. 6J is a graph showing an $IC_{50}$ plot of varying doses of analog 20v against inhibition of NF-κB activity.
Figure 6K:
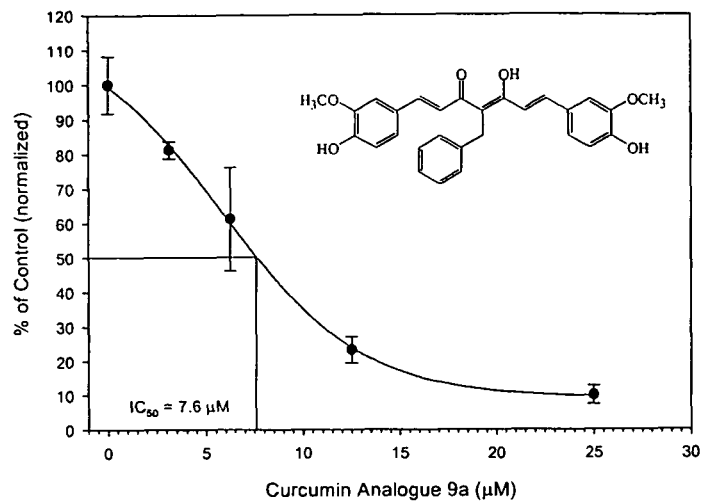
FIG. 6K is a graph showing an $IC_{50}$ plot of varying doses of analog 9a against inhibition of NF-κB activity.
Figure 6L:
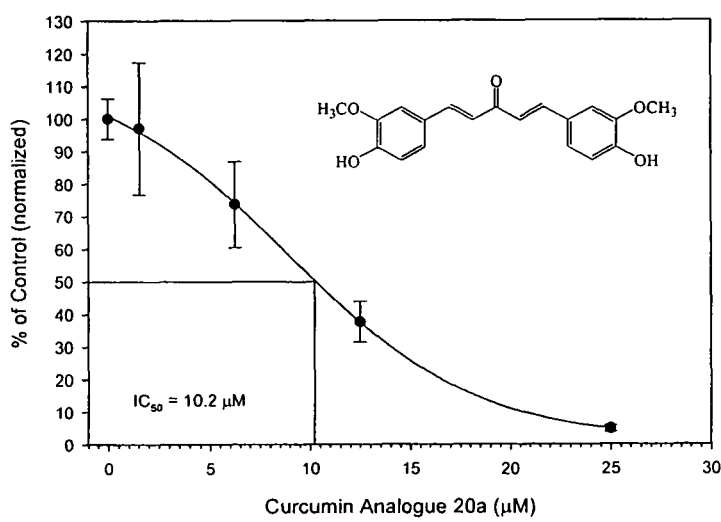
FIG. 6L is a graph showing an $IC_{50}$ plot of varying doses of analog 20a against inhibition of NF-κB activity.

The $IC_{50}$ values for the active analogs against NF-κB were also measured. An $IC_{50}$ value is the concentration of the analog necessary to give 50% inhibition of NF-κB activation. The $IC_{50}$ plot for curcumin is shown in FIG. 6A. $IC_{50}$ plots for additional active analogs are shown in FIGS. 6B-6L. Table 5 shows $IC_{50}$ values for eight of the active analogs from the screening assay. Table 5 also shows if each analog was active as an antioxidant (+) in both the TRAP and FRAP assays. Of the $IC_{50}$ values obtained, curcumin (8.2 μM) is the least potent analog against NF-κB. Analogs 29 and 31 which contain pyridine rings are the most active analogs against NF-κB with $IC_{50}$ values of 3.5 and 3.4 μM. As observed in Table 5, five analogs are active against NF-κB independent of antioxidant activity. This indicates that the analogs are targeting specific proteins in the cell.

TABLE 5

$IC_{50}$ Values and Antioxidant Results for Active Analogs Against NF-κB.

| Structure | Analog Number | $IC_{50}$ (μM) | TRAP | FRAP |
|---|---|---|---|---|
| 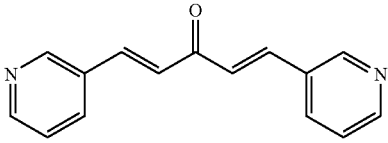 [SMILES: O=C(/C=C/c1cccnc1)/C=C/c1cccnc1] | 31 | 3.4 | − | − |
| 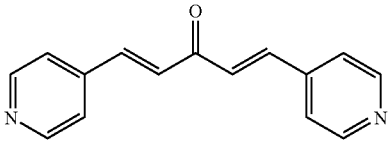 [SMILES: O=C(/C=C/c1ccncc1)/C=C/c1ccncc1] | 29 | 3.5 | − | − |
| 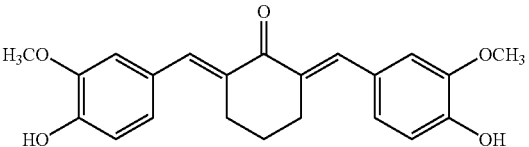 [SMILES: COc1cc(/C=C2\CCC/C(=C\c3ccc(O)c(OC)c3)C2=O)ccc1O] | 38a | 4.2 | + | + |
| 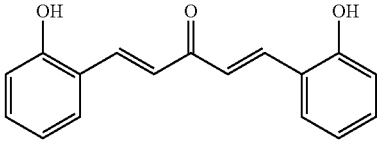 [SMILES: O=C(/C=C/c1ccccc1O)/C=C/c1ccccc1O] | 20q | 4.2 | + | − |
| 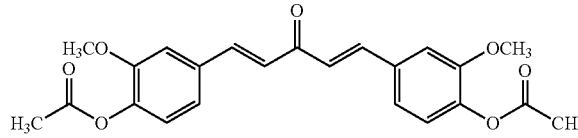 | 20ag | 5.4 | − | + |
| 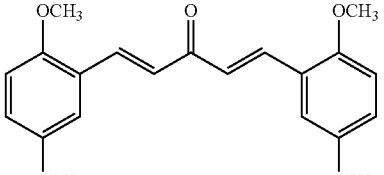 | 20m | 6.4 | − | − |
| 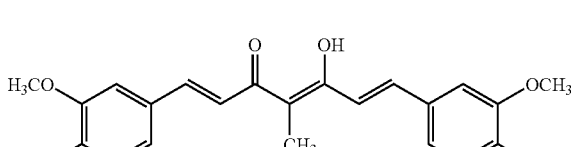 | 6a | 6.8 | + | + |

TABLE 5-continued

IC$_{50}$ Values and Antioxidant Results for Active Analogs Against NF-κB.

| Structure | Analog Number | IC$_{50}$ (μM) | TRAP | FRAP |
|---|---|---|---|---|
| (structure shown) | 9a | 7.6 | + | + |

Example 4

Molecular Modeling of Curcumin Derivatives Binding to NF-κB

Molecular modeling studies can be performed to obtain useful information for the design of potent analogs. Modeling allows the visualization of ligand-protein interactions which can identify a potential inhibitor binding site in a protein. In most cases the substrate binding site is known from crystal structures that contain the native substrate or a substrate analog. Binding sites are also identified through crystal structure data involving bound inhibitors. Removal of the known inhibitor and addition of a potential inhibitor can give useful information concerning inhibitor protein interactions as well as estimated inhibition constants. Estimated inhibition constants ($K_{est}$) can be obtained from the docking studies with the modeling program. These constants can be compared to experimentally obtained inhibition constants ($K_{exp}$). If a correlation between $K_{est}$ and $K_{exp}$ is found then a new potential inhibitor can be docked to obtain $K_{est}$ to determine if synthesis of the analog is warranted.

The dockings were performed using the docking program Autodock 3.0 (Morris et al., J. Comp. Chem. 19(14), 1639-1662 (1998); Morris et al., J. Comput.-Aided Mol. Des. 10(4), 293-304 (1996)) on a cluster of Silicon Graphics workstations consisting of Octanes and O2s. The analogs, prepared using Sybyl 7.0 (Tripos Inc.), were drawn, assigned partial charges using the included Gasteiger-Hückel method and energy minimized using the Broyden, Fletcher, Goldfarb and Shanno (BFGS) optimization method. Minimizations were run for 10,000 iterations and all rotateable bonds were defined before docking. The proteins were prepared before docking in Sybyl by removing non-native substrates and water molecules. Polar hydrogens and Kollman Uni charges were added to the proteins as well. The molecules were docked in an area defined around the protein as a cube of either 60×60×60 Å or 120×120×120 Å.

Since the protein target of the analogs is unknown, molecular modeling was employed to examine a possible correlation between $K_{est}$ and $K_{exp}$. On proteins such as HSP90 (protein data bank code 1YER and 1YES) and glutathione S-transferase (19GS) the location of the analog binding site is known. Docking studies were performed using Autodock 3.0 and the resulting $K_{est}$ was compared to $K_{exp}$.

On proteins such as NF-κB (1IKN and 1SCV) and AP-1 (1FOS), the location of analog binding site is not known. Therefore, it was necessary to identify any and all potential binding areas and model the analogs to these areas. Fortunately, a program has been developed that can identify binding areas (Brown et al., J. Chem. Inf. Comp. Sci. 44(4), 1412-1422 (2004)). The program called the Macromolecule Encapsulating Surface (MES) program generates a flexible surface over the entire protein and determines how much unoccupied volume there is between the generated surface and the surface of the protein. If there is a large space, that area is a potential binding site and it is possible for a potential inhibitor to fill this space. On the other hand, if there is no space the program overlooks that area and dismisses it from future consideration. Once all of the potential binding areas are identified, the program will dock inhibitors in each of these locations and determine the $K_{est}$ for each analog.

Binding to NF-κB

When performing docking studies of the potential analogs against NF-κB, two crystal structures, 1IKN and 1SVC, were selected from the twelve available in the protein databank. These two crystal structures were selected because one (1IKN) contained both the p50 and p65 subunits of NF-κB. The other crystal structure was selected because it contained the p50 subunit of NF-κB bound to a short segment of DNA.

Binding to the 1IKN Form of NF-κB

Figure 7:
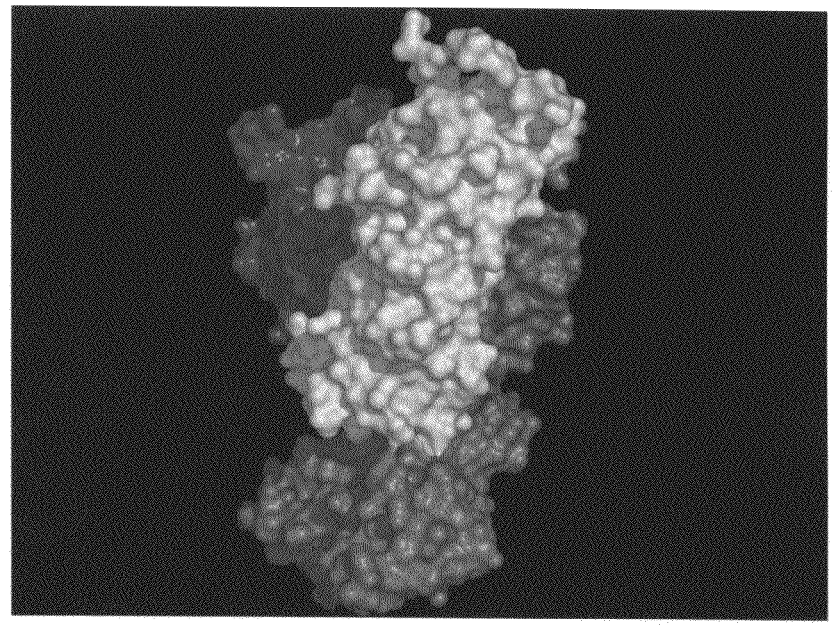
FIG. 7 is a computer-generated image representing NF-κB (1IKN) bound to IκB.

1IKN (Huxford et al., Cell 1998, 95, 759-770) was selected because it contains both the p50 and p65 subunits of NF-κB, the most common heterodimer. The p50 subunit was not the complete subunit. A second reason 1IKN was selected was because it contained I-κB, the natural inhibitor of NF-κB. Since I-κB is phosphorylated at serine residues 32 and 36, in the activation cascade of NF-κB, it was hoped that the crystal structure would contain these residues to see if the potential analogs blocked them from being phosphorylated. Unfortunately, the crystal structure of I-κB did not contain these residues and thus docking studies could not be performed directly on the I-κB subunit. FIG. 7 shows the p50 and p65 NF-κB heterodimer complexed to I-κB. In FIG. 7, the blue protein is the p50 subunit, the red protein is the p65 subunit and the yellow protein is I-κB.

Figure 8:
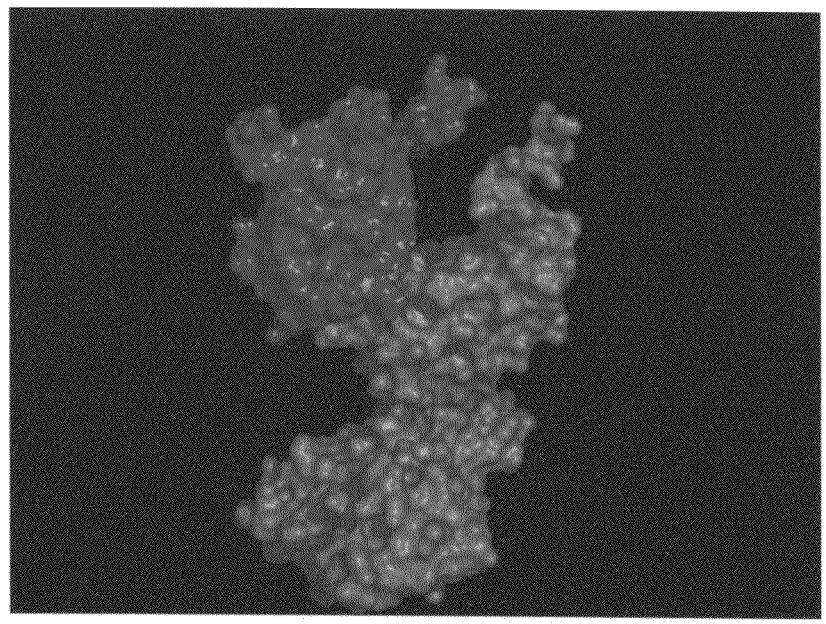
FIG. 8 is a computer-generated image representing NF-κB (1IKN) with IκB removed.
Figure 9:
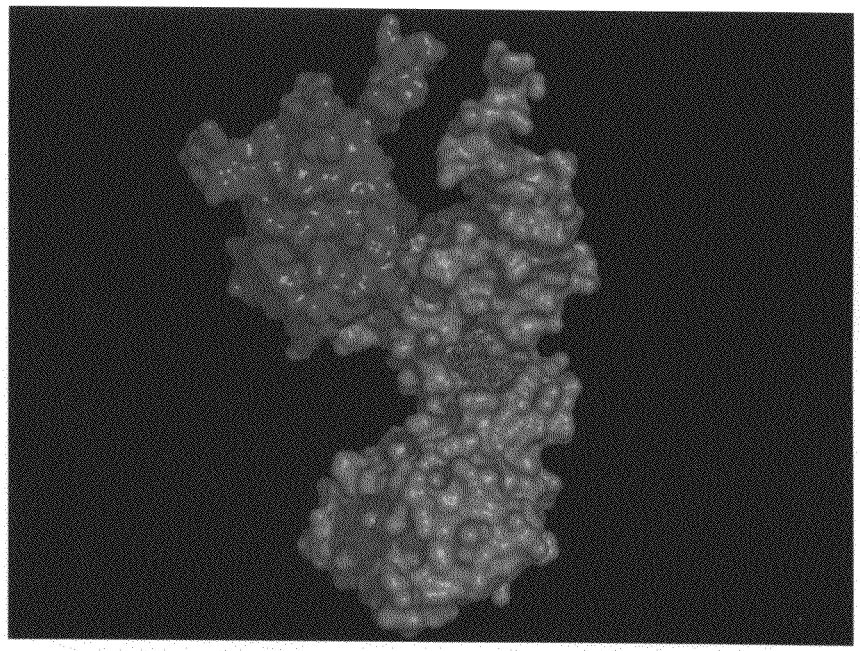
FIG. 9 is a computer-generated image representing the front face of NF-κB (1IKN) with bound analogs.

When I-κB is removed as shown in FIG. 8, a new face of the heterodimer is revealed. It is believed that DNA binds to this new face of the protein after NF-κB translocates to the nucleus. If the potential analogs inhibit NF-κB from binding to DNA and thus stopping transcription from occurring, then the potential analogs should bind to this face of the molecule. However, only analogs 9a, 9b, 12b, 15a, 15b, 17b, 20l and 52l of the analog library bind to the newly exposed face as shown in FIG. 9. Analogs 12b, 15a and 17b have a good $K_{est}$ values and rank in the top nine analogs. Analog 12b binds to NF-κB on this newly exposed face of the molecule and the $K_{est}$ value is good at 2.00E-10 M. These results indicate the analogs should be blocking the NF-κB-DNA interaction. However, there is no correlation between the analogs that bind on this face of the molecule and the experimental results of these analogs. Based on the docking studies, it does not appear that the analogs block a NF-κB-DNA interaction, but it is possible that they inhibit NF-κB in another manner.

Figure 10:
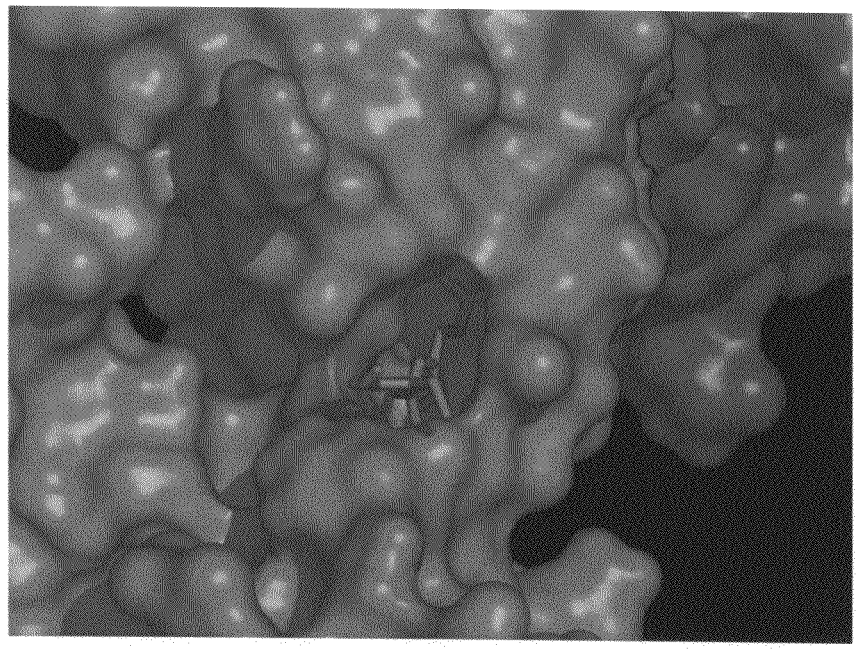
FIG. 10 is a computer-generated image representing curcumin bound to NF-κB (1IKN)
Figure 11:
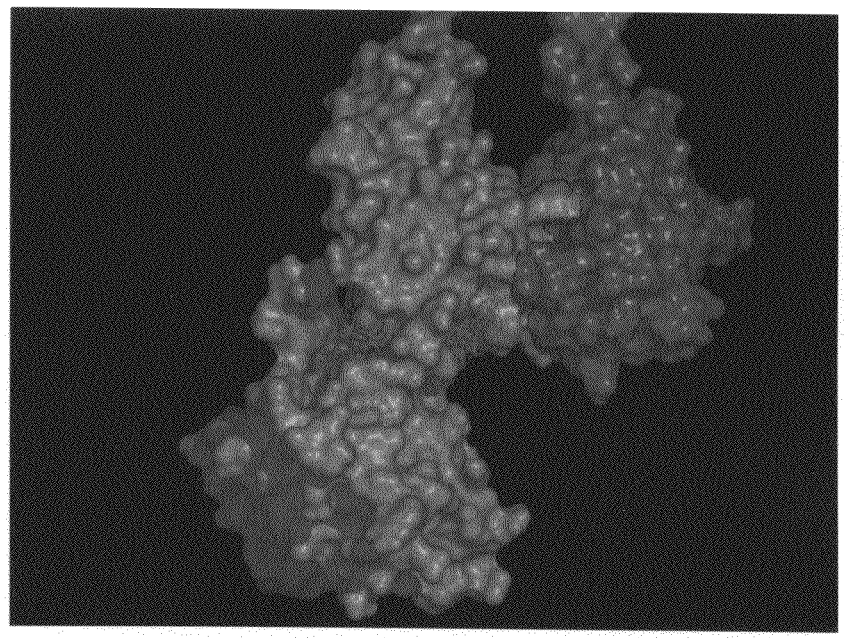
FIG. 11 is a computer-generated image representing the opposite face of NF-κB (1IKN) with bound analogs.

Curcumin (3a), shown in FIG. 10, and the other potential inhibitors bind on the opposite side of the molecule as shown in FIG. 11. Many of the analogs that bind on the opposite side also have good $K_{est}$ values with analogs 3i, 20ag, 23 and 53 being the best. Table 6 shows each analog with its $K_{est}$ value in molar units. Again, there is no correlation between $K_{est}$ and $K_{exp}$. This indicates that the potential inhibitors probably do not bind to the NF-κB heterodimer.

TABLE 6

$K_{est}$ Values of Curcumin Analogs Against NF-κB Without MES.

| | | | | | | | |
|---|---|---|---|---|---|---|---|
| 12b | 2.00E−10 | 11b | 3.31E−09 | 20q | 9.59E−09 | 46a | 3.07E−08 |
| 20ag | 3.07E−10 | 20v | 3.38E−09 | 20ah | 9.80E−09 | 20r | 3.16E−08 |
| 17b | 3.27E−10 | 52e | 3.52E−09 | 20z | 1.11E−08 | 31 | 3.66E−08 |
| 53 | 3.72E−10 | 9b | 4.09E−09 | 45a | 1.20E−08 | 29 | 4.87E−08 |
| 3i | 6.31E−10 | 36a | 4.55E−09 | 40af | 1.29E−08 | 46al | 5.03E−08 |
| 23 | 7.36E−10 | 6a | 4.62E−09 | 20x | 1.35E−08 | 46ak | 5.16E−08 |
| 20n | 7.86E−10 | 20w | 5.08E−09 | 3c | 1.39E−08 | 39b | 5.32E−08 |
| 25 | 1.16E−09 | 20o | 5.32E−09 | 20ab | 1.63E−08 | 20b | 5.82E−08 |
| 15a | 1.20E−09 | 20a | 5.42E−09 | 13b | 1.68E−08 | 20s | 6.08E−08 |
| 3d | 1.34E−09 | 20p | 5.42E−09 | 20ae | 1.75E−08 | 20f | 6.66E−08 |
| 14a | 1.34E−09 | 16b | 5.71E−09 | 52b | 1.76E−08 | 42b | 6.78E−08 |
| 9a | 1.51E−09 | 20k | 6.38E−09 | 38b | 1.87E−08 | 20l | 7.00E−08 |
| 3b | 1.94E−09 | 52aa | 6.52E−09 | 48a | 1.92E−08 | 50b | 7.12E−08 |
| 3g | 2.32E−09 | 52ac | 7.38E−09 | 20t | 2.35E−08 | 34 | 9.37E−08 |
| 38a | 2.36E−09 | 3f | 7.60E−09 | 36e | 2.39E−08 | 40b | 1.23E−07 |
| 14b | 2.38E−09 | 20d | 7.74E−09 | 20g | 2.45E−08 | 43b | 1.41E−07 |
| 20m | 2.49E−09 | 20c | 7.85E−09 | 3e | 2.54E−08 | 52l | 1.76E−07 |
| 15b | 2.89E−09 | 3h | 8.02E−09 | 20e | 2.60E−08 | 45b | 2.19E−07 |
| 3a | 2.94E−09 | 46ad | 8.96E−09 | 48ad | 2.71E−08 | 35a | 5.30E−07 |
| 6b | 3.06E−09 | 20y | 9.03E−09 | 20aa | 2.85E−08 | 35e | 1.66E−06 |
| 13a | 3.17E−09 | 20u | 9.53E−09 | 20ac | 2.90E−08 | 35q | 3.53E−06 |
| 20i | 3.29E−09 | | | | | | |

Figure 12:
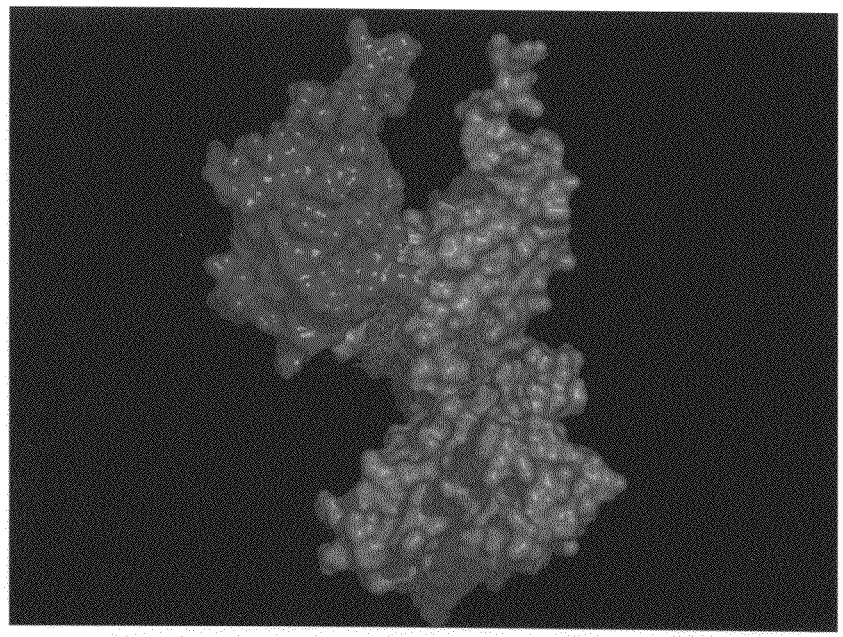
FIG. 12 is a computer-generated image representing NF-κB (1IKN) with MES and bound analogs.
Figure 13:
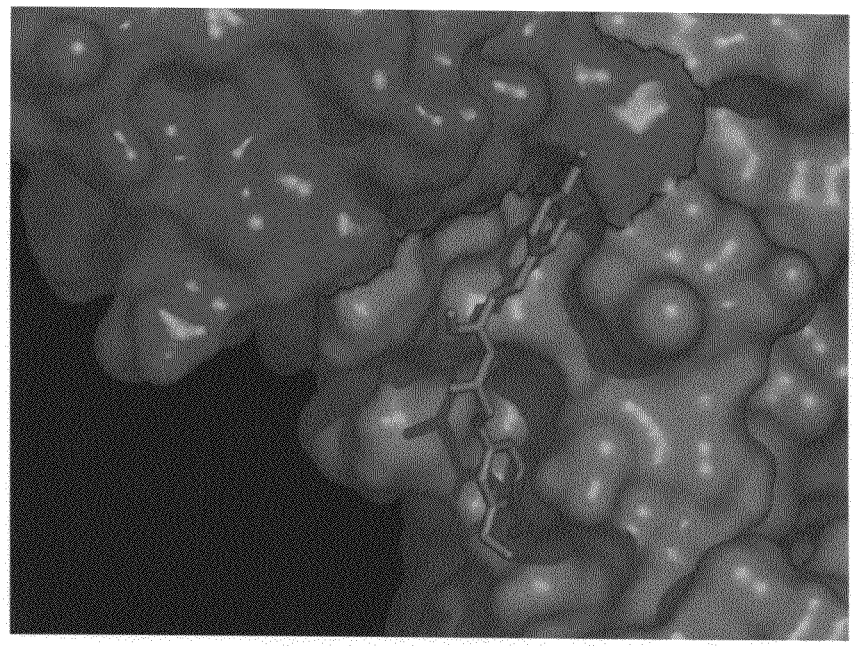
FIG. 13 is a computer-generated image representing curcumin bound to NF-κB (1IKN) with MES.

To verify these findings, the MES program was utilized on the NF-κB heterodimer to identify any potential binding areas for the analogs. The results of this docking study are different than the docking results obtained without the use of the MES program. With the MES program, all the potential inhibitors bind on the new face of the NF-κB heterodimer as shown in FIG. 12. The visual results of this docking study indicate that the analogs should be good inhibitors of NF-κB and in particular of a NF-κB-DNA interaction. Most of the potential inhibitors bind to NF-κB with good Kes,t values with analogs 9a, 12b, 13a, 15a and 20ag showing the best activity as shown in Table 7. Curcumin (3a), as shown in FIG. 13, binds to the heterodimer towards the bottom portion of the p50 subunit and has a $K_{est}$ value of 9.64E-8 M. However, the $K_{est}$ values of curcumin and its analogs do not correlate to $K_{exp}$ values, they probably do not bind to NF-κB.

TABLE 7

$K_{est}$ Values for NF-κB (1IKN) with MES.

| | | | | | | | |
|---|---|---|---|---|---|---|---|
| 20ag | 7.26E−09 | 40af | 8.72E−08 | 6b | 2.19E−07 | 48ad | 7.60E−07 |
| 9a | 7.39E−09 | 14b | 8.86E−08 | 20y | 2.22E−07 | 20t | 8.03E−07 |
| 15a | 1.26E−08 | 20k | 9.43E−08 | 13c | 2.41E−07 | 20l | 8.15E−07 |
| 12b | 1.54E−08 | 3a | 9.64E−08 | 52e | 2.47E−07 | 50b | 8.72E−07 |
| 13a | 1.57E−08 | 15b | 9.69E−08 | 20p | 2.56E−07 | 46ak | 9.22E−07 |
| 17b | 1.65E−08 | 20u | 9.88E−08 | 52l | 2.57E−07 | 42b | 9.44E−07 |
| 9b | 1.93E−08 | 36a | 1.06E−07 | 20aa | 2.71E−07 | 40b | 9.64E−07 |
| 25 | 2.51E−08 | 20w | 1.29E−07 | 3e | 2.74E−07 | 29 | 1.03E−06 |
| 3d | 2.59E−08 | 3h | 1.40E−07 | 20x | 2.81E−07 | 52b | 1.08E−06 |
| 20ae | 2.65E−08 | 3g | 1.47E−07 | 20ab | 2.82E−07 | 46al | 1.14E−06 |
| 20i | 2.69E−08 | 46ad | 1.56E−07 | 20z | 3.78E−07 | 46a | 1.24E−06 |
| 38a | 3.27E−08 | 20o | 1.63E−07 | 52aa | 3.84E−07 | 20b | 1.25E−06 |
| 20a | 4.38E−08 | 20f | 1.74E−07 | 3b | 4.03E−07 | 31 | 1.33E−06 |
| 20ah | 5.27E−08 | 3i | 1.82E−07 | 20q | 4.16E−07 | 39b | 1.42E−06 |
| 20m | 5.61E−08 | 16b | 1.82E−07 | 20c | 4.46E−07 | 43b | 2.01E−06 |
| 53 | 6.06E−08 | 36e | 1.86E−07 | 3f | 4.47E−07 | 38b | 2.41E−06 |
| 14a | 6.10E−08 | 20d | 1.86E−07 | 52ac | 4.61E−07 | 45b | 4.15E−06 |
| 20v | 6.66E−08 | 20g | 1.86E−07 | 20ac | 4.92E−07 | 34 | 4.22E−06 |
| 23 | 7.21E−08 | 20e | 1.87E−07 | 20s | 5.49E−07 | 35a | 4.46E−06 |
| 11b | 7.35E−08 | 13b | 2.03E−07 | 20r | 6.43E−07 | 35e | 4.73E−06 |

TABLE 7-continued $K_{est}$ Values for NF-κB (1IKN) with MES.

| | | | | | | | |
|---|---|---|---|---|---|---|---|
| 20n | 8.21E−08 | 45a | 2.05E−07 | 48a | 6.44E−07 | 35q | 4.81E−06 |
| 6a | 8.63E−08 | | | | | | |

Binding to the 1SVC Form of NF-κB

Figure 14:
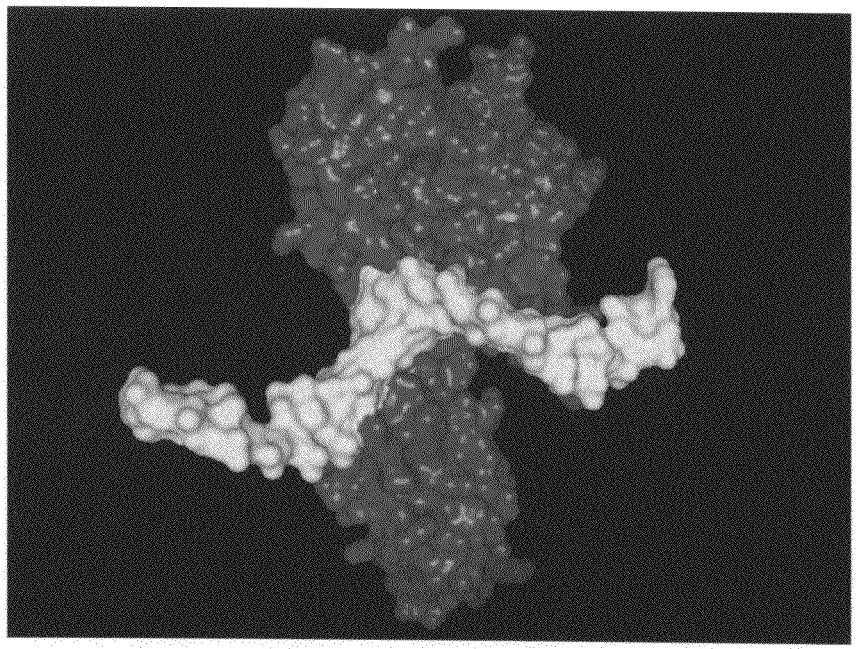
FIG. 14 is a computer-generated image representing NF-κB (1SVC) bound to DNA.
Figure 15:
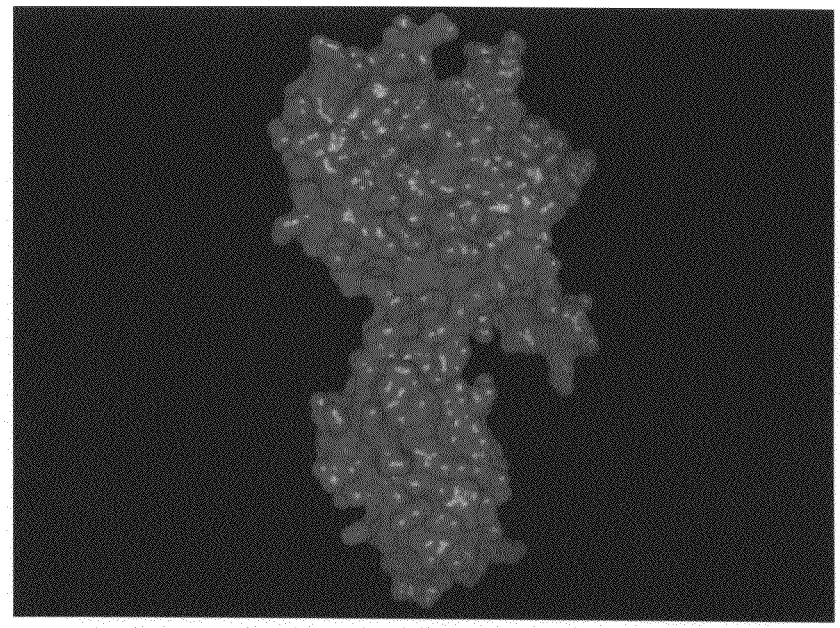
FIG. 15 is a computer-generated image representing NF-κB (1SVC) with DNA removed.

1SVC (Mueller et al., Nature, 373, 311-317 (1995)) was selected because it contains the p50 subunit of NF-κB bound to a small portion of DNA. This crystal structure was important because it contained almost all of the p50 subunit and because it had the exact site of DNA binding. This would provide additional information concerning the blocking of NF-κB-DNA binding interactions of the analogs. FIG. 14 shows the p50 subunit of NF-κB bound to a small portion of DNA. In FIG. 14, the blue protein is the p50 subunit and the yellow segment is the DNA. When the DNA is removed as shown in FIG. 15, a new area is exposed. It is in this location that the analogs will bind if they are preventing a NF-κB-DNA binding interaction.

Figure 16:
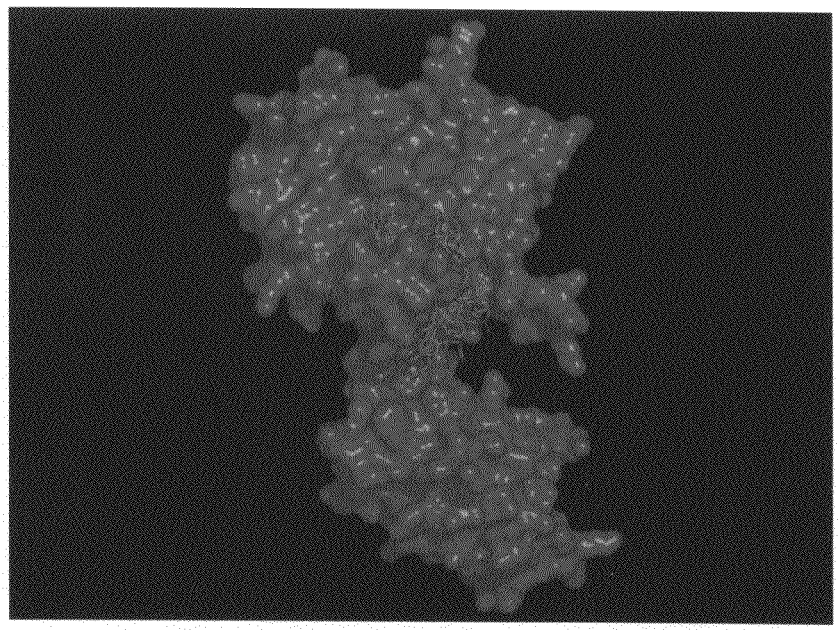
FIG. 16 is a computer-generated image representing NF-κB (1SVC) with bound analogs.
Figure 17:
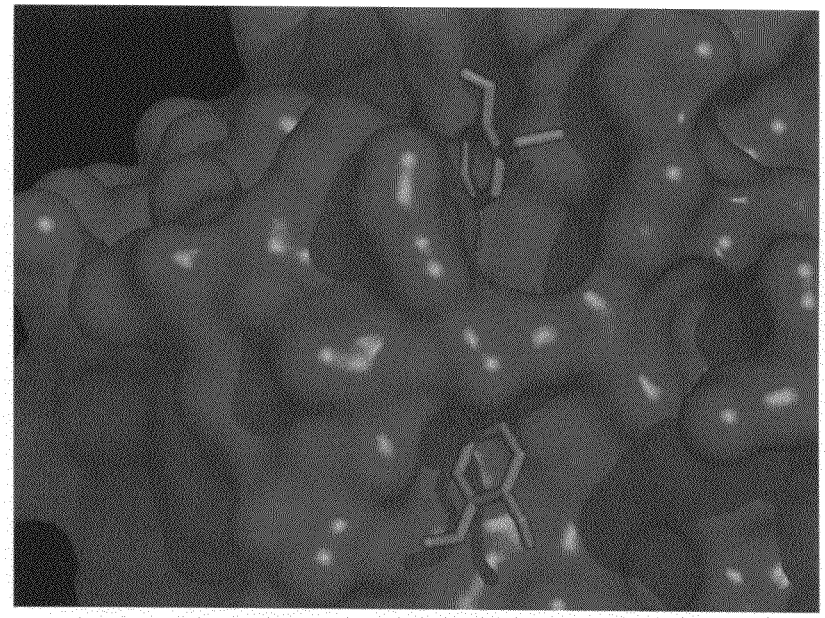
FIG. 17 is a computer-generated image representing curcumin bound to NF-κB (1SVC)

When docking studies were performed, most of the potential inhibitors bind in the general area the DNA once occupied as shown in FIG. 16. It is apparent that in the location of binding, there is a "small hole" to which all of the analogs on this portion of the molecule bind. FIG. 17 shows curcumin (3a) bound in the "small hole".

Figure 18:
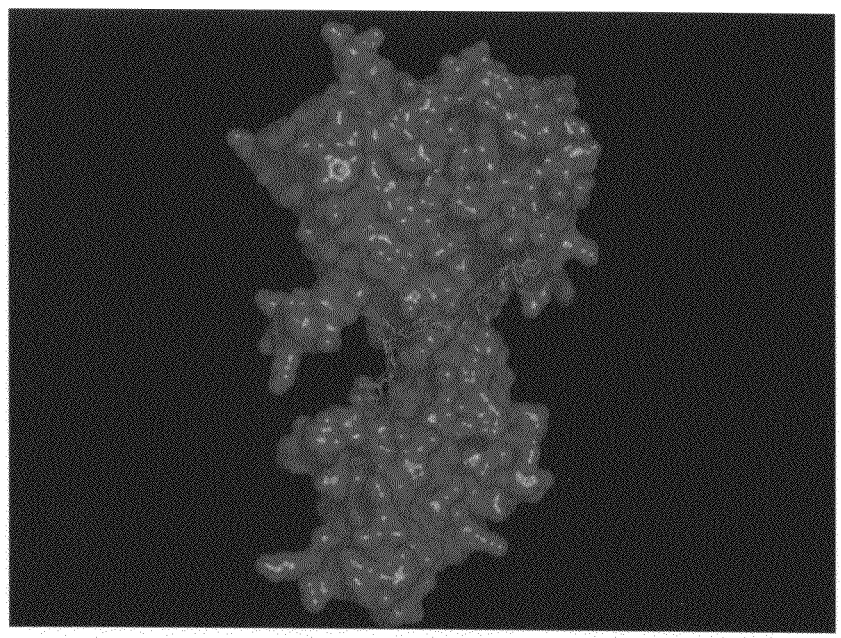
FIG. 18 is a computer-generated image representing the opposite face of NF-κB (1SVC) with bound analogs.

Many of these analogs bind with good $K_{est}$ values with analog 9b displaying the best inhibitory activity at 3.79E-10 M as shown in Table 8. Based on these $K_{est}$ values, several analogs should inhibit the blocking of NF-κB-DNA binding interactions. However, there is no correlation to the $K_{exp}$ results indicating that these analogs probably do not inhibit this type of an interaction. It is possible that there could be another mode of action that potential inhibitors could be displaying since seven analogs bind on the opposite side of the protein as shown in FIG. 18. These seven analogs, 12b, 15a, 15b, 52e, 52l, 52aa and 52ac have rather poor $K_{est}$ values with the exception of analog 12b which was ranked as the third best potential inhibitor. Since these analogs have poor $K_{est}$ values and there is no correlation to any $K_{exp}$ results, they are likely not inhibitors of the NF-κB protein.

TABLE 8

$K_{est}$ Values for NF-κB (1SVC).

| | | | | | | | |
|---|---|---|---|---|---|---|---|
| 9b | 3.79E−10 | 20ag | 1.32E−08 | 20w | 4.68E−08 | 20b | 1.57E−07 |
| 3g | 1.59E−09 | 20u | 1.33E−08 | 20ac | 4.70E−08 | 29 | 1.65E−07 |
| 12b | 3.30E−09 | 20o | 1.34E−08 | 53 | 4.70E−08 | 48ad | 1.85E−07 |
| 25 | 4.39E−09 | 20x | 1.42E−08 | 15a | 4.75E−08 | 40b | 1.86E−07 |
| 6b | 4.40E−09 | 11b | 1.47E−08 | 20t | 5.41E−08 | 38a | 1.87E−07 |
| 3i | 5.53E−09 | 3a | 1.57E−08 | 20r | 6.15E−08 | 46a | 1.94E−07 |
| 6a | 5.62E−09 | 36a | 1.75E−08 | 20l | 6.62E−08 | 50b | 1.94E−07 |
| 23 | 5.67E−09 | 20a | 1.87E−08 | 20n | 7.54E−08 | 45a | 2.03E−07 |
| 20e | 6.09E−09 | 13c | 1.96E−08 | 20p | 7.64E−08 | 34 | 2.89E−07 |
| 3e | 6.84E−09 | 13b | 1.97E−08 | 46ad | 7.96E−08 | 46ak | 2.96E−07 |
| 20m | 7.34E−09 | 20aa | 2.12E−08 | 46al | 8.38E−08 | 52aa | 3.43E−07 |
| 3d | 7.35E−09 | 20y | 2.22E−08 | 20c | 8.47E−08 | 38b | 4.41E−07 |
| 14b | 7.35E−09 | 20q | 2.78E−08 | 42b | 9.25E−08 | 52e | 4.42E−07 |
| 13a | 8.18E−09 | 16b | 2.83E−08 | 20s | 9.78E−08 | 45b | 5.15E−07 |
| 3h | 9.21E−09 | 17b | 2.95E−08 | 31 | 1.11E−07 | 43b | 5.65E−07 |
| 14a | 9.59E−09 | 3f | 3.00E−08 | 20z | 1.13E−07 | 52l | 5.67E−07 |
| 20ah | 9.85E−09 | 36e | 3.34E−08 | 9a | 1.18E−07 | 52ac | 6.59E−07 |
| 20d | 1.07E−08 | 20f | 3.41E−08 | 40af | 1.21E−07 | 35q | 9.89E−07 |
| 20v | 1.11E−08 | 20ab | 3.51E−08 | 15b | 1.27E−07 | 52b | 1.05E−06 |
| 20g | 1.19E−08 | 20i | 4.10E−08 | 48a | 1.45E−07 | 35a | 1.07E−06 |
| 3b | 1.30E−08 | 20k | 4.55E−08 | 39b | 1.55E−07 | 35e | 1.18E−06 |
| 20ae | 1.31E−08 | | | | | | |

Figure 19:
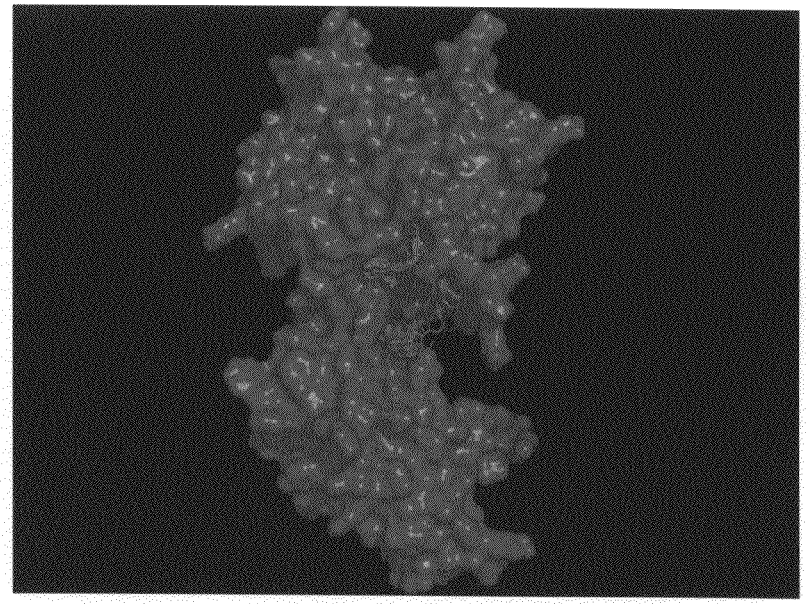
FIG. 19 is a computer-generated image representing NF-κB (1SVC) with MES and bound analogs.

To verify these findings, the MES program was utilized on the p50 subunit of NF-κB to identify any potential binding areas for the analogs. The results of this docking study are slightly different than those when the MES program was not used. All the potential inhibitors bind to an area directly below the DNA binding area and wrap around to the backside of the protein, as shown in FIG. 19, indicating they may inhibit the NF-κB-DNA interaction. None of the potential inhibitors bind in the "small hole" as in the docking results without the MES program (FIG. 17). The $K_{est}$ values for these analogs are mediocre, with the best analog, 15a, having a $K_{est}$ of 2.27E-08 M as shown in Table 9. Since the library of analogs does not display good $K_{est}$ values or correlate with any $K_{exp}$ results, NF-κB does not appear to be the target for curcumin analogs.

TABLE 9

$K_{est}$ Values for NF-κB (1SVC) with MES.

| | | | | | | | |
|---|---|---|---|---|---|---|---|
| 15a | 2.27E−08 | 11b | 4.15E−07 | 20l | 8.98E−07 | 20ac | 2.12E−06 |
| 17b | 2.48E−08 | 3f | 4.22E−07 | 3b | 9.38E−07 | 40b | 2.13E−06 |
| 12b | 2.63E−08 | 40af | 4.26E−07 | 20d | 1.01E−06 | 48ad | 2.31E−06 |
| 20ag | 5.48E−08 | 3g | 4.37E−07 | 20k | 1.19E−06 | 52aa | 2.40E−06 |
| 15b | 6.30E−08 | 3e | 4.45E−07 | 52e | 1.21E−06 | 31 | 2.95E−06 |
| 38a | 7.76E−08 | 20ah | 4.51E−07 | 20e | 1.22E−06 | 20s | 2.98E−06 |
| 9a | 8.10E−08 | 3a | 4.79E−07 | 20f | 1.27E−06 | 39b | 3.04E−06 |
| 6a | 8.37E−08 | 20u | 4.82E−07 | 20g | 1.28E−06 | 46ak | 3.31E−06 |
| 53 | 9.53E−08 | 20ae | 5.00E−07 | 20ab | 1.34E−06 | 20t | 3.52E−06 |
| 3h | 1.01E−07 | 13c | 5.36E−07 | 20y | 1.34E−06 | 36e | 3.67E−06 |
| 3d | 1.29E−07 | 20o | 5.47E−07 | 52l | 1.46E−06 | 20b | 4.27E−06 |
| 9b | 1.32E−07 | 14b | 5.50E−07 | 20aa | 1.47E−06 | 52ac | 4.50E−06 |
| 23 | 1.58E−07 | 20w | 5.71E−07 | 20x | 1.55E−06 | 42b | 6.29E−06 |
| 25 | 2.36E−07 | 20a | 5.80E−07 | 20z | 1.58E−06 | 50b | 6.32E−06 |
| 3i | 2.67E−07 | 20n | 6.46E−07 | 20c | 1.70E−06 | 52b | 7.86E−06 |
| 14a | 2.78E−07 | 46ad | 6.58E−07 | 20q | 1.74E−06 | 35q | 8.52E−06 |
| 20p | 3.01E−07 | 36a | 6.79E−07 | 20r | 1.77E−06 | 45b | 9.20E−06 |
| 13a | 3.13E−07 | 46a | 6.81E−07 | 46al | 1.81E−06 | 35a | 1.11E−05 |
| 20i | 3.22E−07 | 13b | 7.62E−07 | 29 | 1.95E−06 | 35e | 1.30E−05 |
| 16b | 3.31E−07 | 6b | 7.66E−07 | 38b | 2.02E−06 | 34 | 1.84E−05 |
| 20m | 3.58E−07 | 45a | 8.30E−07 | 48a | 2.06E−06 | 43b | 1.88E−05 |
| 20v | 4.08E−07 | | | | | | |

Example 5

Inhibition of AP-1 Activity by Curcumin Derivatives

Curcumin and its analogues were screened for activity against AP-1 by a cellular assay using the AP-1 stable cell line (293/AP1-luc). The cell line is derived from human 293 embryonic kidney cells containing a chromosomal integration of a luciferase reporter construct regulated by 3 copies of the AP-1 response element (Panomics, Inc.). This cell line is obtained by co-transfection of pAP1-luc and pTK-hyg containing plasmids followed by the addition of hygromycin (200 µg/ml) to maintain cell selection.

The cell line was grown in a humidified atmosphere at 37° C. in 5% $CO_2$/95% air and maintained in Dulbecco's Modified Eagle's Medium (DMEM-high glucose containing 4 mM glutamine) containing fetal bovine serum (FBS, 10%), sodium pyruvate (1 mM), penicillin (100 units/ml), streptomycin (100 µg/ml) and hygromycin (100 µg/ml) to maintain cell selection (Gibco/Invitrogen).

The 293/AP1-luc cells were re-plated, 24 hr prior to treatment into, 24-well cell culture plates in media without hygromycin, to prevent it from interfering with the assay. The cells were then allowed to grow and attach, to the wells, for 24 hr in a humidified atmosphere at 37° C. in 5% $CO_2$/95% air. After 24 hr, the cells had reached approximately 60% confluency. The cells were then given media (1 ml) with or without phorbol 12-myristate 13-acetate (PMA, 10 ng/ml, Calciochem) followed by immediate treatments with curcumin or analogue (15 µM in DMSO). The cells were placed again in a humidified atmosphere at 37° C. in 5% $CO_2$/95% air for 24 hr. Plate wells were gently washed with PBS, pH 7.4, and lysed with passive lysis buffer (1x, 100 µl, Promega). The subsequent chemiluminescent lysates were analyzed with the Luciferase Assay System (Promega) utilizing a TD-20/20 luminometer. The relative light units (photons) were determined by the addition of firefly luciferase substrate (75 µl) to cell lysate (10 µl). The light units were then normalized to the amount of protein in the well (mg/ml) with BCA™ Protein Assay Kit (Pierce) and standardized to percent of control (PMA).

To determine cell viability, cells were treated as above but with 15 µM analogue. After gently washing to remove any dead cells, they were given media (100 µl) and CellTiter 96® AQueous One Solution reagent (20 µl) for 1 hour and read at 490 nm with a Spectromax plate reader.

Curcumin is a known inhibitor of the AP-1 activation cascade. Therefore, modification of the structure of curcumin could lead to analogs with enhanced activity. The library consisting of three series of curcumin analogs were used to examine the role of the enone functionality in aryl systems where the spacer is 7-carbons (as in curcumin), 5-carbons or 3-carbons in length. In addition, the importance of aryl ring substituents was assessed. The AP-1 activities of curcumin and analogs were determined by a cellular firefly luciferase assay. This assay utilized a commercially available cell line (Panomics 293-luc cellular assay) developed for screening inhibitors of AP-1. This cell line is stably transfected with a luciferase reporter controlled by an AP-1 dependent promoter. The cell is stimulated with phorbol ester which activates AP-1. AP-1 then binds to one of three promoter regions on the cells DNA leading to the production of a luciferase enzyme. Luciferin is added to the cell lysates and the luciferase enzyme catalyzes a cleavage of luciferin leading to the emission of light.

Figure 20A:
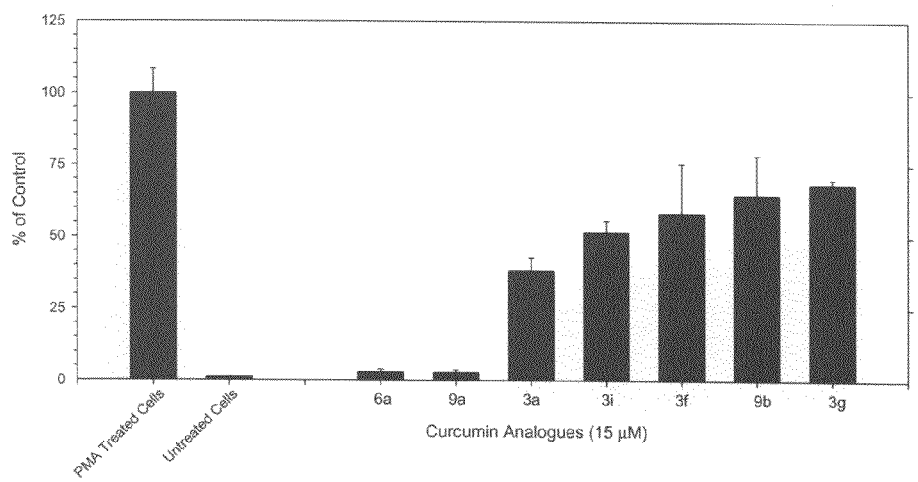
FIG. 20A is a bar graph showing the activities of curcumin analogs including 7-carbon analogs active in the AP-1 assay.
Figure 20B:
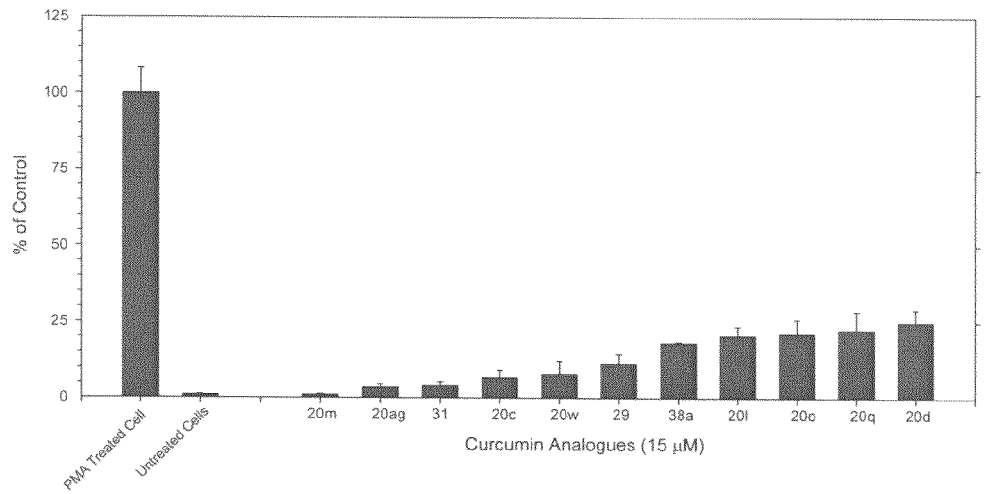
FIG. 20B is a bar graph showing the activities of curcumin analogs including 5-carbon analogs active in the AP-1 assay.
Figure 20C:
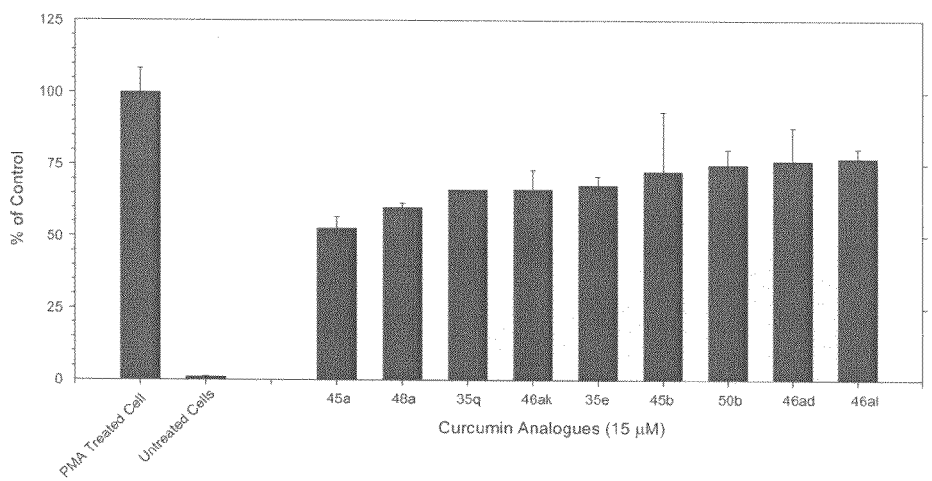
FIG. 20C is a bar graph showing the activities of curcumin analogs including 3-carbon analogs active in the AP-1 assay.
Figure 21A:
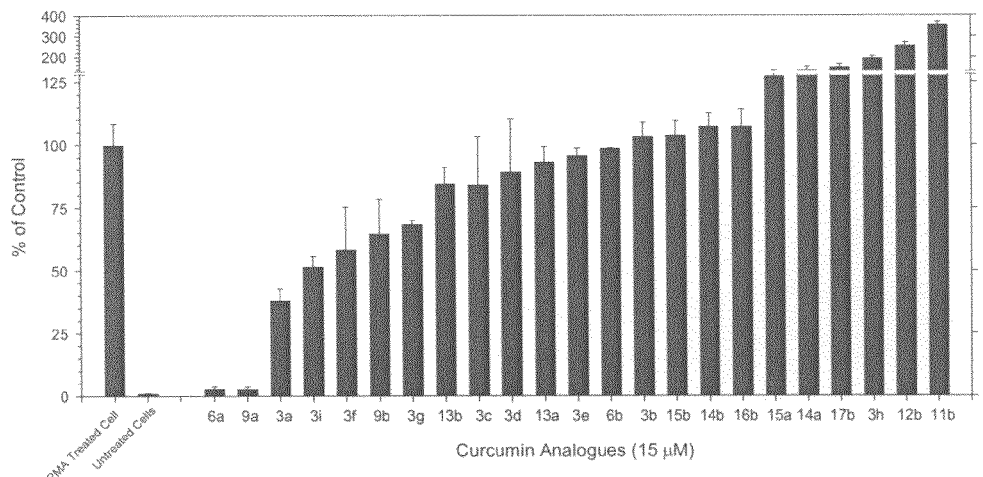
FIG. 21A is a bar graph showing the activities of curcumin analogs including 7-carbon analogues in the AP-1 assay.
Figure 21B:
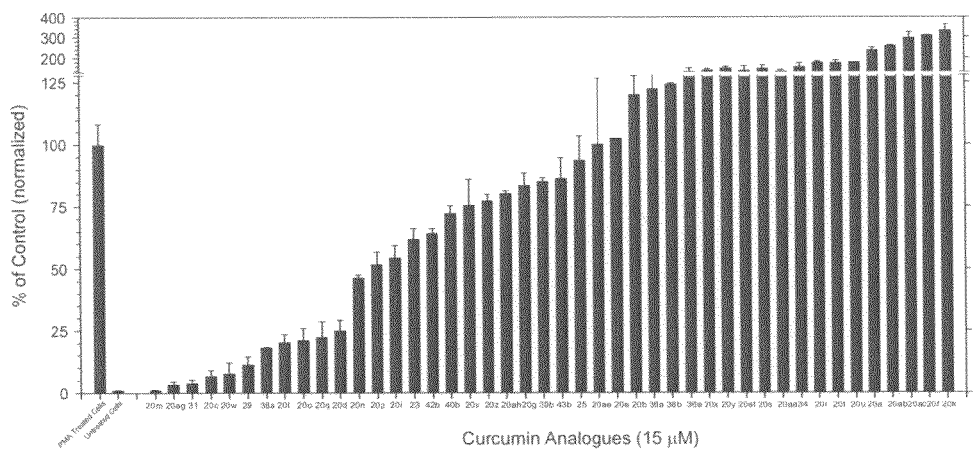
FIG. 21B is a bar graph showing the activities of curcumin analogs including 5-carbon analogues in the AP-1 assay.
Figure 21C:
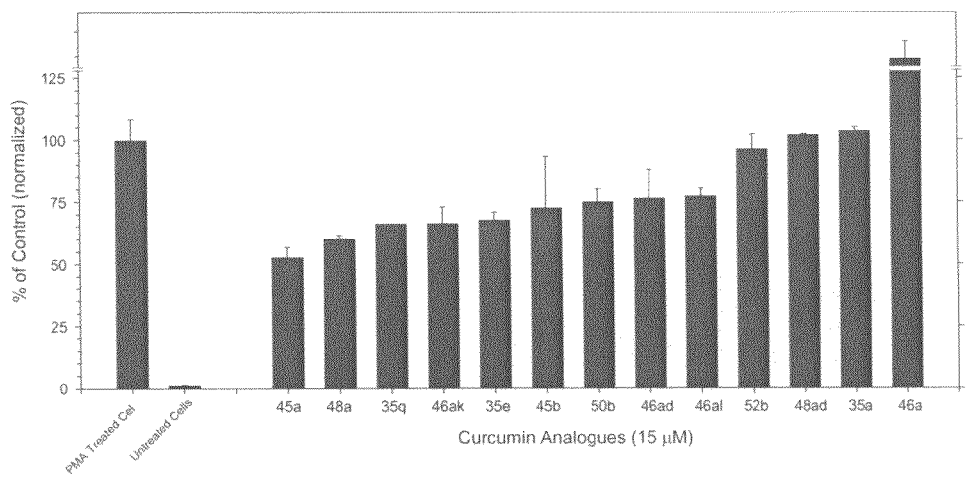
FIG. 21C is a bar graph showing the activities of curcumin analogs including 3-carbon analogues in the AP-1 assay.
Figure 22A:
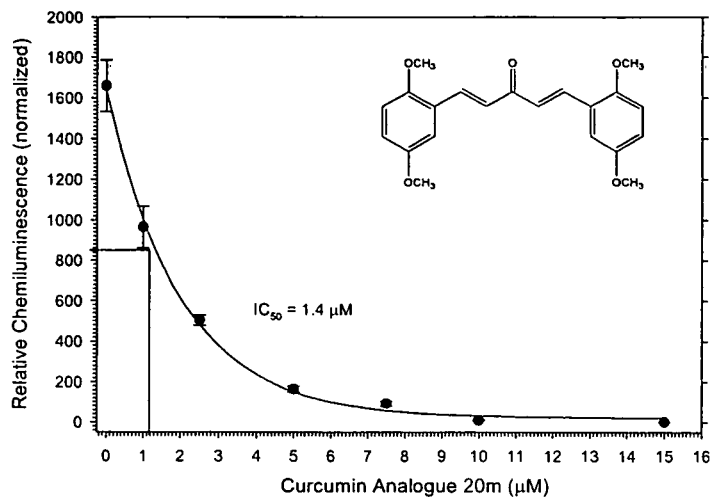
FIG. 22A is a graph showing an $IC_{50}$ plot of varying doses of analog 20m against inhibition of AP-1 activity.
Figure 22B:
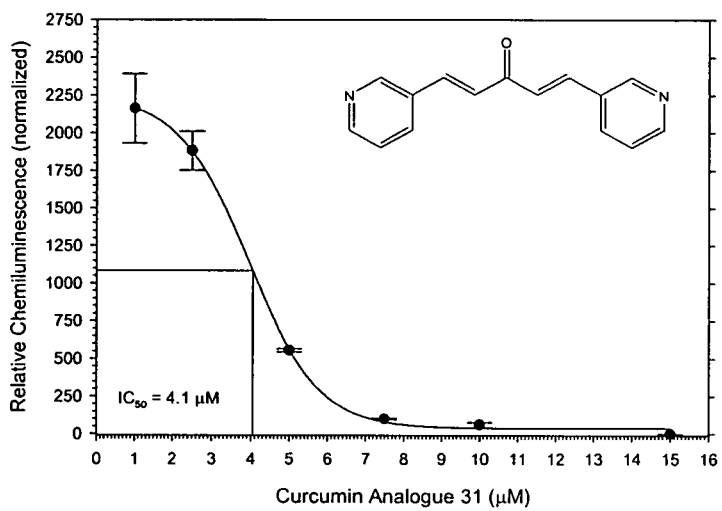
FIG. 22B is a graph showing an $IC_{50}$ plot of varying doses of analog 31 against inhibition of AP-1 activity.
Figure 22C:
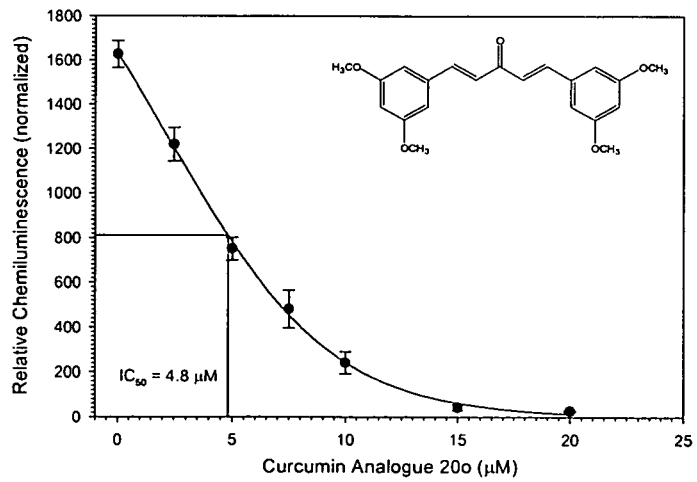
FIG. 22C is a graph showing an $IC_{50}$ plot of varying doses of analog 20o against inhibition of AP-1 activity.
Figure 22D:
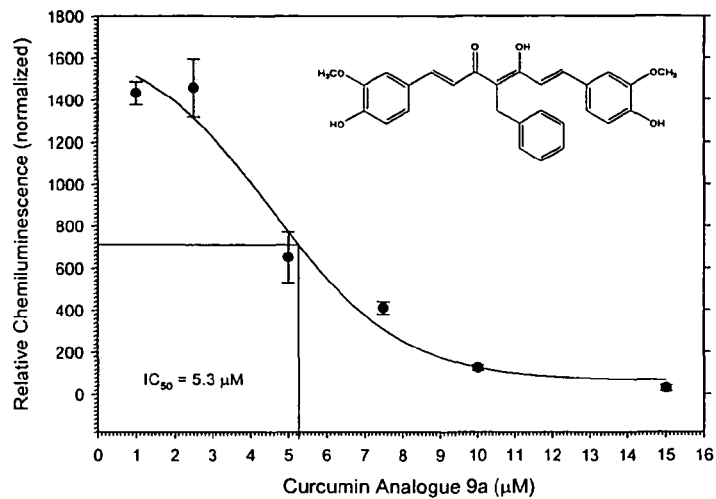
FIG. 22D is a graph showing an $IC_{50}$ plot of varying doses of analog 9a against inhibition of AP-1 activity.
Figure 22E:
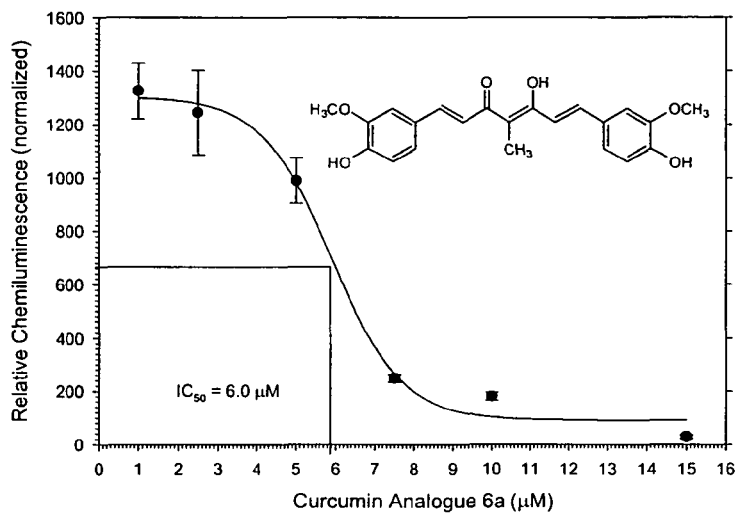
FIG. 22E is a graph showing an $IC_{50}$ plot of varying doses of analog 6a against inhibition of AP-1 activity.
Figure 22F:
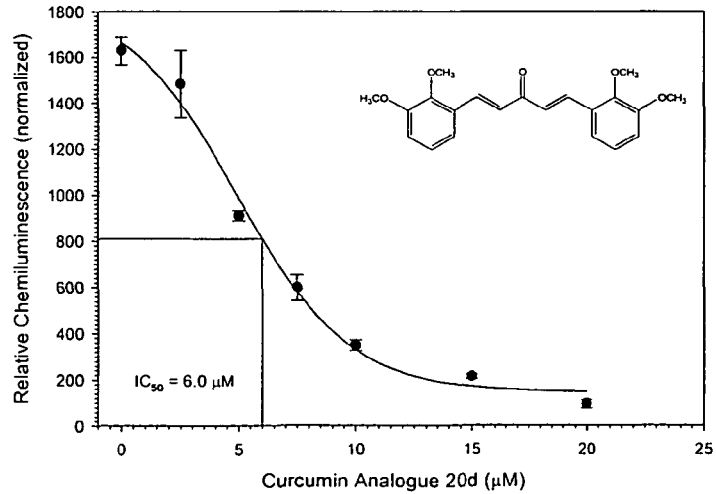
FIG. 22F is a graph showing an $IC_{50}$ plot of varying doses of analog 20d against inhibition of AP-1 activity.
Figure 22G:
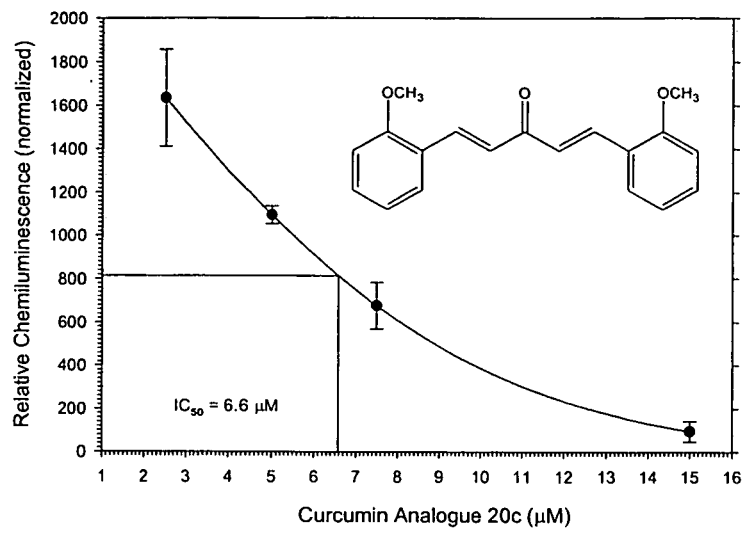
FIG. 22G is a graph showing an $IC_{50}$ plot of varying doses of analog 20c against inhibition of AP-1 activity.
Figure 22H:
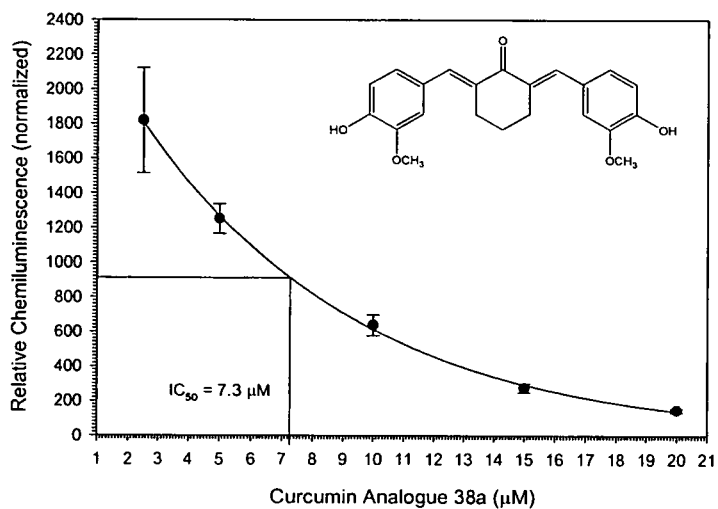
FIG. 22H is a graph showing an $IC_{50}$ plot of varying doses of analog 38a against inhibition of AP-1 activity.
Figure 22I:
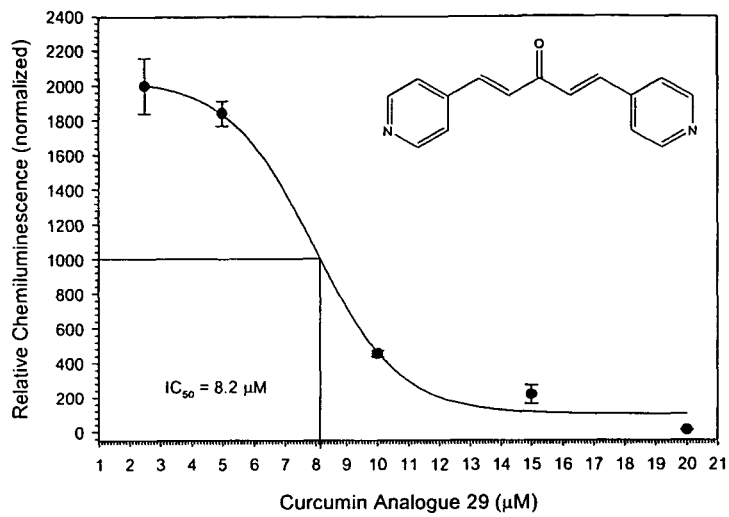
FIG. 22I is a graph showing an $IC_{50}$ plot of varying doses of analog 29 against inhibition of AP-1 activity.
Figure 22J:
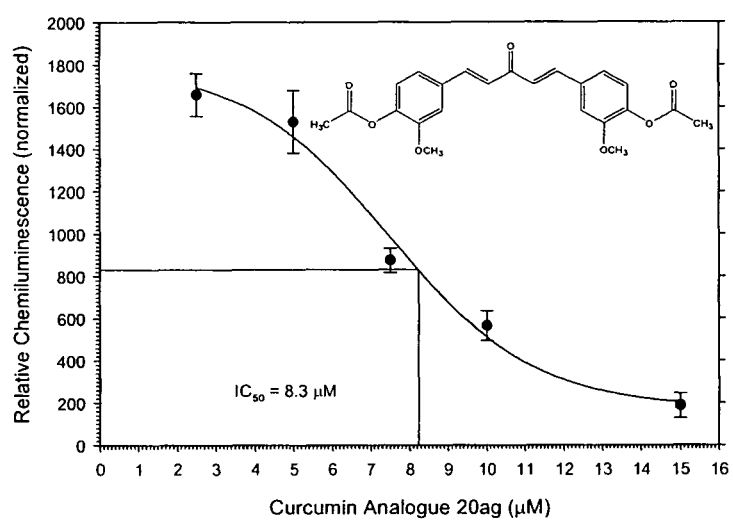
FIG. 22J is a graph showing an $IC_{50}$ plot of varying doses of analog 20ag against inhibition of AP-1 activity.
Figure 22K:
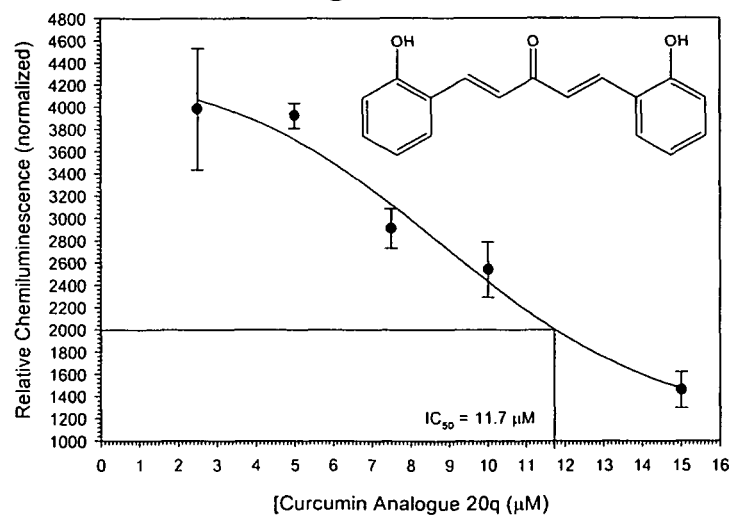
FIG. 22K is a graph showing an $IC_{50}$ plot of varying doses of analog 20q against inhibition of AP-1 activity.
Figure 22L:
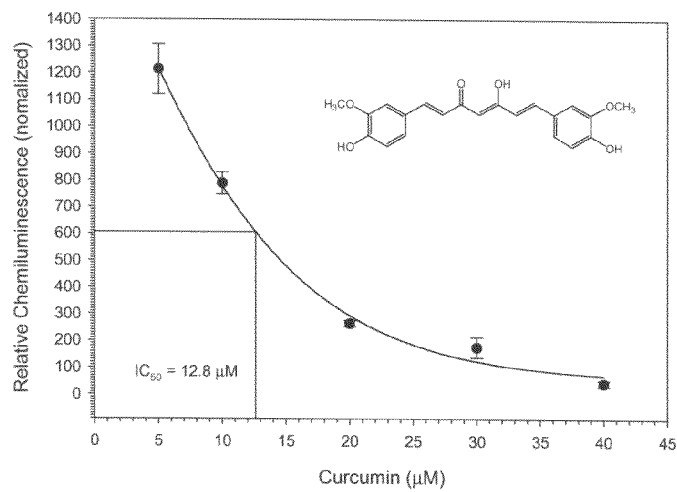
FIG. 22L is a graph showing an $IC_{50}$ plot of varying doses of curcumin against inhibition of AP-1 activity.

FIGS. 20A-C show analogs active in the AP-1 cellular assay. The active analogs in FIGS. 20A-C are arranged from highly active on the left to slightly active on the right. Figures containing all analogs can be found in FIGS. 21A-C.

Active analogs in series 1, which contain a 7-carbon spacer, are shown in FIG. 20A. Two analogs, 6a and 9a, in this series were more active than curcumin (3a). Both of these analogs contain the same aryl ring substituents as curcumin in addition to either a methyl (6a) or benzyl (9a) substituent on the central methylene carbon. A third active analog, 9b, also contains a central methylene benzyl substituent. No active analogs in this series contained a saturated spacer between the aryl groups. Four of the seven analogs in this series display activity in both antioxidant assays. It is important to note that three analogs were active against AP-1 independent of antioxidant activity.

Active analogs in series 2, which contain a 5-carbon spacer, are shown in FIG. 20B. Eleven analogs, 20m, 20ag, 31, 20c, 20w, 29, 38a, 20l, 20o, 20q and 20d, in this series were more active than curcumin. Of these eleven active analogs, nine contain substituted aryl groups. Six analogs contain substituents ortho to the spacer on the aryl group, indicating this position may be important for AP-1 activity. Analogs 29 and 31 contain pyridine rings with no substituents on the ring. These two active analogs indicate that if the analogs in this series have a specific target, the target may contain a hydrogen bond donor in the area of binding. Since only three of the eleven active analogs in this series display antioxidant activities, it is suggested that these analogs are targeting a specific protein.

Active analogs in series 3, which contain a 3-carbon spacer, are shown in FIG. 20C. No analog in this series was more active than curcumin. The active analogs in this series also exhibit good antioxidant activities. The two most active analogs, 45a and 48a, in this series displayed antioxidant activity in both antioxidant assays. Active analogs, 35q, 46ad and 46al, in this series were also active in one or the other antioxidant assay.

The $IC_{50}$ values for the twelve active analogs as well as curcumin against AP-1 were also measured. $IC_{50}$ plots for these active analogs are shown in FIGS. 22A-L. Of the twelve best analogs against AP-1, nine of the analogs also ranked in the top twelve against NF-κB activity. Table 10 shows the $IC_{50}$ values of the nine analogs that were active against both NF-κB and AP-1. Table 10 also shows whether each analog was active as an antioxidant (+) in both the TRAP and FRAP assays.

TABLE 10

$IC_{50}$ Values and Antioxidant Results for Active Analogs Against NF-κB and AP-1.

| Structure | Analog Number | AP-1 $IC_{50}$ (μM) | NF-κB $IC_{50}$ (μM) | TRAP | FRAP |
|---|---|---|---|---|---|
| 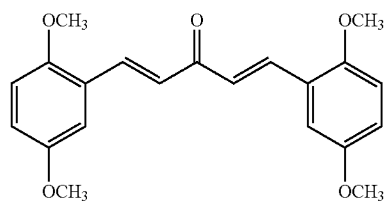 [SMILES: COc1ccc(OC)c(/C=C/C(=O)/C=C/c2cc(OC)ccc2OC)c1] | 20m | 1.4 | 6.4 | − | − |
| 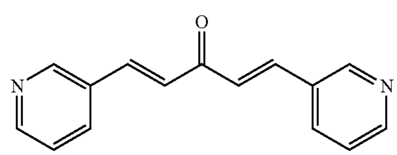 [SMILES: O=C(/C=C/c1cccnc1)/C=C/c1cccnc1] | 31 | 4.1 | 3.4 | − | − |
| 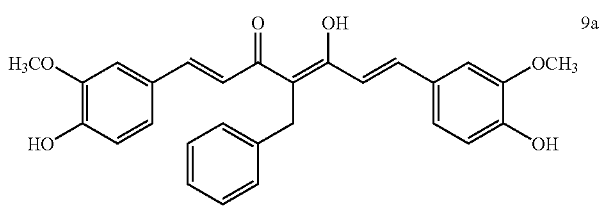 | 9a | 5.3 | 7.6 | + | + |
| 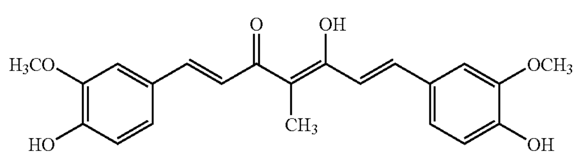 [SMILES: COc1cc(/C=C/C(=O)/C(C)=C(O)/C=C/c2ccc(O)c(OC)c2)ccc1O] | 6a | 6.0 | 6.7 | + | + |
| 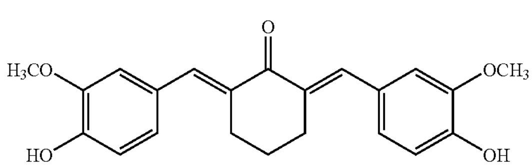 [SMILES: COc1cc(/C=C2\CCC/C(=C\c3ccc(O)c(OC)c3)C2=O)ccc1O] | 38a | 7.3 | 4.2 | + | + |
| 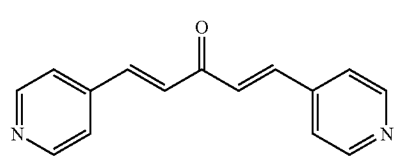 [SMILES: O=C(/C=C/c1ccncc1)/C=C/c1ccncc1] | 29 | 8.2 | 3.5 | − | − |

TABLE 10-continued

IC$_{50}$ Values and Antioxidant Results for Active Analogs Against NF-κB and AP-1.

| Structure | Analog Number | AP-1 IC$_{50}$ (μM) | NF-κB IC$_{50}$ (μM) | TRAP | FRAP |
|---|---|---|---|---|---|
| [structure] | 20ag | 8.3 | 5.4 | − | + |
| [structure] | 20q | 11.7 | 4.2 | + | − |
| [structure] | 3a | 12.8 | 8.2 | + | + |

Of the IC$_{50}$ values obtained, curcumin (12.8 μM) is the least potent analog against AP-1. Analog 20m which has an ortho substituent is the most active analog against AP-1 with an IC50 value of 1.4 μM. As observed in Table 10, several analogs are active against AP-1 independent of antioxidant activity. This indicates that the analogs are targeting specific proteins in the cell. Since nine of the twelve best analogs against AP-1 are also active against NF-κB it is possible that these analogs are acting on a common target involved in both activation cascades and that the analogs are not inhibiting the AP-1 or NF-κB proteins directly.

Example 6

Molecular Modeling of the Binding of Curcumin Derivatives to AP-1

When performing docking studies of the potential inhibitors against AP-1, one crystal structure (1FOS) was selected from the twenty five selections that were available. 1FOS (Glover et al., Nature 373, 257-261 (1995)) was selected because it contained the c-Jun and c-Fos heterodimer, the most common heterodimer, complexed to a segment of DNA. This crystal structure was important because it contained the exact binding site of DNA to this heterodimer. This provided information concerning the blocking of AP-1-DNA binding interactions by the analogs.

Figure 23:
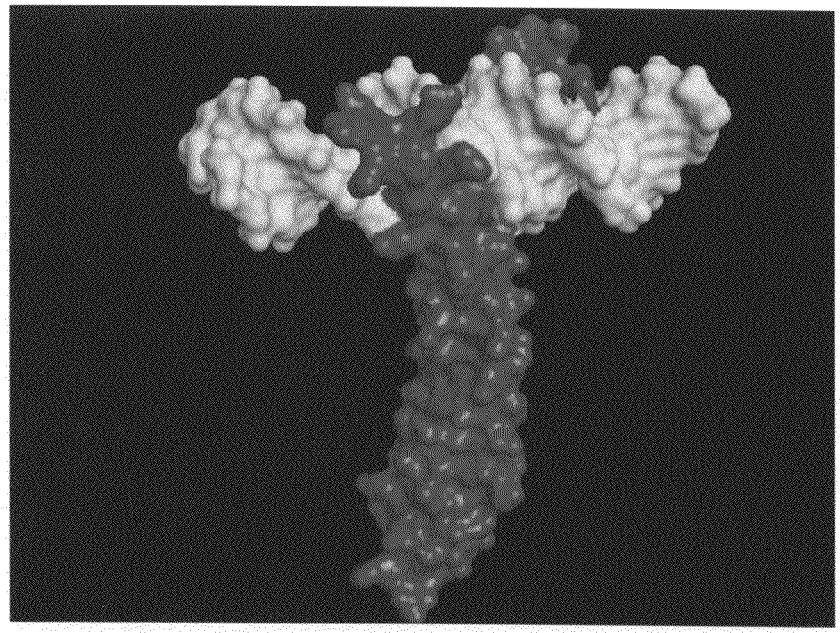
FIG. 23 is a computer-generated image representing AP-1 bound to DNA.
Figure 24:
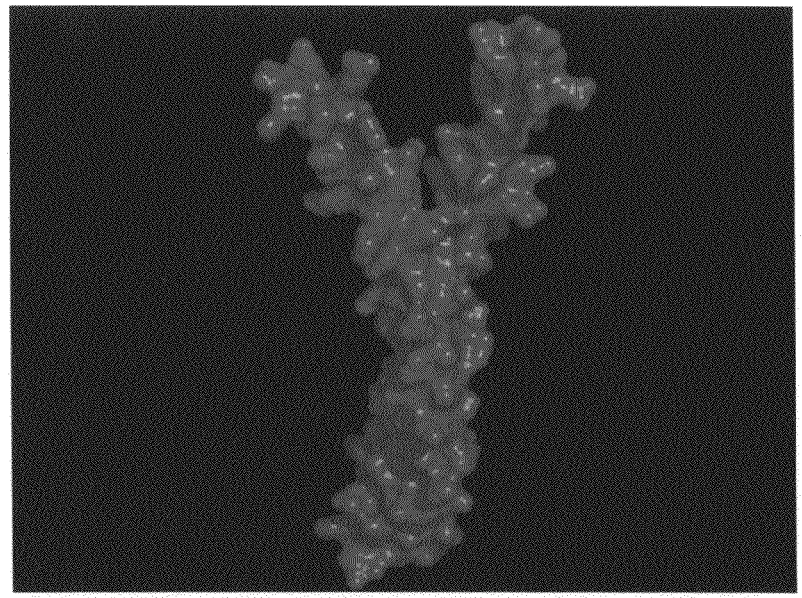
FIG. 24 is a computer-generated image representing AP-1 with DNA removed.

FIG. 23 shows the c-Jun and c-Fos AP-1 heterodimer bound to a segment of DNA. In FIG. 23, the blue protein is the c-Jun/c-Fos heterodimer and the yellow segment is the DNA. When the DNA is removed as shown in FIG. 24, a "Y" shaped area is exposed. It is in this location that the analogs will bind if they are preventing an AP-1-DNA binding interaction. When docking studies were performed, the potential inhibitors bound in the entire DNA interaction region. The front side of these binding interactions is shown in FIG. 25 and the backside of these binding interactions is shown in FIG. 26.

Figure 25:
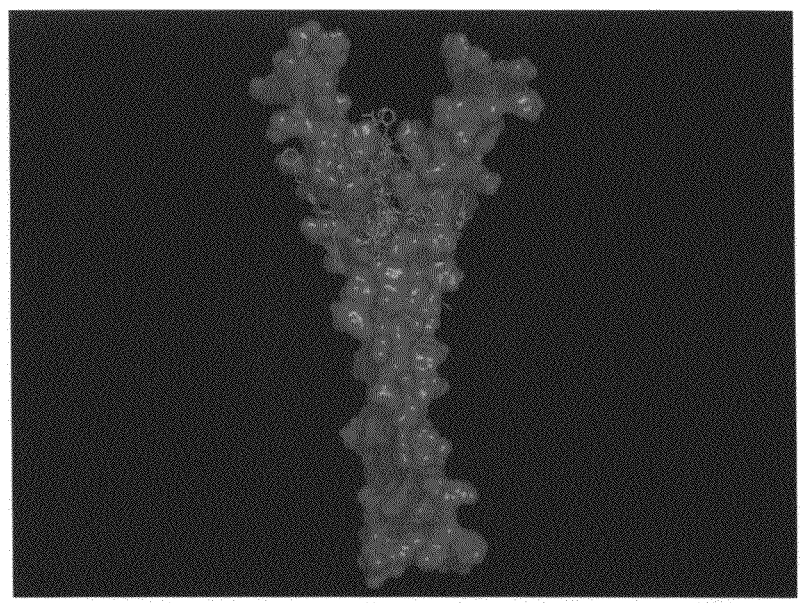
FIG. 25 is a computer-generated image representing the front face of AP-1 with analogs.
Figure 26:
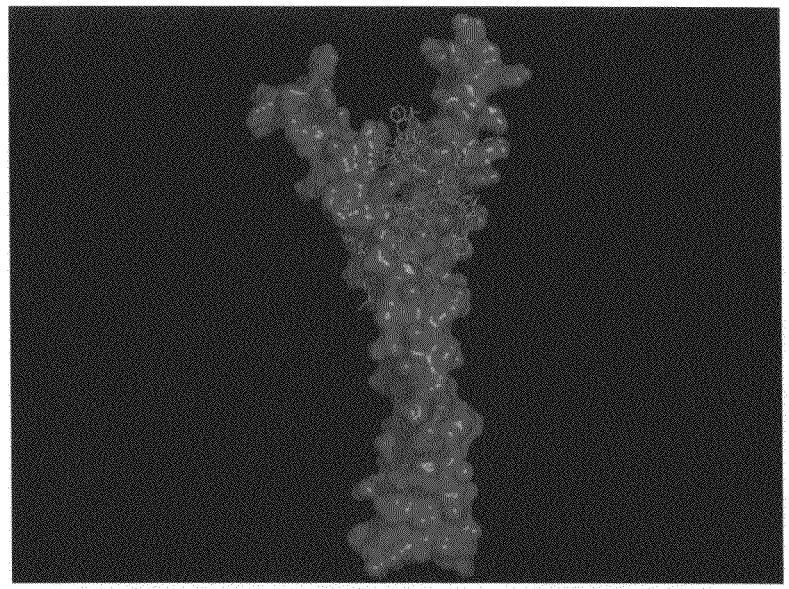
FIG. 26 is a computer-generated image representing the opposite face of AP-1 with analogs.

The analogs that appear to be coming over the top in FIG. 26 are the same analogs as in FIG. 25. Most of these analogs bind in the exact region as the DNA was bound. However, the analogs have mediocre K$_{est}$ values with analog 9b displaying the best inhibition with a K$_{est}$ of 6.53E-8 M as shown in Table 11. There is no correlation to the K$_{exp}$ results. This indicates that the analogs do not bind to the c-Jun and C-Fos heterodimer or at the very least, they do not inhibit DNA from binding to AP-1.

Figure 27:
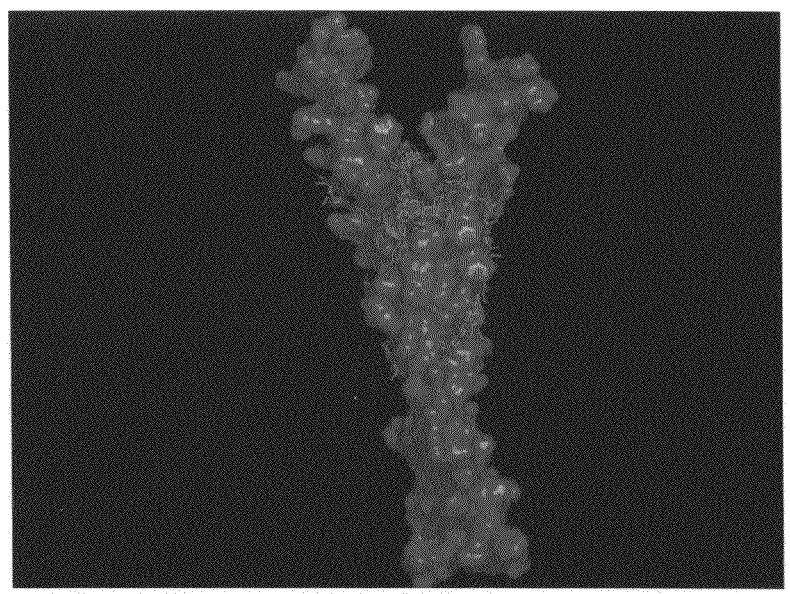
FIG. 27 is a computer-generated image representing AP-1 with MES and analogs.

To verify these findings, the MES program was utilized on the AP-1 heterodimer to identify any potential binding areas for the potential inhibitors. The results of this docking are similar to those from when the MES program was not used (FIG. 27). All of the analogs still bind to the area directly below the DNA binding area and indicate a possible inhibition of AP-1-DNA binding interactions. Once again, the potential inhibitors have mediocre K$_{est}$ values with analog 15a having a K$_{est}$ value of 1.26E-7 M as shown in Table 12. However, there is no correlation to the K$_{exp}$ results which indicates that the analogs do not bind to the c-Jun and C-Fos heterodimer or at the very least, they do not inhibit DNA from binding to AP-1.

TABLE 11

K$_{est}$ Values for AP-1 (1FOS).

| 9b | 6.53E−08 | 38a | 7.53E−07 | 20u | 2.07E−06 | 20r | 4.30E−06 |
|---|---|---|---|---|---|---|---|
| 12b | 9.96E−08 | 3h | 7.73E−07 | 20ah | 2.13E−06 | 13b | 4.60E−06 |
| 15a | 1.57E−07 | 20z | 8.46E−07 | 52l | 2.14E−06 | 20p | 4.90E−06 |
| 3d | 1.71E−07 | 20w | 8.98E−07 | 20t | 2.35E−06 | 45a | 5.01E−06 |
| 6a | 1.73E−07 | 20k | 9.23E−07 | 11b | 2.45E−06 | 20x | 5.14E−06 |

TABLE 11-continued $K_{est}$ Values for AP-1 (1FOS).

| | | | | | | | |
|---|---|---|---|---|---|---|---|
| 53 | 1.95E−07 | 20ac | 9.70E−07 | 36a | 2.54E−06 | 46ak | 5.25E−06 |
| 46ad | 2.37E−07 | 20g | 1.07E−06 | 20c | 2.62E−06 | 20e | 5.33E−06 |
| 20m | 2.43E−07 | 6b | 1.16E−06 | 20aa | 2.72E−06 | 39b | 5.88E−06 |
| 23 | 2.44E−07 | 20ag | 1.20E−06 | 20ab | 2.76E−06 | 46a | 6.66E−06 |
| 20d | 2.88E−07 | 20l | 1.28E−06 | 16b | 2.82E−06 | 52b | 6.83E−06 |
| 20v | 2.99E−07 | 17b | 1.28E−06 | 52e | 2.92E−06 | 42b | 6.84E−06 |
| 48ad | 4.18E−07 | 3e | 1.43E−06 | 20b | 2.93E−06 | 20f | 7.63E−06 |
| 13c | 4.38E−07 | 20ae | 1.53E−06 | 52aa | 2.96E−06 | 50b | 8.05E−06 |
| 9a | 4.49E−07 | 20y | 1.60E−06 | 29 | 3.12E−06 | 48a | 1.10E−05 |
| 3a | 5.01E−07 | 20q | 1.60E−06 | 40af | 3.24E−06 | 34 | 1.11E−05 |
| 25 | 5.31E−07 | 13a | 1.75E−06 | 20s | 3.30E−06 | 45b | 1.19E−05 |
| 15b | 5.38E−07 | 36e | 1.83E−06 | 31 | 3.38E−06 | 43b | 1.91E−05 |
| 3i | 5.42E−07 | 52ac | 1.85E−06 | 20n | 3.57E−06 | 40b | 1.99E−05 |
| 20i | 5.49E−07 | 14b | 1.86E−06 | 20a | 3.93E−06 | 35e | 5.48E−05 |
| 3g | 6.19E−07 | 3b | 1.97E−06 | 38b | 4.02E−06 | 35a | 5.53E−05 |
| 14a | 6.61E−07 | 3f | 1.99E−06 | 46al | 4.17E−06 | 35q | 1.02E−04 |
| 20o | 7.31E−07 | | | | | | |

TABLE 12

$K_{est}$ Values for AP-1 (1FOS) with MES.

| | | | | | | | |
|---|---|---|---|---|---|---|---|
| 15a | 1.26E−07 | 20g | 1.38E−06 | 52e | 2.79E−06 | 20e | 5.33E−06 |
| 13c | 2.05E−07 | 17b | 1.49E−06 | 20y | 2.93E−06 | 20q | 5.40E−06 |
| 23 | 2.96E−07 | 3i | 1.53E−06 | 3f | 2.99E−06 | 52b | 6.00E−06 |
| 46ad | 3.15E−07 | 3d | 1.57E−06 | 20k | 3.28E−06 | 46ak | 6.04E−06 |
| 53 | 3.43E−07 | 3h | 1.59E−06 | 20aa | 3.29E−06 | 20b | 6.33E−06 |
| 3g | 4.75E−07 | 13b | 1.74E−06 | 20x | 3.33E−06 | 20p | 6.38E−06 |
| 20d | 5.74E−07 | 12b | 1.79E−06 | 20ah | 3.40E−06 | 38b | 6.95E−06 |
| 9b | 6.11E−07 | 6a | 1.83E−06 | 11b | 3.58E−06 | 20t | 8.29E−06 |
| 25 | 6.78E−07 | 20s | 1.86E−06 | 20ac | 3.67E−06 | 34 | 8.51E−06 |
| 20z | 7.14E−07 | 52aa | 1.98E−06 | 46a | 3.76E−06 | 20f | 8.58E−06 |
| 20v | 9.80E−07 | 6b | 2.02E−06 | 14b | 3.78E−06 | 40b | 8.61E−06 |
| 38a | 1.04E−06 | 3a | 2.03E−06 | 36e | 3.79E−06 | 36a | 9.23E−06 |
| 48ad | 1.08E−06 | 14a | 2.04E−06 | 31 | 3.81E−06 | 20r | 9.23E−06 |
| 9a | 1.12E−06 | 20ae | 2.07E−06 | 20i | 3.86E−06 | 48a | 1.04E−05 |
| 20w | 1.20E−06 | 52ac | 2.13E−06 | 52l | 3.95E−06 | 50b | 1.07E−05 |
| 20ab | 1.22E−06 | 20m | 2.17E−06 | 3b | 4.00E−06 | 43b | 1.09E−05 |
| 15b | 1.22E−06 | 13a | 2.34E−06 | 29 | 4.08E−06 | 45b | 1.45E−05 |
| 20ag | 1.24E−06 | 42b | 2.58E−06 | 20a | 4.26E−06 | 45a | 1.78E−05 |
| 20o | 1.26E−06 | 20n | 2.60E−06 | 20l | 4.65E−06 | 35a | 4.51E−05 |
| 3e | 1.29E−06 | 46al | 2.74E−06 | 40af | 4.80E−06 | 35e | 4.90E−05 |
| 20u | 1.29E−06 | 20c | 2.76E−06 | 39b | 4.97E−06 | 35q | 1.10E−04 |
| 16b | 1.30E−06 | | | | | | |

Example 7

Evaluation of Curcumin Derivative Pharmacophores Using QSAR

Figure 28:
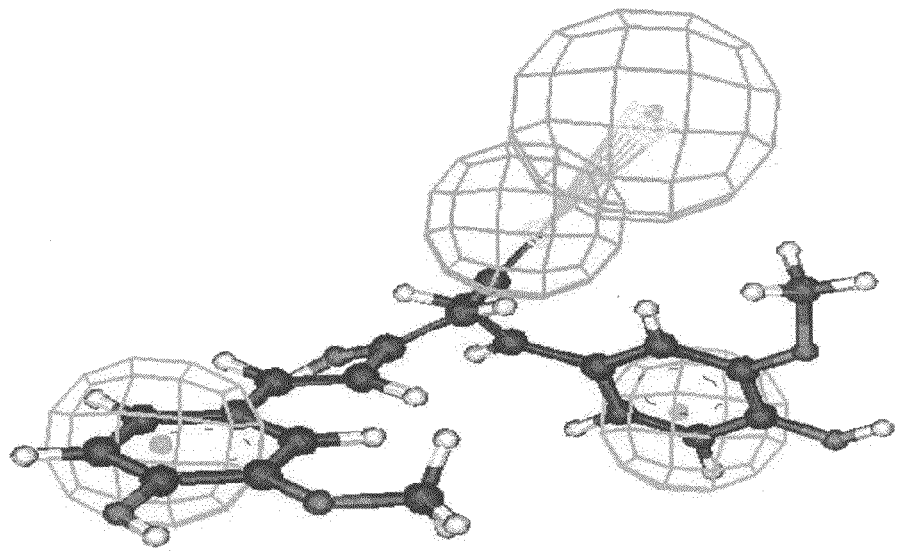
FIG. 28 is a computer generated pharmacophore model with the structure of curcumin superimposed on the model.

A QSAR analysis of the data was carried out using the Catalyst program (Accelrys). A wide range of structures and activities from the results described for FIGS. 3-5 were used to generate multiple pharamcophores. A single pharmacophore did not provide a satisfactory fit of the data. Moreover, pharmacophores that were derived separately from 5-carbon analogs or from 3-carbon analogs did not provide satisfactory fits. However, a single pharmacophore could provide a satisfactory fit of the data for analogs in the 7-carbon series. FIG. 28 shows a pharmacophore on which curcumin is superimposed. In FIG. 28, Curcumin was aligned with the pharmacophore model generated with the Catalyst program, using compounds 3a, 3e, 6a, 9a, 12b, 14a, and 14b as the training set. The pharmacophore model consists of two hydrophobic aromatic regions with centers 11.8 angstroms (Å) apart and a hydrogen bond acceptor 6.2 Å from the nearest hydrophogic aromatic region and 7 Å from the other. The pharmacophore provided an excellent fit (correlation 0.9) of analogs on the 7-carbon series. The inability of a single pharmacophore to provide a satisfactory fit of all of the data or of the data from the 3-carbon or 5-carbon series may mean that there are several different targets for these analogs.

Example 8

Reactivity and Bioavailability of Curcumin Derivatives

Figure 29:
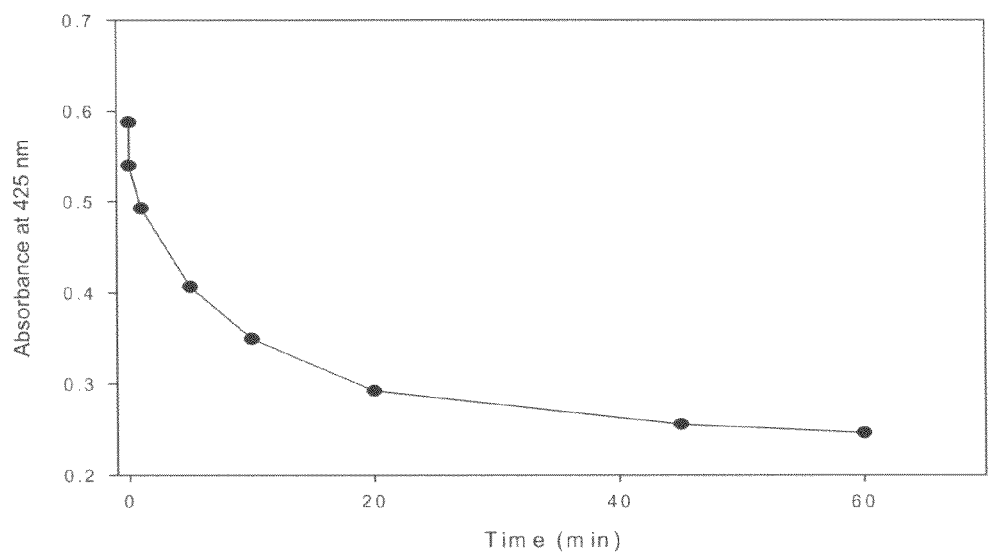
FIG. 29 is a graph showing the high reactivity of curcumin with L-cysteine.

Curcumin is considered a very non-toxic compound but with limited bioavailability. D Ranjan et al., (2004) J Surg Res 121, 171-177. From a medicinal chemistry perspective, a potential concern regarding the structure of curcumin and its analogs is the presence of one or two α,β-unsaturated ketone functional groups. Weber et al., (2005) Bioorg Med Chem 13, 3811-3820. These groups potentially serve as Michael acceptors which are chemically reactive and can form undesirable covalent modifications with biomolecules. Michael acceptors are generally thought to be poor drug compounds because of their high reactivity toward nucleophiles. In order to evaluate the potential of curcumin as a Michael acceptor, its reactivity toward L-cysteine as the nucleophile donor was examined. Curcumin (20 µM) was incubated with 1 mM L-cysteine in 0.1 M sodium phosphate buffer, pH 7.0, and measured curcumin's spectral properties at 425 nm as a function of time. L-Cysteine rapidly reacted with curcumin and quenched absorbance with a $t_{1/2}$ of 7.2 min., as shown in FIG. 29. Thus, curcumin is highly reactive towards nucleophilies; this may explain the poor oral bioavailability of curcumin but also suggests that its toxicity may appear to be deceptively low owing to reactions of curcumin with dietary contents.

The high reactivity of curcumin, presumably through Michael addition to the α,β-unsaturated ketone functionality, and the fact that those analogs that are more active than curcumin are generally α,β-unsaturated ketones raised the question whether any analogs devoid of this functionality retain activity. Screening of the prepared curcumin derivatives identified two analogs (42b and 52b) that show activity comparable to curcumin. Neither 42b nor 52b retain the α,β-unsaturated ketone functionality. This suggests that analogs that are much less reactive than curcumin can be developed as inhibitors of NFκB.

Non-specific inhibition of protein drug targets by small molecule inhibitors can arise by formation of large molecular weight aggregates in an aqueous environment, which provide a microenvironment for protein adsorption that can produce apparent but false inhibition. McGovern et al., (2002) J Med Chem 45, 1712-1722. For example, compounds with multi-aryl ring structures have a tendency to assemble into highly ordered complexes driven by the stacking of their aromatic rings. Compounds that aggregate may have little potential as lead compounds for drug development. Accordingly, whether curcumin aggregates in an aqueous environment was evaluated by measuring the potential aggregation of curcumin using a standard light scattering assay. Curcumin was diluted to 1.0-20.0 uM in 0.1 M phosphate buffered saline, pH 7.0, and its absorbance was measured at 425 nm. The absorbance profile remained linear throughout the concentration range tested, suggesting no aggregation.

Summary of Observations Regarding Activity of Curcumin Derivatives

Curcumin has a broad range of biological activities, some of which may derive from its anti-oxidant activity or ability to quench free radical reactions and some that involve inhibition or inactivation of specific targets. Curcumin can scavenge superoxide radicals, hydrogen peroxide and nitric oxide, and it has been suggested that the ability of curcumin to protect against radiation damage, iron-induced hepatic damage, xanthine oxidase injury and oxidative stress depends upon the anti-oxidant and free radical-scavenging properties of curcumin (Joe et al., Crit. Rev. Food Sci. Nutr. 44, 97 (2004); Bonte et al., Planta Med. 63, 265 (1997); Reddy et al., Toxicology 107, 39 (1996); Cohly et al., Free Radical Biol. Med. 24, 49 (1998)).

Study of the inhibition of activation of NF-κB by analogs of curcumin demonstrated that a) some analogs are more active than curcumin; b) not all analogs that are active need retain the enone functionality, and thus there is reason to expect that some active curcumin derivatives may be much less reactive than curcumin; and c) analogs with heterocyclic rings are active. Furthermore, there appear to be several different targets that are involved in prevention the activation of NF-κB by analogs of curcumin. Also, the anti-oxidant activity of curcumin and analogs is not required for activity against activation of NF-κB.

In Example 2, the abilities of curcumin and derivatives to quench the pre-formed radical monocation of 2,2'-azinobis-(3-ethylbenzothiazoline-6-sulfonic acid), known as the Total Radical-trapping Anti-oxidant Parameter (TRAP) assay, and the abilities of these compounds to reduce the ferric tripyridyltriazine complex, known as the Ferric Reducing/Antioxidant Power (FRAP) assay, were demonstrated (Schlesier et al., Free Radical Res. 36, 177 (2002)). It is noteworthy that many of the most active derivatives with regard to NF-κB show no activity in the TRAP or FRAP assay, which leads to the conclusion that there is no correlation between anti-oxidant activity and ability to inhibit the TNFα-induced activation of NF-κB. While not intending to be bound by theory, the lack of correlation between the anti-oxidant activities of curcumin and derivatives and the abilities of these compounds to inhibit the TNFα-induced activation of NF-κB and the PMA-induced activation of AP-1 suggests that curcumin and its derivatives inhibit a specific target (or targets) rather than function through general redox chemistry.

In summary, derivatives of curcumin in which the two aryl rings are separated by 7-carbon, 5-carbon or 3-carbon spacers are able to inhibit the TNFα-induced activation of AP-1 or NF-κB. However, activities can vary widely. The most active derivatives retain the enone functionality, although this functionality is not essential for activity. In addition, derivatives with the 5-carbon spacer are generally the most active. Ring substituents are not necessary but can affect activity. In addition, the aryl rings can be nitrogen heterocycles. The inhibition of TNFα-induced activation of NF-κB by curcumin and derivatives may occur at the level of the IKK complex.

Example 9

NFκB as a Target for Alzheimer Drugs

New lead compounds as inhibitors of NF-κB will be identified largely based upon the experimental data we will obtain by testing our library of curcumin analogs. We will apply quantitative structure-activity relationship (QSAR) and ligand-based virtual screening (LBVS) technologies, using the available active/rigid hits, to develop a pharmacophore model. At the same time, we will use 2D-fingerprints and 3D properties (e.g., shape, electrostatics, pharmacophore fingerprints) to query the iResearch™ and ChemDiv libraries for additional putative inhibitors of NF-κB. We have access to over 14 million unique structures that are available for synthesis, from the ChemNavigator (http://www.chemnavigator-.com) iResearch™ Library.

The methodology for database preparation, in view of LBVS technologies, has been described in detail. Zamora et al., (2003) J Med Chem 46, 25-33. Briefly, the strategies for compound selection include the following steps: 1. database assembly ('in silico' inventory); 2a. structural integrity verification (keep unique structures only); 2b. limited exploration of alternative chemical representations for unique structures (stereoisomers, tautomers, ionization states); 3. property and structural filtering (remove unwanted structures); 4. 3D-structure generation (for virtual screening or 3D-based similarity); 5a. clustering or statistical design for selection; 5b. similarity-based selection (if bioactives are known); 5c. receptor-based selection (if target binding site is known); 6. add a random subset to the final list. We have developed extensive knowledge in handling large chemical datasets—in particular the iResearch™ library has over 13 million unique structures, whereas ChemDiv has "only" 0.5 million. We will query both databases, using the most active and rigid analogs that we identify, to select a small subset (up to 300 structures) for acquisition.

One of the potential issues related to curcumin, as discussed above, is the presence of two α,β-unsaturated ketone functionalities. Michael acceptors are often considered reactive species that can lead to false hits under biochemical assay conditions. We anticipate that, by using various LBVS methodologies, in particular 3D-similarity and pharmacophore queries, and by having an extensive library of curcumin analogs that include members without this functionality, we will be able to move beyond this particular moiety. There is a list of over 200 substructural filters that we routinely use when selecting compounds for acquisition. Waller et al., (1993) J Med Chem 36, 4152-4160. This list is used by Discovery Partners International, in support of the Molecular Libraries Initiative of the NIH Roadmap for the compound acquisition program. We base this effort on the chemical similarity principle, which states that ligands with similar features are expected to have similar biologic activity. Rishton (1997). Drug Discov. Today 2, 382-338. It is expressed as a number that quantifies the "distance" between a pair of compounds (dissimilarity, or 1 minus similarity), or how related the two compounds are (similarity). By definition, similarity needs a reference: That of a chemical descriptor system (a metric by which similarity is judged), as well as that of an object or class of objects—we need a reference point to which objects can be compared. Similarity depends on the choice of molecular descriptors (Olah et al., (2004) J Comput Aided Mol Des 18, 437-449), the choice of the weighting scheme(s) and the similarity coefficient itself. The coefficient is typically based on Tanimoto's symmetric distance-between-patterns (Tanimoto (1961) Trans NY Acad Sci 23, 576), and on Tversky's asymmetric contrast model. Multiple types of methods are available for evaluation of chemical similarity. See P Willett, 1987, "Similarity and Clustering Techniques in Chemical Information Systems" Letchworth: Research Studies Press; and P Willett (2000) Curr Opin Biotechnol 11, 85-88.

Our approach is to develop composite similarity rankings based on different similarity scores and descriptors. We start with 2D similarity based on the 320-bit MDL keys (Martin (2001) J Comb Chem 3, 231-250), as implemented in software from Mesa Analytics and Computing LLC (http://www.mesaac.com), to which we add the 3D similarity defined by the shape and electrostatics properties derived from ROCS (Rapid Overlay of Chemical Structures (Durant et al., (2002) J Chem Inf Comput Sci 42, 1273-1280), as implemented in software from OpenEye Scientific Software (http://www.eyesopen.com). An additional metric for 3D similarity will be defined by the ALMOND pharmacophore fingerprints; these are generated using software from Molecular Discovery Ltd. (http://moldiscovery.com). For the general subset that matches (to some degree) the above 2D and 3D criteria, we will also use the pharmacophore query to match the curcumin-related molecules using Catalyst™, part of the Accelrys system (http://www.accelrys.com). For 3D structure generation we will use the OMEGA software from Openeye. The overall result will be a small subset of compounds (up to 300), to be acquired and tested as described herein. It is worth noting that, using 17β-estradiol as a query, the Oprea group has performed LBVS searches on a set of 10,000 molecules following exactly the same methodology (i.e., composite similarity ranking using a combination of 2D- and 3D-similarity measures). The top scoring 100 compounds were tested on GPR30 (Revankar et al., (2005) Science 307, 1625-1630), a newly discovered G-protein coupled receptor that binds 17β-estradiol with high affinity, and on the estrogen receptor alpha (ERα); by testing these 100 non-steroidal molecules, Oprea and coworkers were able to identify selective nanomolar ligands for both GPR30 ($K_i$=13 nM, 1 agonist), and ERα ($K_i$<8 nM, 2 antagonists). Bologa et al., (2005) Nature Chem Biol, submitted; Revanka et al., 2005, Science 307:1625-1630).

The following section describes tests of the ability of compounds developed to prevent activation of NFκB and thereby inhibit the up-regulation of pro-inflammatory genes in microglial cells.

Following injury or infection, microglial cells become activated and respond by the release of cytokines, which in turn initiate the inflammatory event. IL1 plays a central role in the inflammatory process and is produced in greatest quantity by microglia. As mentioned above, IL1 is known to affect the expression of over 90 genes including those for cytokines, cytokine receptors, tissue remodeling enzymes and adhesion molecules (O'Neill (1995) Biochim Biophys Acta 1266, 31-44), and both IL1 up-regulation in microglia as well as the IL1 response involve signaling through NF-κB. We will use microglia cell line BV2 to test the curcumin derivatives. We will incubate BV2 cultured microglial cells with the test compound and will monitor the expression of IL6, which is regulated by NF-κB. Pinteaux et al., (2002) J Neurochem 83, 754-763. We have chosen BV2 as our model glial cell because this cell has recently been used to demonstrate curcumin-mediated inhibition of NF-κB activity. Kang et al., (2004) J Pharmacol Sci 94, 325-328. Importantly, this study establishes that the BV2 glial cell line maintains the capacity for NF-κB activation and sensitivity to curcumin treatment, thus providing us with an excellent cell culture model system to improve upon the effectiveness of curcumin therapy with our analog libraries. In addition, the BV2 cell line has been immortalized and exhibits phenotypic and functional properties of reactive microglia. Bocchini et al., (1992) J Neurosci Res 31,616-621. We will incubate BV2 cells with varying concentrations of curcumin analogs and quantitate IL6 gene expression by real-time PCR as a measure of NFκB inhibition. IL6 is a good reporter for NF-κB activity in glia since it shows almost no detectable expression in resting glial cells, yet after stimulation with lipopolysaccharide (LPS) its expression markedly increases (Kang et al., (2004) J Pharmacol Sci 94, 325-328) allowing us to obtain a clear, quantitative evaluation of the effects of our library of analogs. We will separately monitor the effects of the analogs on inhibition of the activation of NF-κB to demonstrate that the effect of a given analog on NF-κB activity correlates with its effect on IL6, as would be predicted if IL6 expression depends upon NF-κB.

Murine BV2 cells are grown in DMEM supplemented with 10% fetal bovine serum, 100 units/ml penicillin, 100 ug/ml streptomycin at 37° C. in 5% $CO_2$/95% air. Cells will be plated in 96-well plates for assay ($5 \times 10^4$ cells/well). When cells reach 80-90% confluency, they will be incubated with lipopolysaccharide (LPS, 0.2 ng/ml) (5) together with varying concentrations of curcumin and its analogs for 6 h at 37° C. 5% $CO_2$/95% air. Total RNA will then be extracted, isolated using an RNeasy kit (Invitrogen) and quantitated by measuring absorbance at 260 nm. One-step reverse transcriptase (RT) coupled to real time PCR analysis will be performed using an Applied Biosystems 7000 System. Primers (designed to amplify <150 bp) and TaqMan probe for IL6 transcript and NFκB transcript will be designed using Applied Biosystems Primer Express software. Primers and TaqMan Probe for β-actin will be used as an internal control. Real-time PCR values obtained for β-actin will be used to normalize values for IL6 and NF-κB expression to correct for loading or cell number differences between wells. Cycling parameters will be determined to optimize IL6, NF-κB and β-actin amplifications. Our starting parameters have been successful for amplification of many different genes currently under study: 50° C. 10 min (RT reaction), 94° C. 2 min (RT enzyme inactivation, Taq Polymerase activation), 40 cycles 92° C. 30 s, 60° C. 30 s, 72° C. 30 s. The 96-well plate format will permit a high efficiency and rapid screen to accurately assess individual analogs as well as obtain quantitative data to determine individual Ki values. The Applied Biosystems 7000 System is capable of multiplexing 96 samples simultaneously in approximately 2 h. To quantitate the effects of analogs on IL6 and NF-κB expression, we will use the comparative $C_T$ method. The amount of target message (IL6 and NF-κB in activated microglial cells with analog incubation) will be normalized to the internal reference (β-actin) and compared to the calibrator (IL6 or NF-κB in activated microglial cells without analog treatment). Since curcumin is an established inhibitor of NF-κB activity, it will serve as our positive control in all experiments.

As an alternative, the Panomics TransBinding NF-κB assay kit will be used. This kit is designed for rapid and sensitive quantization of NF-κB p50 in nuclear extracts of control and treated cells. The ELISA-based kit utilizes oligonucleotide with a consensus NF-κB binding site that has been immobilized on 96-well plates. Complex is detected with antibody to p50 by use of HRP-conjugated second antibody and colorimetric detection. The assay is much more sensitive and rapid than EMSA.

Developing a Reporter Assay in a Format for High Throughput Screening (HTS)

We have already described our directed approach to design of drugs for Alzheimer's disease where curcumin is the starting lead compound for a synthesis/screening approach combined with virtual data base screening to identify improved lead compounds. Here, we describe a HTS approach that is not directed, at least initially, by availability of lead compounds but rather is a mass screening approach. This will be developed as a separate approach that will parallel the directed approach. HTS approaches that are part of the MLSCN of the NIH Roadmap Initiatives require development of a screening assay and then approval for inclusion of the target and assay into the MLSCN.

The brute force approach of screening vast numbers of diverse chemical effectors, which is characteristic of HTS, is often beyond the resources of academic research; however, if the size of a chemical library is too small, the identity of valuable structural details may be missed that could limit our QSAR approach. To circumvent these obstacles, we plan to develop a HTS methodology that incorporates the fundamentals of flow cytometry. Flow cytometry is a sensitive and quantitative method for measuring cell fluorescence and is easily adaptable for assessing the effects of diverse compounds at the single cell level. The sensitivity of this method has been documented at concentrations of fluorescent molecules of 10-100 picomoles. Edwards et al., (2004) Curr Op Chem Biol 8, 392-398. For the University of New Mexico Flow Cytometry Core Facility, it is routine to analyze thousands to tens-of-thousands of particles per second (http://hsc.unm.edu/som/research/flowcyt/hypercyt.shtml). In the past, the ability to use flow cytometry for analysis of multiple samples has been hampered by the need for labor intensive sample handling. Recent generations of instrumentation have incorporated automated sample handling to routinely process in excess of 1 sample/sec. The HyperCyt® high-throughput flow cytometry platform now used by our Core Facility integrates a flow cytometer with rapid autosampling which will allow us the opportunity to develop a HTS protocol to screen a larger chemical library than was possible in the past. This freedom will undoubtedly enable us to obtain more structural information on NFκB inhibitors to more rapidly advance our QSAR methodologies.

To accomplish this objective, we plan to re-engineer the 293T cells, used for the initial screening of curcumin derivatives, to express a reporter system that includes four copies of the NF-κB DNA binding sequence upstream from a green-fluorescent-protein (GFP) gene. We will then use a lentiviral-based vector system that stably integrates into the host genome. Buchschacher et al., (2000) Blood. 95, 2499-2504. TNFα will provide the stimulus for activation of NF-kB as before and cells will be simultaneously treated with varying amounts of curcumin and its analogs. TNFα treatment alone is expected to activate expression of GFP and will serve as our positive control. If curcumin or its analogs are capable of preventing the TNFα-induced activation of NF-κB, we should see quantitative reduction in fluorescence intensity due to diminished GFP expression. Since analysis by flow cytometry is fully quantitative, we will be able to accurately titrate the effectiveness of each chemical toward NFkB inhibition. Analyzing the cells with the HyperCyt® high-throughput flow cytometry platform will allow us to process this endpoint assay at rates of 20 to 40 samples/minute over a 4-fold range of fluorescence intensity.

To engineer a reporter cell line, we will obtain the lentivirus-based reporter vector, pTRF1-NFkB-dscGFP, from System Biosciences (Mountain View, Calif.) and develop a stably transfected 293T cell line. We plan to use 293T cells since they are known to express NF-κB which is fully responsive to TNFα activation as demonstrated by their usefulness in luciferase-based assays. The lentivirus-based expression system contains all of the genetic elements that are necessary for packaging, transduction, stable integration of the viral expression sequence into genomic DNA, and high level expression of the GFP reporter sequence that is completely dependent on NFκB activation. To create a stably transfected 293T cell line, the first step requires generation of functional pseudoviral particles. To generated these particles, the expression vector containing the NFkB binding domains and GFP reporter sequence will be co-transfected with the packaging vector into a packaging cell line, typically 293T cells. The expression vector is then replicated intracellularly and packaged into pseudoviral particles, which contain the coat proteins necessary for delivery to mammalian cells. The pseudoviral particles will then be purified and used to deliver the reporter vector to freshly plated 293T cells. Once delivered, the viral reporter vector integrates into the host genome and expresses the GFP gene following NFkB activation by TNFα. Upon stable integration into the genome, the 5' LTR promoter is inactivated, which prevents replication of the viral sequence and formation of competent viral particles. Dull et al., (1998) J Virol 72, 8463-8471. Also, the transduced cell no longer has the necessary genes to produce viral capsid protein providing an additional safeguard. The efficiency of lentiviral transduction is close to 100% so this system should generate an ideal GFP-based NFkB reporter vector.

293T/NFκB-GFP cells will be plated into 96-well cell culture microtiter plates and, after 24 h, will be incubated with 20 ng/ml recombinant TNFα together with varying concentrations of curcumin and its analogs. The cells will be incubated at 37° C. in 5% CO2/95% air for 7 hours. Flow cytometric analysis will be done as follows. Cells will be rinsed with phosphate buffered saline, pH 7.4, and detached by trypsin treatment. The 96-well microtiter plate will then be placed into the autosampler of the HyperCyt® system. The sampling probe then moves from one well to the next drawing cells into the HyperCyt® system using a peristaltic pump.

Figure 30:
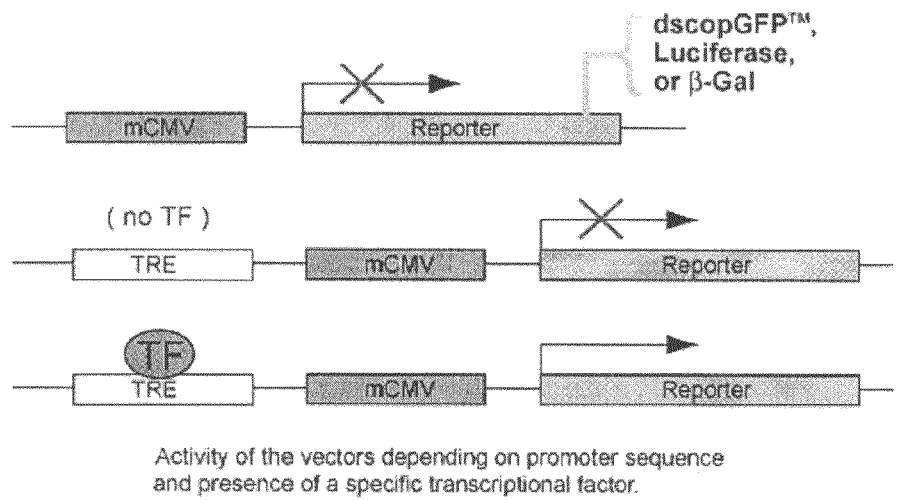
FIG. 30 pictorially represents the design of 293T cells for high throughput screening using flow cytometry.
Figure 30:
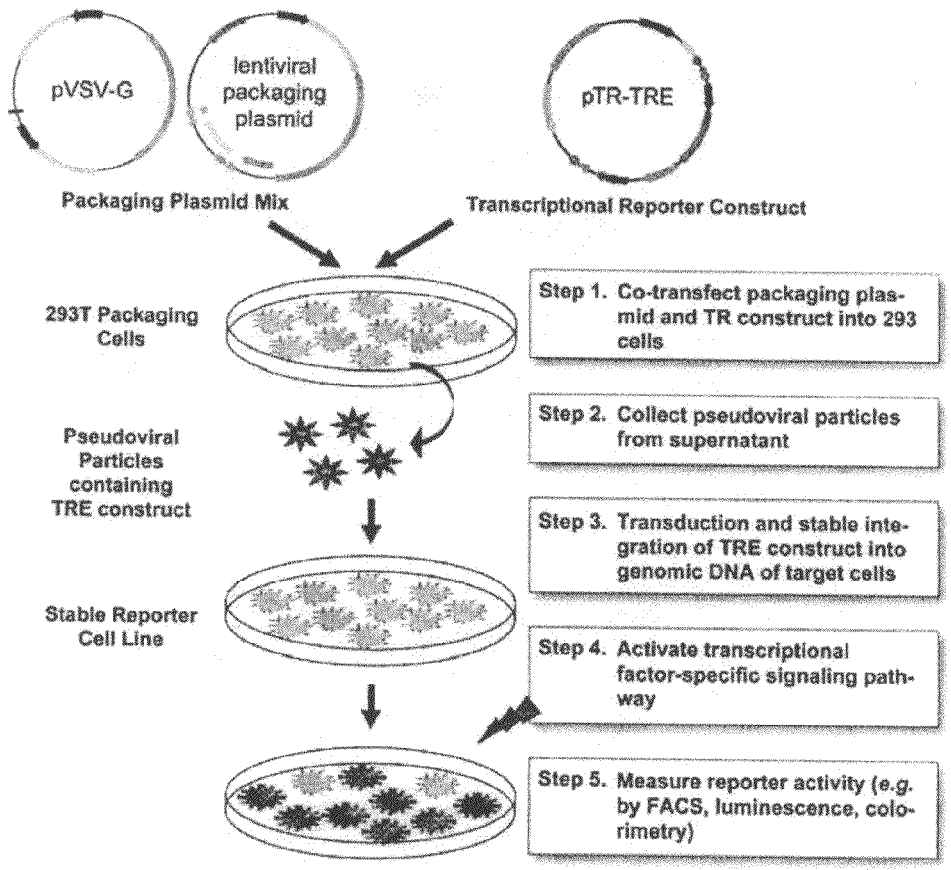
Figure 31:
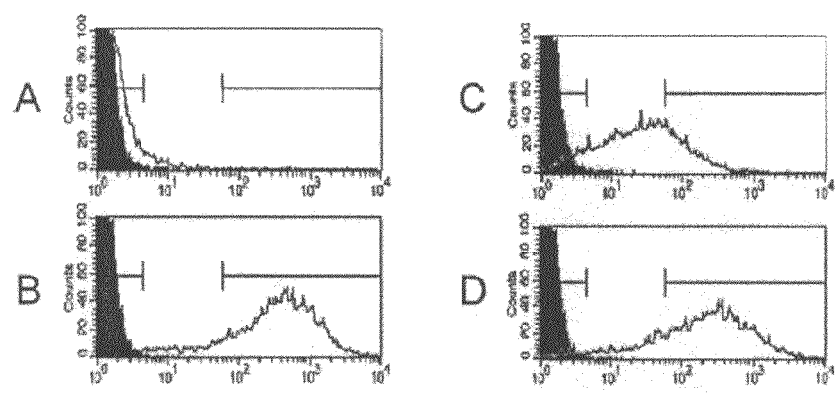
FIG. 31 shows the analysis of p53 activity in HeLa cells transduced with different TR constructs as a sample of the use of flow cytometry for screening.

Between wells, the continuously running pump draws a bubble of air into the sample line. This results in the generation of a tandem series of bubble-separated samples for delivery to the flow cytometer with data being collected in a single uninterrupted stream. The data are then optionally analyzed by proprietary software developed at the University of New Mexico by Dr. Bruce Edwards (Department of Pathology, School of Medicine). With this format, one 96-well plate can be analyzed in approximately 3 min thus achieving the speed necessary for a HTS assay. The procedures for development of the 293T/NF-κB-GFP cell and use of this cell in HTS are summarized in FIGS. 30 and 31.

Example 10

Effects of Curcumin Derivatives on Aβ Peptide Aggregation

Figure 32:
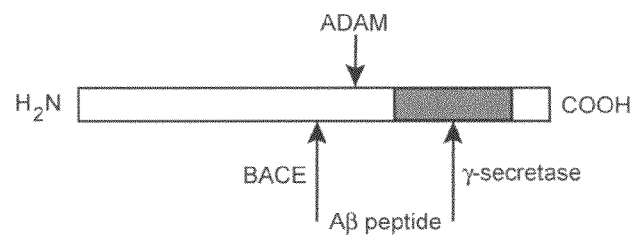
FIG. 32 shows α (ADAM), β (BACE), and γ secretase cleavage sites in the Amyloid Precursor Protein. Proteolytic cleavage of APP by β- and γ-secretases results in Aβ peptide formation. Shaded, transmembrane domain.

The neuropathology that defines Alzheimer's disease has been well studied. One of the earliest histological changes seen in the brains of AD patients is the deposition of amyloid-like plaques. Although many blood-borne proteins have been identified in these plaques, the main constituent is a 40 or 42 amino acid hydrophobic peptide called Aβ (Glenner et al., 1984, Applied Pathology 2:357-369). Deposition of plaques is thought to begin in the entorhinal complex and hippocampus, later progressing into the neocortex (Terry, 2000, Annals of Neurology 47:421). The course of this disorder, which can last from months to well over 10 years, is accompanied by a decrease in neural metabolic activity and increase in neural cell death. Clinically, patients suffer from a variety of unpredictable behaviors including loss in cognition, poor learning and memory, and severe mood changes. The prevalence of the pathology increases from 3% of the population at age 65 to 47% after the age of 85 (Dyrks et al., 1993, FEBS Letters 335:89-93). The amyloid-producing peptide, Aβ, is formed through proteolytic processing of the amyloid precursor protein (APP), a single pass transmembrane protein that is cleaved by two independent aspartyl proteases (FIG. 32).

β-secretase, also knows as BACE (Vassar et al., 1999, Science 286:735-741), cleaves in the ectodomain of APP proximal to the plasma membrane (Cai et al., 2001, Nature Neuroscience 4:233-234). Following β-secretase cleavage, β-secretase performs a unique intramembrane proteolysis giving rise to the Aβ peptide, 40 or 42 amino acids in length depending on β-secretase cleavage site choice within the transmembrane spanning domain (Cai et al., 2001, Nature Neuroscience 4:233-234; Selkoe, 2001, Physiological Reviews 81:741-766). This intramembrane cleavage event requires a multi-protein complex consisting of presenilin, nicastrin, Aph-1 and Pen-2, which together are thought to constitute the β-secretase complex (Periz et al., 2004, J Neurosci Res 77:309-322). Alternative to β-secretase cleavage, proteolysis can also occur by β-secretase, a member of the "A Disintegrin and Metalloproteinase-family" (ADAM) (Hooper et al., 2002, Curr Med Chem 9:1107-1119). Cleavage by this enzyme, prior to the action of β-secretase, generates a non-amyloidogenic peptide approximately 25 amino acids in length.

Although the Aβ peptide is continually produced in individuals of all ages (Funato et al., 1998, Am J Pathol 152:1633-1640; Haass et al., 1992, Nature 359:322-325; Seubert et al., 1992, Nature 359:325-327; Shoji et al., 1992, Science 258:126-129), it has no known normal function. Since the formation of Aβ aggregates is largely dependent on the concentration of available monomeric peptide, amyloid deposition requires a shift in the balance of peptide degradation versus accumulation (Glabe, 2000, Nat Med 6:133-134). Therefore, young, healthy brains are thought to have greater proteolytic catabolism of Aβ (Iwata et al., 2000, Nat Med 6:143-150) or, alternatively, increased endocytic clearance capacities for the peptide (Van Uden et al., 2000, Microsc Res Tech 50:268-272; Van Uden et al., 2000, J Biol Chem 275:30525-30530). Abnormal accumulation of Aβ also appears to exert neurotoxic effects (Emre et al., 1992, Neurobiol Aging 13:553-559; Kowall et al., 1992, Neurobiol Aging 13:537-542; Rush et al., 1992, Neurobiol Aging 13:591-594) by inducing oxidative stress (Yatin et al., 1999, Neurobiol Aging 20:325-330; discussion 339-342) and loss of calcium homeostasis (Etcheberrigaray et al., 1998, Neurobiol Dis 5:37-45; Mattson et al., 1993, Trends Neurosci 16:409-414).

The Aβ fibrillogenesis hypothesis as the primary cause of AD has been challenged; however, the data suggesting that amyloid deposition compromises synaptic integrity, along with memory and behavioral changes, remains compelling (Hardy et al., 2002, Science 297:353-356; Soto, 1999, Mol Med Today 5:343-350). One of the first observations noted supporting this hypothesis was the localization of the gene for APP on chromosome 21 (Goldgaber et al., 1987, Science 235:877-880). One facet of trisomy 21 (Down's Syndrome) consists of a gene dosage error for APP and results in an increase in Aβ amyloid burden and invariably to the neuropathology of AD (Pallister et al., 1997, Neurobiol Aging 18:97-103).

Moreover, a rare case of chromosomal translocation in Down's Syndrome involving chromosome 21 left the patient with a diploid copy of APP resulting in the absence of amyloid deposits and associated neuropathology (Prasher et al., 1998, Ann Neurol 43:380-383). Additional evidence supporting the Aβ hypothesis include; toxicity of Aβ fibrils to hippocampal and cortical neurons (Geula, 1998, Neurology 51:S18-29; discussion S65-67; Lorenzo et al., 1994, Proc Natl Acad Sci USA 91:12243-12247), the natural occurrence of inherited mutations in APP resulting in increased Aβ formation sufficient to cause premature onset of AD (Goate et al., 1991, Nature 349:704-706; Levy et al., 1990, Science 248:1124-1126), and mice transgenic for mutant human APP demonstrate a time-dependent increase in Aβ production that directly correlates with the onset of neuropathological and behavioral changes associated with AD (Games et al., 1995, Nature 373:523-527; Holcomb et al., 1999, Behav Genet 29:177-185; Hsia et al., 1999, Proc Natl Acad Sci USA 96:3228-3233; Hsiao, 1998, Exp Gerontol 33:883-889).

Once formed through β-/γ-secretase cleavage, the Aβ peptide is released from cells where it can aggregate and trigger events leading to neurotoxicity (Walsh et al., 2004, Neuron 44:181-193). NMR studies have provided evidence suggesting that the monomeric form of Aβ 1-40 peptide is initially unstructured and water-solvated between residues 1-14. This is followed by a long α-helical sequence encompassing residues 15-36 and includes a hinge region around amino acids 25-27 (Coles et al., 1998, Biochemistry 37:11064-11077; Watson et al., 1998, Biochemistry 37:12700-12706; Crescenzi et al., 2002, Eur J Biochem 269:5642-5648). Aβ most likely exists in a dynamic flux of different conformations depending on interactions with other molecules and metal ions (Maggio et al., 1995, Science 268:1920-1921; author reply 1921-1923). However, the unstructured peptide may represent a transitional conformation from an α-helix to β-sheet (Soto et al., 1995, Neurosci Lett 200:105-108). It is widely believed that a conformational change in Aβ from an α-helix to random coil to β-sheet configuration is largely responsible for its extracellular aggregation and deposition (Wimley et al., 1998, Journal of Molecular Biology 277:

1091-1110; Chen et al., 1997, FASEB Journal 11:817-823; Gursky et al., 2000, Biochim Biophys Acta 1476:93-102; Roher et al., 2000, Biochim Biophys Acta 1502:31-43).

The initial stages of Aβ aggregation include oligomerization and protofibril formation. Kinetic studies of Aβ fibrillogenesis have pointed to a nucleation-dependent mechanism for Aβ aggregation (Jarrett et al., 1992, Biochemistry 31:12345-12352; Jarrett et al., 1993, Cell 73:1055-1058; Teplow, 1998, Amyloid 5:121-142). The rate of Aβ oligomerization is markedly increased by "seeding" the reaction with other molecular components, such as apolipoprotein E or Aβ dimers, to promote peptide-peptide interactions (Evans et al., 1995, Proc Natl Acad Sci USA 92:763-767). Based on NMR studies, Lansbury and coworkers have proposed that two Aβ monomers dimerize through anti-parallel associations after transitioning into their β-sheet conformations (Lansbury et al., 1995, Nat Struct Biol 2:990-998). Replacing hydrophobic amino acids within residues 17-21 of the Aβ peptide seriously impairs fibril formation, suggesting that anti-parallel associations are stabilized by hydrophobic interactions, in addition to hydrogen bonding. Successive stacking of the anti-parallel structures leads to the creation of a helical protofilament.

Lansbury and colleagues have envisioned Aβ aggregation as proceeding through four separate stages (Harper et al., 1997, Annu Rev Biochem 66:385-407):
1. Protofibril formation requires >20 Aβ molecules,
2. protofibril elongation involves the reversible coalescence of smaller protofibrils,
3. protofibril to fibril transition is the first pathogenic feature of AD detected by dye binding, and
4. fibril elongation process is continuous.

Because the Aβ fibril was the first amyloid entity identified by virtue of dye binding, it was naturally thought to represent the form of Aβ peptide that was neurotoxic. However, more recent evidence suggests that Aβ might be most detrimental to synaptic integrity and neuronal health when it is in the form of soluble oligomers generated during the early stages of the aggregation pathway (Hartley et al., 1999, J Neurosci 19:8876-8884; Lambert et al., 1998, Proc Natl Acad Sci USA 95:6448-6453; McLean et al., 1999, Ann Neurol 46:860-866; Walsh et al., 2002, Nature 416:535-539; Walsh et al., 2004, Protein Pept Lett 11:213-228). Microinjection of human Aβ into rats revealed that Aβ oligomers, in the absence of monomers and amyloid fibrils, inhibit long-term potentiation in the hippocampus (Walsh et al., 2002, Nature 416:535-539). Therefore, because of the complexity of the amyloid deposition process, inhibition of all forms of fibril intermediates-including oligomers and protofibrils-should be addressed when developing therapeutic intervention strategies.

Current therapy of Alzheimer's disease focuses largely on symptomatic aspects of the clinical pathology. Strategies include increasing cholinergic neurotransmission by administering acetylcholine esterase inhibitors (e.g. Tacrine or Donepezil) (Mayeux et al., 1999, N Engl J Med 341:1670-1679), and more recently modulation of NMDA receptor activity by Memantine (Reisberg et al., 2003, N Engl J Med 348:1333-1341). However, although these therapies have shown a modest effect on slowing cognitive decline, they have yet to demonstrate any major impact on the progression of the disease. Other targets in AD include the secretase enzymes. Logically, if one could reduce or eliminate activities of either β- or γ-secretase, then a concomitant reduction in Aβ accumulation would result. Since γ-secretase is an aspartyl protease, inhibitors have been designed to mimic the protease's transition state. Benzodiazepine inhibitors have proven to be highly effective demonstrating $IC_{50}$ values as low as 0.3 nM (Seiffert et al., 2000, J Biol Chem 275:34086-34091). However, inhibition of γ-secretase to treat AD is problematic because this protease has important functions in normal physiologic processing of other critical substrates. One substrate is the Notch receptor, which plays a vital role in cell fate determination during organismic development (Schweisguth, 2004, Curr Biol 14:R129-138). In fact, mice deficient in any of the γ-secretase subunits (Presenilin-1, nicastrin, APH-1, or PEN-2) demonstrate a lethal phenotype due to the absence of Notch processing (De Strooper, 2003, Neuron 38:9-12).

Inhibition of β-secretase has also shown promise, but not without significant challenges (Citron, 2004, Trends Pharmacol Sci 25:92-97). Mice deficient in β-secretase are viable and show no Aβ peptide generation, suggesting that this aspartyl protease may be an attractive target for inhibitor design (Luo et al., 2001, Nat Neurosci 4:231-232; Roberds et al., 2001, Hum Mol Genet 10:1317-1324). Peptidic and peptidomimetic inhibitors, mimicking transition state analogs, have been found (Turner et al., 2001, Biochemistry 40:10001-10006) often demonstrating $IC_{50}$ values in the nanomolar range (Turner et al., 2001, Biochemistry 40:10001-10006; Ghosh et al., 2001, J Med Chem 44:2865-2868). However, although these peptide-based inhibitors have become important and necessary research tools, their low intrinsic stability and inability to cross the blood-brain barrier have hampered studies aimed at assessing their effectiveness in vivo (Citron, 2004, Trends Pharmacol Sci 25:92-97).

It is now well-established that Aβ deposition occurs as a result of changes in peptide structure. Following proteolytic cleavage, the Aβ peptide transitions from a soluble monomeric, α-helical structure to an elongated β-sheet conformer, thus exposing highly interactive hydrophobic amino acid residues. Recognizing the critical nature of this conformational transition, efforts have been focused on developing lead inhibitor compounds that will stabilize the soluble form of Aβ by shifting the equilibrium from β-sheet to α-helix, since the soluble form is a better target for degradation and cellular clearance. Thus, the most promising potential therapies to date focus on compounds that either prevent Aβ fibril formation or reverse the aggregation process, thereby reducing overall amyloid burden. The two most successful approaches toward reducing amyloid burden in vivo have utilized either antibodies specific for the Aβ peptide or non-peptidic small molecule inhibitors. Elan Pharmaceuticals originally injected a transgenic mouse model of AD with a combination of β-amyloid and an immune system activating agent. The injected mice demonstrated significant reductions in amyloid plaques when compared to control animals (Schenk et al., 1999, Nature 400:173-177). Based on this finding, clinical trials were begun using a synthetic form of the Aβ peptide, AN-1792. Unfortunately, Phase IIa trials were terminated when four patients developed symptoms characteristic of encephalitis.

In drug development, non-peptidic small molecules have shown much promise toward Aβ peptide dissolution. These molecules are typically planar, contain a scaffold of 2-4 phenyl rings and have a basic nitrogen on one of the rings. Examples include: Congo Red (Lorenzo et al., 1994, Proc Natl Acad Sci USA 91:12243-12247), naphtylazo derivatives of the dye Congo Red (Talaga, 2001, Mini Rev Med Chem 1:175-186), the well-known antibiotic rifampicin (Tomiyama et al., 1994, Biochem Biophys Res Commun 204:76-83), anthracyclone derivatives (Talaga, 2001, Mini Rev Med Chem 1:175-186), and benzofuran-based compounds (Allsop et al., 1998, Biochem Soc Trans 26:459-463). Although these molecules have demonstrated low µM, and sometimes nM $IC_{50}$ values, they typically do not display ideal drug qualities owing to their charged moieties; such charged groups enhance solubility properties, but restrict passage across the blood-brain barrier (Scherrmann, 2002, Vascul Pharmacol 38:349-354). In addition, many of these compounds have proven to be highly toxic.

Curcumin is a polyphenolic natural product from the spice turmeric, which comes from the root of *Curcuma longa* of the ginger family. Ground turmeric powder as it is used in culinary preparations contains 5% curcumin. The majority of the world's curcumin (80%) is produced and consumed in India. In traditional Indian medicine, curcumin has been used to treat a host of ailments through topical, oral and inhalation administration, and has recently been found safe in six human trials at oral loads up to 8 grams/day for 6 months (Chainani-Wu, 2003, J Altern Complement Med 9:161-168). Most of the clinical trials of curcumin pertain to its anti-tumor activity in colon, skin, stomach, duodenal, soft palate and breast cancers. In addition, curcumin exhibits anti-inflammatory activity and is a potent anti-oxidant and free radical scavenger (Leu et al., 2002, Curr Med Chem Anti-Canc Agents 2:357-370). In APP-overexpressing transgenic mice, curcumin reduces levels of oxidized proteins and inflammatory cytokine interleukin-1$\beta$ (Lim et al., 2001, J Neurosci 21:8370-8377) thus offering a potential therapy against microglial activation, which is routinely detected in brains from AD patients. Curcumin has additional activities of interest: it limits the progression of renal lesions in the STZ-diabetic rat model (Suresh et al., 1998, Mol Cell Biochem 181:87-96), and ameliorates oxidative stress-induced renal injury in mice (Okada et al., 2001, J Nutr 131:2090-2095). Consequently, there has been extensive interest in the anti-oxidant properties of curcumin and the possibility that many of its biological activities are derived from its anti-oxidant properties (Balasubramanyam et al., 2003, J Biosci 28:715-721; Oyama et al., 1998, Eur J Pharmacol 360:65-71).

The large consumption of curcumin by the Indian population may help explain their relatively low (4 times less) incidence of AD compared to the U.S. population (Chandra et al., 2001, Neurology 57:985-989). Although no systematic trials have been preformed using curcumin in India, recent studies have provided valuable insights on curcumin's role in AD (Yang et al., 2005, J Biol Chem 280:5892-5901; Ono et al., 2004, J Neurosci Res 75:742-750). Curcumin was shown to inhibit the formation of A$\beta$ oligomers and fibrils in vitro and reduce A$\beta$ amyloid burden in vivo. The $IC_{50}$ for fibril inhibition is 0.8 $\mu$M and 1.0 $\mu$M for disaggregation of preformed fibrils. Importantly, curcumin administered as a dietary supplement lowered A$\beta$ deposition in aged APP(Swedish)-transgenic mice (Tg2576), clearly demonstrating its ability to cross the blood-brain barrier in sufficient quantities to reduce amyloid burden. Curcumin is structurally similar to other inhibitors of A$\beta$ aggregation such as Congo Red and Chrysamine G, however replacing the charged moieties on these latter compounds with polar groups greatly facilitates blood-brain barrier passage (Klunk et al., 1994, Neurobiol Aging 15:691-698). This study establishes curcumin as one of the most promising lead compounds in recent years that offers real potential for reducing amyloid deposition in AD and in doing so halting or reversing disease progression.

We hypothesize that the base structure of native curcumin provides an excellent starting point to identify chemical analogs that have greater affinity for A$\beta$ peptide oligomers, greater efficiency in fibril disaggregation and inhibition of fibril formation, while improving bioavailability.

A key event in progression of Alzheimer's disease (AD) is aggregation of the A$\beta$ peptide to form amyloid fibrillar deposits. A number of studies have reported on inhibitors that are effective in preventing A$\beta$ aggregation. The usefulness of these inhibitors has been limited due to their toxicity or their inability to cross the blood-brain barrier. However, it was recently reported that the natural product curcumin, a non-toxic component of the spice turmeric, not only prevents A$\beta$ aggregation but also disaggregates preformed A$\beta$ fibrils. Curcumin was reported to cross the blood-brain barrier when injected into the circulation and to reduce amyloid plaque burden in vivo in a transgenic mouse model. Curcumin was less effective, however, when added to the diet, due to limited oral bioavailability. Although curcumin is clearly able to disaggregate A$\beta$ peptide fibrils in vitro, its effectiveness in vivo has considerable room for improvement.

Based upon data presented in the recent literature, we hypothesize that curcumin presents molecular features that make it an excellent lead compound for the development of more effective inhibitors of A$\beta$ aggregation that demonstrate improved $IC_{50}$ values while maintaining or improving bioavailability.

In order to identify and improve upon the structural properties of native curcumin that are essential for its function in reversing amyloid deposition, we have generated chemical analogs that include key modifications to the base structure of curcumin. We plan to obtain detailed information on the functional properties of our library of curcumin-based, chemical analogs toward A$\beta$ peptide oligomerization. We expect to identify useful in vivo therapeutic inhibitors of amyloid plaque formation to halt or reverse cognitive decline.

First, we will identify the molecular features of curcumin that are responsible for inhibition of A$\beta$ peptide oligomerization using chemical analogs of curcumin. We have generated a chemical library of 84 novel compounds based on the molecular structure of curcumin and will test their effectiveness in preventing A$\beta$ peptide oligomerization and disaggregating preformed fibrils. Using biotinylated A$\beta$ (1-40) peptide in an electrophoretic mobility assay, we have obtained informative Preliminary Results examining the effects of select compounds from our curcumin-analog library on preventing A$\beta$ oligomerization. We anticipate that the results obtained will allow us to develop valuable structure-activity relationships that will permit the identification of new compounds that will be effective for the prevention and/or treatment of AD.

Next, we will determine whether analogs of curcumin are more effective than curcumin in reducing cytotoxicity caused by A$\beta$ oligomers in cultured neuronal cells. Depending on their concentration and aggregation state, A$\beta$ oligomers are known to induce neurotoxic effects. We will determine if our curcumin-analogs are biologically active and provide a neuroprotective effect against A$\beta$ toxicity, using a well-characterized neuroblastoma cell line (SY5Y).

Finally, we expect to improve upon the efficacy of chemical analogs of curcumin using ligand-based drug design. Using the curcumin-analog library, we will derive quantitative structure-activity relationship (QSAR) models based on experimental evidence obtained from the A$\beta$ oligomerization assays. We will select the most potent and conformationally rigid analogs to perform a ligand-based virtual screening (LBVS) using several chemical libraries, focusing on the ~0.5 million compounds from Chemical Diversity (ChemDiv). The resulting LBVS hits will be further tested with established in vitro A$\beta$ oligomerization assays and cell-based toxicity assays. We will seek to identify candidates with both high potency and appropriate "drug-like" profile.

Figure 33:
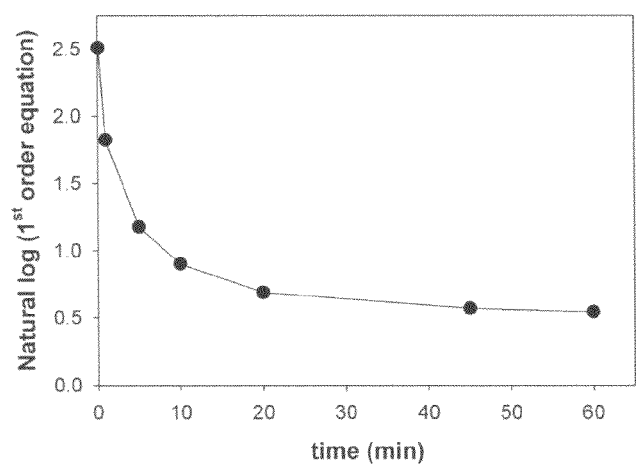
FIG. 33 is a graphical representation of the reactivity of curcumin with L-cysteine. Curcumin (20 µM) was incubated with L-cysteine at the indicated concentrations and absorbance (425 nm) was measured up to 60 minutes. Natural log values were determined based on 1 st order kinetics.

Curcumin reactivity: One potential concern regarding the structure of curcumin is the presence of two $\beta$-ketone-olefin moieties. These groups potentially serve as Michael acceptors which are a chemically reactive species that can form undesirable covalent modifications with binding targets. These types of reactions can lead to false positives in in vitro assays (Rishton, 1997, Drug Discov. Today 2:382-338). Michael acceptors are generally thought to be poor drug compounds because of their high reactivity toward nucleophiles. In order to evaluate curcumin's potential as a Michael acceptor, we examined its reactivity toward L-cysteine as a nucleophile donor. We incubated 20 µM curcumin with 1 mM L-cysteine in 0.1 M sodium phosphate buffer, pH 7.0, and measured curcumin's spectral properties at 425 nm as a function of time. L-Cysteine rapidly reacted with curcumin and quenched absorbance with a $t_{1/2}$ of 7.2 min (FIG. 33). Thus, curcumin is highly reactive to nucleophiles, providing a possible explanation for its poor uptake by intestinal epithelium. However, Aβ peptide contains no cysteine residues so, although curcumin is highly reactive to this amino acid, its inactivation by thiol nucleophiles should not pose a problem in our inhibition studies. In addition, at or below neutral pH, primary amino groups are predominantly in their protonated form and therefore weak nucleophiles that are unlikely to react to any significant extent with curcumin.

Figure 34:
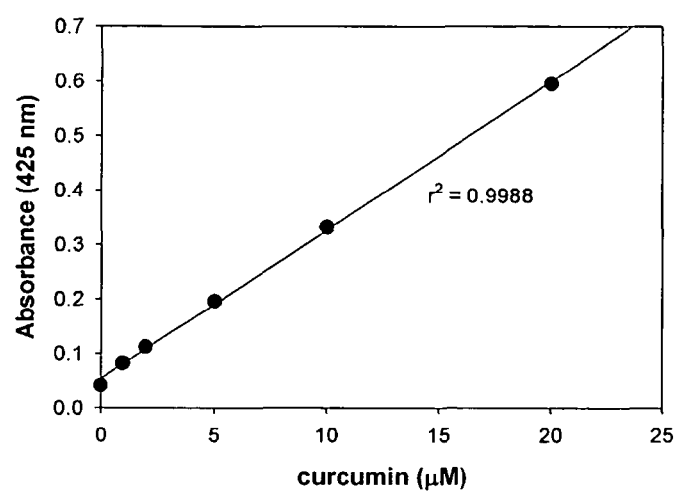
FIG. 34 shows that curcumin does not aggregate in an aqueous environment at concentrations that are effective in preventing Aβ oligomerization. Curcumin was diluted to the indicated concentrations in phosphate buffered saline, pH 7.0. Absorbance (425 nm) was measured and analyzed by linear regression analysis.

Non-specific inhibition of drug targets by small molecule inhibitors can arise by their forming large molecular weight aggregates in an aqueous environment (McGovern et al., 2002, J Med Chem 45:1712-1722). For example, compounds with multi-aryl ring structures have a tendency to assemble into highly ordered complexes driven by the stacking of their aromatic rings (Stopa et al., 1998, Biochimie 80:963-968; Stopa et al., 2003, Acta Biochim Pol 50:1213-1227). Since curcumin is a bi-phenolic molecule, we investigated if it aggregates in an aqueous environment. Such an aggregation property would suggest that curcumin may show poor selectivity and thus have little potential as a lead compound for effective amyloid dissolution in vivo. We measured potential aggregation of curcumin using a standard light scattering assay. Curcumin was diluted to 1.0-20.0 µM in 0.1 M phosphate buffered saline, pH 7.0, and its absorbance was measured at 425 nm. As shown in FIG. 34, the absorbance profile remained linear throughout the concentration range tested indicating no evidence of aggregation. From these data, we conclude that curcumin's ability to inhibit Aβ oligomerization is due to specific interactions and not due to non-specific chemical aggregation effects.

In the last two years, we have constructed a chemical library consisting of 84 curcumin-based analogs to identify the functional groups responsible for curcumin's established anti-oxidant properties (Barclay et al., 2000, Org Lett 2:2841-2843; Weber et al., 2005, Bioorg Med Chem 13:3811-3820). The enone analogs include: 1) those that retain the 7-carbon spacer between the aryl rings, 2) those with a 5-carbon spacer, and 3) those with a 3-carbon spacer. In addition to carbon spacer variations, analogs are also available with monoketone substitution for the native diketone structure, varying degrees of saturation to test the importance of unsaturation and addition of aryl rings to the unsaturated carbon spacer. We also have synthesized analogs that limit rotational flexibility to address if stabilizing interactions with Aβ oligomers will provide greater effectiveness in aggregate dissolution.

In order to perform large-scale screening of our analog library in a rapid, reproducible and cost-effective manner, we are developing novel assays to accurately distinguish between monomeric and oligomeric Aβ peptide. We are in the process of developing an ELISA-based assay using the commercially available anti-Aβ oligomer specific antibody, A11 (Glabe, 2004, Trends Biochem Sci 29:542-547; Kayed, 2003, Science 300:486-489). This antibody clearly distinguishes the oligomeric conformation of the Aβ aggregate, from the fibrillar or monomeric peptide. Since the oligomeric form of Aβ aggregates is receiving increasing attention as a major factor responsible for synaptic dysfunction (Hardy et al., 2002, Science 297:353-356), this antibody will serve a very important diagnostic role due to its ability to specifically recognize Aβ oligomeric conformers. We describe the methodology we are developing for this antibody in Research Plan.

However, as an initial screen of a select number of curcumin analogs for their ability to prevent Aβ aggregation in vitro, we have used the published SDS-PAGE mobility-shift procedure described by Yang, et al., in their original identification of curcumin as an inhibitor of amyloid β-oligomerization (Yang et al., 2005, J Biol Chem 280:5892-5901), with a few modifications. The original procedure relies upon resolving curcumin-treated and non-treated Aβ oligomers by SDS-PAGE, followed by immunoblotting with an anti-Aβ peptide antibody. We have chosen a more direct approach using biotinylated peptide to circumvent the need for antibody detection. Antibody detection can present disadvantages due to variability in detection depending on epitope availability of the Aβ oligomer when it is bound to transfer membranes. We anticipate that use of biotinylated peptide will provide us with greater sensitivity and reproducibility since antibody-epitope recognition is not required; rather very high affinity biotin-streptavidin interactions are utilized for detection.

Figure 35:
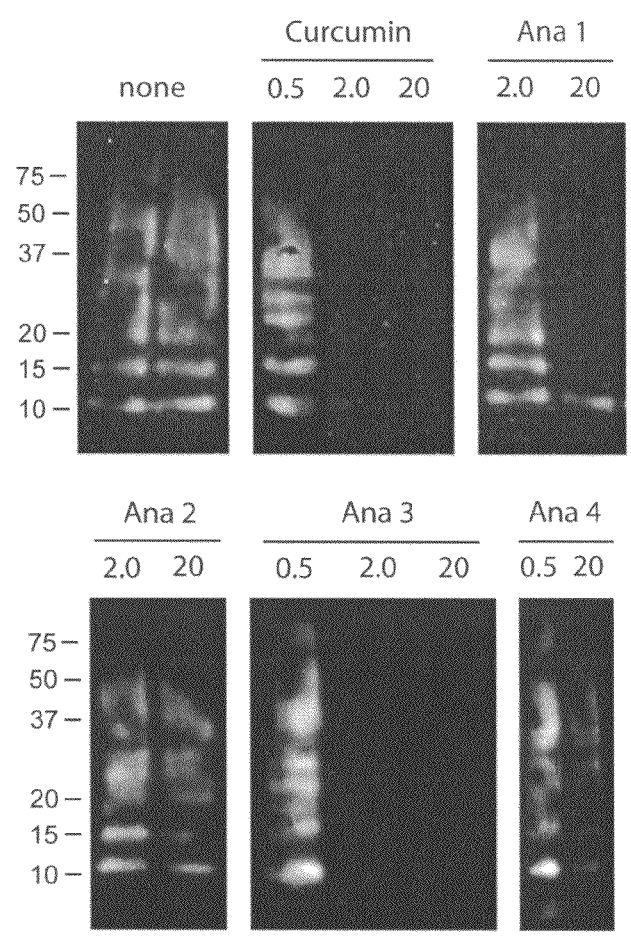
FIG. 35 shows the effect of curcumin and curcumin-based analogs on Aβ(1-40) peptide oligomerization. Biotinylated Aβ(1-40) peptide was diluted from 5 mg/ml DMSO stock to 20 µg/ml in phosphate buffered saline, pH 6.0, and incubated with the indicated concentrations of curcumin or curcumin-analog for 48 h at 37° C. Reactions were mixed with Tricine sample buffer (no heating) and resolved by 10-20% Tris-Tricine gel electrophoresis. Following transfer to PVDF membranes, bound material was probed with streptavidin-HRP (1 µg/ml) and visualized by chemiluminescence detection.

Aβ(1-40) peptide was obtained with biotin coupled to its N-terminus, since structural determinations suggest that the C-terminal residues represent a primary site for β-sheet transitions and oligomerization (Soto, 1999, Mol Med Today 5:343-350; Jarrett et al., 1993, Ann NY Acad Sci 695:144-148; Jarrett et al., 1993, Biochemistry 32:4693-4697). The expectation that biotin attached to the N-terminus of the peptide would have little effect on the oligomerization process was confirmed as follows: Biotin-Aβ(1-40) peptide was diluted to a final concentration of 20 µg/ml into phosphate buffered saline, pH 6.0 and incubated for 48 h at 37° C. in the presence or absence of selected curcumin analogs. Following incubation, the peptide solutions were centrifuged (12,000× g, 2 min) and mixed with an equal volume of 2-fold concentrated Tricine sample buffer and fractionated by electrophoresis on 10-20% precast Tris-Tricine polyacrylamide gels. Fractionated material was then transferred to PVDF membranes using a semi-dry transfer unit (20V, 40 min) and non-specific sites were blocked by incubation with 20 mM Tris, pH 7.4, 150 mM NaCl, 0.1% Tween-20 (TBS-T), 5% calf serum. Membranes were then incubated streptavidin conjugated with horseradish peroxidase and processed for chemiluminescence detection. Images were captured using a Syngene GeneGnome system equipped with a Peltier-cooled 16-bit CCD camera and saturation detection. Without curcumin treatment, we found high molecular weight aggregates resolved by Tris-Tricine PAGE analysis (FIG. 35).

These oligomers ranged in relative molecular mass from 15-75 kDa, as was seen by Yang, et al. (Yang et al., 2005, J Biol Chem 280:5892-5901). When Aβ peptide was incubated with varying concentrations of curcumin, we found that 2.0 and 20 µM concentrations completely inhibited Aβ oligomer formation, whereas 0.5 µM had little effect. Using non-biotinylated Aβ(1-40), Yang, et al., reported an $IC_{50}$ value for curcumin of 1 µM, which is similar to our estimation obtained from PAGE analysis. These results clearly demonstrate that curcumin prevents oligomerization of N-terminal biotinylated Aβ(1-40) peptide in an identical manner as that shown by Yang, et al. (Yang et al., 2005, J Biol Chem 280:5892-5901) using non-biotinylated peptide.

Figure 36:
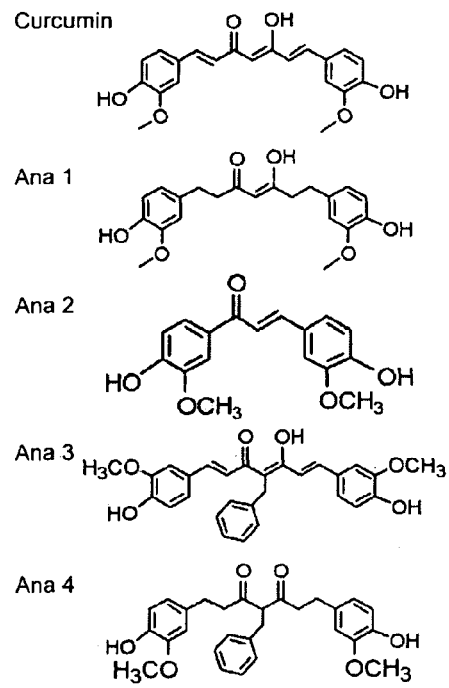
FIG. 36 shows a structural comparison between curcumin and illustrative curcumin derivatives.

We next examined the effect of 4 structurally different analogs of curcumin to determine if oligomer inhibition was restricted to curcumin or if variations could be introduced into its molecular structure that might assist us in identifying the essential chemical groups responsible for its inhibitory properties and guide us in the design of more efficacious inhibitors. From our library of 84 analogs, we chose analogs (Ana) 1-4 for our initial limited screening. These were selected based on their substitutions and degree of unsaturation of the carbon spacer (FIG. 36). As shown in FIG. 36, Ana 1 contains two aryl rings and a saturated 7-carbon spacer designed to test the importance of unsaturation in the spacer arm; Ana 2 contains two aryl rings and an unsaturated 3-carbon spacer to test the importance of spacer length; Ana 3 contains two aryl rings separated by an unsaturated 7-carbon spacer and an additional aryl ring attached to the central methylene carbon to test if additional aryl ring structures impact inhibitory effectiveness; and Ana 4 contains two aryl rings separated by a fully saturated 7-carbon spacer and an aryl ring attached to the central methylene carbon designed to test the importance of unsaturation in the spacer arm together with an additional aryl ring structure.

We applied the same experimental protocol using the 4 different analogs as that described in FIG. 36 for curcumin. Importantly, we found that all 4 analogs demonstrated some degree of inhibition of Aβ oligomerization (FIG. 36). Ana 1 and Ana 4 both inhibited oligomerization with an $IC_{50}$<20 µM, indicating the α,β-unsaturated carbon spacer is not essential to maintain inhibitory properties. This is an important observation due to the potential of α,β-unsaturated groups serving as Michael acceptors. The original work on curcumin by Yang, et al. (Yang et al., 2005, J Biol Chem 280:5892-5901) failed to address this critical concern. Ana 2 also inhibited Aβ oligomerization with an $IC_{50}$ of 20 µM. Although not as effective as curcumin, Ana 2 only has a 3-carbon spacer between the phenolic rings as opposed to the 7-carbon spacer of curcumin suggesting that the bi-phenolic structure may provide the greatest contribution toward the inhibitory properties. These data also demonstrate flexibility in ring spacing since spacer distance can be varied between 3 and 7 carbons. Finally, Ana 3 demonstrates an $IC_{50}$ value <2 µM and is at least as effective as curcumin in preventing Aβ oligomerization. Ana 3 closely resembles curcumin with the addition of an aryl ring attached at the central methylene carbon. The addition of this hydrophobic ring clearly does not interfere with the inhibitory properties of the basic curcumin structure and once accurately titrated in an ELISA-based assay, may prove more effective than curcumin.

From these preliminary results, we are beginning to obtain a picture of the necessary features in the molecular structure of curcumin that are responsible for its inhibitory properties toward Aβ oligomerization. It is our goal to develop more effective aggregation inhibitors by capitalizing on the newly established inhibitory properties of curcumin. Curcumin itself demonstrates $IC_{50}$ values in the low micromolar range leaving much room for improvement. Once we identify the critical features of curcumin that are responsible for prevention of oligomerization, we believe developing synthetic inhibitors with nanomolar $IC_{50}$ values are very possible given the success of our preliminary studies. Developing inhibitors with nanomolar $IC_{50}$ values is imperative when taking into consideration some basic facts of the physiological properties of curcumin. First, curcumin is poorly absorbed by the intestinal epithelium (Ammon et al., 1991, Planta Med 57:1-7; Ravindranath et al., 1980, Toxicology 16:259-265; Sharma et al., 2001, Clin Cancer Res 7:1894-1900) and this is probably the reason why ingesting large doses of curcumin are well tolerated in clinical trials (Chainani-Wu, 2003, J Altern Complement Med 9:161-168). Second, closer examination of the effects of dietary curcumin on in vivo amyloid plaque burden presented by Yang, et al. (Yang et al., 2005, J Biol Chem 280:5892-5901), reveals that, although curcumin significantly reduced hippocampal plaque burden, this effect was limited to a modest 32.5% reduction. We believe that the percent reduction in plaque burden can be increased with analogs demonstrating greater $IC_{50}$ values to offset the poor uptake by intestinal epithelia. Modifications we make to the base curcumin structure may also contribute to the dietary uptake, which will only serve to enhance its biologic effects on Aβ oligomer dissolution.

In order to identify the molecular features of curcumin that are responsible for inhibition of Aβ peptide oligomerization using chemical analogs of curcumin, we will determine whether our library of curcumin-based analogs contains compounds that can inhibit Aβ peptide aggregation and disaggregate preformed Aβ fibrils at sub-micromolar concentrations. Curcumin is a symmetrical diphenolic dienone that exists in equilibrium between diketo and keto-enol forms. We have synthesized a series of three enone analogs of curcumin totaling over 80 compounds that include those: 1) that retain the 7-carbon between the aryl rings, 2) with a 5-carbon spacer, and 3) with a 3-carbon spacer (Weber et al., 2005, Bioorg Med Chem 13:3811-3820). We will compare each of these compounds with curcumin in their abilities to inhibit Aβ peptide aggregation and to disaggregate preformed Aβ oligomers using two in vitro assays. The first assay described below is a novel ELISA-based screening procedure that will allow us to accurately titrate the effectiveness of each curcumin-analog toward preventing Aβ oligomerization. The antibody we will employ for this assay specifically recognizes the oligomeric conformation of the Aβ aggregate, but not the fibrillar or monomeric forms (Glabe, 2004, Trends Biochem Sci 29:542-547; Kayed et al., 2003, Science 300:486-489). We plan to continue using the biotinylated Aβ peptide and use streptavidin-coated plates for capture, rather than anti-Aβ antibodies to ensure efficient binding of aggregates that might otherwise be precluded due to steric hindrance caused by the oligomeric structure.

Other in vitro assays such as use of thioflavin, which rely upon a fluorescent shift following aggregate binding (LeVine 3rd, 1999, Methods Enzymol 309:274-284; Naiki et al., 1989, Anal Biochem 177:244-249), are not practical for our needs because excitation/emission spectra for thioflavin are similar to those of our curcumin-based compounds. Using our ELISA-based assay, which will provide us with a rapid, reproducible and cost-effective screening protocol, we fully anticipate identifying compounds with equal or greater potential than curcumin toward Aβ aggregate disruption. Once identified, we will test these compounds for their ability to prevent Aβ oligomerization using SDS-PAGE analysis.

Figure 37:
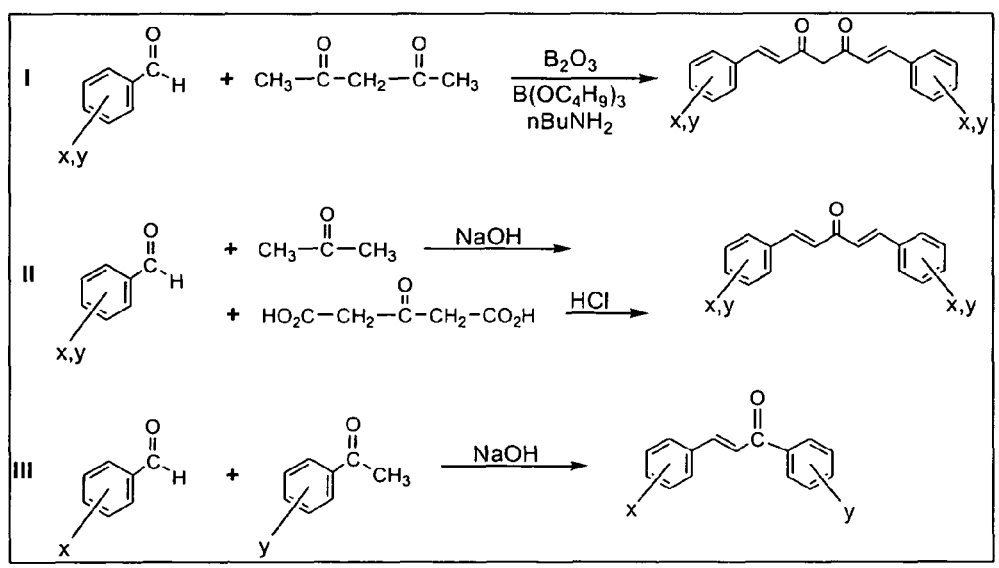
FIG. 37 shows synthesis of illustrative enone analogs of curcumin.

Although we plan to concentrate our initial efforts screening the analogs in our current library, we are not limited to the 84 compounds presently on hand. The syntheses of these 3-, 5-, and 7-carbon spacer analogs, as well as incorporating varying degrees of saturation, are straight forward and the schemes are adaptable. The availability of a large number of substituted benzaldehydes, heterocyclic ring-containing aldehydes and substituted acetophenones adds efficiency and flexibility to the synthetic procedures. In addition, many of the synthetic reactions require only one or two steps as illustrated in FIG. 37. Series I analogues, maintaining the 7-carbon dienone spacer between the aromatic rings as in curcumin, were synthesized from aromatic and heterocyclic aldehydes by condensation with 2,4-pentanedione in an aldol type reaction (Pabon, 1964, Recueil 83:379-386). This involves base-catalyzed condensation in the presence of a trialkylborate to complex with the carbonyl groups, which prevents enolization and guides the reaction. If a mixture of two different aldehydes is used, unsymmetrical analogues are formed. Series II analogues, containing a 5-carbon enone spacer, were synthesized either by base-catalyzed condensation of the appropriate aldehyde with acetone or by acid-catalyzed condensation with 3-oxo-glutaric acid (Masuda et al., 1993, Phytochemistry 32:1557-1560; Zelle et al., 1998, World Patent, 9820891). Series III, containing a 3-carbon enone spacer were synthesized by base-catalyzed condensation of the appropriate aldehyde with a substituted acetophenone (Kohler et al., 1932, Org. Synth., Coll. Vol. 1).

Experimental design: N-terminal biotinylated-Aβ(1-40) peptide will be dissolved in dimethylsulfoxide (DMSO) to a final concentration of 5 mg/ml and sonicated for 30 min. This material will be then centrifuged through a 0.2 μm spin-filter and stored at −80° C. Sonication and filtration are necessary to remove any trace of undissolved seeds that may nucleate aggregate formation (Evans et al., 1995, Proc Natl Acad Sci USA 92:763-767). This preparation remains stable and aggregate-free at −80° C. Immediately before use, the peptide will be diluted to a final concentration of 20 μg/ml into phosphate buffered saline (PBS), pH 6.0 and incubated for 48 h at 37° C. in the presence or absence of varying concentrations of curcumin or curcumin-based analogs (0.01-20 μM). Following this incubation, the reactions will be centrifuged (12,000× g, 5 min) and added to wells of streptavidin-coated 96-well plates for 1 h at 23° C. Wells will be rinsed 3 times with PBS, pH 7.2, to remove unbound biotinylated material and blocked to prevent non-specific adsorption with PBS containing 0.1% Tween-20, 5% calf serum (blocking buffer) for 1 h, 23° C. Wells will then be incubated with rabbit polyclonal antibody A11 (1 μg/ml, available from BioSource International, Camarillo, Calif.) for 1 h, 23° C., followed by rinsing with PBS containing 0.1% Tween-20 and incubated with HRP-conjugated, goat anti-rabbit secondary antibody for 1 h, 23° C. Unbound secondary antibody will be removed by rinsing wells with PBS, 0.1% Tween-20 and developed with peroxidase substrate, 3,3',5,5'-tetramethylbenzidine (TMB). The reaction will be terminated by the addition of 1 N sulfuric acid and spectrophotometric readings will be taken at 450 nm for quantitation. Positive controls will include peptide incubated in the absence of inhibitors to permit fibril formation, and negative controls will consist of peptide freshly diluted just prior to adding reaction mixtures to streptavidin-coated plates. All assays will be performed using varying dilutions of each compound in order to determine $IC_{50}$ values for accurate comparison with native curcumin.

We will then determine whether curcumin-based analogs identified as inhibitors of Aβ peptide aggregation are also able to inhibit Aβ oligomerization. Since soluble Aβ oligomers are more diffusible than amyloid fibrils and viewed as playing an important role in AD pathogenesis, we will also examine if our curcumin analogs are capable of preventing the formation of peptide oligomers. Visualizing Aβ oligomers is best accomplished by Tris-Tricine based SDS-PAGE analysis (Yang et al., 2005, J Biol Chem 280:5892-5901). Using this method, Aβ monomers (~4 kDa) are readily distinguished from 4-5-mers, as well as higher molecular weight oligomers that range in relative molecular masses from 44-127 kDa (Yang et al., 2005, J Biol Chem 280:5892-5901). To permit better comparisons with results obtained by ELISA assays, and for sensitivity in detection, we will continue to use our biotinylated Aβ(1-40) peptide. Toward this end, peptide will be incubated in the presence or absence of varying concentrations of curcumin analogs and, following incubation, resolved by Tris-Tricine SDS-PAGE. Peptide and oligomers will then be transferred to PVDF membrane and probed with HRP-conjugated streptavidin, followed by chemiluminescence detection. We anticipate that one or more of the curcumin analogs identified in our ELISA capture assay will also inhibit Aβ peptide oligomerization in a concentration-dependent manner. With densitometric analyses, we will calculate $IC_{50}$ values for oligomer inhibition and compare these values directly to fibril inhibition derived from our ELISA-based assay.

Experimental design: Biotinylated-Aβ(1-40) peptide will be diluted to a final concentration of 20 μg/ml into PBS, pH 6.0 and incubated for 48 h at 37° C. in the presence or absence of varying concentrations of curcumin or curcumin-based analogs (0.01-20 μM). Following incubation, the reactions will be mixed with an equal volume of 2-fold concentrated Tricine sample buffer without reducing agents and separated on 10-20% Tris-Tricine SDS gels. Peptides will then be transferred to PVDF membranes and incubated with PBS containing 0.1% Tween-20, 5% calf serum for 1 h, 23° C. Membranes will then be incubated with HRP-conjugated streptavidin and processed for chemiluminescence detection according to manufacturer's instructions (SuperSignal, Pierce). Images will be captured using a Syngene GeneGnome system equipped with a Peltier-cooled 16-bit CCD camera. This camera has full saturation detection and a large dynamic linear range for accurate quantitation of chemluminescent signals. Densitometric analysis will be performed using Scion Image, version 4.0.2. All experiments will be done in triplicate and data will be plotted and subjected to regression analysis to determine IC50 values.

We will then determine whether the curcumin-based analogs directly bind Aβ peptide aggregates and, if so, with what affinity. Curcumin has been shown to bind directly to Aβ fibrils and demonstrate little or no affinity for Aβ monomers (80). However, in that study the experimental design was such that affinity measurements could not be made. Determining binding affinity for curcumin and chemical analogs is critical to evaluating their mechanism of inhibition and for future improvements upon inhibitor design. Therefore, we will test curcumin and identified analogs that inhibit Aβ peptide aggregation for their abilities to bind Aβ fibrils and determine affinity measurements for direct comparisons. Toward this end, we will incubate biotinylated-Aβ(1-40) peptide to form aggregates and after which capture the aggregates on streptavidin-coated 96-well plates. Curcumin and curcumin analogs will then be incubated with immobilized aggregates and binding will be quantitated by fluorescence detection taking advantage of the fluorescent properties of curcumin and its chemical analogs. Quantitation of direct binding will allow us to calculate the affinity constant for each inhibitor which will first confirm if the analogs are able to bind Aβ aggregates directly and second, determine if the interaction is of high- or low-affinity.

Experimental design: Biotinylated-Aβ(1-40) peptide will be diluted to a final concentration of 20 μg/ml into PBS, pH 6.0 and incubated for 48 h at 37° C. to permit aggregation. Reaction mixtures will then be incubated in 96-well plates pre-coated with streptavidin for 2 h at 23° C. to capture biotinylated aggregates. Wells will be rinsed 3 times with PBS, pH 7.2 to remove unbound material, followed by incubation with varying concentrations of curcumin or curcumin analogs for 2 h at 23° C. A two hour-incubation period is chosen since this time is insufficient for disaggregation of preformed fibrils, but sufficient to permit curcumin binding to aggregates (Yang et al., 2005, J Biol Chem 280:5892-5901).

Unbound curcumin or curcumin analogs will be removed by rinsing the membrane 3 times with PBS and bound material will be quantitated by fluorescence detection using a fluorescence plate reader (excitation/emission, 355/518 nm). All points will be carried out in triplicate and data will be subjected to regression analysis to determine binding affinities.

We will next determine whether curcumin or its chemical analogs destabilize the β-sheet conformation of Aβ peptide aggregates and stabilize the non-aggregated α-helical/random coil conformation. Because of the chiral properties of the Aβ peptide backbone, circular dichroism spectroscopy can be used to determine its absorption spectra in the far UV range and obtain information about the content of α-helix, β-sheet or random coil within the peptide structure. The wavelengths used range from 190-250 nm, which are well below the excitation/emission spectra of curcumin in an aqueous environment ($\lambda$ex=355 nm, $\lambda$em=518 nm) (Khopde et al., 2000, Photochem Photobiol 72:625-631) or its analogs, thus the presence of these compounds in the sample is not expected to interfere with the measurements. These measurements will provide critical information that will enable us to better define the mechanism of curcumin action. How curcumin disaggregates the Aβ fibril structure is currently unknown. Since Aβ aggregation requires a conformational shift from α-helix/random coil to β-sheet to seed the aggregation process, and as curcumin is known to directly bind Aβ aggregates, we hypothesize that curcumin may bind to and de-stabilize β-sheet conformers, thereby shifting the equilibrium to a greater α-helical/random coil population. To test this hypothesis, we plan to take circular dichroism measurements of Aβ peptide in the presence of varying concentrations of curcumin or its chemical analogs. In the absence of inhibitor, we anticipate measuring predominantly β-sheet conformation of the fibril solution as previous studies have shown (Roher et al., 2000, Biochim Biophys Acta 1502:31-43, Bieler et al., 2004, Curr Drug Targets 5:553-558; Lopez De La Paz et al., 2002, Proc Natl Acad Sci USA 99:16052-16057; Xu et al., 2005, Proc Natl Acad Sci USA 102:5403-5407). With increasing inhibitor concentration, we expect to observe a shift toward α-helical/random coil content, the amount of which will be dependent upon inhibitor structure and concentration.

To ensure that the curcumin- and analog-dependent conformational changes we measure by CD analysis are accompanied by a loss of fibril and oligomeric structure, we will also examine aliquots of Aβ peptide incubated with or without aggregation inhibitors by electron microscopy. We anticipate that a loss of fibril structure resulting from incubation with the aggregation inhibitors will closely correlate with a conformational shift from β-sheet to α-helix/random coil. Such ultrastructural studies will not only confirm the disaggregation properties of our newly discovered inhibitors, but also provide additional mechanistic evidence correlating loss of β-sheet structure with loss of fibril structures.

Experimental design: Biotinylated-Aβ(1-40) peptide will be diluted to a final concentration of 20 μg/ml into PBS, pH 6.0 and incubated for 48 h at 37° C. in the presence or absence of varying concentrations of curcumin or curcumin-based analogs. A minimum of 20 CD scans will be acquired in the range of 190-250 nm by taking points every 0.2 nm. A scan rate of 100 nm/min with band width of 1 nm will be used.

Electron microscopy analysis: A sample of the Aβ aggregates incubated in the presence or absence of curcumin or its analogs will be adsorbed to formvar-coated 400-mesh copper EM grids for 30 min. The grids will then be stained with 2% uranyl acetate and examined with a Hitachi 600 electron microscope.

In order to determine whether analogs of curcumin are more effective than curcumin in reducing cytotoxicity caused by Aβ oligomers in cultured neuronal cells, we will first determine whether the curcumin-based analogs protect against Aβ aggregate-mediated cytotoxicity. AD is ultimately a neurodegenerative disease as it is largely accepted that the progressive deposition of Aβ is directly toxic to neurons and increases their susceptibility to oxidative and metabolic stress, and excitotoxicity (Mattson, 1997, Physiol Rev 77:1081-1132). These insults significantly impact synaptic plasticity and markedly inhibit long-term potentiation. Because of this, it is imperative that inhibitors of Aβ fibrillogenesis be tested for their ability to protect neuronal cells from aggregate-induced cytotoxicity if they are to be considered of any potential therapeutic value. Therefore, we will determine if the curcumin analogs we identify as Aβ aggregate inhibitors are neuroprotective. Toward this end, we will carry out two well-characterized assays to assess: 1) protection against Aβ oligomer-induced cell death by measuring lactate dehydrogenase (LDH) release, and 2) analog-dependent increase in cell viability by determining metabolic activity using the MTT [3-(4,5-dimethylthiazolyl-2)-2,5-diphenyltetrazolium bromide] reduction assay. LDH release is correlated to disruption of cellular integrity and a direct measure of cell death. MTT, a tetrazolium salt, undergoes reduction by dehydrogenases thereby generating intracellular formazan which can be measured spectroscopically. For these studies, we will use the neuroblastoma-derived cell line, SH-SY5Y, which have been previously used for aggregation-dependent cytotoxicity measurements (Datki et al., 2003, Brain Res Bull 62:223-229). Upon addition of retinoic acid (RA) to the culture media, these cells undergo morphological differentiation, growth arrest and develop characteristics of a distinct neuronal phenotype (Pahlman et al., 1984, Cell Differ 14:135-144).

Experimental design: SH-SY5Y cells will be induced to differentiate by supplementing media with 10 μM all-trans-retinoic acid for 7 days. Following differentiation, cells will be incubated with preformed Aβ oligomers (100 nM) in the presence or absence of varying concentrations of curcumin (as our positive control) or curcumin analogs for 48 h at 37° C. LDH assays will then be performed on culture media and MTT assays will be performed on cells.

LDH assay: Standard, reliable kits for measuring LDH activity are commercially available (Promega, Sigma-Aldrich and CalBiochem).

MTT assay: 500 μg/ml MTT is prepared in RPMI-1640 media without phenol red and added to cells for 2-4 h at 37° C. until purple precipitate is seen. Media is then removed and dye is extracted with acidic isopropanol (0.04 M HCl in absolute isopropanol), and absorbance is taken at 570 nm with background subtraction at 650 nm. All experimental points will be done in triplicate to establish statistical significance.

We will then determine whether the curcumin-based analogs protect against Aβ aggregate-mediated glial cell activation. Glial cell activation, both astrocytes and microglia, with subsequent production of proinflammatory mediators, is thought to play a significant role in the pathophysiology of AD (McGeer et al., 1995, Brain Res Brain Res Rev 21:195-218). A number of inflammatory effectors are secreted by microglia in AD brain including nitric oxide, interleukin-6 (IL-6), and tumor necrosis factor-α, among others (Lue et al., 2001, Glia 35:72-79). The centers of these inflammatory responses are the amyloid deposits (Selkoe, 1991, Neuron 6:487-498; Mehlhorn et al., 2000, Int J Dev Neurosci 18:423-431). Importantly for our objectives, Aβ aggregates have been shown to induce the production of inflammatory mediators in cultured glial cells (Araujo et al., 1992, Brain Res 569:141-145; Goodwin et al., 1995, Brain Res 692:207-214; Meda et al., 1995, Nature 374:647-650). Rat C6 glioma cells are a useful model for Aβ aggregate-induced cytokine production (Bales et al., 1998, Brain Res Mol Brain Res 57:63-72; Hu et al., 1998, Brain Res 785:195-206; Pena et al., 1995, Brain Res Mol Brain Res 34:118-126) and with these cells we will examine if curcumin analogs, identified as inhibitory for peptide aggregation, protect against glial cell activation. We will quantitate secreted levels of IL-6 from cultured C6 cells as a measure of inflammatory activation. We anticipate that Aβ-aggregates will induce IL-6 production in these cells, as reported previously (Hu et al., 1998, Brain Res 785:195-206; Pena et al., 1995, Brain Res Mol Brain Res 34:118-126; Gasic-Milenkovic et al., 2003, Eur J Neurosci 17:813-821), and our curcumin analogs will protect cells from activation by virtue of aggregate dissolution. These data will provide important information regarding additional functions for curcumin analogs; in addition to Aβ peptide aggregate dissolution, the analogs may also provide a neuroprotective function by preventing induction of harmful inflammatory mediators.

Experimental design: Rat C6 glioma cells will be seeded in 96-well plates at a density of $5 \times 10^4$ cells per well and grown for 24 h. Culture media will be replaced with 25 μM Aβ peptide with or without varying concentrations of curcumin or curcumin analogs for 48 h. Culture supernatants will be tested for IL-6 secretion using an ELISA specific for rat IL-6 (available from BioSource, Inc.). This particular ELISA system is sensitive to <8 μg/ml IL-6 with a working range of 30-2000 pg/ml.

Next, we will determine whether the curcumin-based analogs that prevent Aβ aggregation and glial cell activation exhibit lipid membrane permeability. Successful drug development methodologies require close attention to physico-chemical properties that ultimately dictate bioavailability. Knowledge obtained regarding these properties, which include absorption, distribution, metabolism and excretion (ADME), are critical for effective and useful drug development. We will carry out a pre-ADME screening process on curcumin analogs that we identify as effective in inhibiting Aβ aggregation and protective in neurotoxicity assays. A pre-ADME screening system is commercially available that permits early characterization of lead compounds in the drug development process. Since lipophilicity is a major determinant of a compounds's inherent bioavailability, the assay quantitatively determines lipid permeability using artificial membranes prepared with a mixture of phospholipids designed to mimic intestinal brush-border membranes (Kansy et al., 1998, J Med Chem 41:1007-1010; Sugano et al., 2001, J Biomol Screen 6:189-196). In addition, passive drug diffusion results will be obtained using artificial membranes of hexane/hexadecane (Wohnsland et al., 2001, J Med Chem 44:923-930). Since our analogs are based on multi-aryl ring structure, we anticipate that each one will display a measurable permeability in these assays. We will compare these results directly to those obtained with curcumin, which will provide us with a comparative assessment with a compound that has already demonstrated some degree of bioavailability and passage of the blood-brain barrier.

Experimental Design:

Parallel Artificial Membrane Permeation Assay (PAMPA): Each well of a 96-well "donor" plate will receive 5 μl lipids prepared in organic solvent (e.g. 2% lecithin in dodecane). Lipids will be of a desired composition to mimic intestinal brush-border membranes. PBS containing 5% DMSO at the desired pH will be added to the "acceptor" plate. Analogs of interest (150 μl) will be prepared at varying concentrations in 5% DMSO/PBS and added to the "donor" plate. The pH of this solution will be varied to resemble intestinal pH changes that occur throughout its length in order to assess the effect of pH on absorption. The "donor" plate is then nested into the "acceptor" plate ensuring that the underside of the lipid membrane is in contact with buffer. The plates will be incubated at 23° C. for 16-24 hours. Absorption will be measured on 100 μL/well from the "donor" plate and 250 μL/well from the "acceptor" plate. Integrity of the artificial lipid membrane will be measured by quantitating the permeability of Lucifer Yellow. This dye demonstrates poor lipid permeability and should be incapable of diffusion into the "acceptor" plate. Lucifer Yellow will be quantitated by fluorescence analysis (λex 425 nm, λem 528 nm).

Passive Drug Permeability Assay: Each well of a 96-well "donor" plate will receive 15 μl of a 5% solution (v/v) of hexadecane in hexane. Plates are then allowed to dry for 1 h in a fume hood to ensure complete evaporation of the hexane allowing for the formation of a uniform layer of hexadecane. PBS containing 5% DMSO is added to each well of the "acceptor plate" and the hexadecane-treated "donor" plate is placed into the acceptor plate ensuring that the underside of the membrane is in contact with the buffer. Analogs of interest will be prepared at varying concentrations in 5% DMSO/PBS and added to the "donor" plate and incubated at 23° C. for 5 hours. Absorption is then measure for samples from both "donor" and "acceptor" plates. Finally, we will continue to improve upon the efficacy of chemical analogs of curcumin using ligand-based drug design.

Example 11

Endothelial Targets and Prevention of Diabetic Complications

Summary

Inflammation and oxidative stress play a major role in the endothelial dysfunction that is associated with diabetes and its microvascular complications. The transcription factor nuclear factor κB (NF-κB) is well known as a regulator of genes controlling the inflammatory response. NF-κB is commonly activated in endothelial cells in diabetes. We propose that limiting the activation of NFκB may be a new approach to the development of therapies for prevention of the microvascular complications of diabetes. We will develop compounds related to curcumin. The polyphenol curcumin, which is the active compound in the spice turmeric, has been used for centuries in Asia as a medicinal for treatment of a wide variety of health problems including inflammation. More recently, curcumin has been found to inhibit activation of NF-κB.

We intend to demonstrate that NF-κB is activated in endothelial cells in response to exposure to agents associated with microvascular complications and that activation of NF-κB results in up-regulation of genes associated with endothelial dysfunction. Human retinal endothelial cells will be exposed to agents or conditions that promote endothelial dysfunction, such as: high glucose; Advanced Glycation Endproducts; angiotensin II; and TNF-α. Activation of NF-κB and up-regulation of genes associated with the pro-inflammatory state (IL-1, IL-6), with extracellular matrix production (collagen, fibronectin) and with leukocyte adherence (E-selectin, ICAM-1) will be determined. Genetic manipulation of the NF-κB pathways will be used to determine if activation of NF-κB is required for the increased expression of these genes that promote endothelial dysfunction.

We will also evaluate curcumin and its analogs as potential therapeutics to prevent activation of NF-κB and to demonstrate that these inhibitors prevent development of endothelial dysfunction. We have developed analog-libraries of curcumin analogs and have demonstrated that a number of these analogs are more active than the parent compounds as inhibitors of the activation of NF-κB. Moreover, we have demonstrated that the anti-oxidant activity of these analogs is not required for inhibition of NF-κB. Endothelial cells will be used to determine the ability of these analogs to inhibit the activation of NF-κB and to prevent the NF-κB-dependent up-regulation of genes that promote endothelial dysfunction.

Endothelial Dysfunction and Diabetic Complications

Endothelial cells (EC), by virtue of their location between the circulation and the vascular tissue, are able to detect humoral changes and to transmit this information to other vascular cells through mechanisms involving altered gene expression both in the EC and in the target cells. EC responses to humoral changes include altering the expression of growth factors, cytokines and adhesion molecules. Thus the endothelium actively regulates vascular tone and permeability, balances coagulation and fibrinolysis, controls the composition of subendothelial matrix, regulates adhesion and extravasation of leukocytes and thereby influences inflammatory activity in vessel walls. Considerable evidence links EC dysfunction with development of microvascular complications in type 1 and type 2 diabetes (Yamagishi et al., 2005, Curr Pharm Des 11:2279-2299; Schalkwijk et al., 2005, Clin Sci 109:143-159; Pomilio et al., 2002, J Pediatr Endocrinol Metab 15:343-361; Hink et al., 2003, Treat Endocrinol 2:293-304). EC dysfunction in diabetes is linked to hyperglycemia (Stenina, 2005, Curr Pharm Des 11:2277-2278). Glucose transport into EC is insulin-independent and appears not to be regulated. Consequently, EC experience high internal concentrations of glucose in response to hyperglycemia with the resulting accumulation of various glucose metabolites. When exposed to high glucose in vitro, EC up-regulate the production of matrix components, including collagen and fibronectin (Cagliero et al., 1988, J Clin Invest 82:735-738), and of pro-coagulant proteins (Boeri et al., 1989, Diabetes 38:212-218). EC exhibit a decrease in proliferation, fibrinolyic potential and increased apoptosis in response to high glucose (Graier et al., 1995, Eur J Pharmacol 294:221-229; Maiello et al., 1992, Diabetes 41:1009-1015), and they up-regulate expression of TGF-β1 which likely controls the expression of many of the genes that code for extracellular matrix (Yevdokimova et al., 2004, J Diabetes Complications 18:300-308). EC also respond to changes in circulating cytokines. The cytokine VEGF, for example, can stimulate differentiation, survival, migration, proliferation and permeability in EC and is especially associated with diabetic retinopathy (Benjamin, 2001, Am J Pathol 158:1181-1184). Likewise, diabetic nephropathy is associated with expression of inflammation markers such as CRP, fibrinogen and IL-6, and with increased expression of adhesion molecules such as ICAM-1, which promote inflammation by increasing leukocyte adherence and infiltration (Dalla Vestra et al., 2005, J Am Soc Nephrol 16:S78-S82). The response of EC to these cytokines commonly involves signaling through transcription factor NF-κB. Additionally, oxidative stress has consistently been shown in experimental models of diabetes (Mohamed et al., 1999, BioFactors 10:157-167), and activation of NF-κB is often observed in response to these stresses.

Curcumin: A Natural Inhibitor of the Activation of NFκB

For centuries, curcumin has been used in India and Southeast Asia as a medicinal for a wide variety of conditions. Curcumin has been reported to possess antioxidant, anti-inflammatory, antiviral, and antimutagenesis activities (Araujo et al., 2001, Mem Inst Oswaldo Cruz 96:723-728). A number of recent studies of curcumin in experimental models of diabetes have reported beneficial effects of these natural products, which were assumed to be due to their anti-oxidant properties (Suranarayana et al., 2005, Invest Ophthalmol Vis Sci 46:2092-2099; Arun et al., 2002, Plant Foods Hum Ntr 57:41-52). However, curcumin can prevent the stress-induced activation of NF-κB in a variety of cells (Bremner et al., 2002, J Pharm Pharmacol 54:453-472; Aggarwal et al., 2004, Ann NY Acad Sci 1030:434-441; Shimizu et al., 2005, Mutat Res 591:147-160), which has been suggested to be the result of inhibition of IKK or of a kinase that activates IKK (Bharti et al., 2003, Blood 101:1053-1062). Since curcumin is a potent antioxidant, the multiple biological activities of these polyphenolic natural products may reflect their general antioxidant properties and/or these compounds may be targeted to specific proteins, such as kinases that regulate the expression of NF-κB. This question is especially relevant to the issue of the role of NF-κB in EC dysfunction in response to hyperglycemia where, as discussed above, oxidative stress often appears inseparable from activation of NF-κB. To address this question, initial studies were carried out to design libraries of analogs of curcumin, to evaluate the anti-oxidant properties of these analogs, and to test whether the ability of these analogs to prevent activation of NF-κB required retention of their anti-oxidant properties.

Preliminary Studies

The observation that simple compounds such as curcumin can block activation of NFκB leads to the hypothesis that synthetic compounds with enhanced activity compared to curcumin can be developed that block NFκB activation. These compounds would be anticipated to exhibit anti-inflammatory activity in EC exposed to high glucose and related stresses associated with diabetic complications and to prevent the up-regulation of genes that promote EC dysfunction. As mentioned above, the biological activities of curcumin are broad and have often been associated with their anti-oxidant activities. On the other hand, the suggestion that these natural products prevent the activation of NF-κB by inhibiting IKK or upstream kinases implies that there are specific targets of curcumin. The anti-oxidant activities of curcumin are derived from the phenolic functional groups. Therefore, synthesis of analogs devoid of the phenolic groups should alter their anti-oxidant activites and should provide analogs that can be used to test whether anti-oxidant activity is necessary for inhibition of the activation of NF-κB. The preliminary results below (recently published, Weber et al., 2005, Bioorg Med Chem 13:3811-3820; Weber et al., 2006, Biorg Med Chem 14:2450-2461) were designed to 1) develop efficient reaction schemes for the synthesis of analogs of curcumin; 2) evaluate the anti-oxidant properties of these analogs; 3) compare these analogs for their abilities to inhibit the activation of NF-κB; and 4) determine whether anti-oxidant activity is required for inhibition of NF-κB. These studies were conducted using a commercial NF-κB reporter stable cell line designed for screening inhibitors of NF-κB.

Synthesis and Biological Activity

Curcumin analog library: We have constructed a chemical library of curcumin analogs; these were used to identify specific functional groups responsible for curcumin's established anti-oxidant properties. These analogs, in general, retain the enone functionality of curcumin. The analogs include: 1) those that retain the 7-carbon spacer between the aryl rings as in curcumin; 2) those with a 5-carbon spacer; and 3) those with a 3-carbon spacer. In addition to carbon spacer variations, analogs were synthesized that have enone or dienone functionality, varying degrees of unsaturation in the spacer, and addition of alkyl or aryl groups to the spacer. We also have synthesized analogs with limited rotational flexibility and with heterocyclic aromatic rings. A brief summary of the synthetic schemes is presented in FIG. 37. These reaction schemes are versatile and efficient, providing us the ability to develop preliminary Structure-Activity Relationships (SAR) and, based upon initial screening with the Panomics NF-κB Reporter Stable Cell Line, the ability to utilize the screening data to design new analogs for hypothesis testing. The chemical basis of the anti-oxidant activities of curcumin and analogs, along with the synthetic schemes, have been reported (Weber et al., 2005, Bioorg Med Chem 13:3811-3820).

Inhibition of the Activation of NF-κB by Analogs of Curcumin

We carried out a screen of our curcumin library, using the commercial Panomics NF-κB Reporter Stable Cell; this is the human 293T embryonic kidney cell line stably transfected with the luciferase gene controlled by an NFκB-dependent promoter (293T/NFκB-luc). This cell line was developed by Panomics for screening potential inhibitors of NF-κB. Cells are stimulated with TNF-α to express luciferase, whose activity is monitored in a chemiluminometer. Screening of curcumin and analogs involves determining the ability of the analogs to inhibit the activation of NFκB, which is detected as diminished chemiluminescence. All of the analogs were separately analyzed for their effects on cell viability and growth and were demonstrated to be non-toxic at the concentrations used in screening. In this preliminary study, we identified a number of analogs that are more active than curcumin (Table 12).

Several points are noteworthy: 1) Derivatives of curcumin, such as analog 2 that contains an alkyl group attached to the central carbon, can retain activity; a large number of different alkyl or aralkyl groups can be attached at this position; 2) Analogs with activity can readily be identified in the C7 (1 and 2) and C5 (3, 4, and 5) series of analogs; 3) Even analogs with heterocyclic rings can retain activity (analog 3); and 4) Analogs that do not exhibit anti-oxidant activity, such as 3 and 5, can prevent activation of NFκB. This demonstrates that the biological activities of curcumin analogs can be separated from their anti-oxidant activities. This suggests that these analogs have specific biological targets rather than acting as general anti-oxidants.

TABLE 12

| Compound | Structure | IC$_{50}$ (μM) |
|---|---|---|
| 1 (curcumin) | 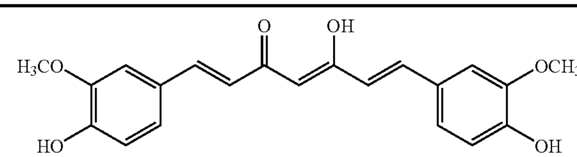 | 8.2 ± 0.4 |
| 2 | 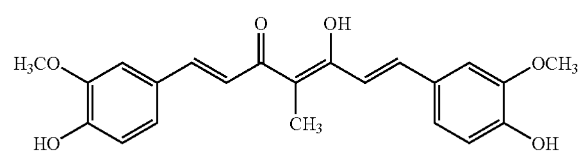 [SMILES: COc1cc(/C=C/C(=O)/C(C)=C(O)/C=C/c2ccc(O)c(OC)c2)ccc1O] | 6.7 ± 1.2 |
| 3 | 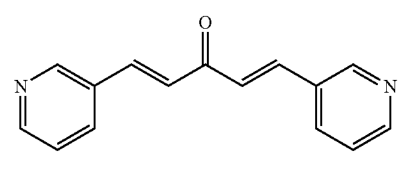 [SMILES: O=C(/C=C/c1cccnc1)/C=C/c1cccnc1] | 3.4 ± 0.2 |
| 4 | 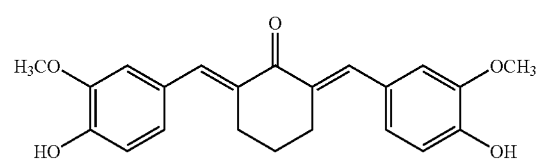 [SMILES: COc1cc(/C=C2\CCC/C(=C\c3ccc(O)c(OC)c3)C2=O)ccc1O] | 4.4 ± 0.8 |
| 5 | 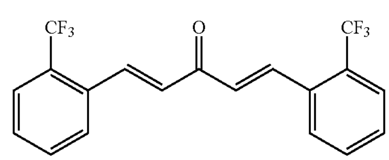 [SMILES: O=C(/C=C/c1ccccc1C(F)(F)F)/C=C/c1ccccc1C(F)(F)F] | 5.0 ± 0.3 |

Summary of Pertinent Initial Results

In summary, our initial studies (Weber et al., 2005, Bioorg Med Chem 13:3811-3820; Weber et al., 2006, Biorg Med Chem 14:2450-2461) of the synthesis and biological activities of curcumin analogs have provided libraries of compounds, some of which are potent anti-oxidants, even more potent than the parent compounds, and some of which are devoid of anti-oxidant activity. Our screening of curcumin analogs for their abilities to prevent the TNF-α-induced activation of NF-κB in a cell-based screening assay indicate that anti-oxidant activity is not necessary for this biological activity, which suggests that there are specific targets for these analogs. We are now in a position to utilize these analogs in studies of EC dysfunction and to determine whether inhibition of the activation of NF-κB is a promising approach to development of new therapeutics for prevention of microvascular complications of diabetes.

Although activation of NF-κB is commonly observed in EC that are exposed to conditions associated with microvascular complications, and although these treatments commonly result in up-regulation of a number of pro-inflammatory genes as well as genes that promote leukocyte adhesion, endothelial permeability and matrix deposition, it remains to be demonstrated that activation of NF-κB is essential for up-regulation of these genes. Therefore, we will examine the role for NF-κB in promoting the alterations in EC gene expression associated with complications.

Our first goal is to demonstrate that activation of NF-κB precedes the up-regulation of genes associated with microvascular complications. We will utilize real-time PCR to monitor the expression of pro-inflammatory factors (IL-1, IL-6), extracellular matrix components (collagen, fibronectin), and leukocyte adhesion factors (E-selectin, ICAM-1). The activation of NF-κB will be analyzed by Western blots of nuclear extracts using p50/RelA-specific and p52/RelB-specific antibodies to monitor both the classical and the alternative pathways. EC cells will be exposed to high glucose, AGE, TNF-α, or angiotensin II to elicite stress. The AGE will include glucose-modified and methylglyoxal-modified albumin prepared by both short- and long-term exposure of albumin to these aldehydes. It is known that methylglyoxal is the main reactive aldehyde produced in diabetes and is the precursor to many of the known AGE (Thornalley, 2002, Int Rev Neurobiol 50:37-57; Vander Jagt et al., 2003, Chem Biol Interact 143-144:341-351). In addition, AGE that form intracellularly in EC exposed to high glucose are derived from methylglyoxal (Shinohara et al., 1998, J Clin Invest 101:1142-1147). Thus both AGE that are administered extracellularly and AGE that are produced intracellularly may contribute to EC dysfunction. In addition, AGE prepared by short-term exposure of proteins to glucose and other aldehydes elicit different effects than AGE prepared from long-term exposure (Mandl-Weber et al., 2001, Perit Dial Int 21:487-494; Schalkwijk et al., 2002, Semin Vasc Med 2:191-197). The experimental cellular system will utilize human retinal EC isolated from human retinas (NDR[1], Philadelphia). As an alternative, human umbilical vein endothelial cells (HUVEC), which are commercially available (Clonetics), will be compared to retinal EC. If the results of initial experiments are similar, HUVEC will be used in place of retinal EC for convenience.

Our second goal is to determine whether activation of NF-κB is essential for up-regulation of this battery of genes. We will utilize siRNA to silence selected components of the IKK/IκB/NF-κB system. As before, real-time PCR will be used to monitor expression of the pro-inflammatory, extracellular matrix and cell adhesion genes in response to the various stresses administered, except that the EC will first be treated with the appropriate siRNA. Real-time PCR and Western analysis will be used to demonstrate that the desired target has been silenced. siRNA targets will include IKKβ and p50/RelA to monitor the classical pathway and IKKα and p52/RelB for the alternative pathway.

Our third goal is to determine whether ROS must be increased in EC before there is activation of NF-κB. This question is related to the observation that increases in ROS are commonly observed in studies of the activation of NF-κB. The production of ROS in response to exposure of EC to the various agents will be monitored by FACS analysis with ROS-sensitive dyes such as dihydrorhodamine 123. Thus, the main question is whether there is a required temporal relationship between exposure of EC to stress, increase of ROS, activation of NF-κB, and up-regulation of complications-associated genes.

We are developing libraries of compounds related to biologically active, polyphenolic natural products including curcumin. Thus, expansion of the analog libraries already described (Weber et al., 2005, Bioorg Med Chem 13:3811-3820; Weber et al., 2006, Biorg Med Chem 14:2450-2461) is an ongoing effort that will provide a range of compounds for use in this project. Analogs of curcumin that are more active than the parent compounds as inhibitors of the activation of NF-κB are available, including compounds devoid of antioxidant activity as well as analogs that are stronger antioxidants than the parent compounds. This range of analogs will be used in studies of the stress response of EC. In addition, analogs are being developed that exhibit improved bioavailability compared to curcumin, which shows poor bioavailability (Garcea et al., 2004, Br J Cancer 9:1011-1015). The poor bioavailability of curcumin is the main reason that attempts to develop this natural product as a drug likely will not succeed. Therefore, there is a need to develop analogs with better pharmacokinetic properties.

We will determine whether the active analogs identified with the Panomics NF-κB Reporter Stable Cell assay also prevent the activation of NF-κB in EC in response to high glucose, AGE, angiotensin II and TNF-α. As before, we will follow the activation of NF-κB by Western analysis of nuclear extracts using p50/RelA-specific or p52/RelB-specific antibodies to assess the two pathways.

We will also determine whether inhibiting the activation of NF-κB in EC by analogs of curcumin prevents the up-regulation of genes associated with microvasculer complications. As before, we will utilize real-time PCR to monitor the expression of pro-inflammatory factors, extracellular matrix components, and leukocyte adhesion factors. To quantitate the effects of analogs on target expression, we will use the comparative $C_T$ method. The amount of target message with analog treatment will be normalized to the internal reference (β-actin) and compared to the calibrator (target expression without analog treatment). Since curcumin is an established inhibitor of NF-κB, it will serve as our positive controls in all experiments. The 96-well plate format will permit a high efficiency and rapid screen to accurately assess individual analogs as well as obtain quantitative data to determine individual $K_i$ values. The Applied Biosystems 7000 System is capable of multiplexing 96 samples simultaneously in approximately 2 h. Comparisons between cells treated with varying concentrations of analogs will be made by Student's t-test. Differences in p-values <0.05 will be considered significant.

We will also identify the site(s) of action of curcumin analogs in preventing the activation of NF-κB in EC. A likely target is IKKβ or IKKα, based upon literature reports that implicate these targets (Bharti et al., 2003, Blood 101:1053-1062). However, it is also possible that a kinase upstream of IKK may be a target. We will initially screen analogs against recombinant human IKK (α and β) to test whether there is a correlation between the cellular data and enzyme inhibition data for either of these kinases. If neither IKK isoform is inhibited by these analogs, then additional kinases will need to be evaluated as likely targets.

Materials and Methods

Cell culture and chemicals: EC will be isolated from retina dissected from human eyes obtained from NDR1 (Philadelphia). Fresh retinas are incubated in DMEM with 0.01% type 1 collagenase, filtered through nylon mesh and the endothelial cells are isolated with antibody-coated magnetic beads for endothelial cells (DynabeadsCD31, Dynal Biotech) (Su et al., 2003, Molec Vision 9:171-178). EC are maintained in Dulbecco's modified Eagle's medium (DMEM, low glucose formulation) supplemented with 4 mM L-glutamine, 10% fetal bovine serum (FBS), 100 units/ml penicillin, 100 µg/ml streptomycin, 0.25 µg/ml amphotericin B). AGE (methylglyoxal (MeG)-modified HSA and glucose-modified HSA, both short (one week)- and long (seven week)-term glycation), are prepared under sterile conditions. MeG is obtained as the dimethylacetal (Aldrich) because commercial MeG is contaminated with formaldehyde. MeG is liberated from the acetal under acid conditions and then purified by azeotropic distillation with water and standardized with the glyoxalase-I reaction, as we described (Vander Jagt et al., 2003, Chem Biol Interact 143-144:341-351).

Real-time PCR: EC will be plated in 96-well plates for assay ($5 \times 10^4$ cells/well). When cells reach 80-90% confluency, they will be stressed with 25 mM glucose, AGE, TNF-α or angiotensin II, together with varying concentrations of either curcumin or its analogs, for varying times depnding on the stressor, at 37° C. 5% $CO_2$/95% air. Total RNA will then be extracted, isolated using an RNeasy kit (Invitrogen) and quantitated by measuring absorbance at 260 nm. One-step reverse transcriptase (RT) coupled to real time PCR analysis will be performed using an Applied Biosystems 7000 System. Primers (designed to amplify <150 bp) and TaqMan probe for the various transcripst will be designed using Applied Biosystems Primer Express software. Primers and TaqMan Probe for β-actin will be used as an internal control. Real-time PCR values obtained for β-actin will be used to normalize values for target expression to correct for loading or cell number differences between wells. Cycling parameters will be determined to optimize target and β-actin amplifications. Our starting parameters have been successful for amplification of many different genes currently under study: 50° C. 10 min (RT reaction), 94° C. 2 min (RT enzyme inactivation, Taq Polymerase activation), 40 cycles 92° C. 30 s, 60° C. 30 s, 72° C. 30 s.

Western analysis: Activation of NF-κB by the classical pathway will be determined with the Panomics TransBinding NF-κB Assay Kit, which quantifies the activation of p50. This ELISA-based assay, which utilizes immobilized oligonucleotide containing NF-κB consensus sites, can be used with whole cell extracts or nuclear extracts; nuclear extracts will be prepared using the Panomics Nuclear Extraction Kit. Activation of NF-κB by the alternative pathway will be determined by Western analysis with human RelB antibody (ab12013, Ancam) as the primary antibody (rabbit polyclonal) and HRP-conjugated goat anti-rabbit IgG as the second antibody.

siRNA

Cellular oxidative stress: ROS determinations by FACS analysis will be carried out with dihydrorhodamine 123 (or alternatively with 2',7'-dichlorodihydrofluorescein). Cells from the various experimental protocols are treated with the nonfluorescent, permeable form of the indicator which is trapped intracellularly following uptake and hydrolysis. After oxidation of the dye to the fluorescent form by intracellular ROS, cells are analyzed by Becton Dickenson FACSCAN with excitation 495, emission 525 nm, respectively, carried out in the University New Mexico Flow Cytometry Facility. Cells are treated with stress-inducer for varying periods, incubated with dye for 30 min, trypsinized and then subjected to FACS, with at least 20,000 events analyzed.

Synthesis: Our recent report on the anti-oxidant properties of curcumin and its analogs (Weber et al., 2005, Bioorg Med Chem 13:3811-3820) included description of a wide range of synthetic procedures as described in FIG. 37. Currently there are about 100 analogs in our curcumin library.

Screening with the Panomics NF-κB Reporter Stable Cell: The following procedure was used to obtain the data reported recently (Weber et al., 2006, Biorg Med Chem 14:2450-2461). An NF-κB reporter stable cell line from human 293T embryonic kidney cells (293T/NFκB-luc) (Panomics) was grown in a humidified atmosphere at 37° C. in 5% $CO_2$/95% air. The cells were maintained in Dulbecco's Modified Eagle's Medium (DMEM—high glucose containing 4 mM glutamine) supplemented with 10% fetal bovine serum (FBS), 1 mM sodium pyruvate, 100 units/ml penicillin, 100 µg/ml streptomycin and 100 µg/ml hygromycin (Gibco/Invitrogen, Carlsbad, Calif.)) to maintain cell selection. One day prior to treatment, the 293T/NFκB-luc cells were plated into 24-well cell culture plates (Costar) at approximately 70% confluency in the above media without hygromycin. The following day cells were fed fresh media 1 hour prior to treatment. Media with or without recombinant tumor necrosis factor alpha (TNF-α) (R&D Biosciences/Clontech) was then applied to the cells at 20 ng/ml followed by immediate treatment with curcumin or analog. The cells were placed again in a humidified atmosphere at 37° C. in 5% $CO_2$/95% air for 7 hours. Plate wells were gently washed with phosphate buffered saline, pH 7.4, and lysed with 1× passive lysis buffer (Promega). The subsequent lysates were analyzed with the Luciferase Assay System (Promega) utilizing a TD-20/20 luminometer (Turner Designs). The firefly luciferase relative light units were normalized to protein (mg/ml) with BCA™ Protein Assay Kit (Pierce) and standardized to TNF-α control.

Screening against IKKα and IKKβ: It is likely that some of the analogs in the curcumin libraries may inhibit IKK, based upon reports in the literature (Shimizu et al., 2005, Mutat Res 591:147-160; Bharti et al., 2003, Blood 101:1053-1062). Recombinant human IKKα and IKKβ are now available (Upstate). Therefore, we will screen our library against these two kinases. We anticipate that we may identify a subset of compounds that are inhibitors of these kinases. If this is the case, then these subsets of analogs will be used separately to develop IKK-specific SAR to identify new, more potent inhibitors that may be highly specific for each IKK. The IKK screening will be carried out as follows: Enzyme reactions are conducted in 40 mM MOPS buffer, pH7, containing 1mM EDTA. The substrate is a commercial IKK peptide substrate (named IKKtide) from Upstate, used at 100 µM. The reaction is initiated with 100 µM [γ-$^{32}$P]ATP (3000 Ci/mmol, Perkin Elmer). Reactions mixtures with and without added analog are incubated for 10 min at 30° C., transferred to P81 paper, washed with 0.75% phosphoric acid, then acetone, and counted in standard scintillation cocktail. For analogs that are active, kinetic runs to obtain dissociation constants will be conducted using a range of IKKtide concentrations, with and without added analog. CPM will be converted into initial rates and analyzed by non-linear regression (ENZFITTER, Elsevier-Biosoft).

Bioavailability: Analogs of curcumin that are promising drug candidates from studies of inhibition of activation of NF-κB in EC cells will be examined for predicted oral bioavailability by use of the Parallel Artificial Membrane Permeability Assay (PAMPA), which uses a hexadecane-filled membrane (Millipore MultiScreen Permeability Plate) as a lipophilic barrier in a 96-well format. This is then combined with a 96-well plate reader for quantitation of material that passes through the membrane (Kansy et al., 1998, J Med Chem 41:1007-1010).

Anticipated Problems and Alternative Procedures: The synthetic strategies are straightforward and have been used in our preliminary studies; these will allow us to synthesize a wide variety of analogs. The determinations of ROS levels use standard procedures. HUVECS are available as a backup to EC. The various treatments (high glucose, AGE, TNF-α, angiotensin II) provide overlap between the two pathways for activation of NF-κB and, therefore, some redundancy. The siRNA procedure is not anticipated to present any problems; use of antisense oligonucleotides is available as a backup. Likewise the real-time PCR procedure is not anticipated to present any problems; conventional use of Northerns is available as a backup.

Example 12

Glutathione-S-Transferase P1-1: An Anticancer Drug Target

Introduction

Glutathione-S-Transferase (GSTP1-1) belongs to the glutathione-S-transferase family of detoxification enzymes. It catalyzes the addition of glutathione, an important biological antioxidant, to toxic electrophiles including anti-cancer drugs. GSTP1-1 has been shown to be over expressed in many cancers, which leads to increased resistance to anti-cancer drugs. We propose that inhibition of GSTP1-1 will increase susceptibility of the cancer to the anti-cancer drug.

Curcumin has been shown to inhibit GSTP1-1. Curcumin and analogues or curcumin were analyzed for their ability to inhibit GSTP1-1 activity.

Materials and Methods

Computer modeling was used to screen 63 curcumin compounds for promising inhibitors of GSTP1-1. Computer modeling used a crystal structure of GSTP1-1 from the Protein Data Bank. Inhibitors were drawn using Sybyl molecular modeling software. Inhibitors were docked to GSTP1-1 using Autodock3, which estimates the binding constant of the inhibitor to the protein.

Kinetic analysis assays were conducted. In photometric assays, curcumin and 63 curcumin analogues were screened. GSTP1-1 activity was measured at pH 6.5 in 1 ml volumes of 20 mM potassium phosphate buffer containing 100 mM NaCl, 1 mM CDNB and 1 mM GSH. Curcumin and curcumin analogues were screened at a concentration of 25 μM and the reaction was initiated with 70 ng of GSTP1-1 enzyme and monitored at 340 nm, 25° C. (Perkin/Elmer Lambda 2S spectrophotometer). These activities were plotted as percent of control (GSTP1-1 activity without inhibitors). Kinetic analysis (dissociation constants) of inhibitors was determined by linear regression analysis of the Dixon, plots. Routinely, assays were carried out as above, however, at two different constant concentrations of GSH (0.25 and 1.25 mM) varying the concentration of analogue. Ki's were calculated utilizing SigmaPlot's Enzyme Kinetics Module™ (Chicago, Ill., USA).

Results

Figure 38:
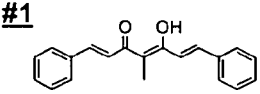
FIG. 38 shows curcumin analogs, as well as estimated binding constants.
Figure 38:
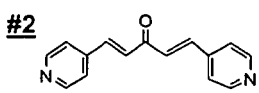
Figure 39:
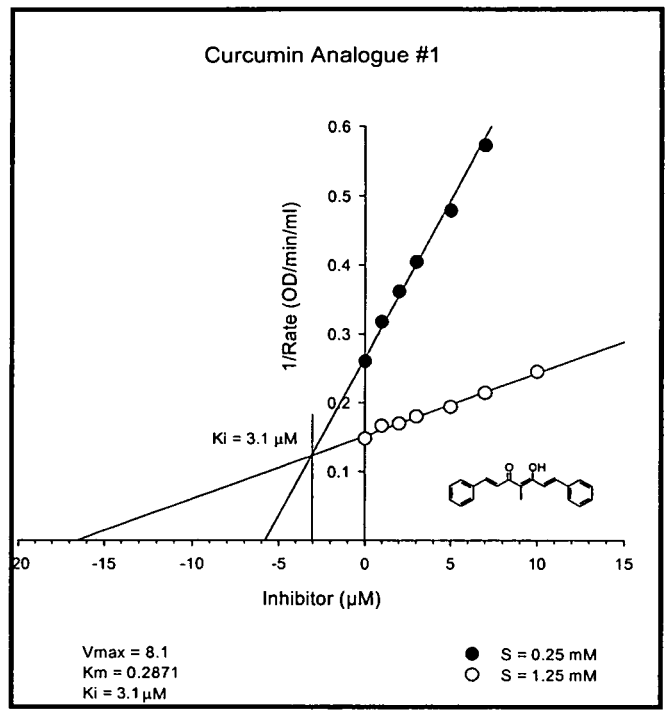
FIG. 39 shows GSTP1-1 inhibitory activity of a curcumin analog.
Figure 40:
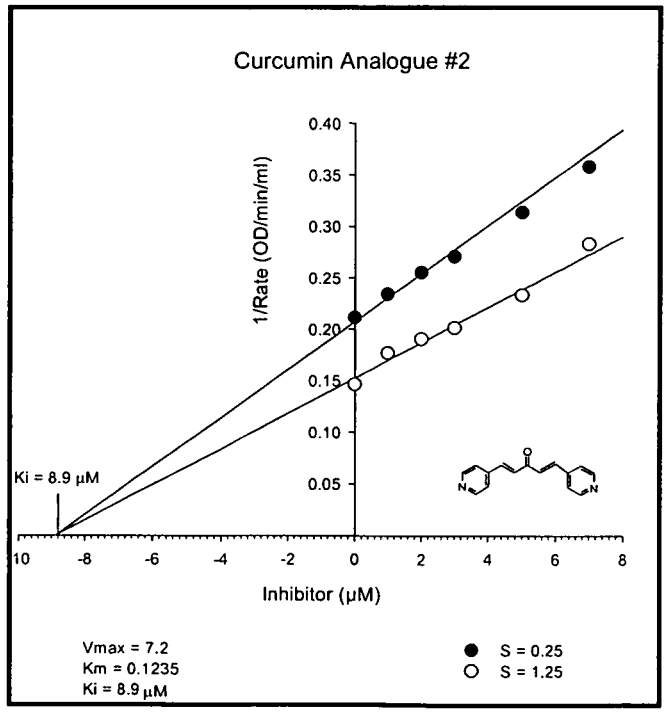
FIG. 40 shows GSTP1-1 inhibitory activity of a curcumin analog.

FIG. 38 and FIG. 39 show curcumin analogues #1 and #2, respectively, and some estimated Ki binding constants from computer modeling with their molecular structures. Dixon plots for curcumin analogues #1 (left) and #2 (right) showing inhibition of GSTP1-1 are shown in FIG. 40. These two analogues were shown to exhibit better inhibition than curcumin. Ki values for these analogues were similar to the predicted Ki values from computer modeling.

Conclusions

In kinetic analysis experiments, assays of the natural product curcumin analogues of curcumin were tested for inhibition of GSTP1-1. Experiments showed that curcumin analogues inhibit GSTP1-1 well. Many analogues of curcumin inhibit GSTP1-1 activity better than curcumin itself. In general, computer modeling predicted inhibition results that were in agreement with experimental results. Curcumin analogues that inhibit GSTP1-1 will be tested for their abilities to sensitize breast cancer cells to anti-cancer drugs in culture.

Example 13

Inhibitory Activity of Curcumin Derivatives in GSTP1-1 Assay and Computer Modeling Curcumin is known to inhibit GSTP1-1 activity. Therefore, it was thought that modification of the structure of curcumin could lead to enhanced activity. The library consisting of three series of curcumin analogues examined the role of the enone functionality in aryl systems where the spacer is 7-carbons (as in curcumin), 5-carbons or 3-carbons in length. In addition, the importance of aryl ring substituents was assessed. The GSTP1-1 inhibitory activities of curcumin and analogues were determined by the inhibition of the formation of product of a reaction between the electrophilic 1-chloro-2,4-dinitrobenzene (CDNB) and the nucleophilic glutathione (GSH) at 340 nm which is catalyzed by GSTP1-1.

Curcumin and its analogues were tested for glutathione S-transferase inhibitory activity by an enzyme assay. Glutathione S-transferase activity was measured at pH 6.5 in 1 ml volume aliquots of potassium phosphate buffer (20 mM, Fluka; Sigma/Aldrich), containing sodium chloride (100 mM, Fluka; Sigma/Aldrich), 1-chloro-2,4-dinitrobenzene (CDNB, 1 mM, Fluka; Sigma/Aldrich) and glutathione (GSH, 1 mM, Fluka; Sigma/Aldrich) followed by the addition of curcumin and analogues (10 μl). The reaction was initiated with recombinant glutathione S-transferase P1-1 enzyme (70 ng/ml final concentration, Calciochem) and monitored at 340 nm at 25° C. for 1 min. These activities were plotted as percent of control (GSTP1-1 activity without inhibitors).

Figure 41:
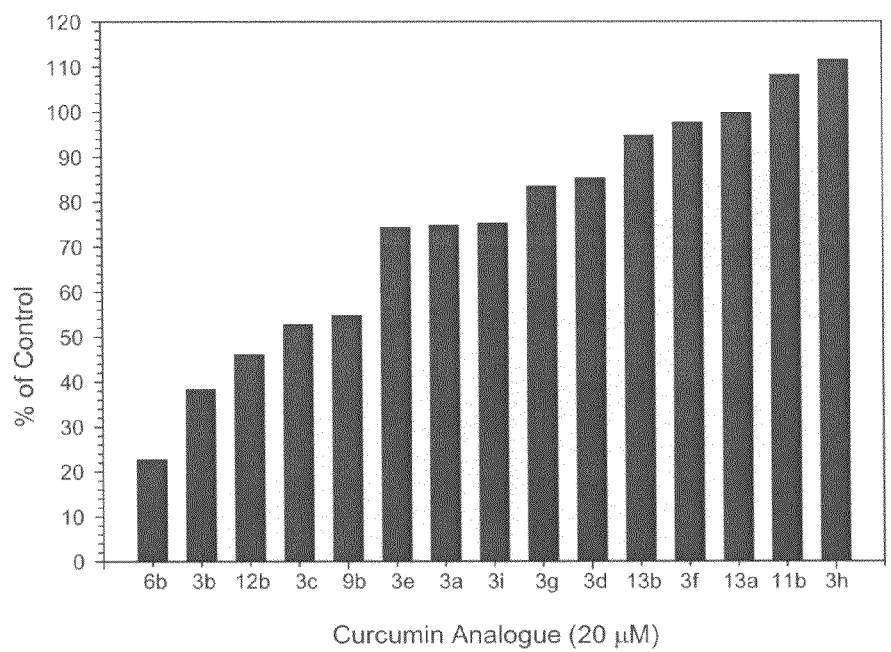
FIG. 41 shows the activity of 7-carbon analogues in the GSTP1-1 assay.
Figure 42:
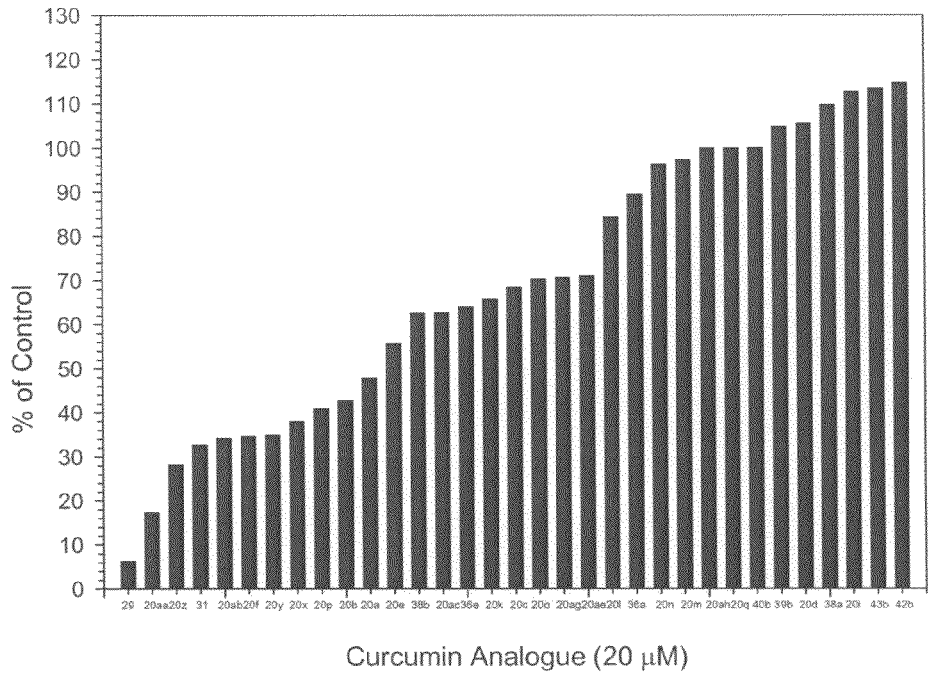
FIG. 42 shows the activity of 5-carbon analogues in the GSTP1-1 assay
Figure 43:
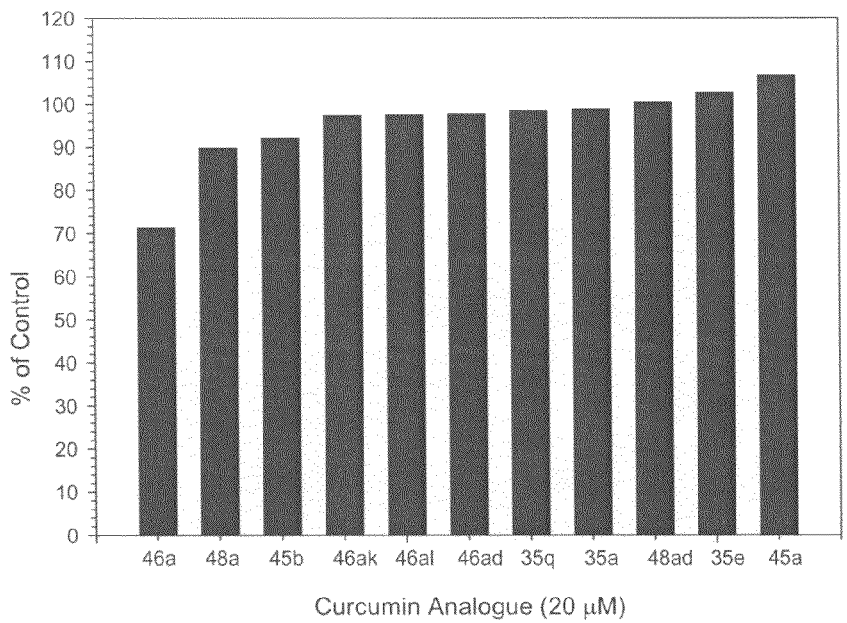
FIG. 43 shows the activity of 3-carbon analogues in the GSTP1-1 assay

FIG. 41, FIG. 42 and FIG. 43 show analogues active in the GSTP1-1 screening assay. The active analogues are arranged from highly active on the left to slightly active on the right.

Active analogues in series 1, which contain a 7-carbon spacer, are shown in FIG. 41. Five analogues, 6b, 3b, 12b, 3c and 9b in this series were more active than curcumin. Four of the active analogues in this series contain aryl groups with no substituents. Three of these analogues also contain a central methylene substituent with one of these analogues, 12b, containing two benzyl substituents. The active analogues in this series are all very hydrophobic. There is very little correlation to antioxidant activity in these analogues.

Active analogues in series 2, which contain a 5-carbon spacer, are shown in FIG. 42. Twenty analogues including 29, 20aa, 20z, 31, 20ab, 20f, 20y, 20x, 20p and 20b show better inhibitory activity than curcumin. Eight of the ten most active analogues contain an aryl group with a substituent in either the para or meta position. Just as in the 7-carbon series when the most active analogues were hydrophobic, analogues in the 5-carbon series also follow this trend. Some of the active analogues in this series also Analogues in series 3, which contain a 3-carbon spacer, are shown in FIG. 43. No analogue in this series was more active than curcumin. Many of the analogues in this series exhibit antioxidant activity.

We performed a similar assay using 2.5 mM glutathione and 1mM 1-chloro-2,4-dinitrobenzene as the electrophile. In this assay GSTP1-1 was activated with TNFα. The reaction was monitored at 340 nm. Curcumin and each analogue were analyzed at 25 µM concentration. In that assay, it appeared that that analogues of curcumin in which the two aryl groups are separated by 7-carbon, 5-carbon, or 3-carbon enone spacers are able to inhibit the TNFα-induced activation of GSTP1-1 and, possibly, ultimately NFκB. However, activities can vary widely. The most active analogues are those that retain the enone functionality, so, surprisingly, it is found that this enone functionality is very important and preferred for the inventive small molecules and its method of application. Many of the analogues are more active than curcumin. Ring substituents are not necessary for activity but can affect it. The analogues need not have the same substituents on each of the aromatic or heterocyclic rings.

Computer Modeling

An additional docking study was performed on glutathione S-transferase P1-1 (GSTP1-1). Curcumin is a known inhibitor of GSTP1-1. One crystal structure was selected from the protein data bank of the thirty one available selections. 19GS[12] was selected because it contained a large portion of the GSTP1-1 protein and was complexed to its natural substrate glutathione.

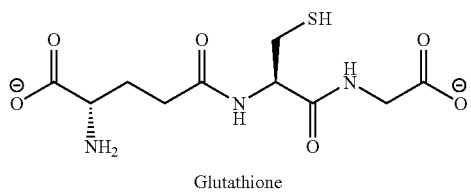 [SMILES: N[C@@H](CCC(=O)N[C@@H](CS)C(=O)NCC(=O)[O-])C(=O)[O-]]
Glutathione

When glutathione was removed and docked back to GSTP1-1, glutathione bound in the same location and with the same orientation it had before being removed from the protein. When the analogues were docked, they all docked to the same binding area and most of the analogues docked into the actual binding pocket. Many of these analogues have good $K_{est}$ values with analogue 14a having the most potent $K_{est}$ value at 3.51 E-9 M as shown in Table 14. Nine of the docked analogues display better $K_{est}$ values than glutathione. Therefore, there is the potential that any of these analogues could block glutathione from entering GSTP1-1. There is no correlation to the $K_{exp}$ values.

TABLE 14

| $K_{est}$ Values for GSTP1-1 (19GS) | | | | | | | |
|---|---|---|---|---|---|---|---|
| 14a | 3.51E-09 | 6a | 1.09E-07 | 20i | 3.16E-07 | 40b | 8.56E-07 |
| 15a | 6.57E-09 | 52e | 1.13E-07 | 20k | 3.18E-07 | 46ak | 8.66E-07 |
| 15b | 9.61E-09 | 3g | 1.17E-07 | 3e | 3.22E-07 | 45b | 9.34E-07 |
| 12b | 1.26E-08 | 20l | 1.20E-07 | 16b | 3.37E-07 | 50b | 9.37E-07 |
| 9b | 1.33E-08 | 3b | 1.23E-07 | 20y | 3.74E-07 | 20z | 1.00E-06 |
| 9a | 3.33E-08 | 20o | 1.25E-07 | 20q | 3.92E-07 | 52ac | 1.08E-06 |
| 17b | 3.35E-08 | 3a | 1.36E-07 | 36a | 4.10E-07 | 31 | 1.09E-06 |
| 23 | 4.63E-08 | 13a | 1.53E-07 | 20c | 4.27E-07 | 52l | 1.14E-06 |
| 53 | 4.79E-08 | 3d | 1.64E-07 | 46a | 4.41E-07 | 20p | 1.24E-06 |
| gluta | 5.26E-08 | 20ab | 1.77E-07 | 40af | 4.55E-07 | 20aa | 1.29E-06 |
| 20ag | 5.34E-08 | 20m | 2.03E-07 | 20n | 4.68E-07 | 20b | 1.33E-06 |
| 20w | 5.67E-08 | 13b | 2.19E-07 | 6b | 4.72E-07 | 36e | 1.40E-06 |
| 20v | 5.87E-08 | 45a | 2.22E-07 | 20a | 4.86E-07 | 29 | 1.45E-06 |
| 20ae | 6.81E-08 | 20u | 2.25E-07 | 20r | 5.30E-07 | 42b | 1.57E-06 |
| 38a | 6.84E-08 | 48ad | 2.28E-07 | 20ac | 5.39E-07 | 20t | 1.97E-06 |
| 14b | 7.09E-08 | 20e | 2.54E-07 | 48a | 6.36E-07 | 39b | 2.06E-06 |
| 3i | 7.75E-08 | 13c | 2.61E-07 | 46ad | 6.38E-07 | 34 | 2.57E-06 |
| 20g | 8.88E-08 | 52aa | 2.67E-07 | 20f | 7.40E-07 | 43b | 3.25E-06 |
| 25 | 9.45E-08 | 11b | 2.68E-07 | 38b | 7.61E-07 | 35a | 4.00E-06 |
| 3f | 9.68E-08 | 46al | 2.80E-07 | 20s | 7.90E-07 | 35q | 5.83E-06 |
| 20ah | 1.05E-07 | 52b | 2.84E-07 | 20x | 8.01E-07 | 35e | 1.12E-05 |
| 3h | 1.07E-07 | 20d | 3.01E-07 | | | | |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of treating a subject afflicted with Alzheimer's disease, the method comprising administering to the subject a therapeutically effective amount of a composition comprising a curcumin derivative according to the chemical structure:

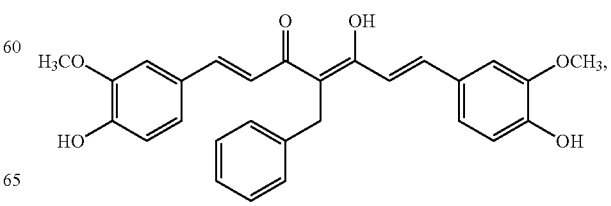

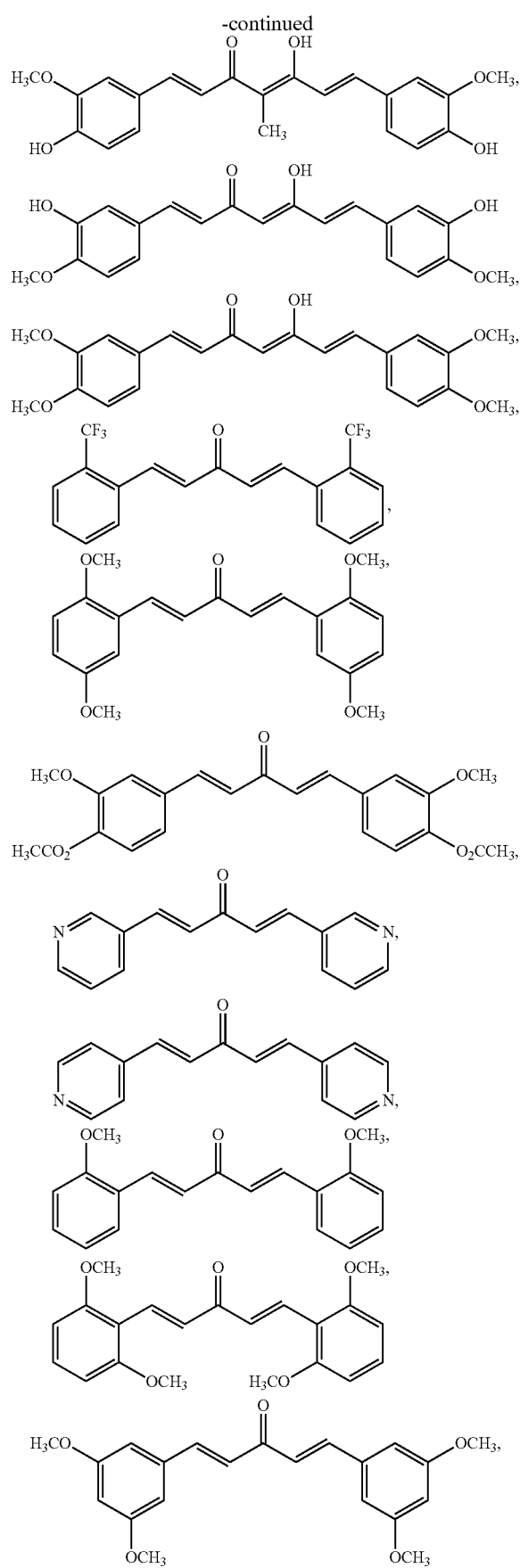
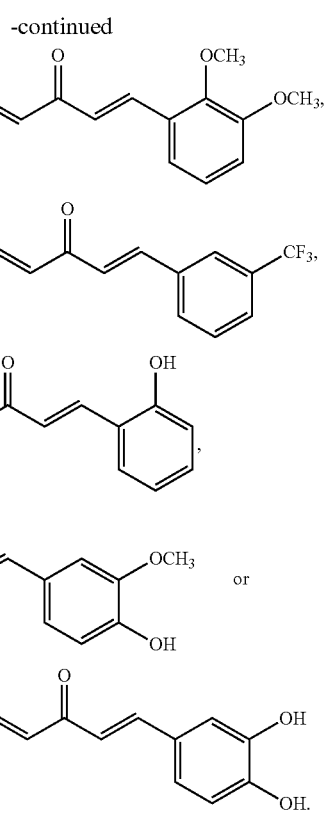
2. The method according to claim 1 wherein said compound is
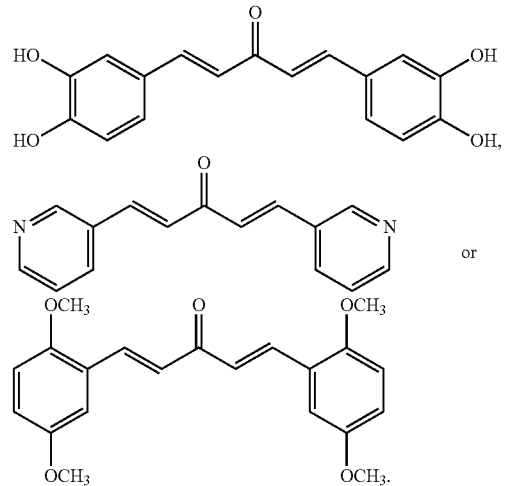
3. The method according to claim 1 wherein said compound is
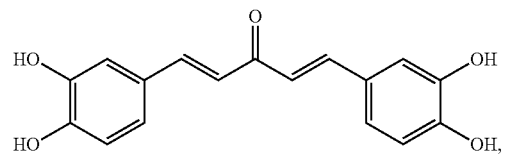

-continued

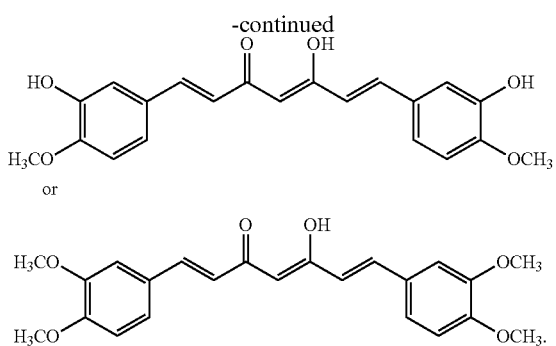

or

4. The method according to claim 1 wherein said compound is

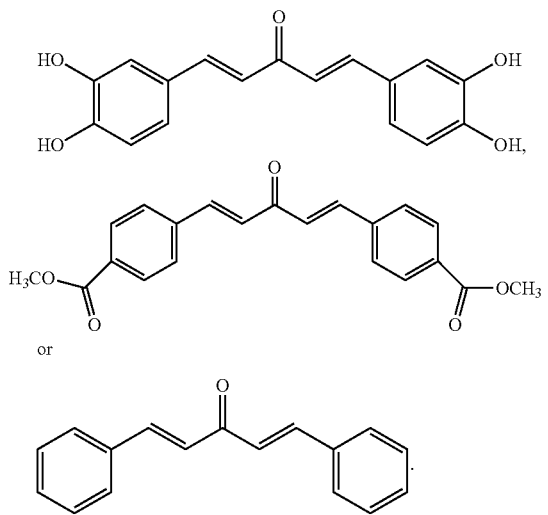

5. The method of claim 1, wherein the composition further comprises a pharmaceutically acceptable carrier.

6. The method of claim 1, wherein the curcumin derivative inhibits at least one of AP-1 or NF-κB.

7. The method of claim 1, wherein the curcumin derivative inhibits amyloid plaque formation.

8. The method of claim 1, wherein the curcumin derivative inhibits aggregation of a plurality of Aβ peptides.

9. The method of claim 1, wherein the curcumin derivative inhibits oligomerization of a plurality of Aβ peptides.

10. The method of claim 1, wherein the curcumin derivative decreases the cytotoxicity of an Aβ peptide aggregate.

11. The method of claim 1, wherein the curcumin derivative decreases activation of a glial cell by an Aβ peptide aggregate.

12. The method according to claim 1 wherein said curcumin derivative is a compound according to the chemical structure:

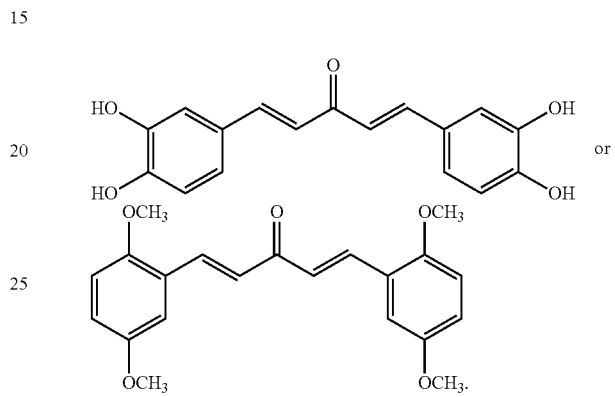

13. The method according to claim 1 wherein said curcumin derivative is a compound according to the chemical structure:

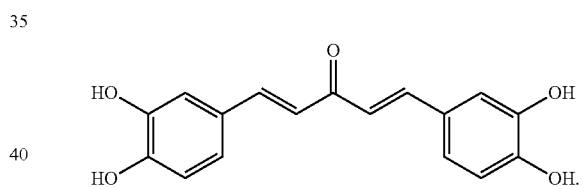

* * * * *